(12) United States Patent
Arnold et al.

(10) Patent No.: US 8,575,164 B2
(45) Date of Patent: Nov. 5, 2013

(54) COMBINATION CANCER THERAPY

(75) Inventors: Lee D. Arnold, East Islip, NY (US);
Qun-Sheng Ji, Babylon, NY (US);
Elizabeth Buck, Farmingdale, NY (US);
John D. Haley, Farmingdale, NY (US);
Mark J. Mulvihill, Farmingdale, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 895 days.

(21) Appl. No.: 12/072,269

(22) Filed: Feb. 25, 2008

(65) Prior Publication Data

US 2008/0267957 A1 Oct. 30, 2008

Related U.S. Application Data

(63) Continuation-in-part of application No. 11/787,236, filed on Apr. 13, 2007, now abandoned, which is a continuation-in-part of application No. 11/641,346, filed on Dec. 18, 2006, now abandoned.

(60) Provisional application No. 60/752,243, filed on Dec. 19, 2005.

(51) Int. Cl.
| | | |
|---|---|---|
| A01N 43/64 | (2006.01) | |
| A01N 43/58 | (2006.01) | |
| A01N 43/60 | (2006.01) | |
| A61K 31/53 | (2006.01) | |
| A61K 31/50 | (2006.01) | |
| A61K 31/495 | (2006.01) | |

(52) U.S. Cl.
USPC .......................................... 514/243; 514/249

(58) Field of Classification Search
USPC .................................. 514/243, 249
See application file for complete search history.

(56) References Cited

U.S. PATENT DOCUMENTS

| | | | |
|---|---|---|---|
| 5,217,999 A | 6/1993 | Levitzki et al. | |
| 5,302,606 A | 4/1994 | Spada et al. | |
| 5,397,787 A | 3/1995 | Buzzetti et al. | |
| 5,556,874 A | 9/1996 | Dobrusin et al. | |
| 6,194,439 B1 | 2/2001 | Dow | |
| 6,265,411 B1 | 7/2001 | Thomas et al. | |
| 6,337,338 B1 | 1/2002 | Kozlowski et al. | |
| 6,362,336 B1 | 3/2002 | Lohmann et al. | |
| 6,486,179 B2 | 11/2002 | Jirousek et al. | |
| 6,939,874 B2 | 9/2005 | Harmange et al. | |
| 7,087,602 B2 | 8/2006 | Thomas et al. | |
| 7,087,613 B2 | 8/2006 | Norris | |
| 7,115,617 B2 | 10/2006 | Buchanan et al. | |
| 7,202,243 B2 | 4/2007 | Hendrix et al. | |
| 7,244,733 B2 | 7/2007 | Hunt et al. | |
| 7,271,262 B2 | 9/2007 | La Greca | |
| 7,326,699 B2 | 2/2008 | Capraro | |
| 7,332,497 B2 | 2/2008 | Hirst et al. | |
| 7,345,038 B2 | 3/2008 | Bright et al. | |
| 2002/0076408 A1 | 6/2002 | Buchsbaum | |
| 2003/0108545 A1 | 6/2003 | Rockwell | |
| 2003/0114467 A1 | 6/2003 | Shakespeare | |
| 2003/0144252 A1 | 7/2003 | Furr | |
| 2003/0153752 A1 | 8/2003 | Hirst | |
| 2003/0157104 A1 | 8/2003 | Waksal | |
| 2003/0175763 A1 | 9/2003 | Degenhardt | |
| 2004/0014774 A1 | 1/2004 | Myers et al. | |
| 2004/0052785 A1 | 3/2004 | Goodman | |
| 2004/0057950 A1 | 3/2004 | Waksal | |
| 2004/0092546 A1 | 5/2004 | Wei | |
| 2004/0102655 A1 | 5/2004 | Liang | |
| 2004/0106605 A1 | 6/2004 | Carboni | |
| 2004/0180911 A1 | 9/2004 | Capraro | |
| 2004/0220189 A1 | 11/2004 | Sun et al. | |
| 2005/0032759 A1 | 2/2005 | Massimini | |
| 2005/0037999 A1 | 2/2005 | La Greca | |

(Continued)

FOREIGN PATENT DOCUMENTS

| | | |
|---|---|---|
| WO | 97/28161 | 8/1997 |
| WO | 0112227 A1 | 2/2001 |

(Continued)

OTHER PUBLICATIONS

Adachi et. al. (Novartis Foundation Symposium (2004) 262 (biology of IGF-1), 177-192).*

(Continued)

*Primary Examiner* — Marcos Sznaidman
(74) *Attorney, Agent, or Firm* — Frank W. Forman; Astellas US LLC

(57) ABSTRACT

Methods and compositions for treating tumors or tumor metastases in a patient, comprising administering to the patient simultaneously or sequentially (a) a therapeutically effective amount of an anti-cancer agent and (b) an IGF1R inhibitor compound of Formula I, with or without additional agents or treatments, such as other anti-cancer drugs or radiation therapy. Suitable IGF1R inhibitor may be represented by Formula I:

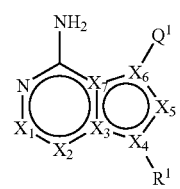

wherein $X_1$, $X_2$, $X_3$, $X_4$, $X_5$, $X_6$, $X_7$, $R^1$, and $Q^1$ are defined herein.

14 Claims, 22 Drawing Sheets

(56) References Cited

U.S. PATENT DOCUMENTS

| | | | |
|---|---|---|---|
| 2005/0054638 A1 | 3/2005 | Barlaam et al. | |
| 2005/0136063 A1 | 6/2005 | Wang | |
| 2005/0153966 A1 | 7/2005 | Gangloff | |
| 2005/0215530 A1 | 9/2005 | Ryan | |
| 2005/0215564 A1 | 9/2005 | Stiles et al. | |
| 2005/0271747 A1* | 12/2005 | Higgins et al. | 424/649 |
| 2006/0019957 A1 | 1/2006 | Crew | |
| 2006/0046977 A1 | 3/2006 | Nunes | |
| 2006/0069084 A1 | 3/2006 | Burns et al. | |
| 2006/0084654 A1 | 4/2006 | Beck | |
| 2006/0154982 A1 | 7/2006 | Larsson et al. | |
| 2006/0166992 A1 | 7/2006 | Hendrix et al. | |
| 2006/0235031 A1 | 10/2006 | Arnold | |
| 2007/0112005 A1 | 5/2007 | Chen | |
| 2007/0149521 A1 | 6/2007 | Crew | |
| 2007/0202101 A1 | 8/2007 | Rosen | |
| 2007/0238734 A1 | 10/2007 | Nemecek et al. | |
| 2008/0014200 A1 | 1/2008 | Arnold | |
| 2008/0254040 A1 | 10/2008 | Stefanic | |
| 2008/0267957 A1 | 10/2008 | Arnold | |

FOREIGN PATENT DOCUMENTS

| | | | |
|---|---|---|---|
| WO | 01/72751 | | 10/2001 |
| WO | 02/079192 | | 10/2002 |
| WO | 03/080064 | | 10/2003 |
| WO | WO2005/097800 | * | 10/2005 |
| WO | 2006004703 A2 | | 1/2006 |
| WO | 2008076143 A1 | | 6/2008 |
| WO | 2008/106168 | | 9/2008 |

OTHER PUBLICATIONS

Galisteo, M.L. et al. (2006) PNAS 103 (26): 9796-9801.
Mahajan, N.P.(2005) Cancer Research 65 (22):10514-10523.
Mahajan, N.P.(2007) PNAS 104 (20): 8438-8443.
Manser, E. et al. (1993) Nature 363 (6427):364-367.
Mulvihill, M.J. et al (2007) Bioorganic & Medicinal Chemistry 17(4): 1091-1097.
van der horst, E.T. et al. (2005) PNAS 102 (44):15901-15906.
Yang, et al. (1999) The Journal of Biological Chemistry 274 (13): 8524-8530.
Akio, et al. (1995) Machine English Translation of JP 071333280.
Albert, A. et al. (1969) Chem. Biol. Pterdines.Proc.Int.Symp., 4th, 4:1-5.
Albert, A. et al. (1970) Journal of the Chemical Society, vol. 11, pp. 1540-1547.
Austrian Search Report Dec. 23, 2008.
Baserga R. (1999) Exp.Cell.Res, vol. 253, pp. 1-6.
Hartz, R. A. et al (2002) Bioorganic & Medicinal Chemistry Letters, vol. 12, pp. 291-294.
ISR in PCT/US2004/034219—May 6, 2005.
ISR in PCT/US2005/010606—Aug. 19, 2005.
IPRP in PCT/US2004/034219—May 6, 2005.
IPRP in PCT/US2005/010606—Jul. 6, 2006.
National Library of Medicine—Medical Subject Headings definition of Sarcoma (http://www.nlm.nih.gov/mesh/2008/MBrowser.html, then type "sarcoma"); last accessed Jul. 1, 2008.
Parrizas et al (1997) Endocrinology, vol. 138, pp. 1427-1433.
Stein, J.H. et al (1994) Internal Medicine 4th Edition, Chapters 71 and 72, pp. 699-729.
Thomas, et al. (1998) Expert Opinion Ther. Pat., vol. 8, pp. 475-478.
WOSA in PCT/US2004/034219—May 6, 2005.
Holbro, T. and Hynes, N.E. (2004) Annu Rev Pharmacol Toxicol 44:195-217.
Kurmasheva, R. T. and Houghton, P. J. (2006) Biochim Biophys Acta 1766:1-22.
Levitzki, A. (2003) Lung Cancer 41 Suppl 1, S9-14.
Roskoski, R., Jr. (2004) Biochem Biophys Res Commun 319:1-11.
Chakravarti, A. et al. Cancer Research 62: 200-207.
Jones, H.E. et al. (2004) Endocr Relat Cancer 11:793-814.
Lu, Y. at al. (2001) Journal of the National Cancer Institute 93: 1852-1857.
Nahta, R. (2005) Cancer Research 65:11118-11128.
Valeriote, et al. (1975) Cancer Chemotherapy Reports (5):895-900.
de Bono, J.S. and Rowinsky, E.K. (2002) Trends in Mol. Medicine 8:S19-S26.
Dancey, J. and Sausville, E.A. (2003) Nature Rev. Drug Discovery 2:296-313.
Raben, D. et al. (2002) Semin. Oncol. vol. 29, No. 1, suppl 4 (February): pp. 37-46.
Herbst, R.S. et al. (2001) Expert Opin. Biol. Ther. 1:719-732.
Magne, N. et al. (2003) Clin. Can. Res. 9:4735:4732.
Magne, N. et al. (2002) British Journal of Cancer 86:819-827.
Torrance, C.J. et al. (2000) Nature Med. 6:1024-1028.
Gupta, R.A. and DuBois, R.N. (2000) Nature Med. 6:974-975.
Tortora, et al. (2003) Clin. Cancer Res. 9:1566-1572.
Solomon, B. et al (2003) Int. J. Radiat. Oncol. Biol. Phys. 55:713-723.
Krishnan, S. et al. (2003) Frontiers in Bioscience 8, e1-13.
Huang, S. et al. (1999) Cancer Res. 59:1935-1940.
Contessa, J. N. et al. (1999) Clin. Cancer Res. 5:405-411.
Li, M. et al. (2002) Clin.Cancer Res. 8:3570-3578.
Ciardiello, F. et al. (2003) Clin. Cancer Res. 9:1546-1556.
Ciardiello, F. et al. (2000) Clin. Cancer Res. 6:3739-3747.
Grunwald, V. and Hidalgo, M. (2003) J. Nat. Cancer Inst. 95:851-867.
Seymour, L. (2003) Current Opin. Investig. Drugs 4(6):658-666.
Khalil, M.Y. et al. (2003) Expert Rev. Anticancer Ther. 3:367-380.
Bulgaru, A.M. et al. (2003) Expert Rev. Anticancer Ther.3:269-279.
Kim, E.S. et al. (2001) Current Opinion Oncol. 13:506-513.
Arteaga, C.L. and Johnson, D.H. (2001) Current Opinion Oncol. 13:491-498.
Ciardiello, F. et al. (2000) Clin. Cancer Res. 6:2053-2063.
Liu, B. (2001) Oncogene 20:1913-1922.
Morgillo, F. et al. (2006) Cancer Res 66(20):10100-10111.
Knowlden, J. M. (2005) Endocrinology 146(11):4609-4618.
Hurbin, A. et al. (2003) Ann. N. Y. Acad. Sci 1010:354-357.
International Search Report and Written Opinion of the International Search Authority in PCT/US2006/048222.
International Search Report and Written Opinion of the International Search Authority in PCT/US2007/009178.
International Search Report and Written Opinion of the International Search Authority in PCT/US2008/002593.
Gura, et al. (1997) Science 278:1041-1042 on Oct. 29, 2008 U.S. Appl. No. 11/787,236.
Johnson, et al. (2001) British Journal of Cancer 84:1424-1431 on Oct. 29, 2008 U.S. Appl. No. 11/787,236.
Adachi, et al. (2004) CAS Accession #2005:366557, corresponding to Novartis Foundation Symposium 262 (biology of IGF-1), 177-192 on Oct. 29, 2008 U.S. Appl. No. 11/787,236.
Camirand, A. et al. (2005) Breast Cancer Research 2005, 7:R570-R579.
Lu, D. et al. (2004) J. Biol. Chem. Jan. 23; 279(4): 2856-65.
McCarty, M. F. (2004) Integrative Cancer Therapies 3(4): 349-380.
Steinbeck, J. P. et al.(2004) Biochem Biophys Res Commun. Aug. 27;321 (3): 524-30.

* cited by examiner

Figure 1. Activation of IGF-1R pathways protected cells from growth inhibition and apoptosis by Tarceva, and Combination of IGF-1R inhibitor (compound-A) with Tarceva enhanced ability to inhibit cell proliferation (A), induce apoptosis (B) and block signaling pathways (C) in NSCLC H292 cells
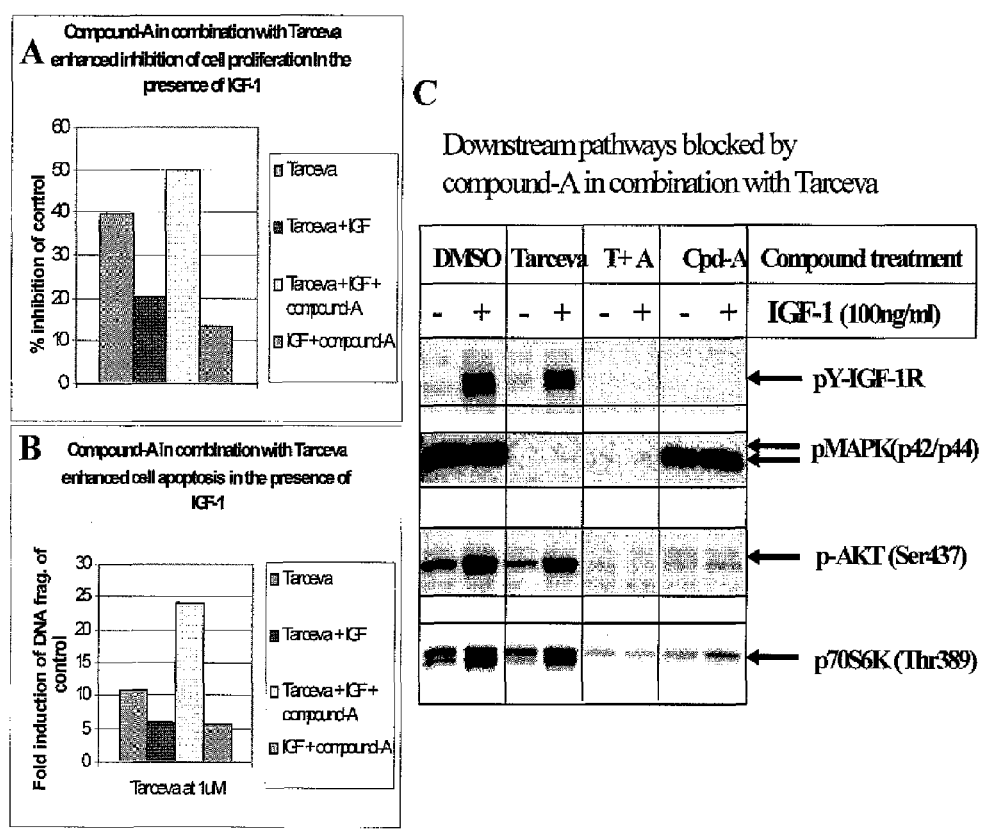

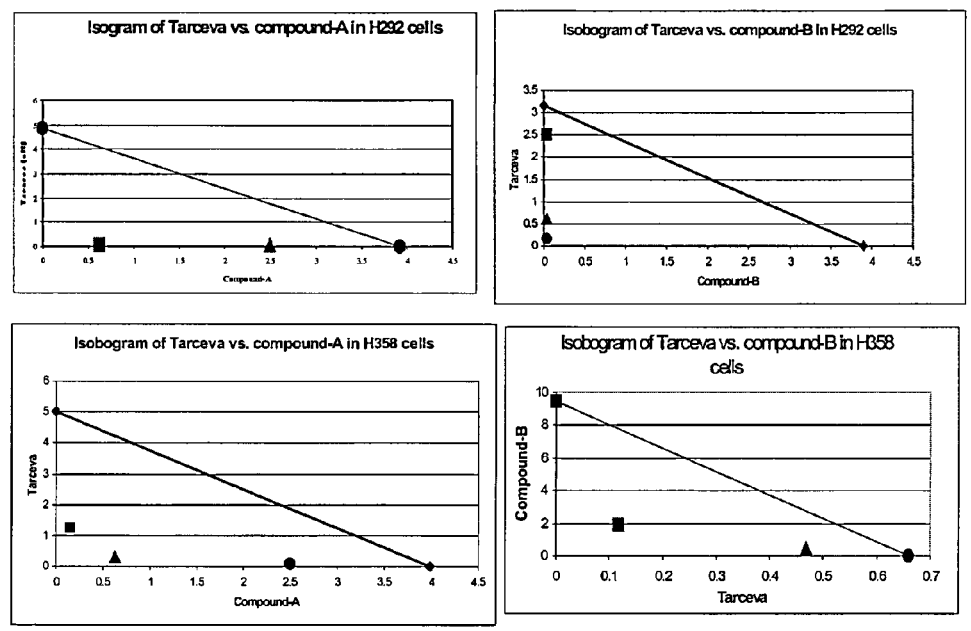
Figure 2. Synergistic effect of IGF-1R inhibitors (compound-A & -B) in combination with Tarceva on inhibition of cell proliferation in NSCLC cell lines

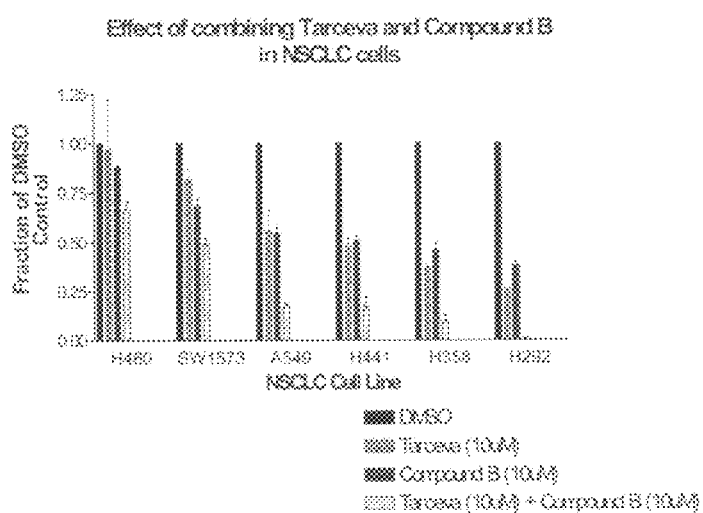
Figure 3. Effects on inhibition of cell proliferation by IGF-1R inhibitor (compound-B) with Tarceva in NSCLC cells at single concentration

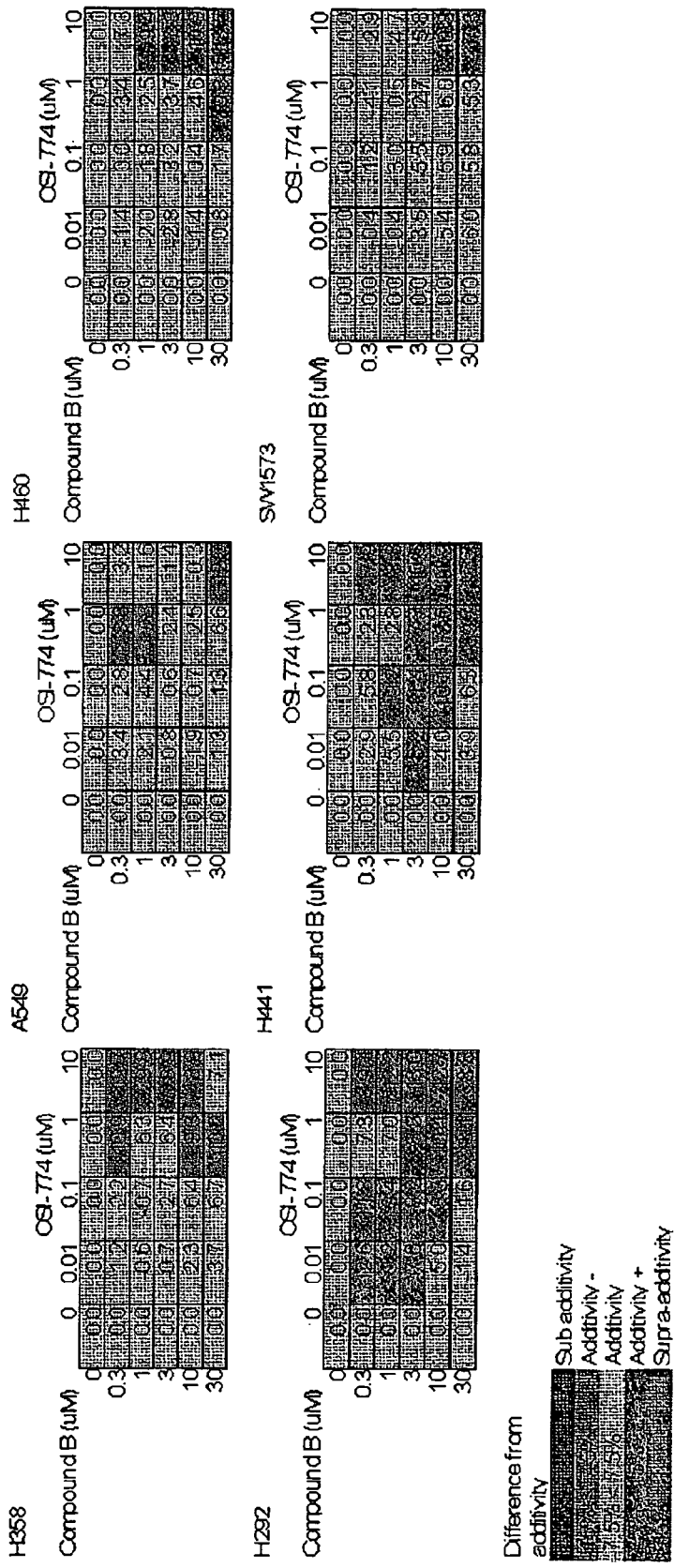
Figure 4. Bliss independence model of IGF-1R inhibitor (coumpound-B) in combination with Tarceva in NSCLC cells

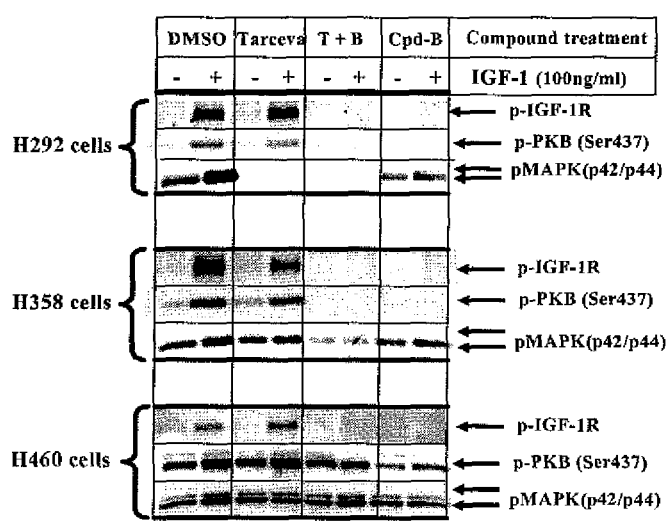
Figure 5. Influence on downstream pathways by IGF-1R inhibitor (compound-B) in combination with Tarceva in NSCLC cells in the presence of IGF-1

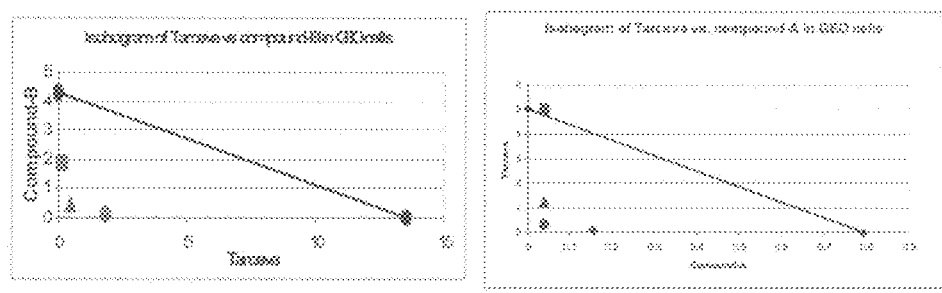
Figure 6. Synergistic effect of Tarceva in combination with IGF-1R inhibitors on cell proliferation in GEO cells

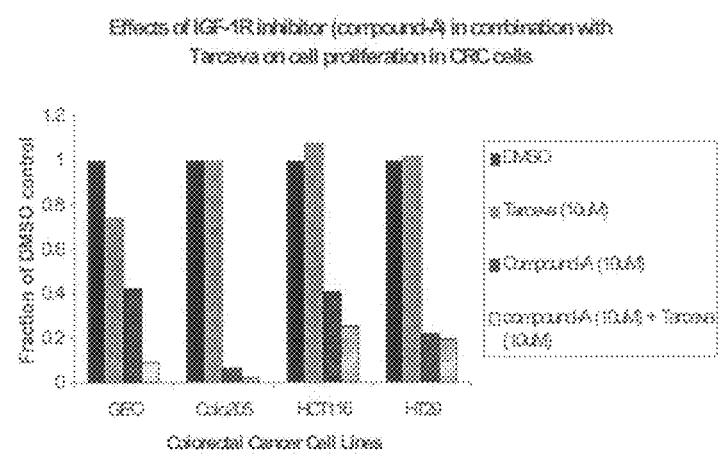
Figure 7. Effects on inhibition of cell proliferation by IGF-1R inhibitor (compound-A) with Tarceva in CRC cells at single concentration

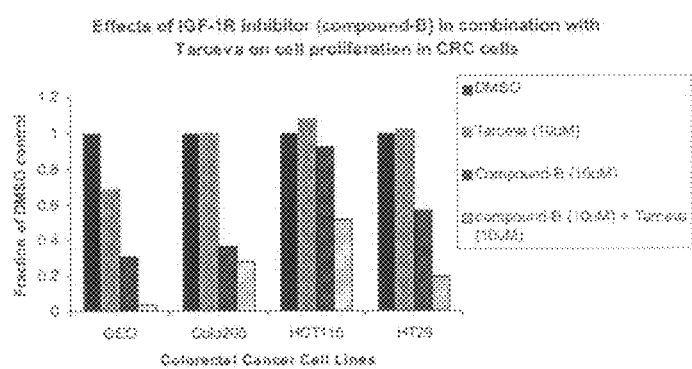
Figure 8. Effects on inhibition of cell proliferation by IGF-1R inhibitor (compound-8) with Tarceva in CRC cells at single concentration.

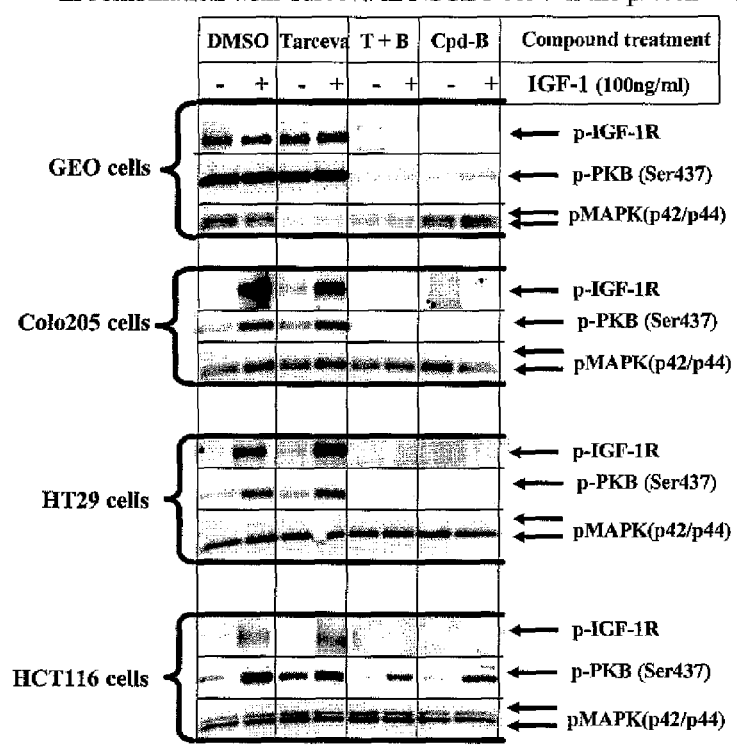
Figure 9. Influence on downstream pathways by IGF-1R inhibitor (compound-B) in combination with Tarceva in NSCLC cells in the presence of IGF-1

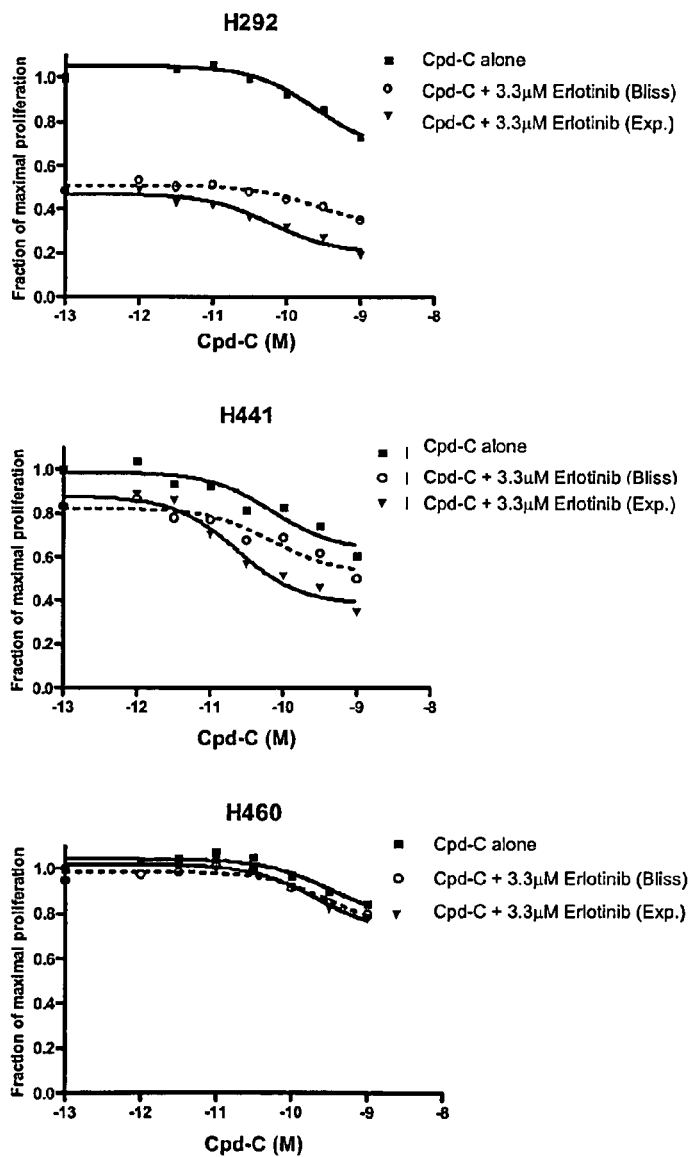
Figure 10. Synergistic effect of IGF-1R inhibitors (compound-C) in combination with Tarceva on inhibition of cell proliferation in NSCLC cell lines

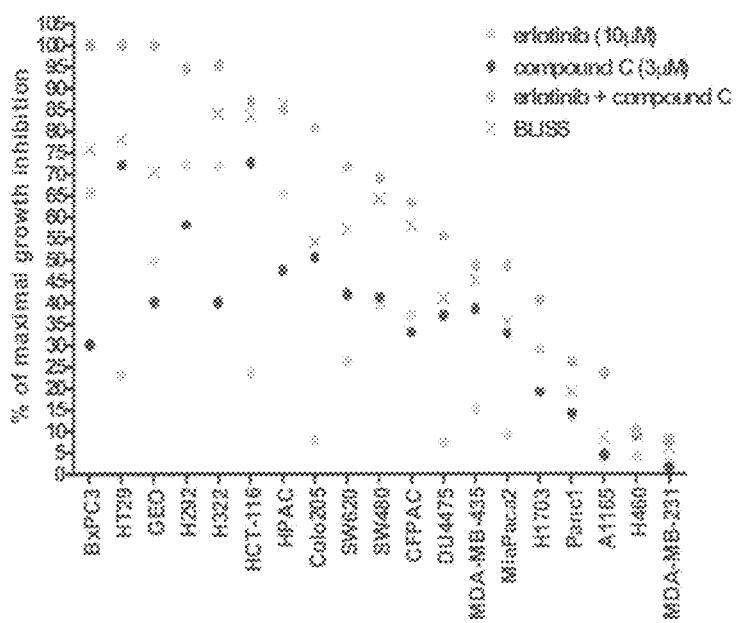
Figure 11. Synergistic effect of IGF-1R inhibitors (compound-C) in combination with Tarceva on inhibition of cell proliferation in NSCLC, colorectal, breast and pancreatic cancer cell lines

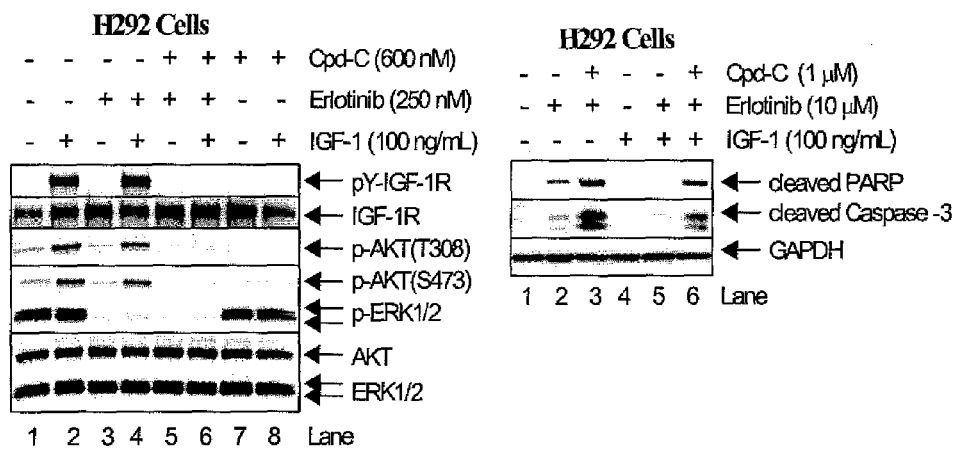
Figure 12A. Influence on downstream pathways and induction of apoptosis by IGF-1R inhibitor (compound-C) in combination with Tarceva in NSCLC H292 cells in the presence of IGF-1

Figure 12B. Influence on downstream pathways and induction of apoptosis by IGF-1R inhibitor (compound-C) in combination with Tarceva in NSCLC H441 cells in the presence of IGF-1
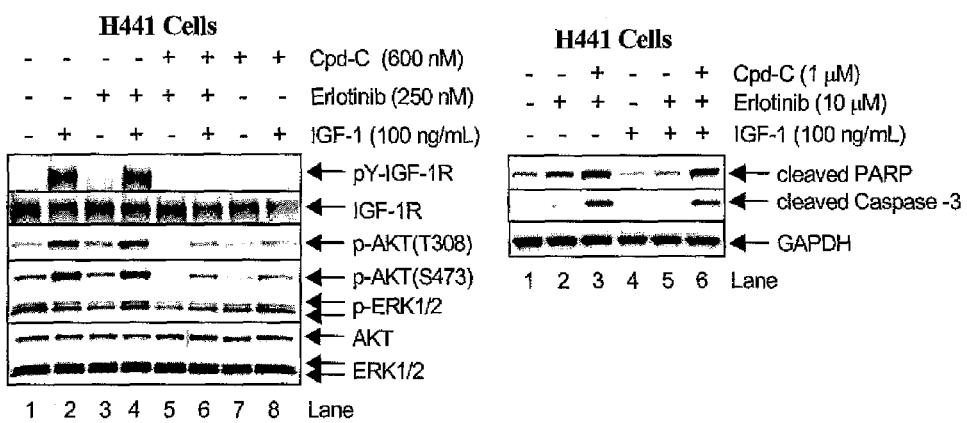

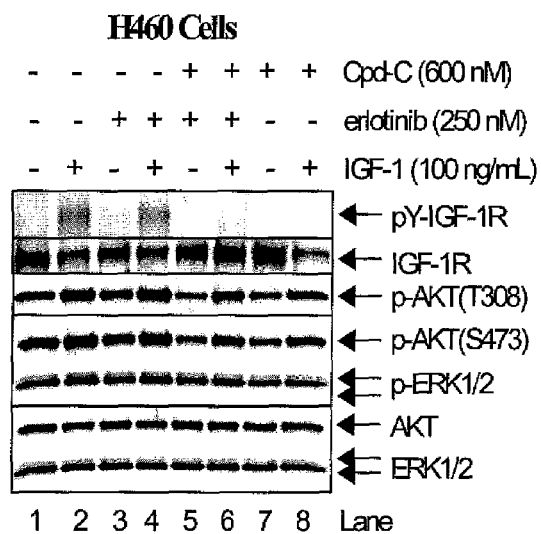
Figure 12C. Influence on downstream pathways by IGF-1R inhibitor (compound-C) in combination with Tarceva in NSCLC H460 cells in the presence of IGF-1

Figure 13. Anti-tumor efficacy of oral co-administration of compound-C with Tarceva in NSCLC xenograft tumor models
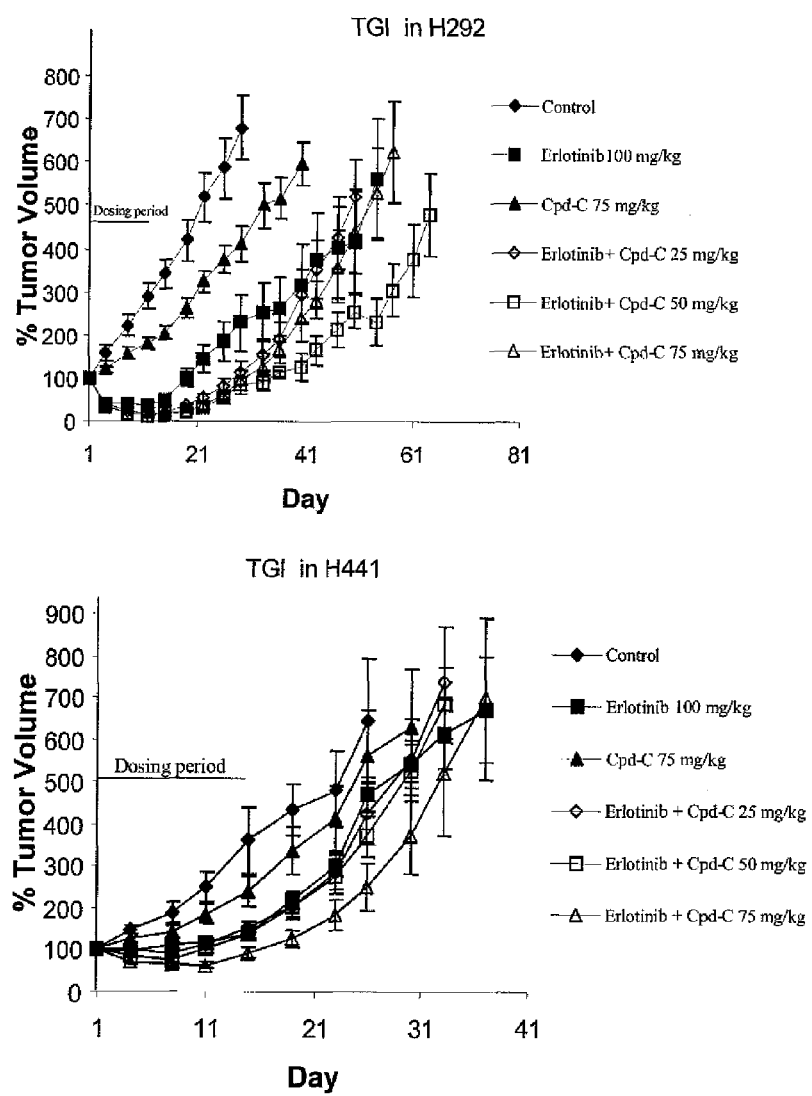

Fig. 13A Anti-tumor efficacy of compound-C in combination with Tarceva in NSCLC and colorectal cancer xenograft tumor models
(Note: TGI=tumor growth inhibition; GD=growth delay; BWL=body weight loss)

| Model | Group | TGI (%)[a] | GD[b] | Regression (%) | BWL (%)[c] | Cures |
|---|---|---|---|---|---|---|
| NCI-H292 | Control | 0 | 0 | 0 | 0 | 0 |
| | Erlotinib (100 mg/kg) | 157 | 29 | 51.3 | ~5 | 1 |
| | Cpd-C (75 mg/kg) | 66 | 10 | 0 | <10 | 0 |
| | Erlotinib + Cpd-C (25 mg/kg) | 163 | 27.6 | 81.4 | <10 | 1 |
| | Erlotinib + Cpd-C (50 mg/kg) | 167 | 43.7 | 83.9 | ~17 | 3 |
| | Erlotinib + Cpd-C (75 mg/kg) | 170 | 30.5 | 87.1 | ~23 | 0 |
| NCI-H441 | Control | 0 | 0 | 0 | 0 | 0 |
| | Erlotinib (100 mg/kg) | 104 | 7.6 | 0 | <5 | 0 |
| | Cpd-C (75 mg/kg) | 65 | 5.1 | 0 | 5-10 | 0 |
| | Erlotinib + Cpd-C (25 mg/kg) | 100 | 8.4 | 0 | ~10 | 0 |
| | Erlotinib + Cpd-C (50 mg/kg) | 113 | 9.6 | 0 | ~23 | 0 |
| | Erlotinib + Cpd-C (75 mg/kg) | 127 | 13.4 | 36.4 | ~25 | 0 |
| NCI-H460 | Control | 0 | 0 | 0 | 0 | 0 |
| | Erlotinib (100 mg/kg) | 8 | 1.0 | 0 | 0 | 0 |
| | Cpd-C (75 mg/kg) | 8 | 2.0 | 0 | 0 | 0 |
| | Erlotinib + Cpd-C (25 mg/kg) | 17 | 1.7 | 0 | <10 | 0 |
| | Erlotinib + Cpd-C (50 mg/kg) | 43 | 3.5 | 0 | ~12 | 0 |
| | Erlotinib + Cpd-C (75 mg/kg) | 56 | 6.4 | 0 | ~22 | 0 |
| GEO | Control | 0 | NA | 0 | 0 | 0 |
| | Erlotinib (100 mg/kg) | 79 | NA | 0 | 3.5 | 0 |
| | Cpd-C (75 mg/kg) | 76 | NA | 0 | 4.3 | 0 |
| | Erlotinib + Cpd-C (25 mg/kg) | 89 | NA | 0 | 16 | 0 |
| | Erlotinib + Cpd-C (50 mg/kg) | 100 | NA | 9 | 18.2 | 0 |
| | Erlotinib + Cpd-C (75 mg/kg) | 110 | NA | 15 | 21.8 | 0 |
| HT-29 | Control | 0 | NA | 0 | 0 | 0 |
| | Erlotinib (100 mg/kg) | 39 | NA | 0 | 2.4 | 0 |
| | Cpd-C (75 mg/kg) | 38 | NA | 0 | 9.8 | 0 |
| | Erlotinib + Cpd-C (25 mg/kg) | 41 | NA | 0 | 11.6 | 0 |
| | Erlotinib + Cpd-C (50 mg/kg) | 81 | NA | 0 | 21.1 | 0 |
| | Erlotinib + Cpd-C (75 mg/kg) | 72 | NA | 0 | 25.3 | 0 |

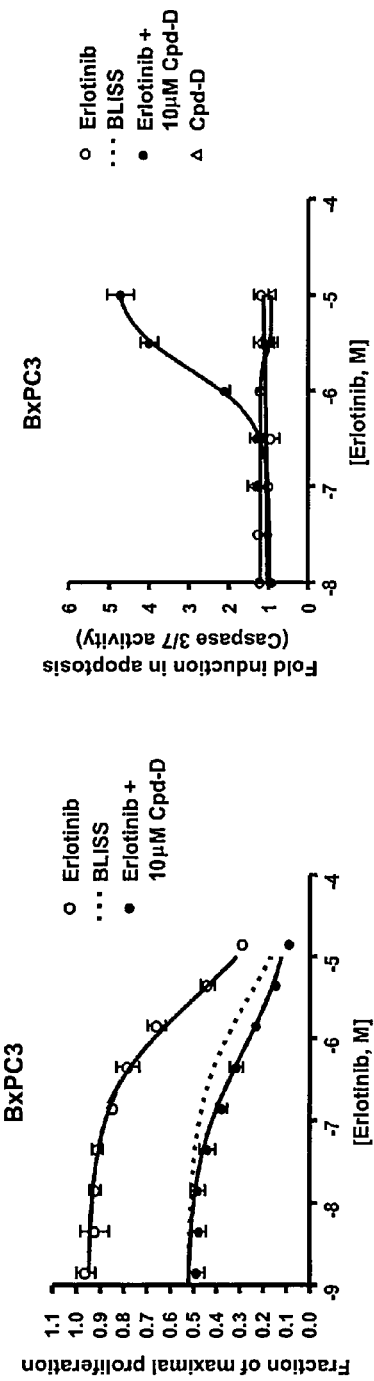

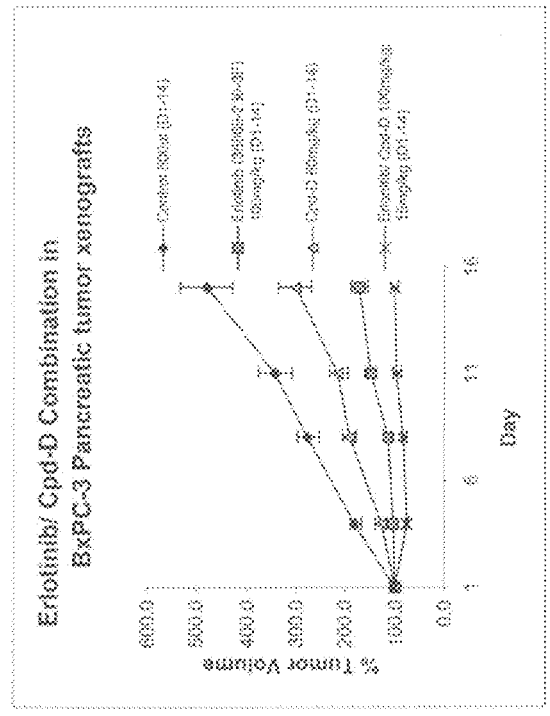

Figure 18.

| GEO colorectal cancer xenograft | Dose | Schedule | %TGI (treatment period) | Maximum % Regression (day8) | % regression (dosing period) |
|---|---|---|---|---|---|
| Control | | QD 1-14 | N/A | N/A | |
| Erlotinib | 100mg/kg | QD 1-14 | 79 | 0 | |
| Compound D | 60mg/kg | QD 1-14 | 90 | 0 | |
| Erlotinib + Compound D | 100mg/kg, 7.5mg/kg | QD 1-14, BID 1-14 | >100 | 18 | 9.7 |
| Erlotinib + Compound D | 100mg/kg, 15mg/kg | QD 1-14, QD 1-14 | >100 | 4.6 | 3.7 |
| Erlotinib + Compound D | 100mg/kg, 30mg/kg | QD 1-14, QOD 1-14 | >100 | 20.4 | 13.1 |

COMBINATION CANCER THERAPY

CROSS-REFERENCES

This application is a CIP of U.S. application Ser. No. 11/787,236 (filed Apr. 13, 2007) now abandoned, which is a CIP of U.S. application Ser. No. 11/641,346 (filed Dec. 18, 2006) now abandoned, which claim the benefit of U.S. Prov. Appl. No. 60/752,243 (filed Dec. 19, 2005), all of which are incorporated by reference herein in their entireties for all purposes. This application also claims the benefit of U.S. Prov. Appl. Nos. 60/966,966 (filed Aug. 31, 2007) and 60/903,593 (filed Feb. 27, 2007), which are also incorporated by reference herein in their entireties for all purposes.

BACKGROUND

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

A multitude of therapeutic agents have been developed over the past few decades for the treatment of various types of cancer. The most commonly used types of anticancer agents include: DNA-alkylating agents (e.g., cyclophosphamide, ifosfamide), anti-metabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide).

Colorectal cancer is among the leading causes of cancer-related morbidity and mortality in the U.S. Treatment of this cancer depends largely on the size, location and stage of the tumor, whether the malignancy has spread to other parts of the body (metastasis), and on the patient's general state of health. Options include surgical removal of tumors for early stage localized disease, chemotherapy and radiotherapy. However, chemotherapy is currently the only treatment for metastatic disease. 5-fluorouracil is currently the most effective single-agent treatment for advanced colorectal cancer, with response rates of about 10%. Additionally, new agents such as the topoisomerase I inhibitor irinotecan (CPT11), the platinum-based cytotoxic agent oxaliplatin (e.g. ELOXATIN™), and the EGFR kinase inhibitor erlotinib ([6,7-bis(2-methoxy-ethoxy)-4-quinazolin-4-yl]-(3-ethynylphenyl)amine, e.g. erlotinib HCl, TARCEVA™) have shown promise in treatment.

Over-expression of the epidermal growth factor receptor (EGFR) kinase, or its ligand TGF-alpha, is frequently associated with many cancers, including breast, lung, colorectal and head and neck cancers (Salomon D. S., et al. (1995) Crit. Rev. Oncol. Hematol. 19:183-232; Wells, A. (2000) Signal, 1:4-11), and is believed to contribute to the malignant growth of these tumors. A specific deletion-mutation in the EGFR gene has also been found to increase cellular tumorigenicity (Halatsch, M-E. et al. (2000) J. Neurosurg. 92:297-305; Archer, G. E. et al. (1999) Clin. Cancer Res. 5:2646-2652). Activation of EGFR stimulated signaling pathways promote multiple processes that are potentially cancer-promoting, e.g. proliferation, angiogenesis, cell motility and invasion, decreased apoptosis and induction of drug resistance. The development for use as anti-tumor agents of compounds that directly inhibit the kinase activity of the EGFR, as well as antibodies that reduce EGFR kinase activity by blocking EGFR activation, are areas of intense research effort (de Bono J. S, and Rowinsky, E. K. (2002) Trends in Mol. Medicine. 8:S19-S26; Dancey, J. and Sausville, E. A. (2003) Nature Rev. Drug Discovery 2:92-313). Several studies have demonstrated or disclosed that some EGFR kinase inhibitors can improve tumor cell or neoplasia killing when used in combination with certain other anti-cancer or chemotherapeutic agents or treatments (e.g. Raben, D. et al. (2002) Semin. Oncol. 29:37-46; Herbst, R. S. et al. (2001) Expert Opin. Biol. Ther. 1:719-732; Magne, N et al. (2003) Clin. Can. Res. 9:4735-4732; Magne, N. et al. (2002) British Journal of Cancer 86:819-827; Torrance, C. J. et al. (2000) Nature Med. 6:1024-1028; Gupta, R. A. and DuBois, R. N. (2000) Nature Med. 6:974-975; Tortora, et al. (2003) Clin. Cancer Res. 9:1566-1572; Solomon, B. et al (2003) Int. J. Radiat. Oncol. Biol. Phys. 55:713-723; Krishnan, S. et al. (2003) Frontiers in Bioscience 8, e1-13; Huang, S et al. (1999) Cancer Res. 59:1935-1940; Contessa, J. N. et al. (1999) Clin. Cancer Res. 5:405-411; Li, M. et al. Clin. (2002) Cancer Res. 8:3570-3578; Ciardiello, F. et al. (2003) Clin. Cancer Res. 9:1546-1556; Ciardiello, F. et al. (2000) Clin. Cancer Res. 6:3739-3747; Grunwald, V. and Hidalgo, M. (2003) J. Nat. Cancer Inst. 95:851-867; Seymour L. (2003) Current Opin. Investig. Drugs 4(6):658-666; Khalil, M. Y. et al. (2003) Expert Rev. Anticancer Ther. 3:367-380; Bulgaru, A. M. et al. (2003) Expert Rev. Anticancer Ther. 3:269-279; Dancey, J. and Sausville, E. A. (2003) Nature Rev. Drug Discovery 2:92-313; Kim, E. S. et al. (2001) Current Opinion Oncol. 13:506-513; Arteaga, C. L. and Johnson, D. H. (2001) Current Opinion Oncol. 13:491-498; Ciardiello, F. et al. (2000) Clin. Cancer Res. 6:2053-2063; Patent Publication Nos: US 2003/0108545; US 2002/0076408; and US 2003/0157104; and International Patent Publication Nos: WO 99/60023; WO 01/12227; WO 02/055106; WO 03/088971; WO 01/34574; WO 01/76586; WO 02/05791; and WO 02/089842).

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well.

Thus, there is a need for more efficacious treatment for neoplasia and other proliferative disorders. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone). For example, when combined with 5-FU and leucovorin, oxaliplatin exhibits response rates of 25-40% as first-line treatment for colorectal cancer (Raymond, E. et al. (1998) Semin Oncol. 25(2 Suppl. 5):4-12).

Growth factors acting through receptor tyrosine kinases (RTKs) drive tumor initiation and progression by accelerating cell proliferation and promoting cell survival. The RTKs for epidermal growth factor (EGF) and insulin-like growth factor (IGF) contribute to tumorigenesis for a multitude of tumor types including non-small cell lung cancer (NSCLC), colorectal, pancreatic, and breast tumors (Holbro, T., and Hynes, N. E. (2004). ErbB receptors: directing key signaling networks throughout life. Annu Rev Pharmacol Toxicol 44, 195-217; Kurmasheva, R. T., and Houghton, P. J. (2006). IGF-I mediated survival pathways in normal and malignant cells. Biochim Biophys Acta 1766, 1-22; Levitzki, A. (2003). EGF receptor as a therapeutic target. Lung Cancer 41 Suppl 1, S9-14; Roskoski, R., Jr. (2004). The ErbB/HER receptor protein-tyrosine kinases and cancer. Biochem Biophys Res Commun 319, 1-11.) Tumor cells can exhibit redundancy surrounding RTKs that contributes to de novo resistance to a single RTK inhibitor, and crosstalk between RTKs can confer acquired resistance whereby the inhibition of one RTK is compensated by enhanced activity through an alternative RTK. It has been shown that IGF-1R signaling is associated with acquired resistance of cancer cells to chemo or radiation therapies, and molecular targeted therapies including epidermal growth factor receptor (EGFR) inhibition. Indeed, it has recently been shown that in several different cancer types the efficacy of EGFR and ErbB2 signal transduction inhibitors could be acutely attenuated by IGF-1R activation of the PI3-kinase/Akt pathway (Chakravarti, A., Loeffler, J. S., and Dyson, N.J. (2002). Insulin-like growth factor receptor I mediates resistance to anti-epidermal growth factor receptor therapy in primary human glioblastoma cells through continued activation of phosphoinositide 3-kinase signaling. Cancer research 62, 200-207; Jones, H. E., Goddard, L., Gee, J. M., Hiscox, S., Rubini, M., Barrow, D., Knowlden, J. M., Williams, S., Wakeling, A. E., and Nicholson, R. I. (2004). Insulin-like growth factor-I receptor signaling and acquired resistance to gefitinib (ZD1839; Iressa) in human breast and prostate cancer cells. Endocr Relat Cancer 11, 793-814; Lu, Y., Zi, X., Zhao, Y., Mascarenhas, D., and Pollak, M. (2001). Insulin-like growth factor-I receptor signaling and resistance to trastuzumab (Herceptin). Journal of the National Cancer Institute 93, 1852-1857; Nahta, R., Yuan, L. X., Zhang, B., Kobayashi, R., and Esteva, F. J. (2005). Insulin-like growth factor-I receptor/human epidermal growth factor receptor 2 heterodimerization contributes to trastuzumab resistance of breast cancer cells. Cancer research 65, 11118-11128). For instance, IGF-1R activation correlates with acquired resistance of breast and prostate cancer cells to EGFR inhibition (Jones et al., 2004). IGF-IR has also been shown to mediate resistance to anti-EGFR therapies in glioblastoma, colorectal, and NSCLC tumor cells (Chakravarti et al., 2002; Liu et al., 2001; Jones et al., 2004; Morgillo et al., 2006; Hurbin et al., 2003; Knowiden et al., 2005).

US2006/0235031 refers to 6,6-bicyclic ring substituted heterobicyclic protein kinase inhibitors as IFG1R inhibitors and uses thereof, including for treating cancer. Valeriote et al., *Cancer Chemotherapy Reports,* 59(5), 895-900 (1975), states that "extensive literature describing additivity and synergism in anticancer agents exists." US2003/0114467; US2003/0153752; and US2005/0037999 refer to pyrazolo- and pyrrolo-pyrimidines and uses thereof, including for cancer treatment, and generally refer to various combinations with other anticancer agents. US2005/0153966 refers to heterocyclic compounds said to be kinase inhibitors and uses thereof, including for cancer treatment. US2004/0180911 refers to pyrimidine derivatives and uses thereof, including for tumors and proliferative diseases, and states that the compounds can be used in combination with other chemotherapy drugs. WO2004/056830 refers to pyrrolopyrimidine derivatives and uses thereof, including for cancer treatment, and states that the compounds can be used in combination with other anti-cancer agents. US2004/0106605 is entitled "Synergistic Methods and Compositions for Treating Cancer," and generally refers to combinations of IGF1R inhibitors with EGFR inhibitors.

SUMMARY

The present invention includes compositions and methods for treating cancer. In particular, the present invention is directed to combination compositions and dual therapy or combined treatment of patients with substituted heterobicyclic IGF1R protein kinase inhibitors and anti-cancer agents. The invention described herein provides new drug combinations, and methods for using drug combinations in the treatment of cancer.

This invention provides anti-cancer combination therapies that reduce the dosages for individual components required for efficacy, thereby decreasing side effects associated with each agent, while maintaining or increasing therapeutic value.

The present invention includes a method for treating tumors or tumor metastases in a patient, comprising administering to the patient simultaneously or sequentially a therapeutically effective amount of (a) at least one anti-cancer agent such as an agent which inhibits serine phosphorylation of IRS1 (IRS1 agent) such as an EGFR inhibitor and (b) at least one IGF1R inhibitor in combination, with or without additional agents or treatments, such as other anti-cancer drugs or radiation therapy, wherein the IGF1R inhibitor relates to compounds of Formula I, as defined herein:

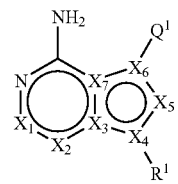

I or a pharmaceutically acceptable salt thereof.

The invention also encompasses a pharmaceutical composition that is comprising (a) at least one anti-cancer agent such as IRS1 agent such as an EGFR inhibitor, and (b) at least one IGF1R inhibitor in combination with a pharmaceutically acceptable carrier wherein the IGF1R inhibitor is selected from compounds and salts of Formula I above.

DESCRIPTION OF DRAWINGS

FIG. 1: Activation of IGF-1R pathways protected cells from growth inhibition and apoptosis by TARCEVA™, and Combination of IGF-1R inhibitor (Compound A: 3-(4-Aminomethyl-cyclohexyl)-1-(2-phenyl-quinolin-7-yl)-imidazo[1,5-a]pyrazin-8-ylamine) with TARCEVA™ enhanced ability to inhibit cell proliferation (A), induce apoptosis (B) and block signaling pathways (C) in NSCLC H292 cells.

FIG. 2: Synergistic effect of IGF-LR inhibitors (Compound A: 3-(4-Aminomethyl-cyclohexyl)-1-(2-phenyl-quinolin-7-yl)-imidazo[1,5-a]pyrazin-8-ylamine & Compound B: 3-(3-Azetidin-1-ylmethyl-cyclobutyl)-1-(2-phenyl-quinolin-7-yl)-imidazo[1,5-a]pyrazin-8-ylamine) in combination with TARCEVA™ on inhibition of cell proliferation in NSCLC cell lines.

FIG. 3: Effects on inhibition of cell proliferation by IGF-1R inhibitor (Compound B: 3-(3-Azetidin-1-ylmethyl-cyclobutyl)-1-(2-phenyl-quinolin-7-yl)-imidazo[1,5-a]pyrazin-8-ylamine) with TARCEVA™ in NSCLC cells at single concentration.

FIG. 4: Bliss independence model of IGF-1R inhibitor (Compound B: 3-(3-Azetidin-1-ylmethyl-cyclobutyl)-1-(2-phenyl-quinolin-7-yl)-imidazo[1,5-a]pyrazin-8-ylamine) in combination with TARCEVA™ in NSCLC cells.

FIG. 5: Influence on downstream pathways by IGF-IR inhibitor (Compound B: 3-(3-Azetidin-1-ylmethyl-cyclobutyl)-1-(2-phenyl-quinolin-7-yl)-imidazo[1,5-a]pyrazin-8-ylamine) in combination with TARCEVA™ in NSCLC cells in the presence of IGF-1.

FIG. 6: Synergistic effect of TARCEVA™ in combination with IGF-1R inhibitors on cell proliferation in GEO cells.

FIG. 7: Effects on inhibition of cell proliferation by IGF-1R inhibitor (Compound A: 3-(4-Aminomethyl-cyclohexyl)-1-(2-phenyl-quinolin-7-yl)-imidazo[1,5-a]pyrazin-8-ylamine) with TARCEVA™ in CRC cells at single concentration.

FIG. 8: Effects on inhibition of cell proliferation by IGF-1R inhibitor (Compound B: 3-(3-Azetidin-1-ylmethyl-cyclobutyl)-1-(2-phenyl-quinolin-7-yl)-imidazo[1,5-a]pyrazin-8-ylamine) with TARCEVA™ in CRC cells at single concentration.

FIG. 9: Influence on downstream pathways by IGF-1R inhibitor (Compound B: 3-(3-Azetidin-1-ylmethyl-cyclobutyl)-1-(2-phenyl-quinolin-7-yl)-imidazo[1,5-a]pyrazin-8-ylamine) in combination with TARCEVA™ in NSCLC cells in the presence of IGF-1.

FIG. 10: Synergistic Effect of IGF-LR inhibitor (Compound C: cis-3-[3-(4-Methyl-piperazin-1-yl)-cyclobutyl]1-(2-phenyl-quinolin-7-yl)-imidazo[1,5-a]pyrazin-8-ylamine) in combination with TARCEVA™ on inhibition of cell proliferation in NSCLC cell lines.

FIG. 11: Synergistic Effect of IGF-1R inhibitor (Compound C: cis-3-[3-(4-Methyl-piperazin-1-yl)-cyclobutyl]1-(2-phenyl-quinolin-7-yl)-imidazo[15-a]pyrazin-8-ylamine) in combination with TARCEVA™ on inhibition of cell proliferation in NSCLC, colorectal, breast, and pancreatic cancer cell lines.

FIG. 12A: Influence on downstream pathways and induction of apoptosis by IGF-1R inhibitor (Compound C: cis-3-[3-(4-Methyl-piperazin-1-yl)-cyclobutyl]1-(2-phenyl-quinolin-7-yl)-imidazo[1,5-a]pyrazin-8-ylamine) in combination with TARCEVA™ in NSCLC H292 cells in the presence of IGF-1.

FIG. 12B: Influence on downstream pathways and induction of apoptosis by IGF-1R inhibitor (Compound C: cis-3-[3-(4-Methyl-piperazin-1-yl)-cyclobutyl]1-(2-phenyl-quinolin-7-yl)-imidazo[1,5-a]pyrazin-8-ylamine) in combination with TARCEVA™ in NSCLC H441 cells in the presence of IGF-1.

FIG. 12C: Influence on downstream pathways and induction of apoptosis by IGF-1R inhibitor (Compound C:. cis-3-[3-(4-Methyl-piperazin-1-yl)-cyclobutyl]1-(2-phenyl-quinolin-7-yl)-imidazo[1,5-a]pyrazin-8-ylamine) in combination with TARCEVA™ in NSCLC H460 cells in the presence of IGF-1.

FIG. 13: Anti-tumor efficacy or oral co-administration of Compound C (cis-3-[3-(4-Methyl-piperazin-1-yl)-cyclobutyl]1-(2-phenyl-quinolin-7-yl)-imidazo[1,5-a]pyrazin-8-ylamine) with TARCEVA™ in NSCLC xenograft tumor models.

FIG. 13A: Anti-tumor efficacy of Compound C (cis-3-[3-(4-Methyl-piperazin-1-yl)-cyclobutyl]1-(2-phenyl-quinolin-7-yl)-imidazo[1,5-a]pyrazin-8-ylamine) in combination with TARCEVA™ in NSCLC and colorectal cancer xenograft tumor models.

FIGS. 14A and 14B: Plots depicting synergistic effect of IGF-1R inhibitor Compound D (cis-3-[8-Amino-1-(2-phenyl-quinolin-7-yl)-imidazo[1,5-a]pyrazin-3-yl]-1-methyl-cyclobutanol) in combination with Erlotinib (TARCEVA) on inhibiting cell proliferation (1A) and promoting apoptosis (1B) in the epithelial pancreatic cancer cell line BxPC3.

FIGS. 15A and 15B: Plot and table depicting anti-tumor efficacy of oral co-administration of Compound D (cis-3-[8-Amino-1-(2-phenyl-quinolin-7-yl)-imidazo[1,5-a]pyrazin-3-yl]-1-methyl-cyclobutanol) with Erlotinib (TARCEVA) in BxPC3 human pancreatic cancer xenograft model.

FIG. 18: Table representing anti-tumor efficacy of oral co-administration of Compound D (cis-3-[8-Amino-1-(2-phenyl-quinolin-7-yl)-imidazo[1,5-a]pyrazin-3-yl]-1-methyl-cyclobutanol) with Erlotinib (TARCEVA) in GEO human colorectal cancer xenograft model. The combination of Compound D and Erlotinib is more efficacious than either drug alone in vivo, and only the combination achieves growth regression of the tumor during the treatment period.

DETAILED DESCRIPTION

Figure 16A:
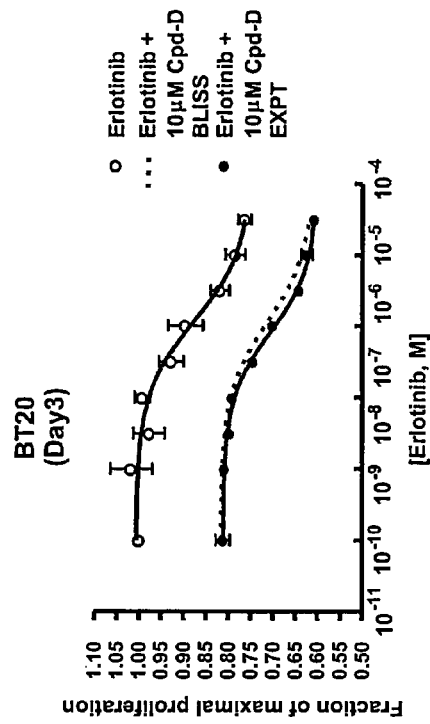
FIGS. 16A and 16B: Plots depicting synergistic effect of IGF-1R inhibitor Compound D (cis-3-[8-Amino-1-(2-phenyl-quinolin-7-yl)-imidazo[1,5-a]pyrazin-3-yl]-1-methyl-cyclobutanol) in combination with Erlotinib (TARCEVA) on inhibiting cell proliferation in the epithelial breast tumor cell line MDA-MB-468 (A), and additive effect of the combination in the breast tumor cell line BT20 (B).

It has been discovered by the present inventors that agents that prevent serine phosphorylation of the IGF-1R adaptor protein IRS1 potentiate IGF-driven Akt, thereby enhancing sensitivity to IGF-1R inhibition. As a result, the present invention is directed to methods for treating cancer patients comprising administering to the patient simultaneously or sequentially a therapeutically effective amount of an a IGF1R protein kinase inhibitor compound of Formula I in combination with an agent which inhibits serine phosphorylation of IRS1, with or without additional agents or treatments such as other anti-cancer drugs or radiation therapy. According to the invention, agents that inhibit serine phosphorylation of IRS1 include inhibitors of the MAPK pathway, including for example EGFR inhibitors, MEK inhibitors, Ras inhibitors, Raf inhibitors, and PKC inhibitors.

As further described below, EGFR and IGF-IR can cooperate to regulate tumor growth and survival. The present inventors have found that for epithelial tumor cells, but not for mesenchymal-like tumor cells, Akt is controlled synergistically by EGFR and IGF-IR. Two molecular aspects contributing to synergy were identified: 1) inhibition of EGFR or IGF-1R individually promotes activation of the reciprocal receptor, and 2) inhibition of EGFR-directed MAPK shifts regulation of Akt from EGFR towards IGF-1R. Specifically, inhibition of the MAPK pathway by EGFR blockade circumvents a negative feedback loop imposed on the IGF-1R-IRS-1 signaling complex. The synergistic inhibition of Akt achieved by co-targeting EGFR and IGF-1R in epithelial tumor cells conferred synergistic apoptosis and growth inhibition in vitro and growth regression in vivo.

Without being bound by a particular theory, the present inventors find that the ability of an agent which inhibits serine phosphorylation of IRS1, such as erlotinib, to inhibit the MAPK pathway is responsible for the potentiation of IGF-driven Akt, and this is likely mediated by augmented coupling of IGF-1R to Akt through IRS-1. The ability of IRS-1 phosphorylation at select serine sites to tightly regulate activity has been observed. Serine phosphorylation of IRS-1 promotes a decrease in the ability of IGF-1R to couple to downstream effectors including PI3K by affecting either the stability of IRS-1 or by affecting protein-protein interactions between receptor and effector. It was found by the present inventors that inhibition of EGFR conferred a decrease in IRS-1 serine phosphorylation only in tumor cells for which Erk activity was inhibited by erlotinib, and a specific inhibitor of the MAPK pathway evoked an increase in Akt phosphorylation that was associated with a decrease in IRS-1 serine phosphorylation. According to an aspect of the present invention, this increase in Akt phosphorylation could be blocked by the combination of an IGF-1R inhibitor, and synergistic growth inhibition for the combination of IGFR inhibitors with inhibitors of the MAPK pathway, such as EGFR inhibitors and MEK inhibitors, was observed. The ability of the MAPK pathway to affect the serine-phosphorylation of IRS-1 could be mediated either directly through Erk, or indirectly through Erk's ability to transactivate p70S6K. Therefore, inhibition of the MAPK pathway, such as by EGFR inhibition or MEK inhibition, primes signaling through the IGF-1R to sustain Akt activity and cell survival.

An aspect of the present invention is directed to methods for treating cancer patients comprising administering to the patient simultaneously or sequentially a therapeutically effective amount of an agent which inhibits serine phosphorylation of IRS1 and a IGF1R protein kinase inhibitor compound of Formula I combination, with or without additional agents or treatments, such as other anti-cancer drugs or radiation therapy. This aspect of the present invention is also directed to combined treatment of patients with the IGF1R protein kinase inhibitors of Formula I, and their salts, and epidermal growth factor receptor (EGFR) kinase inhibitors, and their salts.

The present invention is directed to compositions and methods for treating cancer patients comprising administering to the patient simultaneously or sequentially a therapeutically effective amount of an epidermal growth factor receptor (EGFR) kinase inhibitor and a novel heterobicyclic IGF1R protein kinase inhibitor compound of Formula I combination, with or without additional agents or treatments, such as other anti-cancer drugs or radiation therapy. The present invention is also directed to compositions and combined or sequential treatment of patients with novel heterobicyclic IGF1R protein kinase inhibitors, their salts, and compositions comprising them and epidermal growth factor receptor (EGFR) kinase inhibitors, their salts, or compositions comprising them. The invention further encompasses a pharmaceutical composition that is comprised of an EGFR kinase inhibitor and IGF1R inhibitor combination with a pharmaceutically acceptable carrier.

The present invention includes compositions and methods for treating cancer patients comprising administering to the patient simultaneously or sequentially a therapeutically effective amount of an IRS1 agent such as an EGFR kinase inhibitor and an IGF1R inhibitor combination, with or without additional agents or treatments, such as other anti-cancer drugs or radiation therapy, wherein the IGF1R inhibitor is a compound of Formula I:

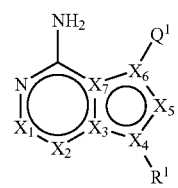

I or a pharmaceutically acceptable salt thereof, wherein:
$X_1$ and $X_2$ are each independently N or $-C-(E^1)_{aa}$;
$X_5$ is N, $-C-(E^1)_{aa}$, or $-N-(E^1)_{aa}$;
$X_3$, $X_4$, $X_6$, and $X_7$ are each independently N or C;
wherein at least one of $X_3$, $X_4$, $X_5$, $X_6$, and $X_7$ is independently N or $-N-(E^1)_{aa}$;
$Q^1$ is

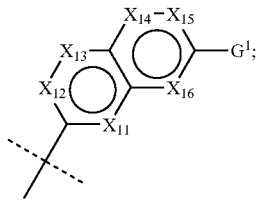

$X_{11}$, $X_{12}$, $X_{13}$, $X_{14}$, $X_{15}$, and $X_{16}$ are each independently N, $-C-(E^{11})_{bb}$, or $-N^+-O^-$;
wherein at least one of $X_{11}$, $X_{12}$, $X_{13}$, $X_{14}$, $X_{15}$, and $X_{16}$ is N or $-N^+-O^-$;
$R^1$ is absent, $C_{0-10}$alkyl, cyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents;
$E^1$, $E^{11}$, $G^1$, and $G^{41}$ are each independently halo, $-CF_3$, $-OCF_3$, $-OR^2$, $-NR^2R^3(R^{2a})_{j1}$, $-C(=O)R^2$, $-CO_2R^2$, $-CONR^2R^3$, $-NO_2$, $-CN$, $-S(O)_{j1}R^2$, $-SO_2NR^2R^3$, $-NR^2C(=O)R^3$, $-NR^2C(=O)OR^3$, $-NR^2C(=O)NR^3R^{2a}$, $-NR^2S(O)_{j1}R^3$, $-C(=S)OR^2$, $-C(=O)SR^2$, $-NR^2C(=NR^3)NR^{2a}R^{3a}$, $-NR^2C(=NR^3)OR^{2a}$, $-NR^2C(=NR^3)SR^{2a}$, $-OC(=O)OR^2$, $-OC(=O)NR^2R^3$, $-OC(=O)SR^2$, $-SC(=O)OR^2$, $-SC(=O)NR^2R^3$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, oxo, $-CF_3$, $-OCF_3$, $-OR^{222}$, $-NR^{222}R^{333}(R^{222a})_{j1a}$, $-C(=O)R^{222}$, $-CO_2R^{222}$, $-C(=O)NR^{222}R^{333}$, $-NO_2$, $-CN$, $-S(=O)_{j1a}R^{222}$, $-SO_2NR^{222}R^{333}$, $-NR^{222}C(=O)R^{333}$, —N$^{222}$C(=O)OR$^{333}$, —NR$^{222}$C(=O)NR$^{333}$R$^{222a}$, —NR$^{222}$S(O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$, or —SC(=O)NR$^{222}$R$^{333}$ substituents;

or E$^1$, E$^{11}$, or G$^1$ optionally is —(W$^1$)$_n$—(Y$^1$)$_m$—R$^4$;

or E$^1$, E$^{11}$, G$^1$, or G$^{41}$ optionally independently is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$, —NR$^{222}$R$^{333}$(R$^{222a}$)$_{j2a}$, —C(O)R$^{222}$, —CO$_2$R$^{222}$, —C(=O)NR$^{222}$R$^{333}$, —NO$_2$, —CN, —S(O)$_{j2a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(O)SR$^{222}$, SC(=O)OR$^{222}$, or —SC(=O)NR$^{222}$R$^{333}$ substituents;

G$^{11}$ is halo, oxo, —CF$_3$, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, —NO$_2$, —CN, —S(O)$_{j4}$R$^{21}$, —SO$_2$NR$^{21}$R$^{31}$, NR$^{21}$C(=O)R$^{31}$, NR$^{21}$C(=O)OR$^{31}$, NR$^{21}$C(=O)NR$^{31}$R$^{2a1}$, NR$^{21}$S(O)$_{j4}$R$^{31}$, —C(=S)OR$^{21}$, —C(=O)SR$^{21}$, —NR$^{21}$C(=NR$^{31}$)NR$^{2a1}$R$^{3a1}$, —NR$^{21}$C(=NR$^{31}$)OR$^{2a1}$, —NR$^{21}$C(=NR$^{31}$)SR$^{2a1}$, —OC(=O)OR$^{21}$, —OC(=O)NR$^{21}$R$^{31}$, —OC(=O)SR$^{21}$, —SC(=O)OR$^{21}$, —SC(=O)NR$^{21}$R$^{31}$, —P(O)OR$^{21}$OR$^{31}$, C$_{1-10}$alkylidene, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)R$^{2221}$OR$^{3331}$, or —SC(=O)NR$^{2221}$R$^{3331}$ substituents;

or G$^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{222}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)R$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

or G$^{11}$ is C, taken together with the carbon to which it is attached forms a C=C double bond which is substituted with R$^5$ and G$^{111}$;

R$^2$, R$^{2a}$, R$^3$, R$^{3a}$, R$^{222}$, R$^{222a}$, R$^{333}$, R$^{333a}$, R$^{21}$, R$^{2a1}$, R$^{31}$, R$^{3a1}$, R$^{2221}$, R$^{222a1}$, R$^{3331}$, and R$^{333a1}$ are each independently C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted by one or more independent G$^{111}$ substituents;

or in the case of —NR$^2$R$^3$(R$^{2a}$)$_{j1}$ or —NR$^{222}$R$^{333}$(R$^{222a}$)$_{j1a}$ or —NR$^{222}$R$^{333}$(R$^{222a}$)$_{j2a}$ or —NR$^{21}$R$^{31}$(R$^{2a1}$)$_{j4}$ or NR$^{2221}$R$^{3331}$(R$^{222a1}$)$_{j4a}$ or —NR$^{2221}$R$^{3331}$(R$^{222a1}$)$_{j5a}$, then R$^2$ and R$^3$, or R$^{222}$ and R$^{333}$, or R$^{2221}$ and R$^{3331}$, respectfully, are optionally taken together with the nitrogen atom to which they are attached to form a 3-10 membered saturated or unsaturated ring, wherein said ring is optionally substituted by one or more independent G$^{1111}$ substituents and wherein said ring optionally includes one or more heteroatoms other than the nitrogen to which R$^2$ and R$^3$, or R$^{222}$ and R$^{333}$, or R$^{2221}$ and R$^{3331}$ are attached;

W$^1$ and Y$^1$ are each independently —O—, —NR$^7$—, —S(O)$_{j7}$—, —CR$^5$R$^6$—, —N(C(O)OR$^7$)—, —N(C(O)R$^7$)—, —N(SO$_2$R$^7$)—, —CH$_2$O—, —CH$_2$S—, —CH$_2$N(R$^7$)—, —CH(NR$^7$)—, —CH$_2$N(C(O)R$^7$)—, —CH$_2$N(C(O)OR$^7$)—, —CH$_2$N(SO$_2$R$^7$)—, —CH(NHR$^7$)—, —CH(NHC(O)R$^7$)—, —CH(NHSO$_2$R$^7$)—, —CH(NHC(O)OR$^7$)—, —CH(OC(O)R$^7$)—, —CH(OC(O)NHR$^7$)—, —CH=CH—, —C≡C—, —C(=NOR$^7$)—, —C(O)—, —CH(OR$^7$)—, —C(O)N(R$^7$)—, —N(R$^7$)C(O)—, —N(R$^7$)S(O)—, —N(R$^7$)S(O)$_2$— —OC(O)N(R$^7$)—, —N(R$^7$)C(O)N(R$^8$)—, —NR$^7$C(O)O—, —S(O)N(R$^7$)—, —S(O)$_2$N(R$^7$)—, —N(C(O)R$^7$)S(O)—, —N(C(O)R$^7$)S(O)$_2$—, —N(R$^7$)S(O)N(R$^8$)—, —N(R$^7$)S(O)$_2$N(R$^8$)—, —C(O)N(R$^7$)C(O)—, —S(O)N(R$^7$)C(O)—, —S(O)$_2$N(R$^7$)C(O)—, —OS(O)N(R$^7$)—, —OS(O)$_2$N(R$^7$)—, —N(R$^7$)S(O)O—, —N(R$^7$)S(O)$_2$O—, —N(R$^7$)S(O)C(O)—, —N(R$^7$)S(O)$_2$C(O)—, —SON(C(O)R$^7$)—, —SO$_2$N(C(O)R$^7$)—, —N(R$^7$)SON(R$^8$)—, —N(R$^7$)SO$_2$N(R$^8$)—, —C(O)O—, —N(R$^7$)P(OR$^8$)O—, —N(R$^7$)P(OR$^8$)—, —N(R$^7$)P(O)(OR$^8$)O—, —N(R$^7$)P(O)(OR$^8$)—, —N(C(O)R$^7$)P(OR$^8$)O—, —N(C(O)R$^7$)P(OR$^8$)—, —N(C(O)R$^7$)P(O)(OR$^8$)O—, —N(C(O)R$^7$)P(OR$^8$)—, —CH(R$^7$)S(O)—, —CH(R$^7$)S(O)$_2$—, —CH(R$^7$)N(C(O)OR$^8$)—, —CH(R$^7$)N(C(O)R$^8$)—, —CH(R$^7$)N(SO$_2$R$^8$)—, —CH(R$^7$)O—, —CH(R$^7$)S—, —CH(R$^7$)N(R$^8$)—, —CH(R$^7$)N(C(O)R$^8$)—, —CH(R$^7$)N(C(O)OR$^8$)—, —CH(R$^7$)N(SO$_2$R$^8$)—, —CH(R$^7$)C(=NOR$^8$)—, —CH(R$^7$)C(O)—, —CH(R$^7$)CH(OR$^8$)—, —CH(R$^7$)C(O)N(R$^8$)—, —CH(R$^7$)N(R$^8$)C(O)—, —CH(R$^7$)N(R$^8$)S(O)—, —CH(R$^7$)N(R$^8$)S(O)$_2$—, —CH(R$^7$)OC(O)N(R$^8$)—, —CH(R$^7$)N(R$^8$)C(O)N(R$^{7a}$)—, —CH(R$^7$)NR$^8$C(O)O—, —CH(R$^7$)S(O)N(R$^8$)—, —CH(R$^7$)S(O)$_2$N(R$^8$)—, —CH(R$^7$)N(C(O)R$^8$)S(O)—, —CH(R$^7$)N(C(O)R$^8$)S(O)—, —CH(R$^7$)N(R$^8$)S(O)N(R$^{7a}$)—, —CH(R$^7$)N(R$^8$)S(O)$_2$N(R$^{7a}$)—, —CH(R$^7$)C(O)N(R$^8$)C(O)—, —CH(R$^7$)S(O)N(R$^8$)C(O)—, —CH(R$^7$)S(O)$_2$N(R$^8$)C(O)—, —CH(R$^7$)OS(O)N(R$^8$)—, —CH(R$^7$)OS(O)$_2$N(R$^8$)—, —CH(R$^7$)N(R$^8$)S(O)O—, —CH(R$^7$)N(R$^8$)S(O)$_2$O—, —CH(R$^7$)N(R$^8$)S(O)C(O)—, —CH(R$^7$)N(R$^8$)S(O)$_2$C(O)—, —CH(R$^7$)SON(C(O)R$^8$)—, —CH(R$^7$)SO$_2$N(C(O)R$^8$)—, —CH(R$^7$)N(R$^8$)SON(R$^{7a}$)—, —CH(R$^7$)N(R$^8$)SO$_2$N(R$^{7a}$)—, —CH(R$^7$)C(O)O—, —CH(R$^7$)N(R$^8$)P(OR$^{7a}$)O—, —CH(R$^7$)N(R$^8$)P(OR$^{7a}$)—, —CH(R$^7$)N(R$^8$)P(O)(OR$^{7a}$)O—, —CH(R$^7$)N(R$^8$)P(O)(OR$^{7a}$)—, —CH($R^7$)N(C(O)$R^8$)P(O$R^{7a}$)O—, —CH($R^7$)N(C(O)$R^8$)P(O$R^{7a}$)—, —CH($R^7$)N(C(O)$R^8$)P(O)(O$R^{7a}$)O—, or —CH($R^7$)N(C(O)$R^8$)P(O$R^{7a}$)—;

$R^5$, $R^6$, $G^{111}$, and $G^{1111}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{77}$, —$NR^{77}R^{87}$, —C(O)$R^{77}$, —$CO_2R^{77}$, —CON$R^{77}R^{87}$, —$NO_2$, —CN, —S(O)$_{j5a}R^{77}$, —$SO_2NR^{77}R^{87}$, —$NR^{77}$C(=O)$R^{87}$, —$NR^{77}$C(=O)O$R^{87}$, —$NR^{77}$C(=O)N$R^{78}R^{87}$, —$NR^{77}$S(O)$_{j5a}R^{87}$, —C(=S)O$R^{77}$, —C(=O)S$R^{77}$, —$NR^{77}$C(=N$R^{87}$)N$R^{78}R^{88}$, —$NR^{77}$C(=N$R^{87}$)O$R^{78}$, —$NR^{77}$C(=N$R^{87}$)S$R^{78}$, —OC(=O)O$R^{77}$, —OC(=O)N$R^{77}R^{87}$, —OC(=O)S$R^{77}$, —SC(=O)O$R^{77}$, —P(O)O$R^{77}O R^{87}$ or —SC(=O)N$R^{77}R^{87}$ substituents;

or $R^5$ with $R^6$ are optionally taken together with the carbon atom to which they are attached to form a 3-10 membered saturated or unsaturated ring, wherein said ring is optionally substituted with one or more independent $R^{69}$ substituents and wherein said ring optionally includes one or more heteroatoms;

$R^7$, $R^{7a}$, and $R^8$ are each independently acyl, $C_{0-10}$alkyl, $C_{2-10}$alkenyl, aryl, heteroaryl, heterocyclyl or cyclo$C_{3-10}$alkyl, any of which is optionally substituted by one or more independent $G^{111}$ substituents;

$R^4$ is $CO_{0-10}$alkyl, $C_{2-10}$alkenyl, $C_{2-10}$alkynyl, aryl, heteroaryl, cyclo$C_{3-10}$alkyl, heterocyclyl, cyclo$C_{3-8}$alkenyl, or heterocycloalkenyl, any of which is optionally substituted by one or more independent $G^{41}$ substituents;

$R^{69}$ is halo, —$OR^{78}$, —SH, —$NR^{78}R^{88}$, —$CO_2R^{78}$, —C(=O)N$R^{78}R^{88}$, —$NO_2$, —CN, —S(O)$_{j8}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{778}$, —$SO_2NR^{778}R^{888}$ or —$NR^{778}R^{888}$ substituents;

or $R^{69}$ is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —C(=O)N$R^{778}R^{888}$, —$SO_2NR^{778}R^{888}$, or —$NR^{778}R^{888}$ substituents;

or in the case of —$NR^{78}R^{88}$, $R^{78}$ and $R^{88}$ are optionally taken together with the nitrogen atom to which they are attached to form a 3-10 membered saturated or unsaturated ring, wherein said ring is optionally substituted with one or more independent halo, cyano, hydroxy, nitro, $C_{1-10}$alkoxy, —$SO_2NR^{778}R^{888}$, or —$NR^{778}R^{888}$ substituents, and wherein said ring optionally includes one or more heteroatoms other than the nitrogen to which $R^{78}$ and $R^{88}$ are attached;

$R^{77}$, $R^{78}$, $R^{87}$, $R^{88}$, $R^{778}$, and $R^{888}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2$N($C_{0-4}$alkyl)($C_{0-4}$alkyl), or —N($C_{0-4}$alkyl)($C_{0-4}$alkyl) substituents;

or $R^{77}$, $R^{78}$, $R^{87}$, $R^{88}$, $R^{778}$, and $R^{888}$ are each independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl)($C_{0-10}$alkyl), —$SO_2$N($C_{0-4}$alkyl)($C_{0-4}$alkyl), or —N($C_{0-4}$alkyl)($C_{0-4}$alkyl) substituents;

n, m, j1, j1a, j2a, j4, j4a, j5a, j7, and j8 are each independently 0, 1, or 2; and aa and bb are each independently 0 or 1.

In an aspect of the present invention, the IGF1R inhibitor is represented by Formula I, or a pharmaceutically acceptable salt thereof, wherein $X_3$ is N; $X_1$, $X_2$, and $X_5$ are C-($E^1$)$_{aa}$; $X_4$, $X_6$, and $X_7$ are C; and the other variables are described as above for Formula I.

In a second aspect of the present invention, the IGF1R inhibitor is represented by Formula I, or a pharmaceutically acceptable salt thereof, wherein $X_4$ is N; $X_1$, $X_2$, and $X_5$ are C-($E^1$)$_{aa}$; and $X_3$, $X_6$, and $X_7$ are C; and the other variables are described as above for Formula I.

In a third aspect of the present invention, the IGF1R inhibitor is represented by Formula I, or a salt thereof, wherein $X_5$ is N-($E^1$)$_{aa}$; $X_1$ and $X_2$ are C-($E^1$)$_{aa}$; $X_3$, $X_4$, $X_6$, and $X_7$ are C; and the other variables are described as above for Formula I.

In a fourth aspect of the present invention, the IGF1R inhibitor is represented by Formula I, or a salt thereof, wherein $X_6$ is N; $X_1$, $X_2$, and $X_5$ are C-($E^1$)$_{aa}$; $X_3$, $X_4$, and $X_7$ are C; and the other variables are described as above for Formula I.

In a fifth aspect of the present invention, the IGF1R inhibitor is represented by Formula I, or a salt thereof, wherein $X_7$ is N; $X_1$, $X_2$, and $X_5$ are C-($E^1$)$_{aa}$; $X_3$, $X_4$, and $X_6$ are C; and the other variables are described as above for Formula I.

In a sixth aspect of the present invention, the IGF1R inhibitor is represented by Formula I, or a salt thereof, wherein $X_1$ and $X_3$ are N; $X_2$ and $X_5$ are C-($E^1$)$_{aa}$; $X_4$, $X_6$, and $X_7$ are C; and the other variables are described as above for Formula I.

In a seventh aspect of the present invention, the IGF1R inhibitor is represented by Formula I, or a salt thereof, wherein $X_1$ and $X_4$ are N; $X_2$ and $X_5$ are C-$(E^1)_{aa}$; $X_3$, $X_6$, and $X_7$ are C; and the other variables are described as above for Formula I.

In an eighth aspect of the present invention, the IGF1R inhibitor is represented by Formula I, or a salt thereof, wherein $X_1$ is N; $X_5$ is N-$(E^1)_{aa}$; $X_2$ is C-$(E^1)_{aa}$; $X_3$, $X_4$, $X_6$, and $X_7$ are C; and the other variables are described as above for Formula I.

In a ninth aspect of the present invention, the IGF1R inhibitor is represented by Formula I, or a salt thereof, wherein $X_1$ and $X_6$ are N; $X_2$ and $X_5$ are C-$(E^1)_{aa}$; $X_3$, $X_4$, and $X_7$ are C; and the other variables are described as above for Formula I.

In a tenth aspect of the present invention, the IGF1R inhibitor is represented by Formula I, or a salt thereof, wherein $X_1$ and $X_7$ are N; $X_2$ and $X_5$ are C-$(E^1)_{aa}$; $X_3$, $X_4$, and $X_6$ are C; and the other variables are described as above for Formula I.

In a eleventh aspect of the present invention, the IGF1R inhibitor is represented by Formula I, or a salt thereof, wherein $X_2$ and $X_3$ are N; $X_1$ and $X_5$ are C-$(E^1)_{aa}$; $X_4$, $X_6$, and $X_7$ are C; and the other variables are described as above for Formula I.

In a twelfth aspect of the present invention, the IGF1R inhibitor is represented by Formula I, or a salt thereof, wherein $X_2$ and $X_4$ are N; $X_1$ and $X_5$ are C-$(E^1)_{aa}$; $X_3$, $X_6$, and $X_7$ are C; and the other variables are described as above for Formula I.

In a thirteenth aspect of the present invention, the IGF1R inhibitor is represented by Formula I, or a salt thereof, wherein $X_2$ is N; $X_5$ is N-$(E^1)_{aa}$, $X_1$ is C-$(E^1)_{aa}$; $X_3$, $X_4$, $X_6$, and $X_7$ are C; and the other variables are described as above for Formula I.

In a fourteenth aspect of the present invention, the IGF1R inhibitor is represented by Formula I, or a salt thereof, wherein $X_2$ and $X_6$ are N; $X_1$ and $X_5$ are C-$(E^1)_{aa}$; $X_3$, $X_4$, and $X_7$ are C; and the other variables are described as above for Formula I.

In a fifteenth aspect of the present invention, the IGF1R inhibitor is represented by Formula I, or a salt thereof, wherein $X_2$ and $X_7$ are N; $X_1$ and $X_5$ are C-$(E^1)_{aa}$; $X_3$, $X_4$, and $X_6$ are C; and the other variables are described as above for Formula I.

In a sixteenth aspect of the present invention, the IGF1R inhibitor is represented by Formula I, or a salt thereof, wherein $X_3$ and $X_4$ are N; $X_1$, $X_2$, and $X_5$ are C-$(E^1)_{aa}$; $X_6$ and $X_7$ are C; $R^1$ is absent; and the other variables are described as above for Formula I.

In a seventeenth aspect of the present invention, the IGF1R inhibitor is represented by Formula I, or a salt thereof, wherein $X_3$ and $X_5$ are N; $X_1$ and $X_2$ are C-$(E^1)_{aa}$; $X_4$, $X_6$, and $X_7$ are C; and the other variables are described as above for Formula I.

In an eighteenth aspect of the present invention, the IGF1R inhibitor is represented by Formula I, or a salt thereof, wherein $X_4$ and $X_5$ are N; $X_1$ and $X_2$ are C-$(E^1)_{aa}$; $X_3$, $X_6$, and $X_7$ are C; and the other variables are described as above for Formula I.

In a nineteenth aspect of the present invention, the IGF1R inhibitor is represented by Formula I, or a salt thereof, wherein $X_4$ and $X_6$ are N; $X_1$, $X_2$, and $X_5$ are C-$(E^1)_{aa}$; $X_3$ and $X_7$ are C; $R^1$ is absent; and the other variables are described as above for Formula I.

In a twentieth aspect of the present invention, the IGF1R inhibitor is represented by Formula I, or a salt thereof, wherein $X_4$ and $X_7$ are N; $X_1$, $X_2$, and $X_5$ are C-$(E^1)_{aa}$; $X_3$ and $X_6$ are C; $R^1$ is absent; and the other variables are described as above for Formula I.

In a twenty-first aspect of the present invention, the IGF1R inhibitor is represented by Formula I, or a salt thereof, wherein $X_5$ and $X_6$ are N; $X_1$ and $X_2$ are C-$(E^1)_{aa}$; $X_3$, $X_4$, and $X_7$ are C; and the other variables are described as above for Formula I.

In a twenty-second aspect of the present invention, the IGF1R inhibitor is represented by Formula I, or a salt thereof, wherein $X_5$ and $X_7$ are N; $X_1$ and $X_2$ are C-$(E^1)_{aa}$; $X_3$, $X_4$, and $X_6$ are C; and the other variables are described as above for Formula I.

In a twenty-third aspect of the present invention, the IGF1R inhibitor is represented by Formula I, or a salt thereof, wherein $X_2$, $X_3$, and $X_4$ are N; $X_1$ and $X_5$ are C-$(E^1)_{aa}$; $X_6$ and $X_7$ are C; $R^1$ is absent; and the other variables are described as above for Formula I.

In a twenty-fourth aspect of the present invention, the IGF1R inhibitor is represented by Formula I, or a salt thereof, wherein $X_2$, $X_3$, and $X_5$ are N; $X_1$ is C-$(E^1)_{aa}$; $X_4$, $X_6$ and $X_7$ are C; and the other variables are described as above for Formula I.

In a twenty-fifth aspect of the present invention, the IGF1R inhibitor is represented by Formula I, or a salt thereof, wherein $X_3$, $X_4$, and $X_5$ are N; $X_1$ and $X_2$ are C-$(E^1)_{aa}$; $X_6$ and $X_7$ are C; $R^1$ is absent; and the other variables are described as above for Formula I.

In a twenty-sixth aspect of the present invention, the IGF1R inhibitor is represented by Formula I, or a salt thereof, wherein $X_1$, $X_3$, and $X_4$ are N; $X_2$ and $X_5$ are C-$(E^1)_{aa}$; $X_6$ and $X_7$ are C; $R^1$ is absent; and the other variables are described as above for Formula I.

In a twenty-seventh aspect of the present invention, the IGF1R inhibitor is represented by Formula I, or a salt thereof, wherein $X_1$, $X_4$, and $X_5$ are N; $X_2$ is C-$(E^1)_{aa}$; $X_3$, $X_6$ and $X_7$ are C; and the other variables are described as above for Formula I.

In a twenty-eighth aspect of the present invention, the IGF1R inhibitor is represented by Formula I, or a salt thereof, wherein $X_2$, $X_4$, and $X_5$ are N; $X_1$ is C-$(E^1)_{aa}$; $X_3$, $X_6$ and $X_7$ are C; and the other variables are described as above for Formula I.

In a twenty-ninth aspect of the present invention, the IGF1R inhibitor is represented by Formula I, or a salt thereof, wherein $X_1$, $X_5$, and $X_6$ are N; $X_2$ is C-$(E^1)_{aa}$; $X_3$, $X_4$, and $X_7$ are C; and the other variables are described as above for Formula I.

In a thirtieth aspect of the present invention, the IGF1R inhibitor is represented by Formula I, or a salt thereof, wherein $X_2$, $X_5$, and $X_6$ are N; $X_1$ is C-$(E^1)_{aa}$; $X_3$, $X_4$, and $X_7$ are C; and the other variables are described as above for Formula I.

In a thirty-first aspect of the present invention, the IGF1R inhibitor is represented by Formula I, or a salt thereof, wherein $X_4$, $X_5$, and $X_6$ are N; $X_1$ and $X_2$ are C-$(E^1)_{aa}$; $X_3$ and $X_7$ are C; $R^1$ is absent; and the other variables are described as above for Formula I.

In a thirty-second aspect of the present invention, the IGF1R inhibitor is represented by Formula I, or a salt thereof, wherein $X_1$, $X_3$, and $X_5$ are N; $X_2$ is C-$(E^1)_{aa}$; $X_4$, $X_6$ and $X_7$ are C; and the other variables are described as above for Formula I.

In a thirty-third aspect of the present invention, the IGF1R inhibitor is represented by Formula I, or a salt thereof, wherein $X_1$, $X_4$, and $X_6$ are N; $X_2$ and $X_5$ are C-$(E^1)_{aa}$; $X_3$ and $X_7$ are C; $R^1$ is absent; and the other variables are described as above for Formula I.

In a thirty-fourth aspect of the present invention, the IGF1R inhibitor is represented by Formula I, or a salt thereof, wherein $X_1$, $X_5$, and $X_7$ are N; $X_2$ is C-$(E^1)_{aa}$; $X_3$, $X_4$, and $X_6$ are C; and the other variables are described as above for Formula I.

In a thirty-fifth aspect of the present invention, the IGF1R inhibitor is represented by Formula I, or a salt thereof, wherein $X_1$, $X_4$, and $X_7$ are N; $X_2$ and $X_5$ are C-$(E^1)_{aa}$; $X_3$ and $X_6$ are C; $R^1$ is absent; and the other variables are described as above for Formula I.

In a thirty-sixth aspect of the present invention, the IGF1R inhibitor is represented by Formula I, or a salt thereof, wherein $X_2$, $X_4$, and $X_6$ are N; $X_1$ and $X_5$ are C-$(E^1)_{aa}$; $X_3$ and $X_7$ are C; $R^1$ is absent; and the other variables are described as above for Formula I.

In a thirty-seventh aspect of the present invention, the IGF1R inhibitor is represented by Formula I, or a salt thereof, wherein $X_2$, $X_4$, and $X_7$ are N; $X_1$ and $X_5$ are C-$(E^1)_{aa}$; $X_3$ and $X_6$ are C; $R^1$ is absent; and the other variables are described as above for Formula I.

In a thirty-eighth aspect of the present invention, the IGF1R inhibitor is represented by Formula I, or a salt thereof, wherein $X_2$, $X_5$, and $X_7$ are N; $X_1$ is C-$(E^1)_{aa}$; $X_3$, $X_4$, and $X_6$ are C; and the other variables are described as above for Formula I.

In a thirty-ninth aspect of the present invention, the IGF1R inhibitor is represented by Formula I, or a salt thereof, wherein $X_1$, $X_4$, $X_5$, and $X_6$ are N; $X_2$ is C-$(E^1)_{aa}$; $X_3$ and $X_7$ are C; $R^1$ is absent; and the other variables are described as above for Formula I.

In a fortieth aspect of the present invention, the IGF1R inhibitor is represented by Formula I, or a salt thereof, wherein $X_2$, $X_4$, $X_5$, and $X_6$ are N; $X_1$ is C-$(E^1)_{aa}$; $X_3$ and $X_7$ are C; $R^1$ is absent; and the other variables are described as above for Formula I.

In a forty-first aspect of the present invention, the IGF1R inhibitor is represented by Formula I, or a salt thereof, wherein $X_1$, $X_3$, $X_4$, and $X_5$ are N; $X_2$ is C-$(E^1)_{aa}$; $X_6$ and $X_7$ are C; $R^1$ is absent; and the other variables are described as above for Formula I.

In a forty-second aspect of the present invention, the IGF1R inhibitor is represented by Formula I, or a salt thereof, wherein $X_2$, $X_3$, $X_4$, and $X_5$ are N; $X_1$ is C-$(E^1)_{aa}$; $X_6$ and $X_7$ are C; $R^1$ is absent; and the other variables are described as above for Formula I.

The following embodiments refer to all of the forty-two aspects above:

In an embodiment of each of the above aspects, the IGF1R inhibitor is represented by Formula I, or a pharmaceutically acceptable salt thereof, wherein $X_{11}$, $X_{12}$, and $X_{13}$ are N; $X_{14}$, $X_{15}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{11}$, $X_{12}$, and $X_{14}$ are N; $X_{13}$, $X_{15}$, and $X_{16}$ are C-$(E^{11})_{bb}$; and the other variables are as described in each of the above aspects.

In yet another embodiment of each of the above aspects, the IGF1R inhibitor is represented by Formula I, or a pharmaceutically acceptable salt thereof, wherein $X_{11}$, $X_{12}$, and $X_{15}$ are N; $X_{13}$, $X_{14}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{11}$, $X_{12}$, and $X_{16}$ are N; $X_{13}$, $X_{14}$, and $X_{15}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{11}$, $X_{13}$, and $X_{14}$ are N; $X_{12}$, $X_{15}$, and $X_{16}$ are C-$(E^{11})_{bb}$; and the other variables are as described in each of the above aspects.

In yet still another embodiment of each of the above aspects, the IGF1R inhibitor is represented by Formula I, or a pharmaceutically acceptable salt thereof, wherein $X_{11}$, $X_{13}$, and $X_{15}$ are N; $X_{12}$, $X_{14}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{11}$, $X_{13}$, and $X_{16}$ are N; $X_{12}$, $X_{14}$, and $X_{15}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{11}$, $X_{14}$, and $X_{15}$ are N; $X_{12}$, $X_{13}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{11}$, $X_{14}$, and $X_{16}$ are N; $X_{12}$, $X_{13}$, and $X_{15}$ are C-$(E^{11})_{bb}$; and the other variables are as described in each of the above aspects.

In yet another embodiment of each of the above aspects, the IGF1R inhibitor is represented by Formula I, or a pharmaceutically acceptable salt thereof, wherein $X_{11}$, $X_{15}$, and $X_{16}$ are N; $X_{12}$, $X_{13}$, and $X_{14}$ are C-$(E^{11})_{bb}$; and the other variables are as described in each of the above aspects.

In yet still another embodiment of each of the above aspects, the IGF1R inhibitor is represented by Formula I, or a pharmaceutically acceptable salt thereof, wherein $X_{12}$, $X_{13}$, and $X_{14}$ are N; $X_{11}$, $X_{15}$, and $X_{16}$ are C-$(E^{11})_{bb}$; and the other variables are as described in each of the above aspects.

In still yet another embodiment of each of the above aspects, the IGF1R inhibitor is represented by Formula I, or a pharmaceutically acceptable salt thereof, wherein $X_{12}$, $X_{13}$, and $X_{15}$ are N; $X_{11}$, $X_{14}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{12}$, $X_{13}$, and $X_{16}$ are N; $X_{11}$, $X_{14}$, and $X_{15}$ are C-$(E^{11})_{bb}$; and the other variables are as described in each of the above aspects.

In yet another embodiment of each of the above aspects, the IGF1R inhibitor is represented by Formula I, or a pharmaceutically acceptable salt thereof, wherein $X_{12}$, $X_{14}$, and $X_{15}$ are N; $X_{11}$, $X_{13}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{12}$, $X_{14}$, and $X_{16}$ are N; $X_{11}$, $X_{13}$, and $X_{15}$ are C-$(E^{11})_{bb}$; and the other variables are as described in each of the above aspects.

In yet still another embodiment of each of the above aspects, the IGF1R inhibitor is represented by Formula I, or a pharmaceutically acceptable salt thereof, wherein $X_{12}$, $X_{15}$, and $X_{16}$ are N; $X_{11}$, $X_{13}$, and $X_{14}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{13}$, $X_{14}$, and $X_{15}$ are N; $X_{11}$, $X_{12}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{13}$, $X_{14}$, and $X_{16}$ are N; $X_{11}$, $X_{12}$, and $X_{15}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{14}$, $X_{15}$, and $X_{16}$ are N; $X_{11}$, $X_{12}$, and $X_{13}$ are C-$(E^{11})_{bb}$; and the other variables are as described in each of the above aspects.

In yet another embodiment of each of the above aspects, the IGF1R inhibitor is represented by Formula I, or a pharmaceutically acceptable salt thereof, wherein $X_{13}$, $X_{15}$, and $X_{16}$ are N; $X_{11}$, $X_{12}$, and $X_{14}$ are C-$(E^{11})_{bb}$; and the other variables are as described in each of the above aspects.

In yet still another embodiment of each of the above aspects, the IGF1R inhibitor is represented by Formula I, or a pharmaceutically acceptable salt thereof, wherein $X_{11}$ and $X_{12}$ are N; $X_{13}$, $X_{14}$, $X_{15}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{11}$ and $X_{13}$ are N; $X_{12}$, $X_{14}$, $X_{15}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{11}$ and $X_{14}$ are N; $X_{12}$, $X_{13}$, $X_{15}$, and $X_{16}$ are C-$(E^{11})_{bb}$; and the other variables are as described in each of the above aspects.

In still yet another embodiment of each of the above aspects, the IGF1R inhibitor is represented by Formula I, or a pharmaceutically acceptable salt thereof, wherein $X_{11}$ and $X_{15}$ are N; $X_{12}$, $X_{13}$, $X_{14}$, and $X_{16}$ are C-$(E^{11})_{bb}$; and the other variables are as described in each of the above aspects.

In yet another embodiment of each of the above aspects, the IGF1R inhibitor is represented by Formula I, or a pharmaceutically acceptable salt thereof, wherein $X_{11}$ and $X_{16}$ are N; $X_{12}$, $X_{13}$, $X_{14}$, and $X_{15}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{12}$ and $X_{13}$ are N; $X_{11}$, $X_{14}$, $X_{15}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{12}$ and $X_{14}$ are N; $X_{11}$, $X_{13}$, $X_{15}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{12}$ and $X_{15}$ are N; $X_{11}$, $X_{13}$, $X_{14}$, and $X_{16}$ are C-$(E^{11})_{bb}$; and the other variables are as described in each of the above aspects.

In still yet another embodiment of each of the above aspects, the IGF1R inhibitor is represented by Formula I, or a pharmaceutically acceptable salt thereof, wherein $X_{12}$ and $X_{16}$ are N; $X_{11}$, $X_{13}$, $X_{14}$, and $X_{15}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{13}$ and $X_{14}$ are N; $X_{11}$, $X_{12}$, $X_{15}$, and $X_{16}$ are C-$(E^{11})_{bb}$; and the other variables are as described in each of the above aspects.

In yet still another embodiment of each of the above aspects, the IGF1R inhibitor is represented by Formula I, or a pharmaceutically acceptable salt thereof, wherein $X_{13}$ and $X_{15}$ are N; $X_{11}$, $X_{12}$, $X_{14}$, and $X_{16}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{13}$ and $X_{16}$ are N; $X_{11}$, $X_{12}$, $X_{14}$, and $X_{15}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{14}$ and $X_{15}$ are N; $X_{11}$, $X_{12}$, $X_{13}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{14}$ and $X_{16}$ are N; $X_{11}$, $X_{12}$, $X_{13}$, and $X_{15}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{15}$ and $X_{16}$ are N; $X_{11}$, $X_{12}$, $X_{13}$, and $X_{14}$ are C-$(E^{11})_{bb}$; and the other variables are as described in each of the above aspects.

In another embodiment of each of the above aspects, the IGF1R inhibitor is represented by Formula I, or a pharmaceutically acceptable salt thereof, wherein $X_{11}$ is N; $X_{12}$, $X_{13}$, $X_{14}$, $X_{15}$, and $X_{16}$ are C-$(E^{11})_{bb}$; and the other variables are as described in each of the above aspects.

In yet another embodiment of each of the above aspects, the IGF1R inhibitor is represented by Formula I, or a pharmaceutically acceptable salt thereof, wherein $X_{12}$ is N; $X_{11}$, $X_{13}$, $X_{14}$, $X_{15}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{13}$ is N; $X_{11}$, $X_{12}$, $X_{14}$, $X_{15}$, and $X_{16}$ are C-$(E^{11})_{bb}$; and the other variables are as described in each of the above aspects.

In yet still another embodiment of each of the above aspects, the IGF1R inhibitor is represented by Formula I, or a pharmaceutically acceptable salt thereof, wherein $X_{14}$ is N; $X_{11}$, $X_{12}$, $X_{13}$, $X_{15}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{15}$ is N; $X_{11}$, $X_{12}$, $X_{13}$, $X_{14}$, and $X_{16}$ are C-$(E^{11})_{bb}$; and the other variables are as described in each of the above aspects.

In still another embodiment of each of the above aspects, the IGF1R inhibitor is represented by Formula I, or a pharmaceutically acceptable salt thereof, wherein $X_{16}$ is N; $X_{11}$, $X_{12}$, $X_{13}$, $X_{14}$, and $X_{15}$ are C-$(E^{11})_{bb}$; and the other variables are as described in each of the above aspects.

Advantageous embodiments of the above aspects include:

An embodiment of each of the above aspects, wherein the IGF1R inhibitor is represented by Formula I, or a pharmaceutically acceptable salt thereof, wherein $X_{11}$ and $X_{16}$ are N; $X_{12}$, $X_{13}$, $X_{14}$, and $X_{15}$ are C-$(E^{11})_{bb}$; and the other variables are as described in each of the above aspects.

An embodiment of each of the above aspects, wherein the IGF1R inhibitor is represented by Formula I, or a pharmaceutically acceptable salt thereof, wherein $X_{14}$ and $X_{16}$ are N; $X_{11}$, $X_{12}$, $X_{13}$, and $X_{15}$ are C-$(E^{11})_{bb}$; and the other variables are as described in each of the above aspects.

An embodiment of each of the above aspects, wherein the IGF1R inhibitor is represented by Formula I, or a pharmaceutically acceptable salt thereof, wherein $X_{15}$ and $X_{16}$ are N; $X_{11}$, $X_{12}$, $X_{13}$, and $X_{14}$ are C-$(E^{11})_{bb}$; and the other variables are as described in each of the above aspects.

An embodiment of each of the above aspects, wherein the IGF1R inhibitor is represented by Formula I, or a pharmaceutically acceptable salt thereof, wherein $X_{11}$ is N; $X_{12}$, $X_{13}$, $X_{14}$, $X_{15}$, and $X_{16}$ are C-$(E^{11})_{bb}$; and the other variables are as described in each of the above aspects.

An embodiment of each of the above aspects, wherein the IGF1R inhibitor is represented by Formula I, or a pharmaceutically acceptable salt thereof, wherein $X_{16}$ is N; $X_{11}$, $X_{12}$, $X_{13}$, $X_{14}$, and $X_{15}$ are C-$(E^{11})_{bb}$; and the other variables are as described in each of the above aspects.

An aspect of the present invention includes compositions and methods for treating cancer patients comprising administering to the patient simultaneously or sequentially a therapeutically effective amount of an agent that inhibits serine phosphorylation of IRS1 (IRS1 agent) such as an EGFR inhibitor, and an IGF1R inhibitor combination, with or without additional agents or treatments, such as other anti-cancer drugs or radiation therapy, wherein the IGF1R inhibitor is a compound of Formula I:

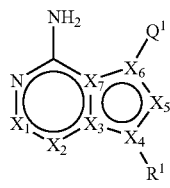

I or a pharmaceutically acceptable salt thereof, wherein:
$X_1$, $X_2$, $X_4$, $X_6$, and $X_7$ are C;
$X_3$ and $X_5$ are N;

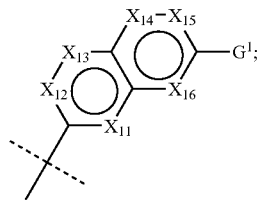

$Q^1$ is $X_{11}$, $X_{12}$, $X_{13}$, $X_{14}$, and $X_{15}$ are C;
$X_{16}$ is N;
$R^1$ is cycloC$_{3-10}$alkyl substituted by one or more independent $G^{11}$ substituents;

$G^1$ and $G^{41}$ are each independently halo, —CF$_3$, —OCF$_3$, —OR$^2$, —NR$^2$R$^3$(R$^{2a}$)$_{j1}$, —C(=O)R$^2$, —CO$_2$R$^2$, —CONR$^2$R$^3$, —NO$_2$, —CN, —S(O)$_{j1}$R$^2$, —SO$_2$NR$^2$R$^3$, —NR$^2$C(=O)R$^3$, —NR$^2$C(=O)OR$^3$, —NR$^2$C(=O)NR$^3$R$^{2a}$, —NR$^2$S(O)$_{j1}$R$^3$, —C(=S)OR$^2$, —C(=O)SR$^2$, —NR$^2$C(=NR$^3$)NR$^{2a}$R$^{3a}$, —NR$^2$C(=NR$^3$)OR$^{2a}$, —NR$^2$C(=NR$^3$)SR$^{2a}$, —OC(=O)OR$^2$, —OC(=O)NR$^2$R$^3$, —OC(=O)SR$^2$, —SC(=O)OR$^2$, —SC(=O)NR$^2$R$^3$, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{222}$, —NR$^{222}$R$^{333}$(R$^{222a}$)$_{j1a}$, —C(=O)R$^{222}$, —CO$_2$R$^{222}$, —C(=O)NR$^{222}$R$^{333}$, —NO$_2$, —CN, —S(=O)$_{j1a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j1a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$, or —SC(=O)NR$^{222}$R$^{333}$ substituents;

or $G^1$ optionally is —(W$^1$)$_n$—(Y$^1$)$_m$—R$^4$;

or $G^1$ or $G^{41}$ optionally independently is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{222}$—NR$^{222}$R$^{333}$(R$^{2a}$)$_{j2a}$, —C(O)R$^{222}$, —CO$_2$R$^{222}$, —C(=O)NR$^{222}$R$^{333}$, —NO$_2$, —CN, S(O)$_{j2a}$R$^{222}$, —SO$_2$NR$^{222}$R$^{333}$, —NR$^{222}$C(=O)R$^{333}$, —NR$^{222}$C(=O)OR$^{333}$, —NR$^{222}$C(=O)NR$^{333}$R$^{222a}$, —NR$^{222}$S(O)$_{j2a}$R$^{333}$, —C(=S)OR$^{222}$, —C(=O)SR$^{222}$, —NR$^{222}$C(=NR$^{333}$)NR$^{222a}$R$^{333a}$, —NR$^{222}$C(=NR$^{333}$)OR$^{222a}$, —NR$^{222}$C(=NR$^{333}$)SR$^{222a}$, —OC(=O)OR$^{222}$, —OC(=O)NR$^{222}$R$^{333}$, —OC(=O)SR$^{222}$, —SC(=O)OR$^{222}$ or —SC(=O)NR$^{222}$R$^{333}$ substituents;

$G^{11}$ is halo, oxo, —CF$_3$, —OCF$_3$, —OR$^{21}$, —NR$^{21}$R$^{31}$(R$^{2a1}$)$_{j4}$, —C(O)R$^{21}$, —CO$_2$R$^{21}$, —C(=O)NR$^{21}$R$^{31}$, —NO$_2$, —CN, —S(O)$_{j4}$R$^{21}$, —SO$_2$NR$^{21}$R$^{31}$, NR$^{21}$(C=O)R$^{31}$, NR$^{21}$C(=O)OR$^{31}$, NR$^{21}$C(=O)NR$^{31}$R$^{2a1}$, NR$^{21}$S(O)$_{j4}$R$^{31}$, —C(=S)OR$^{21}$, —C(=O)SR$^{21}$, —NR$^{21}$C(=NR$^{31}$)NR$^{2a1}$R$^{3a1}$, —NR$^{21}$C(=NR$^{31}$)OR$^{2a1}$, —NR$^{21}$C(=NR$^{31}$)SR$^{2a1}$, —OC(=O)OR$^{21}$, —OC(=O)NR$^{21}$R$^{31}$, —OC(=O)SR$^{21}$, —SC(=O)OR$^{21}$, —SC(=O)NR$^{21}$R$^{31}$, —P(O)OR$^{21}$OR$^{31}$, C$_{1-10}$alkylidene, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j4a}$R$^{3331}$, C(=S)R$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

or $G^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —COR$^{2221}$, —C(=O)NR$^{2221}$R$^{3331}$, NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —OC(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

or $G^{11}$ is C, taken together with the carbon to which it is attached forms a C=C double bond which is substituted with $R^5$ and $G^{111}$;

$R^2$, $R^{2a}$, $R^3$, $R^{3a}$, $R^{222}$, $R^{222a}$, $R^{333}$, $R^{333a}$, $R^{21}$, $R^{2a1}$, $R^{31}$, $R^{3a1}$, $R^{2221}$, $R^{222a1}$, $R^{3331}$, and $R^{333a1}$ are each independently $C_{0-10}$alkyl, $C_{2-10}$alkenyl, $C_{2-10}$alkynyl, $C_{1-10}$alkoxy $C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted by one or more independent $G^{111}$ substituents;

or in the case of $-NR^2R^3(R^{2a})_{j1}$ or $-NR^{222}R^{333}$ $(R^{222a})_{j1a}$ or $-NR^{222}R^{333}(R^{222a})_{j2a}$ or $-NR^{21}R^{31}(R^{2a1})_{j4}$ or $-NR^{2221}R^{3331}(R^{222a1})_{j4a}$ or $-NR^{2221}R^{3331}(R^{222a1})_{j5a}$, then $R^2$ and $R^3$, or $R^{222}$ and $R^{333}$, or $R^{2221}$ and $R^{3331}$, respectfully, are optionally taken together with the nitrogen atom to which they are attached to form a 3-10 membered saturated or unsaturated ring, wherein said ring is optionally substituted by one or more independent $G^{1111}$ substituents and wherein said ring optionally includes one or more heteroatoms other than the nitrogen to which $R^2$ and $R^3$, or $R^{222}$ and $R^{333}$ or $R^{2221}$ and $R^{3331}$ are attached;

$W^1$ and $Y^1$ are each independently $-O-$, $-NR^7-$, $-S(O)_{j7}-$, $-CR^5R^6-$, $-N(C(O)OR^7)-$, $-N(C(O)R^7)-$, $-N(SO_2R^7)-$, $-CH_2O-$, $-CH_2S-$, $-CH_2N(R^7)-$, $-CH(NR^7)-$, $-CH_2N(C(O)R^7)-$, $-CH_2N(C(O)OR^7)-$, $-CH_2N(SO_2R^7)-$, $-CH(NHR^7)-$, $-CH(NHC(O)R^7)-$, $-CH(NHSO_2R^7)-$, $-CH(NHC(O)OR^7)-$, $-CH(OC(O)R^7)-$, $-CH(OC(O)NHR^7)-$, $-CH=CH-$, $-C\equiv C-$, $-C(=NOR^7)-$, $-C(O)-$, $-CH(OR^7)-$, $-C(O)N(R^7)-$, $-N(R^7)C(O)-$, $-N(R^7)S(O)-$, $-N(R^7)S(O)_2-$, $-OC(O)N(R^7)-$, $-N(R^7)C(O)N(R^8)-$, $-NR^7C(O)O-$, $-S(O)N(R^7)-$, $-S(O)_2N(R^7)-$, $-N(C(O)R^7)S(O)-$, $-N(C(O)R^7)S(O)_2-$, $-N(R^7)S(O)N(R^8)-$, $-N(R^7)S(O)_2N(R^8)-$, $-C(O)N(R^7)C(O)-$, $-S(O)N(R^7)C(O)-$, $-S(O)_2N(R^7)C(O)-$, $-OS(O)N(R^7)-$, $-OS(O)_2N(R^7)-$, $-N(R^7)S(O)O-$, $-N(R^7)S(O)_2O-$, $-N(R^7)S(O)C(O)-$, $-N(R^7)S(O)_2C(O)-$, $-SON(C(O)R^7)-$, $-SO_2N(C(O)R^7)-$, $-N(R^7)SON(R^8)-$, $-N(R^7)SO_2N(R^8)-$, $-C(O)O-$, $-N(R^7)P(OR^8)O-$, $-N(R^7)P(OR^8)-$, $-N(R^7)P(O)(OR^8)-$, $-N(R^7)P(O)(OR^8)-$, $-N(C(O)R^7)P(OR^8)O-$, $-N(C(O)R^7)P(OR^8)-$, $-N(C(O)R^7)P(O)(OR^8)O-$, $-N(C(O)R^7)P(OR^8)-$, $-CH(R^7)S(O)-$, $-CH(R^7)S(O)_2-$, $-CH(R^7)N(C(O)OR^8)-$, $-CH(R^7)N(C(O)R^8)-$, $-CH(R^7)N(SO_2R^8)-$, $-CH(R^7)O-$, $-CH(R^7)S-$, $-CH(R^7)N(R^8)-$, $-CH(R^7)N(C(O)R^8)-$, $-CH(R^7)N(C(O)OR^8)-$, $-CH(R^7)N(SO_2R^8)-$, $-CH(R^7)C(=NOR^8)-$, $-CH(R^7)C(O)-$, $-CH(R^7)CH(OR^8)-$, $-CH(R^7)C(O)N(R^8)-$, $-CH(R^7)N(R^8)C(O)-$, $-CH(R^7)N(R^8)S(O)-$, $-CH(R^7)N(R^8)S(O)_2-$, $-CH(R^7)OC(O)N(R^8)-$, $-CH(R^7)N(R^8)C(O)N(R^{7a})-$, $-CH(R^7)NR^8C(O)O-$, $-CH(R^7)S(O)N(R^8)-$, $-CH(R^7)S(O)_2N(R^8)-$, $-CH(R^7)N(C(O)R^8)S(O)-$, $-CH(R^7)N(C(O)R^8)S(O)-$, $-CH(R^7)N(R^8)S(O)N(R^{7a})-$, $-CH(R^7)N(R^8)S(O)_2N(R^{7a})-$, $-CH(R^7)C(O)N(R^8)C(O)-$, $-CH(R^7)S(O)N(R^8)C(O)-$, $-CH(R^7)S(O)_2N(R^8)C(O)-$, $-CH(R^7)OS(O)N(R^8)-$, $-CH(R^7)OS(O)_2N(R^8)-$, $-CH(R^7)N(R^8)S(O)O-$, $-CH(R^7)N(R^8)S(O)_2O-$, $-CH(R^7)N(R^8)S(O)C(O)-$, $-CH(R^7)N(R^8)S(O)_2C(O)-$, $-CH(R^7)SON(C(O)R^8)-$, $-CH(R^7)SO_2N(C(O)R^8)-$, $-CH(R^7)N(R^8)SON(R^{7a})-$, $-CH(R^7)N(R^8)SO_2N(R^{7a})-$, $-CH(R^7)C(O)O-$, $-CH(R^7)N(R^8)P(OR^{7a})O-$, $-CH(R^7)N(R^8)P(OR^{7a})-$, $-CH(R^7)N(R^8)P(O)(OR^{7a})O-$, $CH(R^7)N(R^8)P(O)(OR^{7a})$, $-CH(R^7)N(C(O)R^8)P(OR^{7a})O$, $-CH(R^7)N(C(O)R^8)P(OR^{7a})$, $-CH(R^7)N(C(O)R^8)P(O)(OR^{7a})O-$, or $-CH(R^7)N(C(O)R^8)P(OR^{7a})-$;

$R^5$, $R^6$, $G^{111}$, and $G^{1111}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, $-CF_3$, $-OCF_3$, $-OR^{77}$, $-NR^{77}R^{87}$, $-C(O)R^{77}$, $-CO_2R^{77}$, $-CONR^{77}R^{87}$, $-NO_2$, $-CN$, $-S(O)_{j5a}R^{77}$, $-SO_2NR^{77}R^{87}$, $-NR^{77}C(=O)R^{87}-NR^{77}C(=O)OR^{87}$, $-NR^{77}C(=O)NR^{78}R^{87}$, $-NR^{77}S(O)_{j5a}R^{87}$, $-C(=S)OR^{77}$, $-C(=O)SR^{77}$, $-NR^{77}C(=NR^{87})NR^{78}R^{88}$, $-NR^{77}C(=NR^{87})OR^{78}$, $-NR^{77}C(=NR^{87})SR^{78}$, $-OC(=O)OR^{77}$, $-OC(=O)NR^{77}R^{87}$, $-OC(=O)SR^{77}$, $-SC(=O)OR^{77}$, $-P(O)OR^{77}R^{87}$, or $-SC(=O)NR^{77}R^{87}$ substituents;

or $R^5$ with $R^6$ are optionally taken together with the carbon atom to which they are attached to form a 3-10 membered saturated or unsaturated ring, wherein said ring is optionally substituted with one or more independent $R^{69}$ substituents and wherein said ring optionally includes one or more heteroatoms;

$R^7$, $R^{7a}$, and $R^8$ are each independently acyl, $C_{0-10}$alkyl, $C_{2-10}$alkenyl, aryl, heteroaryl, heterocyclyl or cyclo$C_{3-10}$alkyl, any of which is optionally substituted by one or more independent $G^{111}$ substituents;

$R^4$ is $C_{0-10}$alkyl, $C_{2-10}$alkenyl, $C_{2-10}$alkynyl, aryl, heteroaryl, cyclo$C_{3-10}$alkyl, heterocyclyl, cyclo$C_{3-8}$alkenyl, or heterocycloalkenyl, any of which is optionally substituted by one or more independent $G^{41}$ substituents;

$R^{69}$ is halo, $-OR^{78}$, $-SH$, $-NR^{78}R^{88}$, $-CO_2R^{78}$, $-C(=O)NR^{78}R^{88}$, $-NO_2$, $-CN$, $-S(O)_{j8}R^{78}$, $-SO_2NR^{78}R^{88}$, $C_{0-10}$alkyl, $C_{2-10}$alkenyl, $C_{2-10}$alkynyl, $C_{2-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, $-OR^{778}$—$SO_2NR^{778}R^{888}$, or $-NR^{778}R^{888}$ substituents;

or $R^{69}$ is aryl-$C_{0-10}$-alkyl, aryl-$C_{2-10}$alkenyl, aryl-$C_{2-10}$alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or $-N(C_{1-6}$alkyl)-$C_{1-6}$alkyl-aryl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-C(=O)NR^{778}R^{888}$, $-SO_2NR^{778}R^{888}$ or $-NR^{778}R^{888}$ substituents;

or in the case of —NR$^{78}$R$^{88}$, R$^{78}$ and R$^{88}$ are optionally taken together with the nitrogen atom to which they are attached to form a 3-10 membered saturated or unsaturated ring, wherein said ring is optionally substituted with one or more independent halo, cyano, hydroxy, nitro, C$_{1-10}$alkoxy, —SO$_2$NR$^{778}$R$^{888}$, or —NR$^{778}$R$^{888}$ substituents, and wherein said ring optionally includes one or more heteroatoms other than the nitrogen to which R$^{78}$ and R$^{88}$ are attached;

R$^{77}$, R$^{78}$, R$^{87}$, R$^{88}$, R$^{778}$, and R$^{888}$ are each independently C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, C$_{1-10}$alkylcarbonyl, C$_{2-10}$alkenylcarbonyl, C$_{2-10}$alkynylcarbonyl, C$_{1-10}$alkoxycarbonyl, C$_{1-10}$alkoxycarbonylC$_{1-10}$alkyl, monoC$_{1-6}$alkylaminocarbonyl, diC$_{1-6}$alkylaminocarbonyl, mono(aryl)aminocarbonyl, di(aryl)aminocarbonyl, or C$_{1-10}$alkyl(aryl)aminocarbonyl, any of which is optionally substituted with one or more independent halo, cyano, hydroxy, nitro, C$_{1-10}$alkoxy, —SO$_2$N(C$_{0-4}$alkyl)(C$_{0-4}$alkyl), or —N(C$_{0-4}$alkyl)(C$_{0-4}$alkyl) substituents;

or R$^{77}$, R$^{78}$, R$^{87}$, R$^{88}$, R$^{778}$, and R$^{888}$ are each independently aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, hetaryl-C$_{2-10}$alkynyl, mono(C$_{1-6}$alkyl)aminoC$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, or —N(C$_{1-6}$alkyl)-C$_{1-6}$alkyl-aryl, any of which is optionally substituted with one or more independent halo, cyano, nitro, —O(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CON(C$_{0-4}$alkyl)(C$_{0-10}$alkyl), —SO$_2$N(C$_{0-4}$alkyl)(C$_{0-4}$alkyl), or —N(C$_{0-4}$alkyl)(C$_{0-4}$alkyl) substituents; and n, m, j1, j1a, j2a, j4, j4a, j5a, j7, and j8 are each independently 0, 1, or 2.

In an aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is an EGFR kinase inhibitor.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is an EGFR kinase inhibitor wherein the EGFR kinase inhibitor is erlotinib, cetuximab, gefitinib, or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is an EGFR kinase inhibitor wherein the EGFR kinase inhibitor is erlotinib or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is an inhibitor of the MAPK pathway or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a Ras, Raf, MEK or PKC inhibitor; or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a MEK inhibitor or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a MEK inhibitor wherein the MEK inhibitor is ARRY-142886, PD-184352, PD-98059, PD-0325901, XL518, or MEK1; or a salt thereof.

1. In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a Ras inhibitor; or a salt thereof.

2. In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a Ras inhibitor; or a salt thereof, wherein the Ras inhibitor is BMS-214662, SCH 66336, L-778, 123, R115777, 6-[(4-chlorophenyl)-hydroxy-(3-methyl-3H-imidazol-4-yl)-methyl]-4-(3-ethynyl-phenyl)-1-methyl-1H-quinolin-2-one; or a salt thereof.

3. In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a Raf inhibitor; or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a Raf inhibitor; or a salt thereof, wherein the Raf inhibitor is sorafenib; or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a PKC inhibitor; or a salt thereof.

In another aspect of the present invention, the IGF1R inhibitor is represented by Formula I, or a salt thereof, wherein X$_3$ and X$_5$ are N; X$_1$, X$_2$, X$_4$, X$_6$, and X$_7$ are C; and the other variables are described as above for Formula I; and the agent that inhibits serine phosphorylation of IRS1 is a PKC inhibitor; or a salt thereof, wherein the PKC inhibitor is Byrostatin, staurosporine, staurosporine analog including UCN-01 or CGP41251, safingol; or a salt thereof.

In further embodiments according to the above aspects of the invention, the IGF1R inhibitor is represented by Formula I, or a pharmaceutically acceptable salt thereof, wherein $X_{16}$ is N; $X_{11}$, $X_{12}$, $X_{13}$, $X_{14}$, and $X_{15}$ are C; and the other variables are as described in each of the above aspects.

In further embodiments according to the above aspects of the invention, the IGF1R inhibitor is represented by Formula I, or a pharmaceutically acceptable salt thereof, wherein $X_{16}$ is N; $X_{11}$, $X_{12}$, $X_{13}$, $X_{14}$, and $X_{15}$ are C; $G_1$ is aryl-$C_{0-10}$alkyl; and the other variables are as described in each of the above aspects.

In further embodiments according to the above aspects of the invention, the IGF1R inhibitor is represented by Formula I, or a pharmaceutically acceptable salt thereof, wherein $X_{16}$ is N; $X_{11}$, $X_{12}$, $X_{13}$, $X_{14}$, and $X_{15}$ are C; $G_1$ is aryl; $R^1$ is cyclo$C_{3-10}$ alkyl substituted by one or more independent $G^{11}$ substituents; and the other variables are as described in each of the above aspects.

The IGF1R inhibitors included in the present invention include any of,

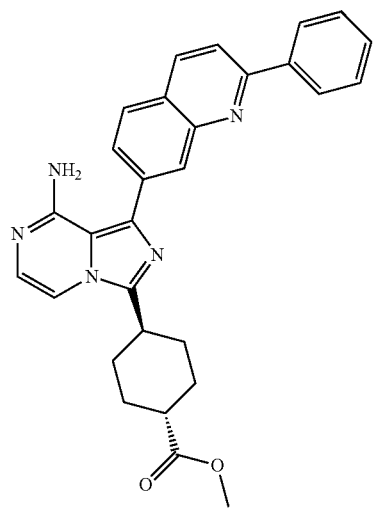

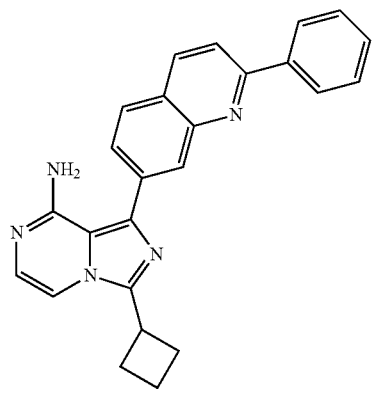

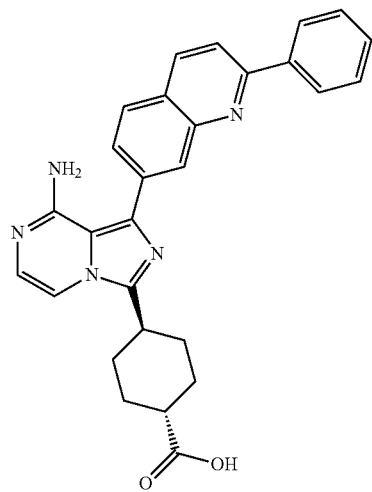

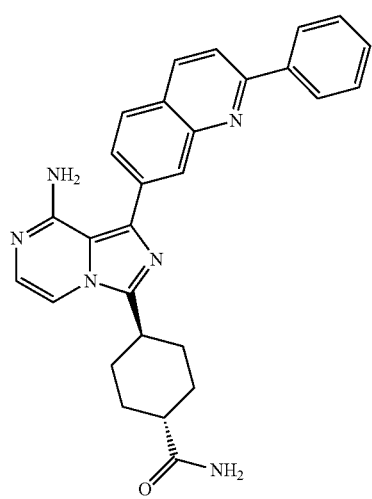

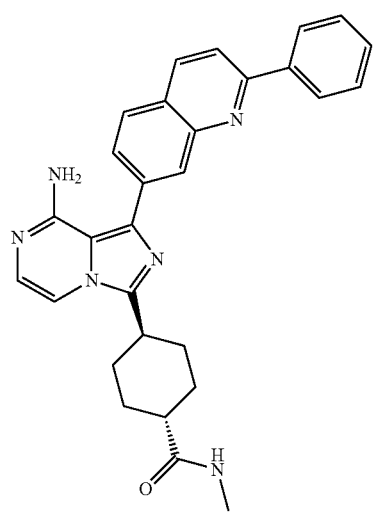

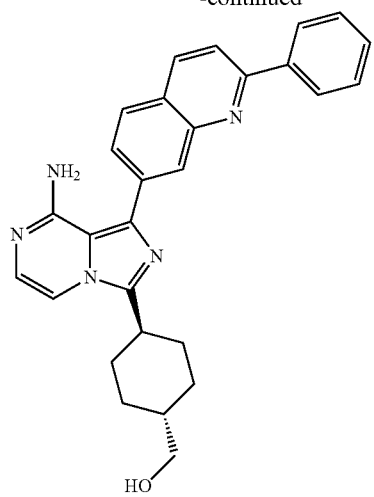
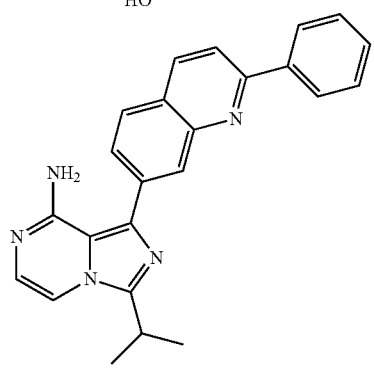
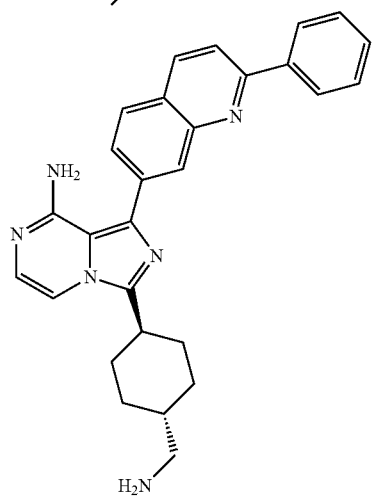
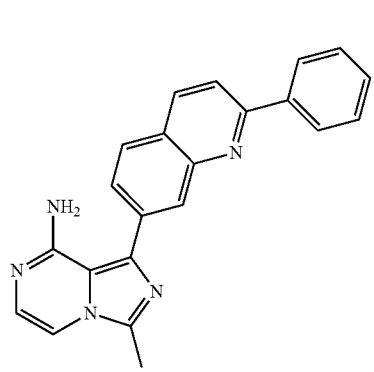
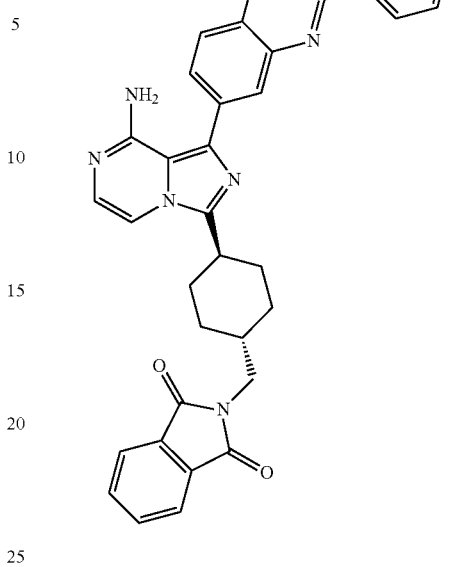
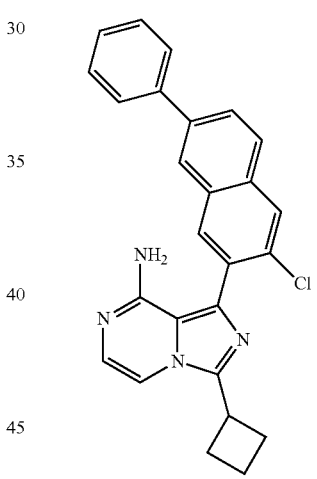
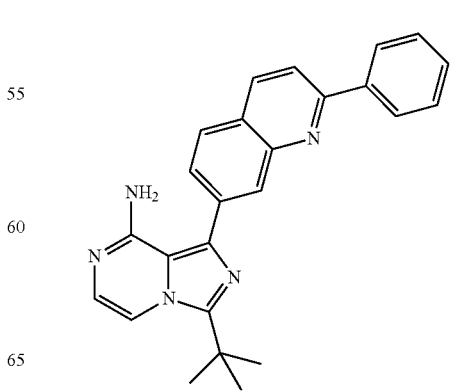

29
-continued
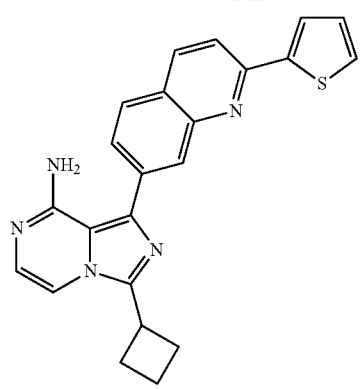
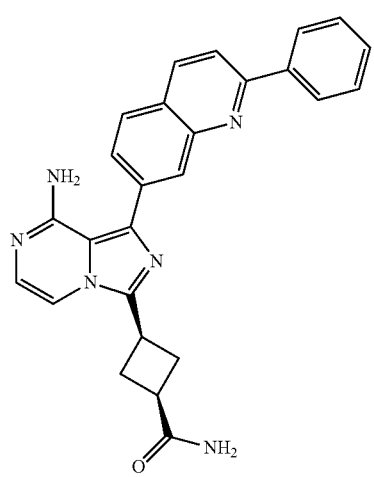
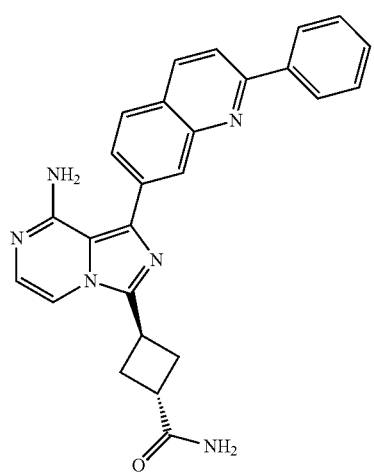
30
-continued
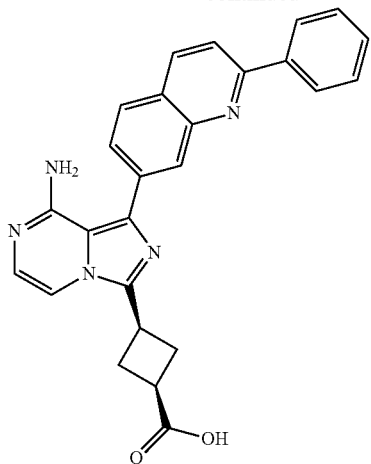
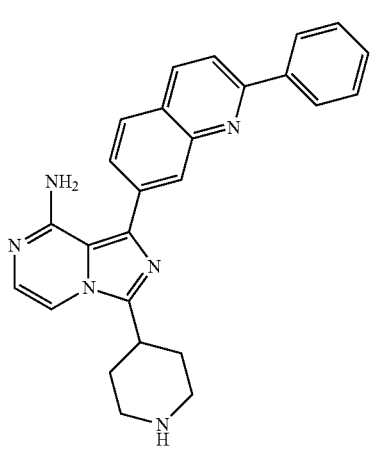
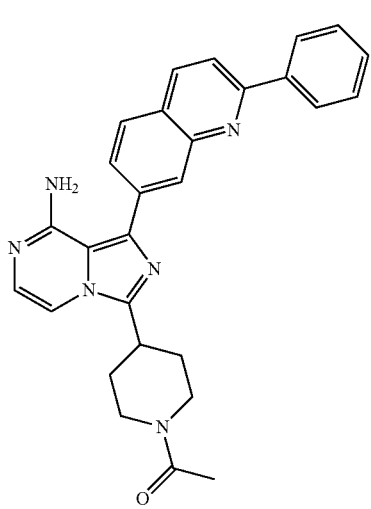

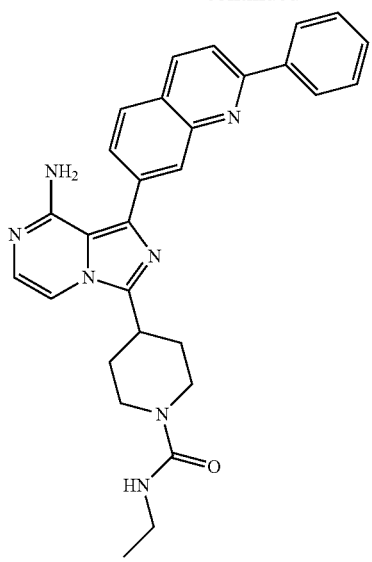
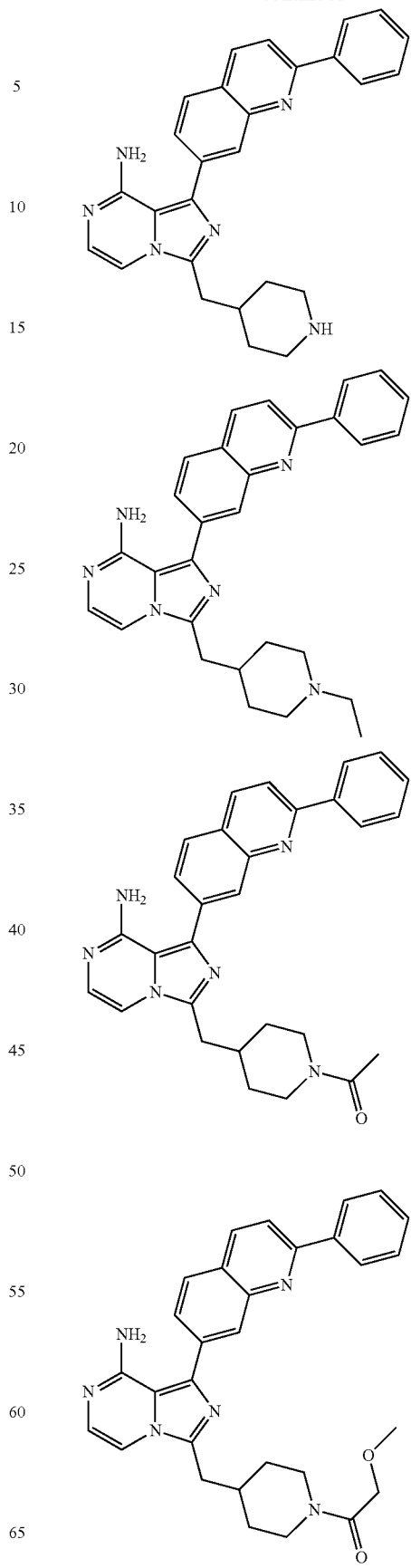

33
-continued
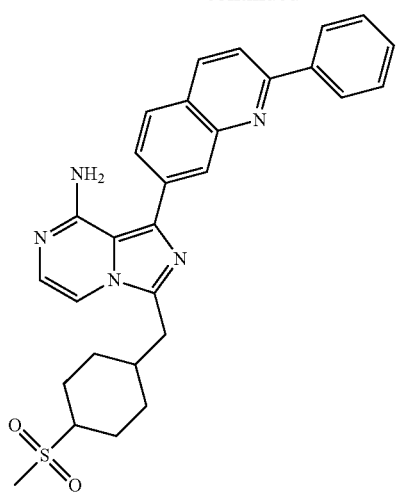
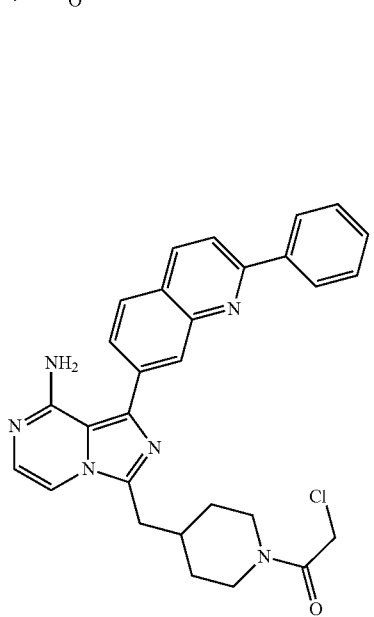
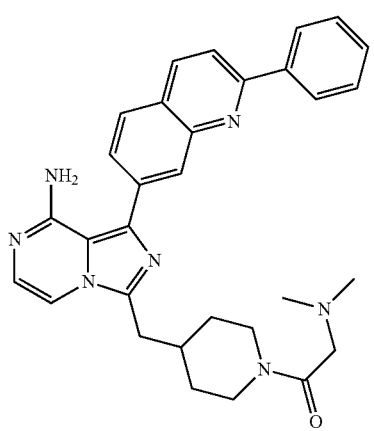
34
-continued
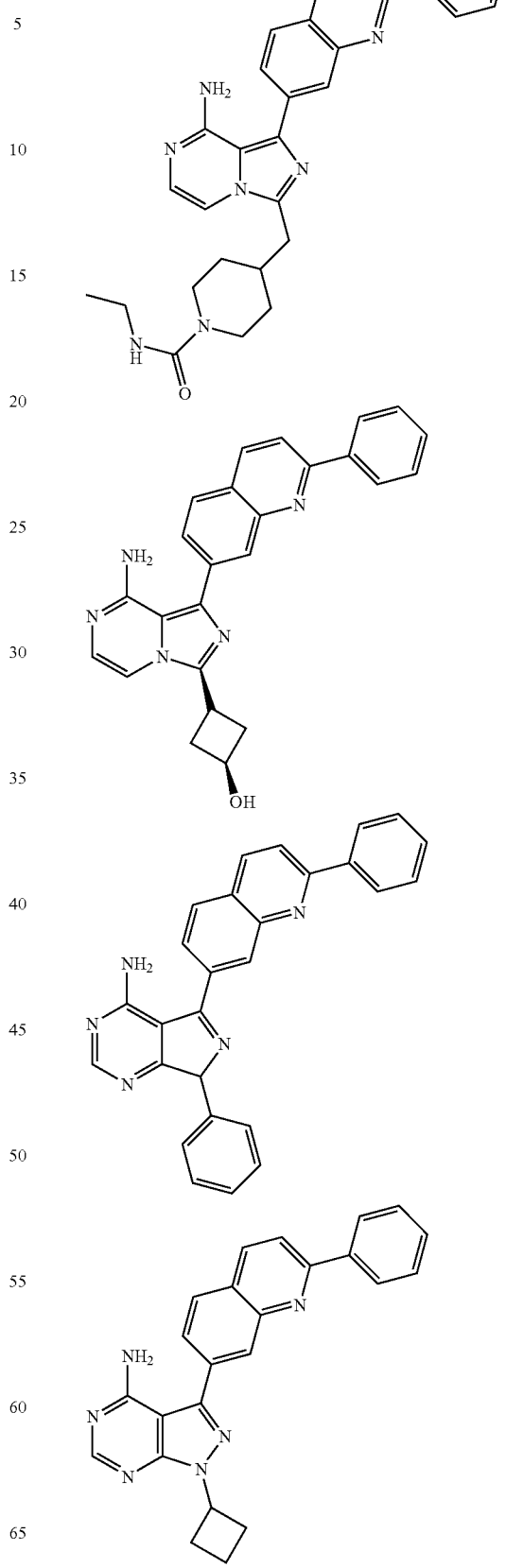

35
-continued
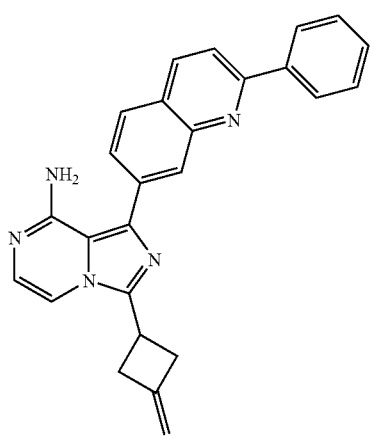
36
-continued
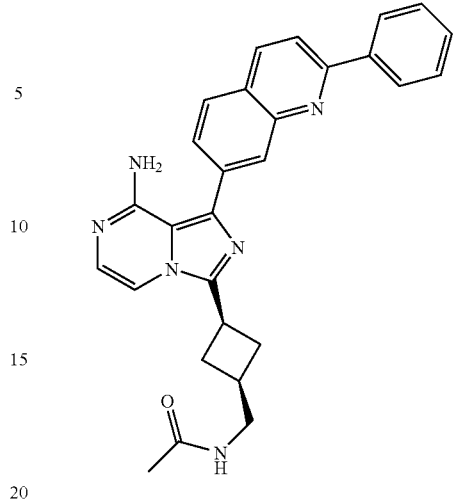
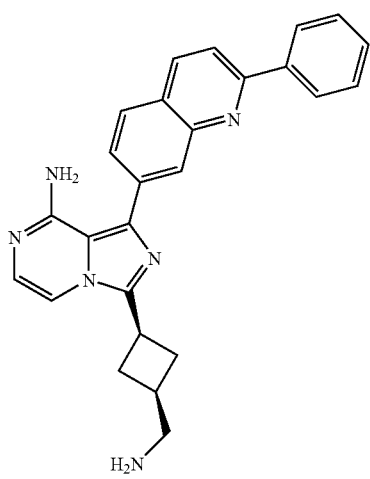
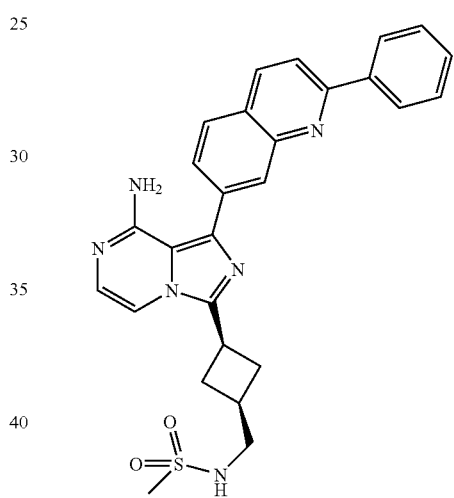
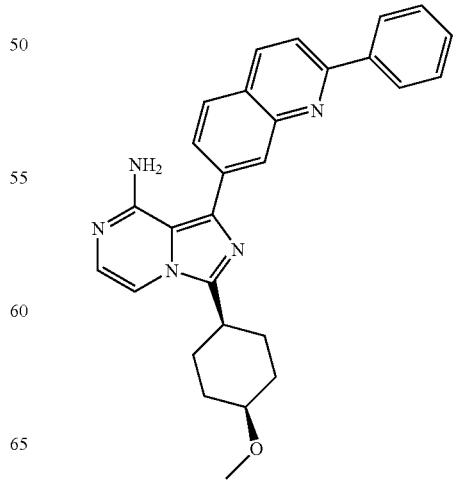

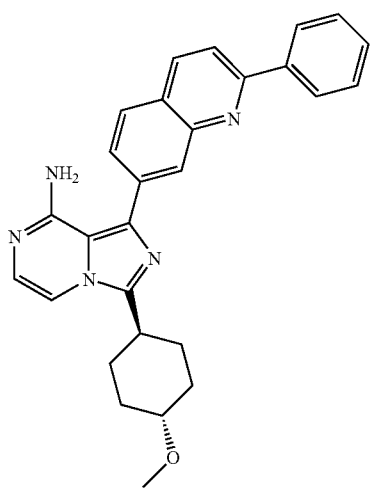
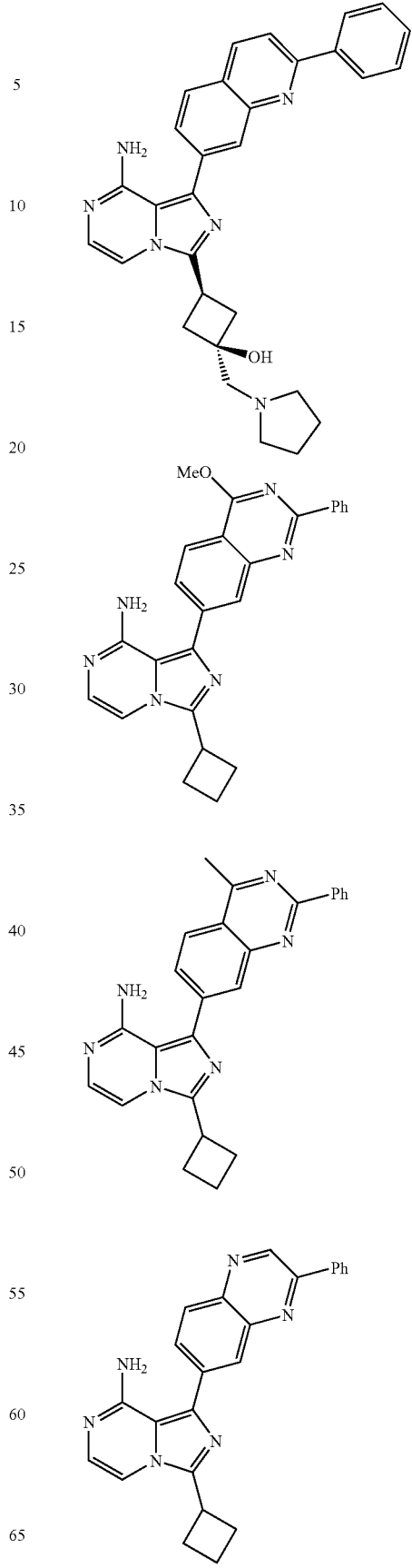

39
-continued
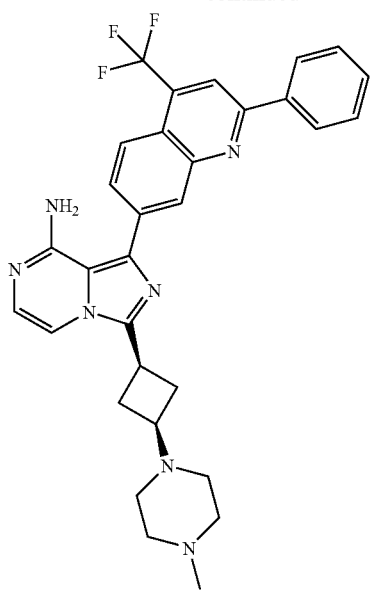
40
-continued
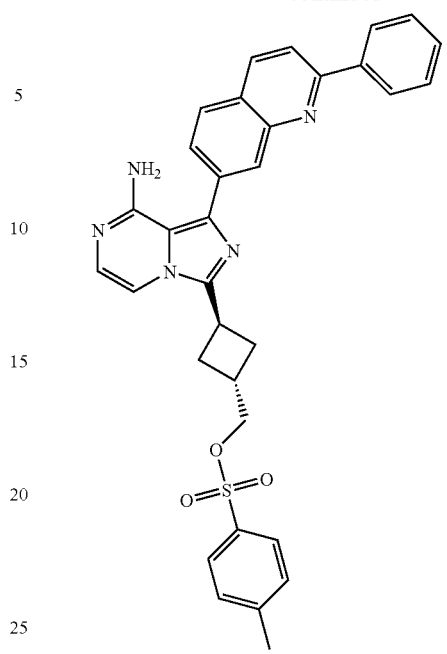
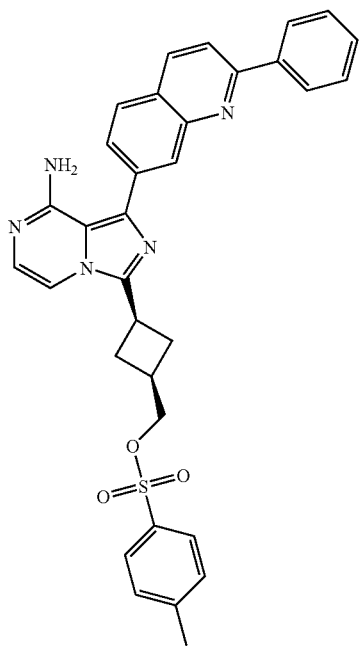
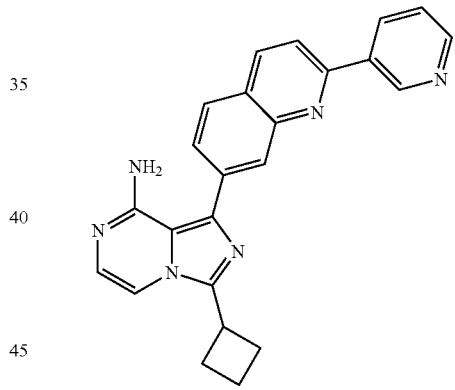
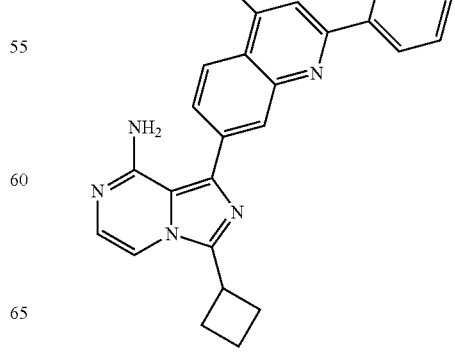

41
-continued
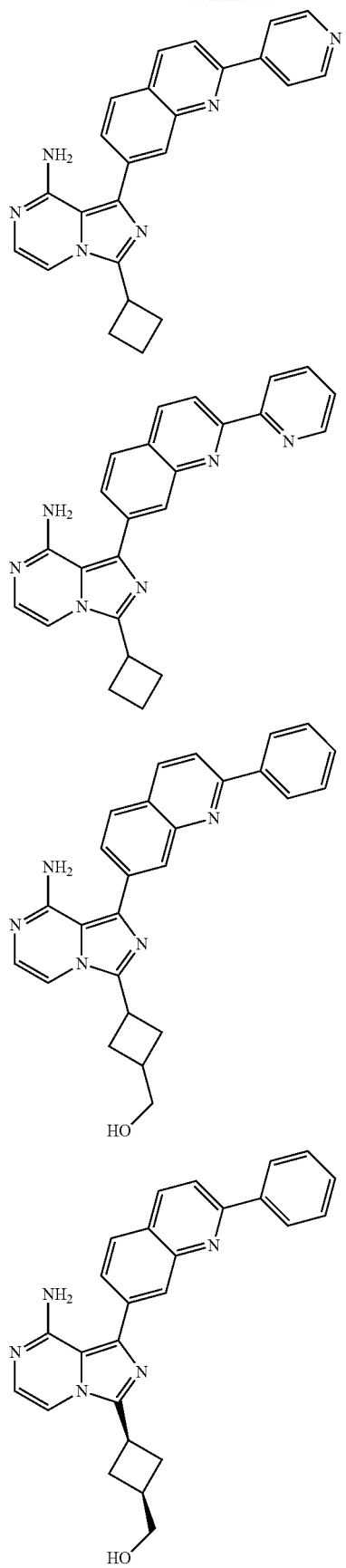
42
-continued
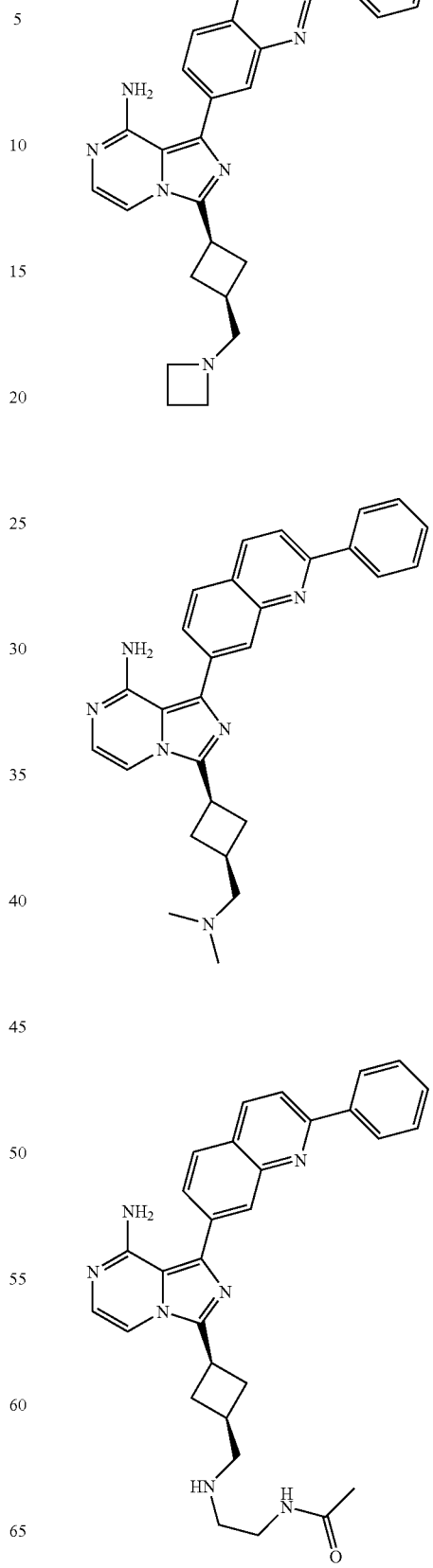

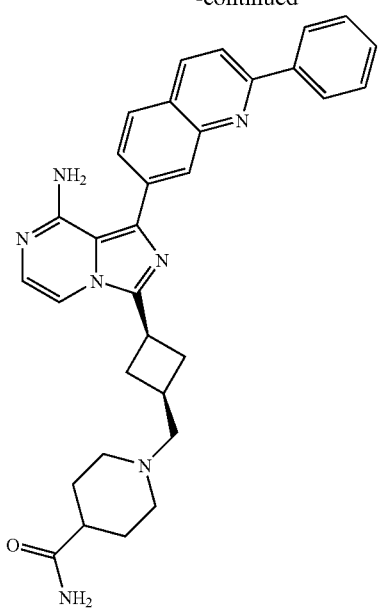
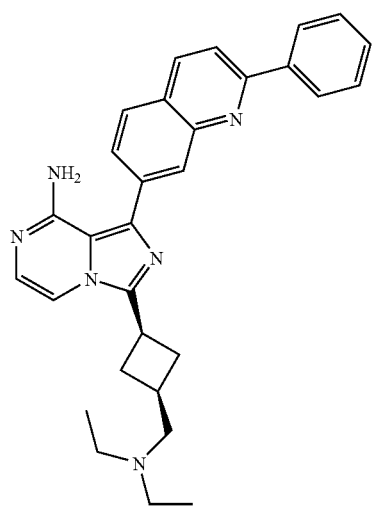
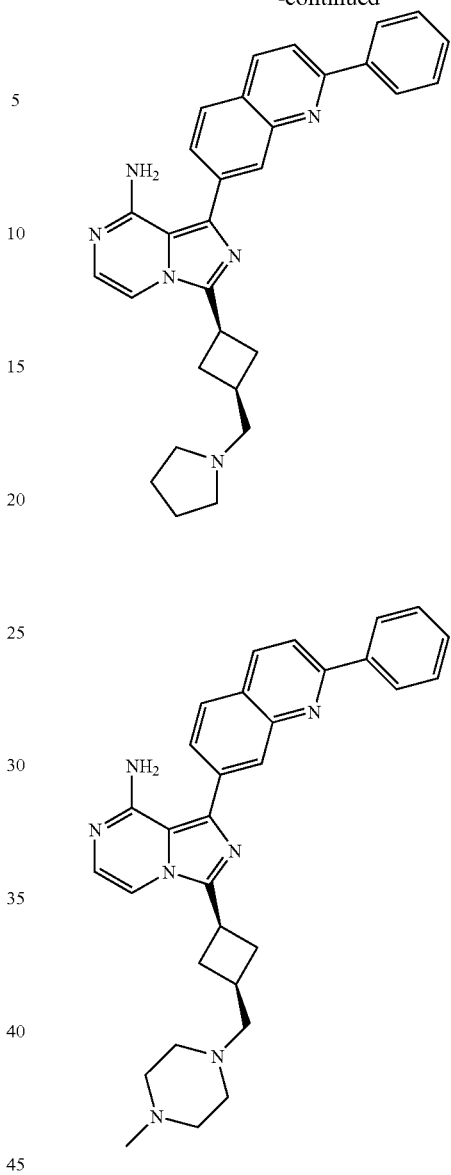

45
-continued
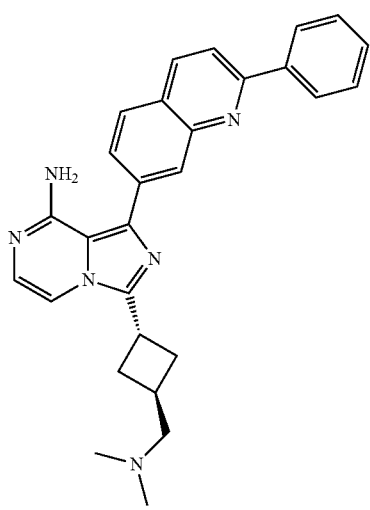
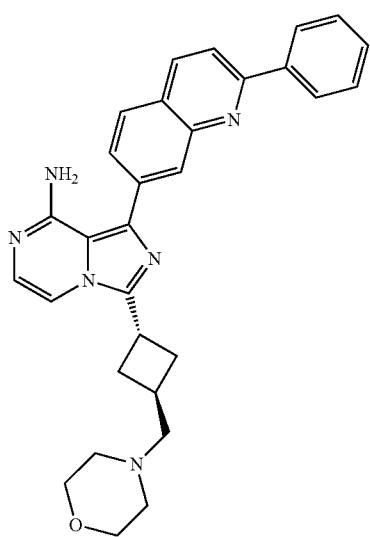
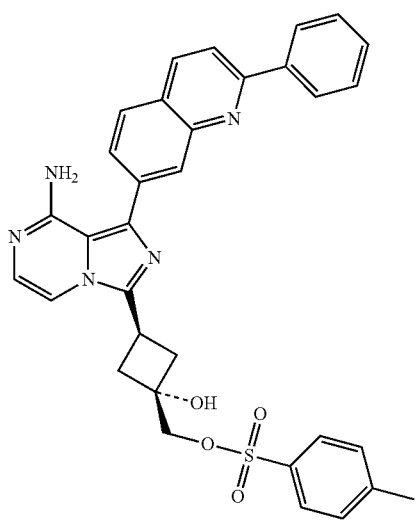
46
-continued
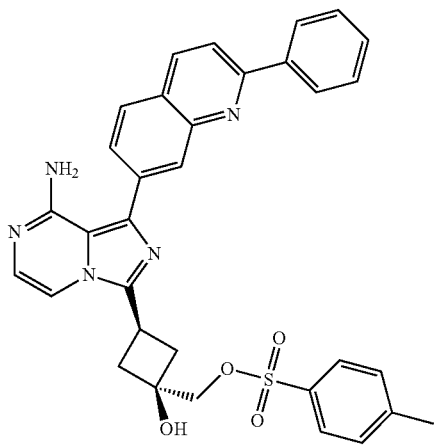
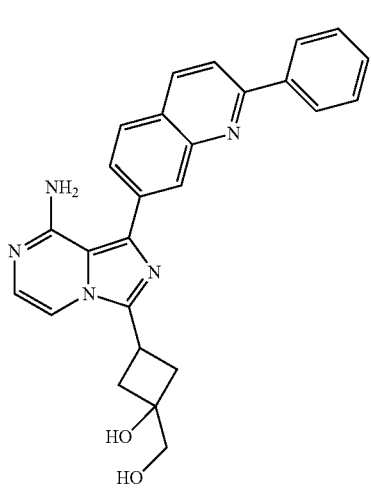

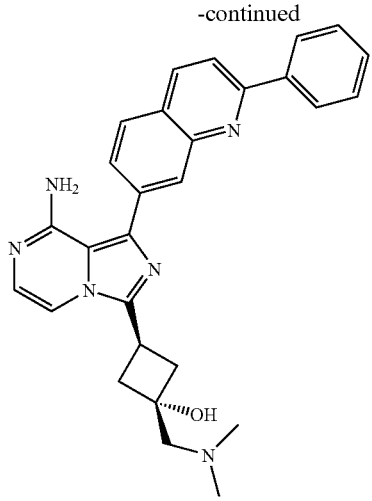
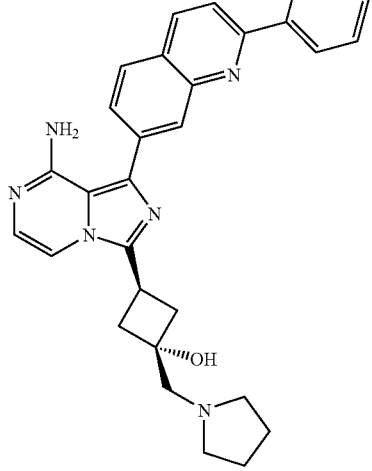
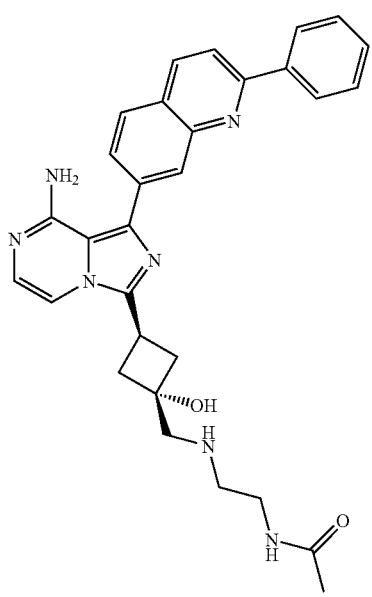
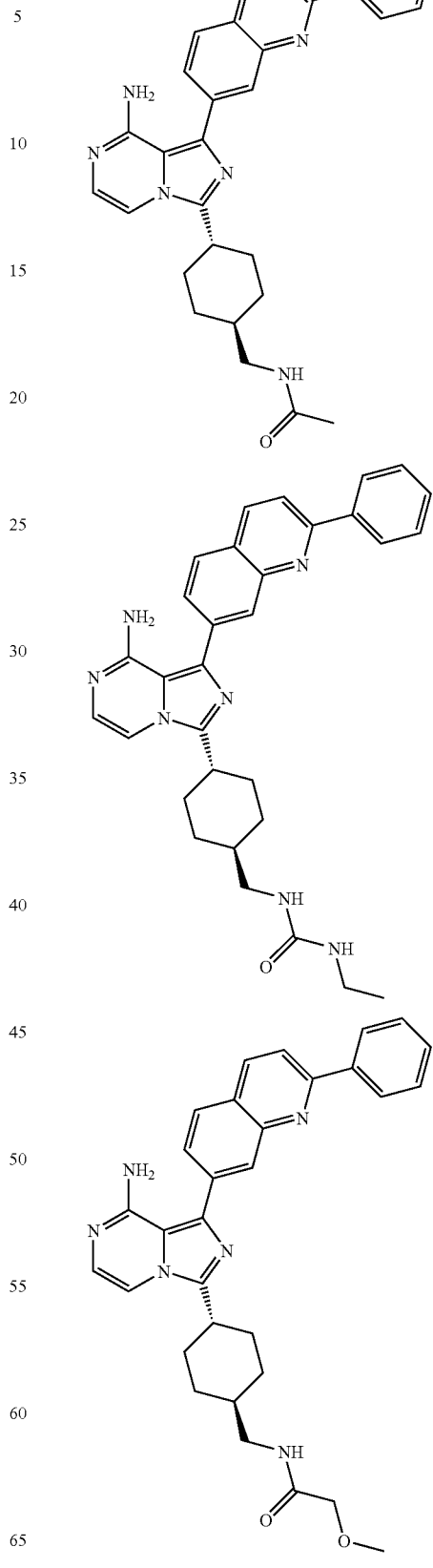

49
-continued
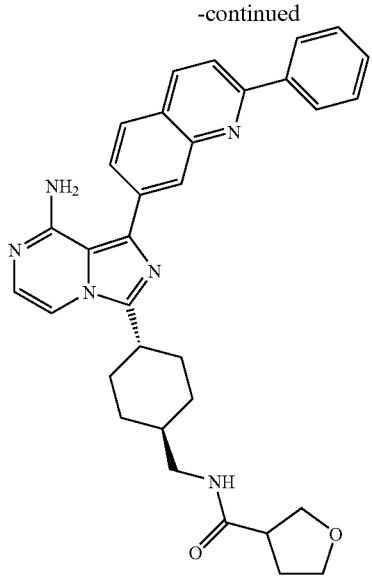
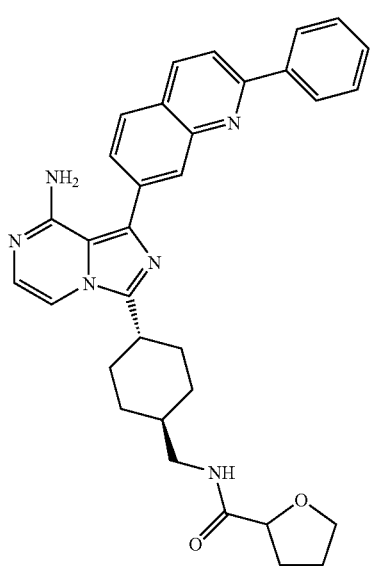
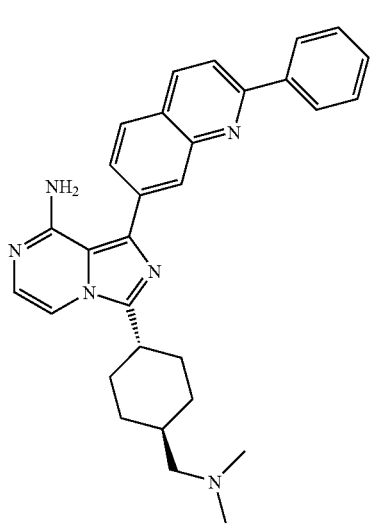
50
-continued
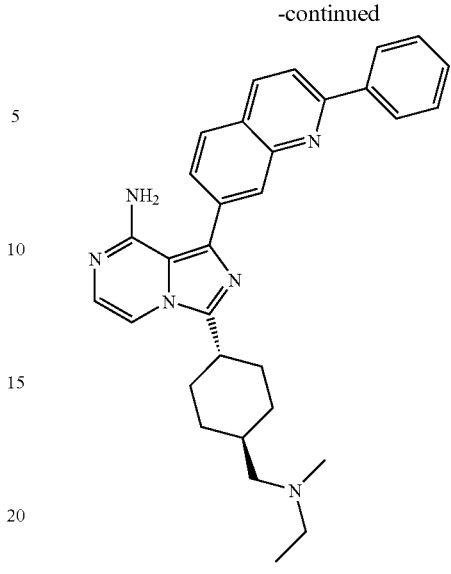
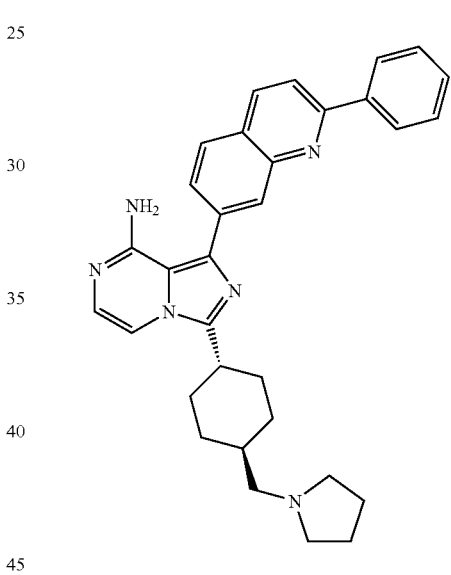
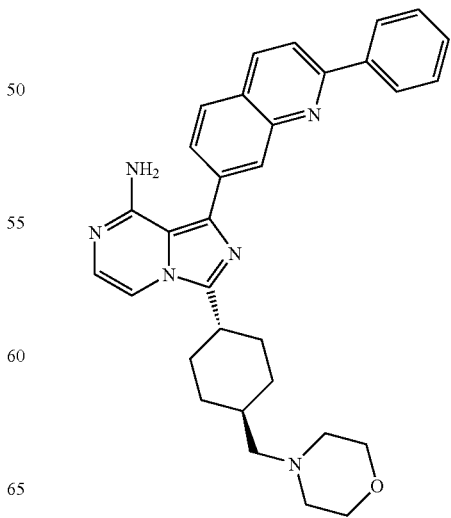

51
-continued
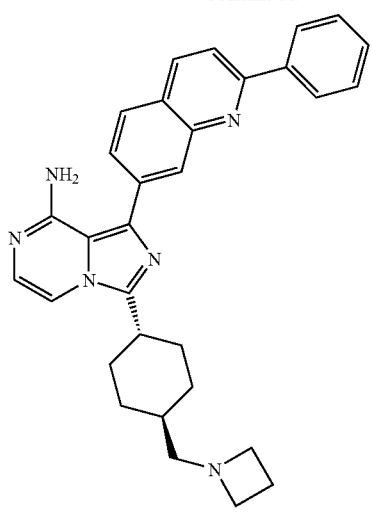
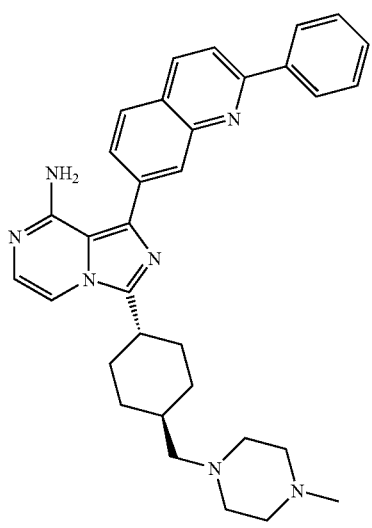
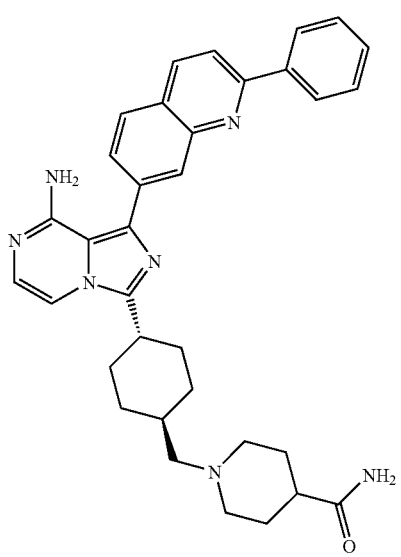
52
-continued
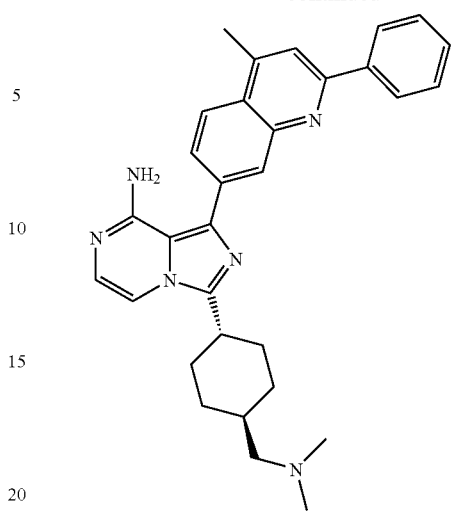
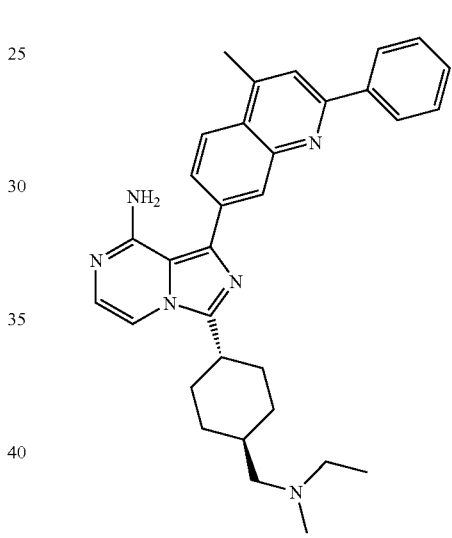
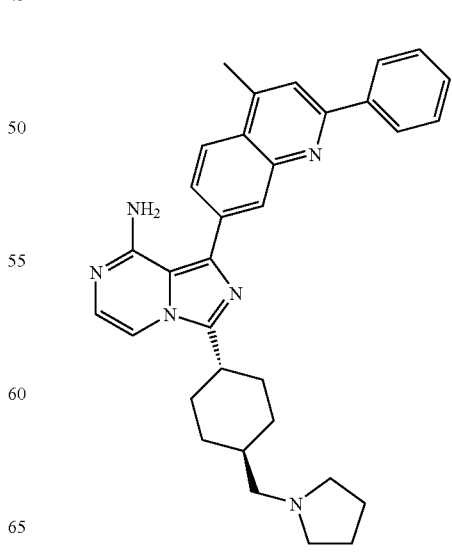

53
-continued
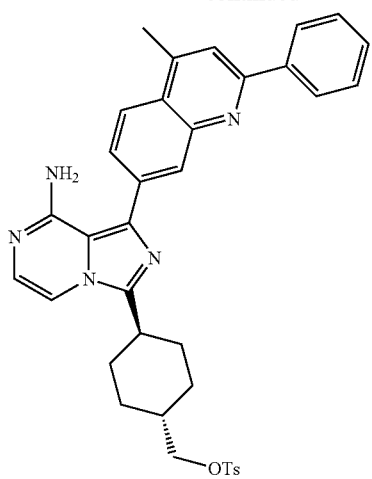
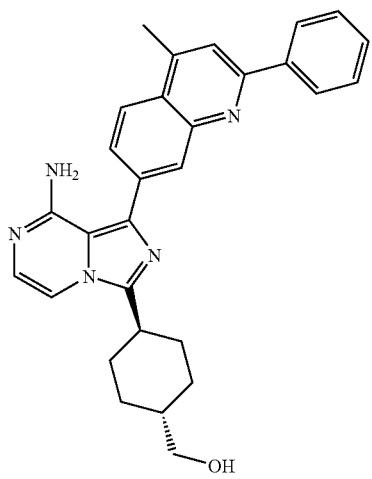
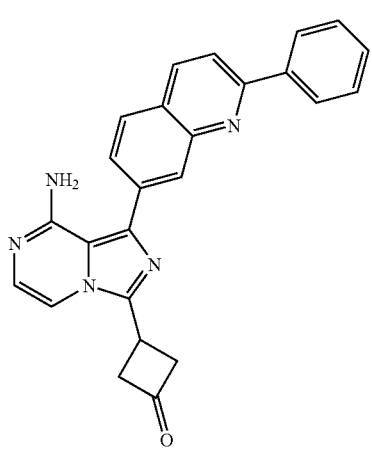
54
-continued
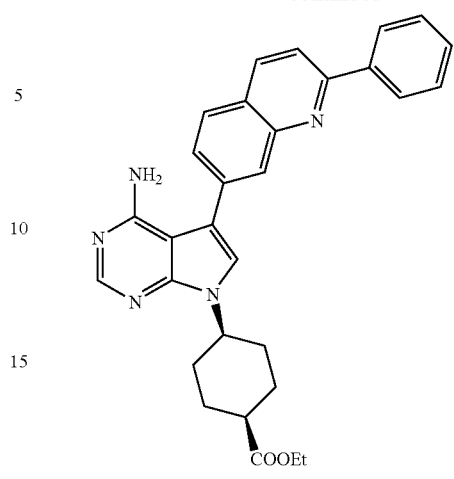
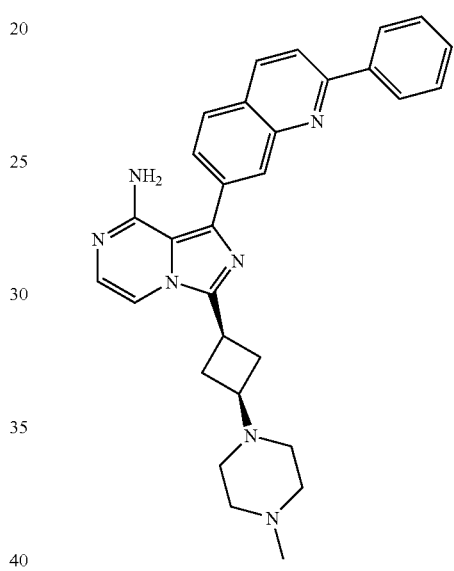
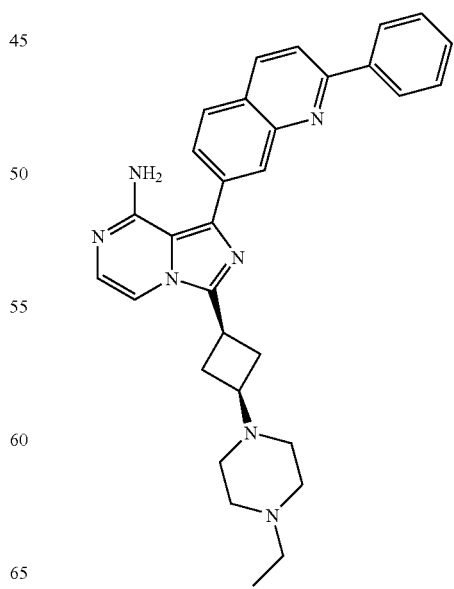

55
-continued
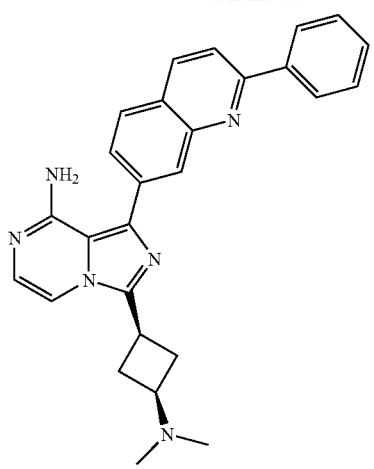
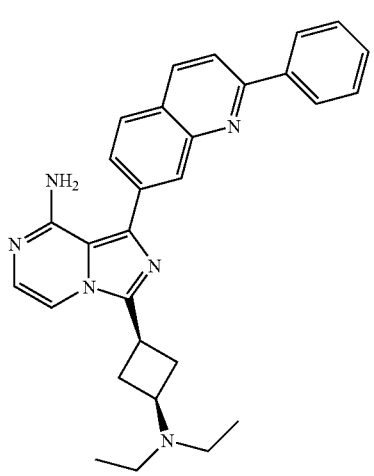
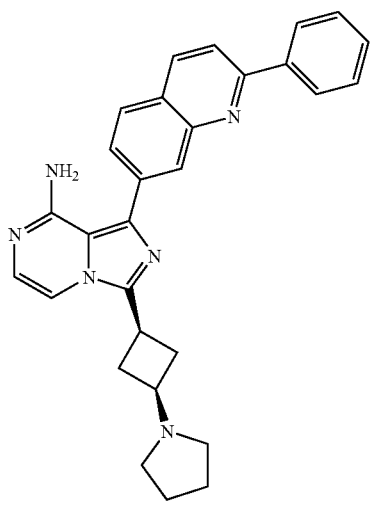
56
-continued
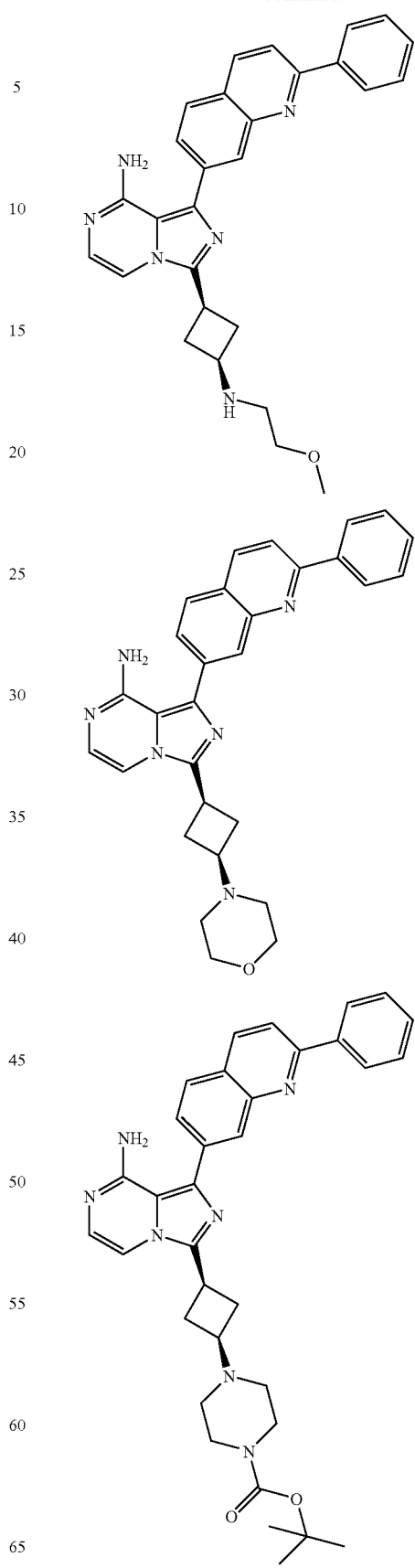

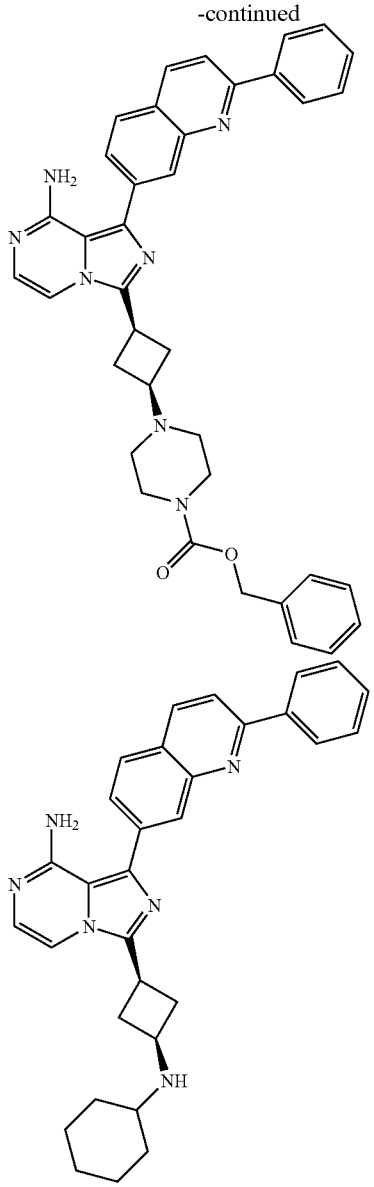
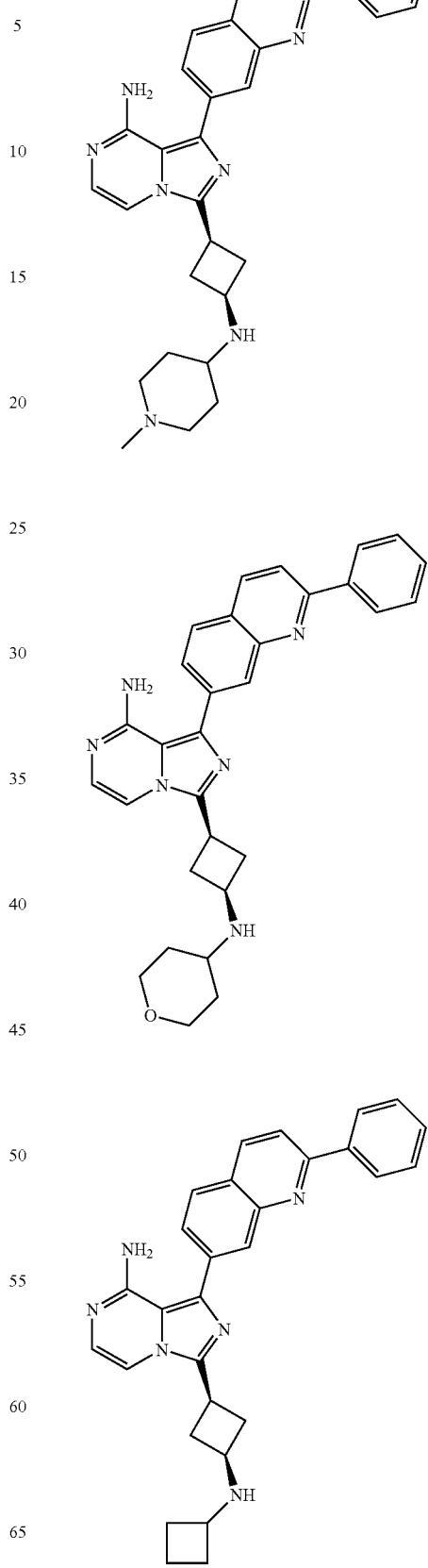
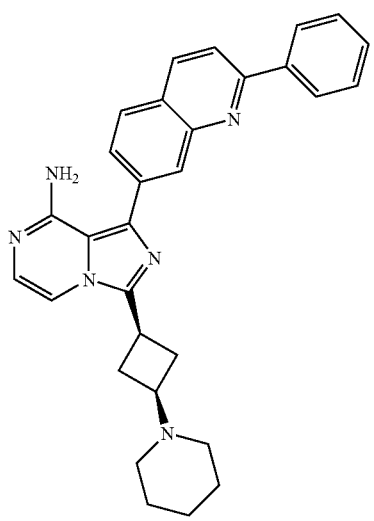
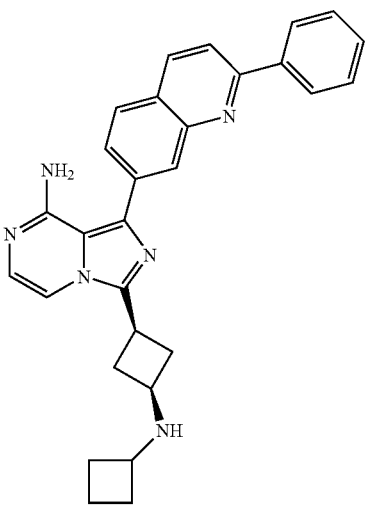

59
-continued
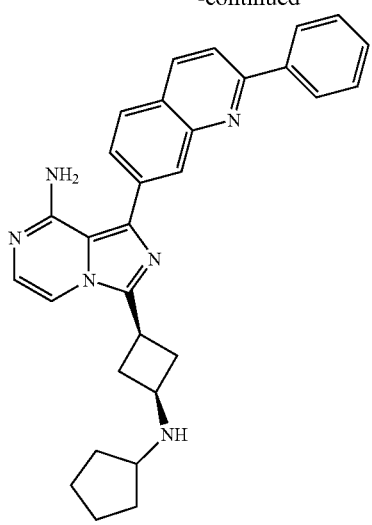
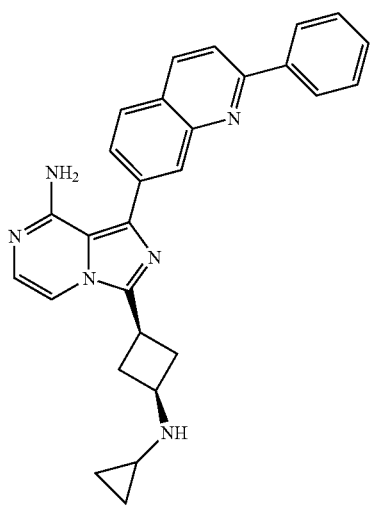
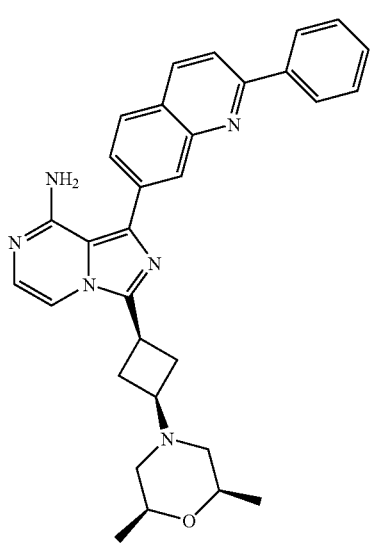
60
-continued
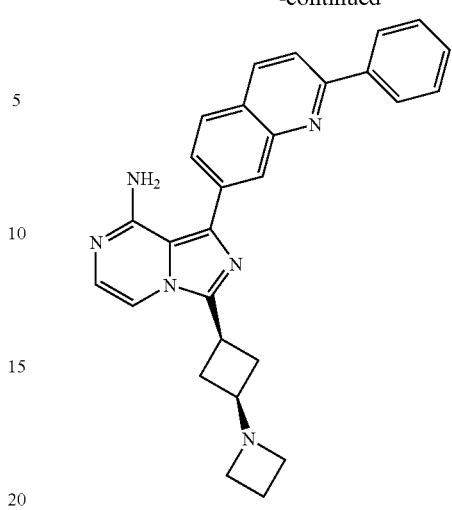
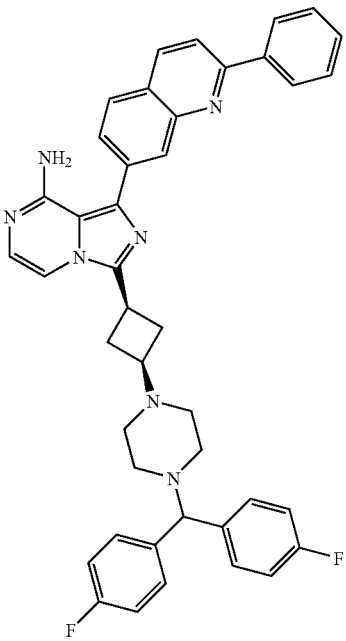

61
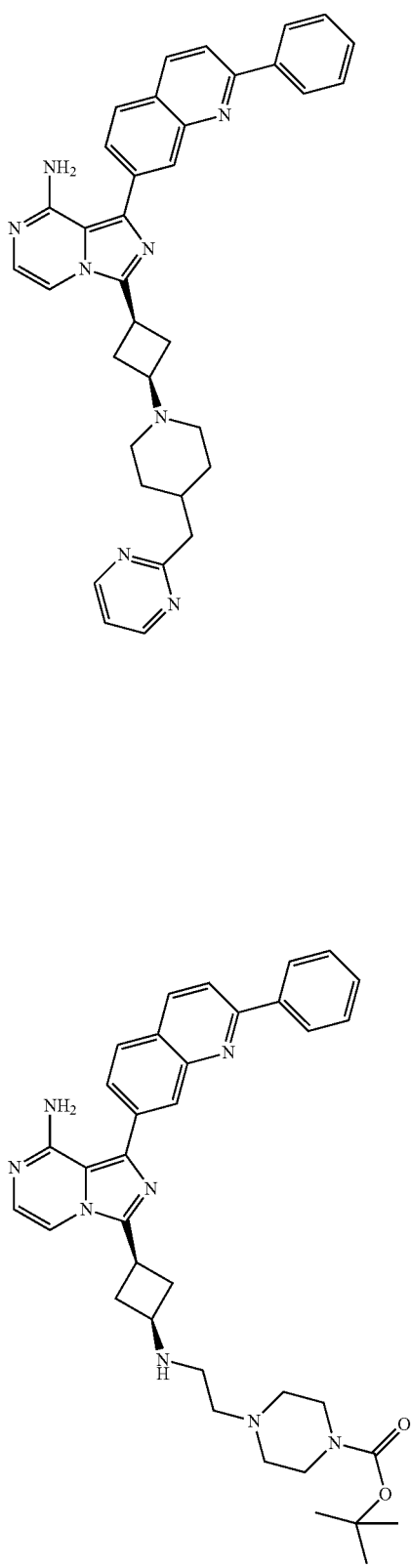
62
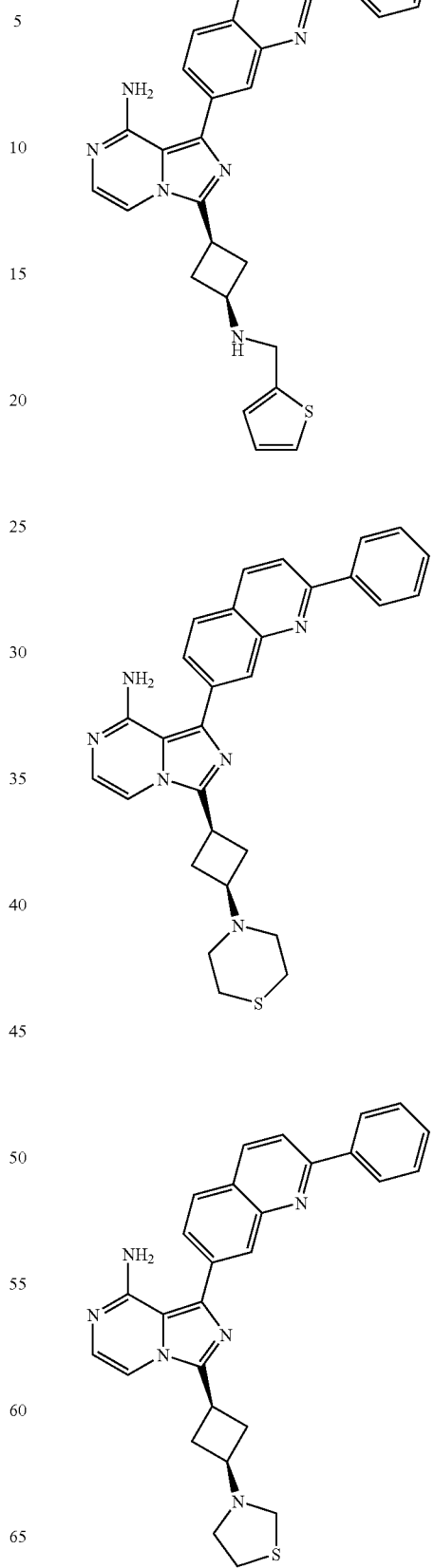

63
-continued
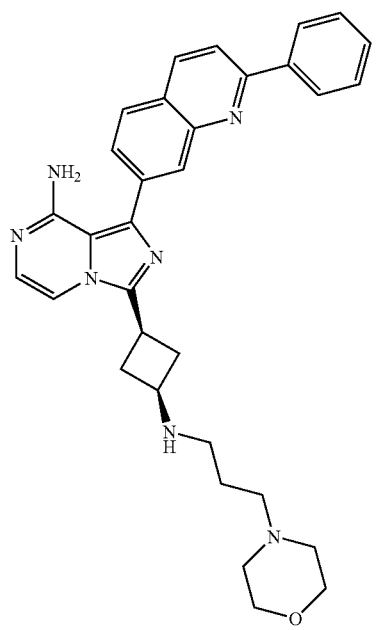
64
-continued
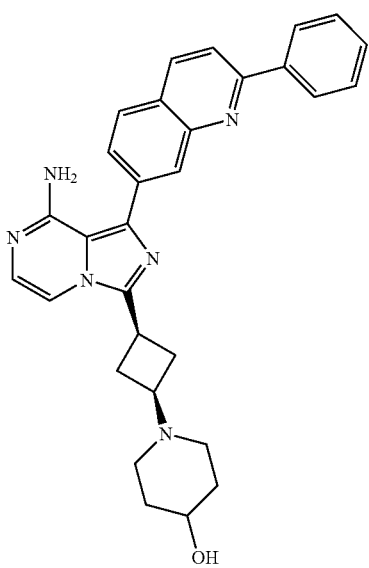
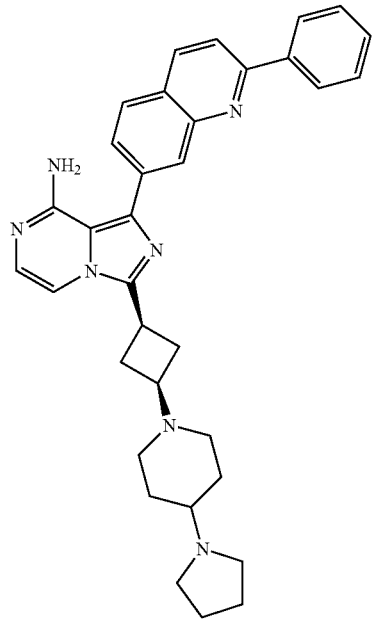

65
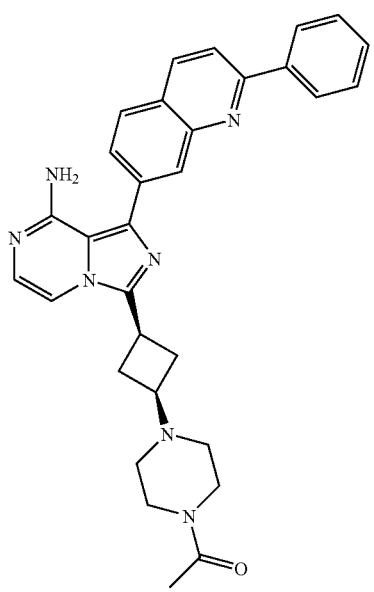
66
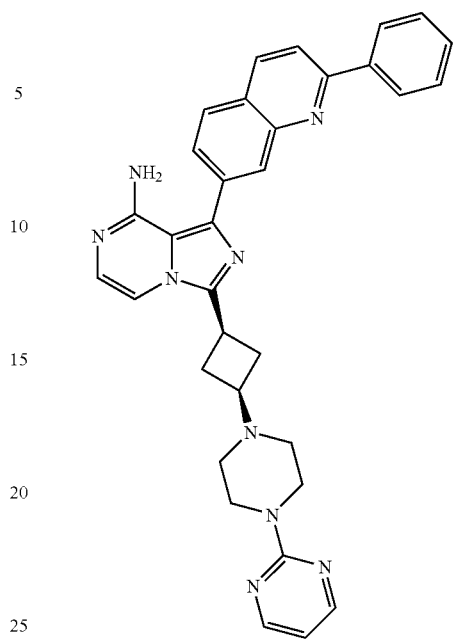
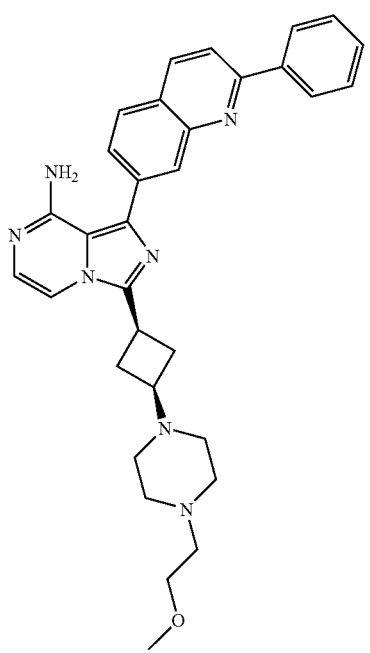

67
68
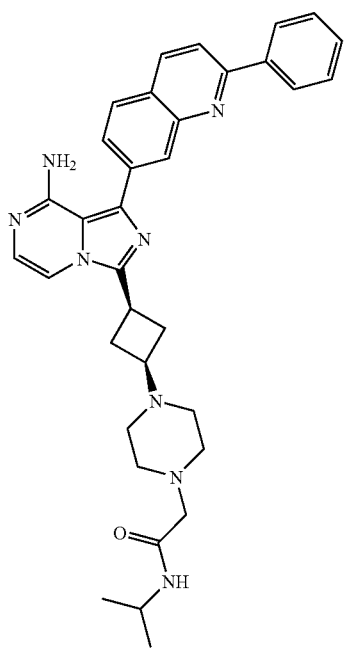
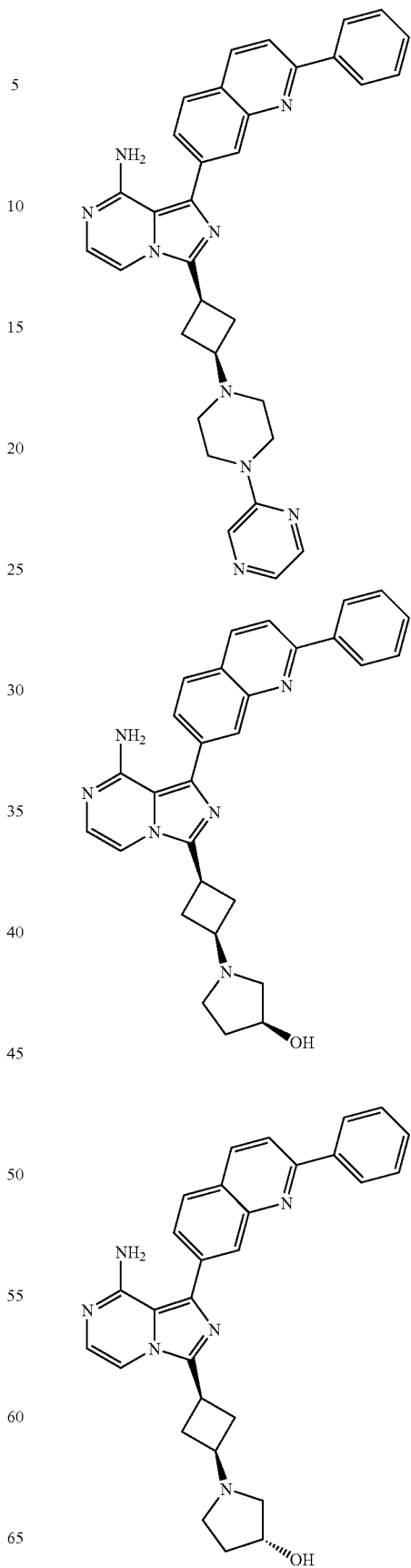

69
-continued
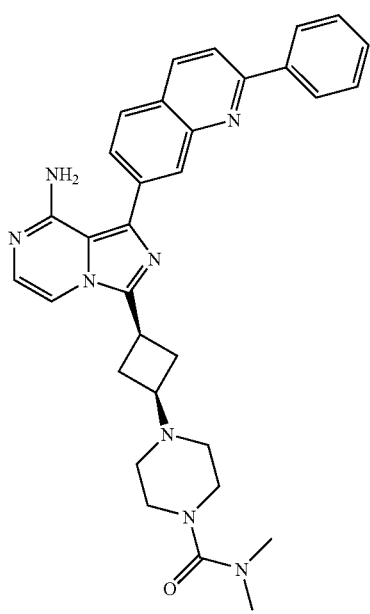
70
-continued
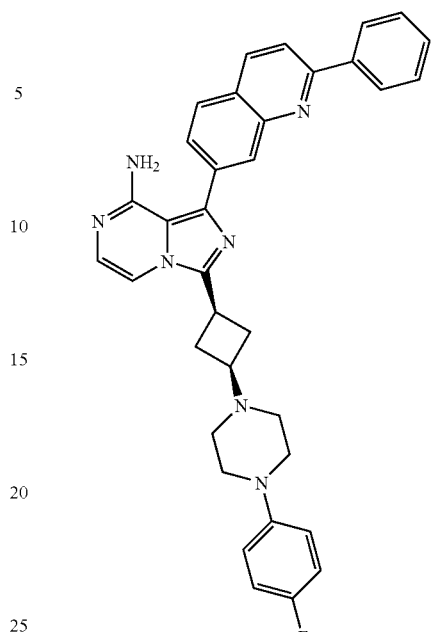
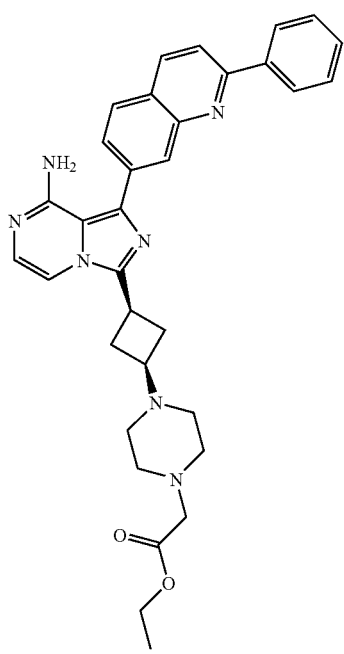
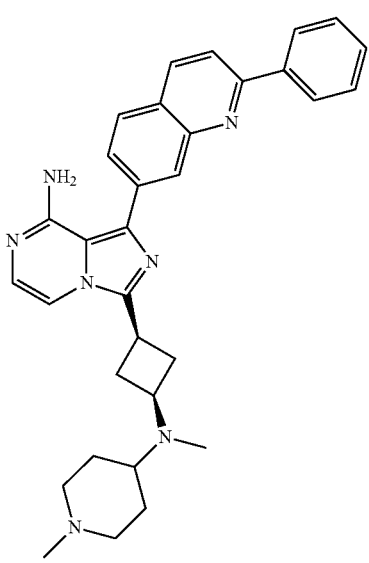

71
-continued
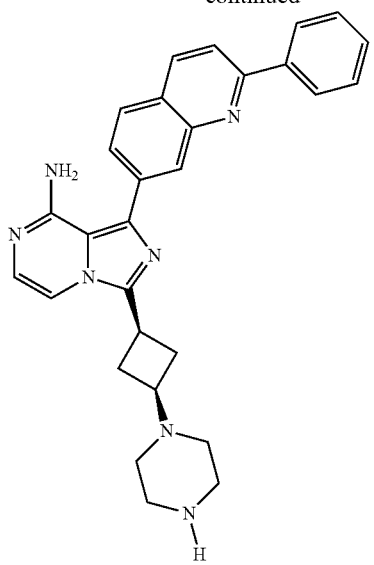
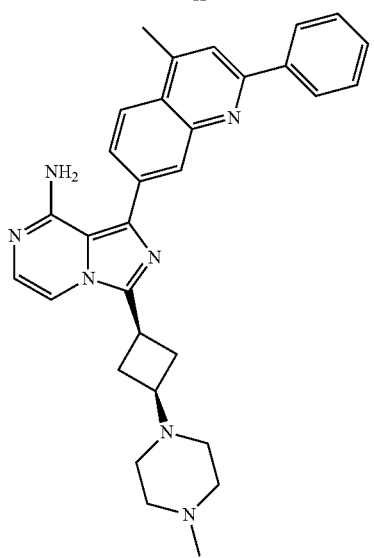
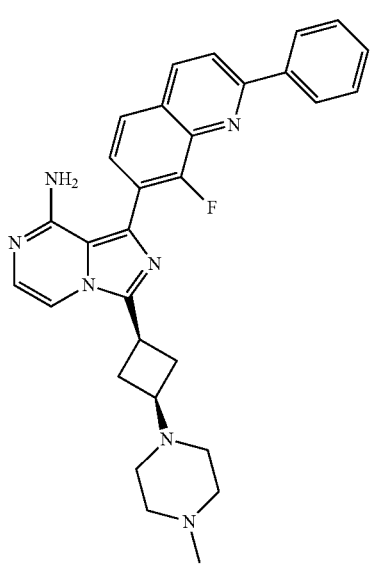
72
-continued
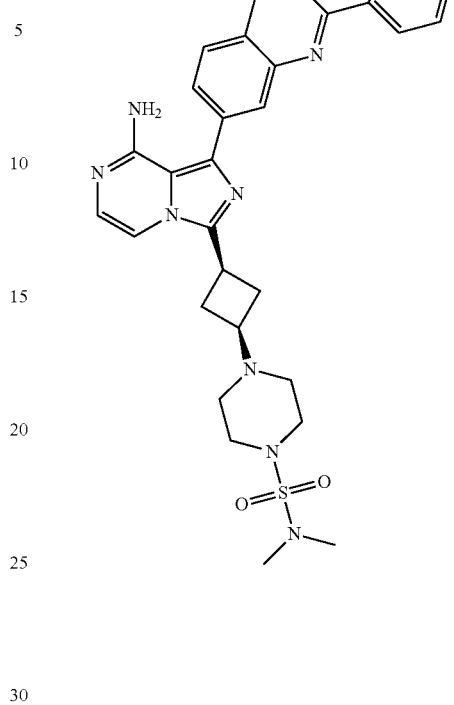
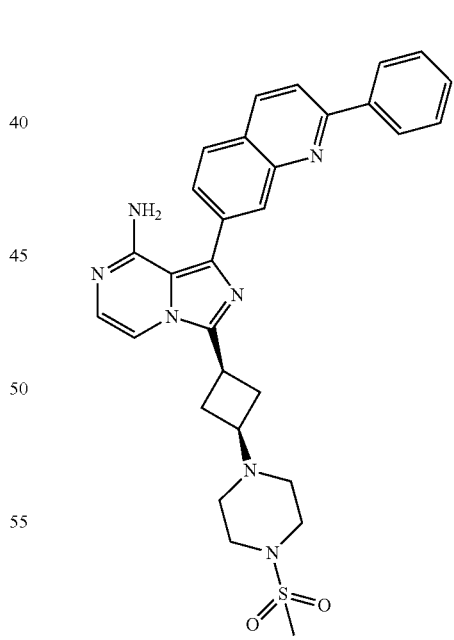

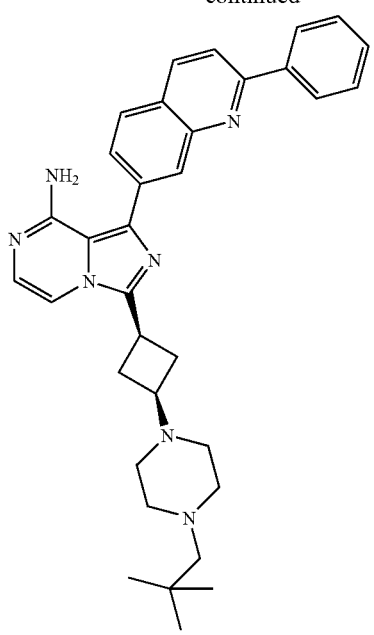
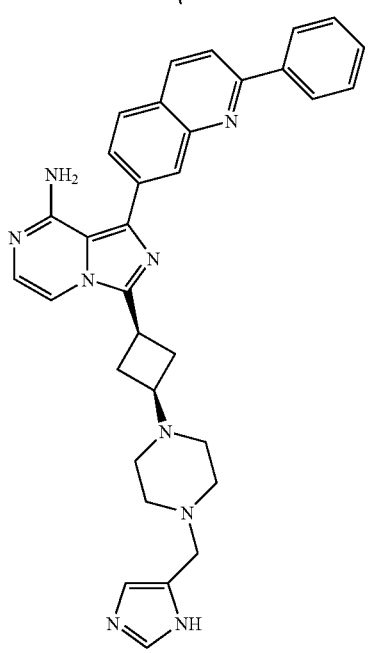
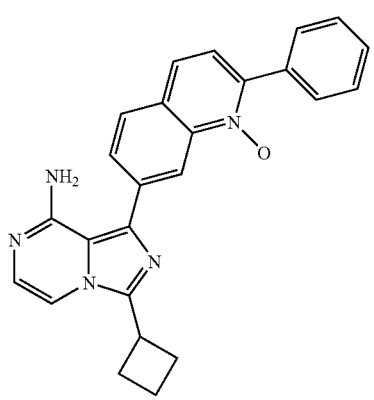
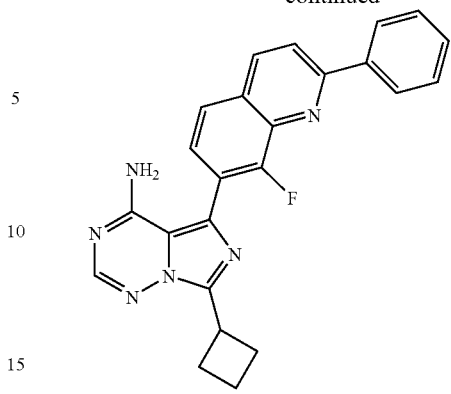
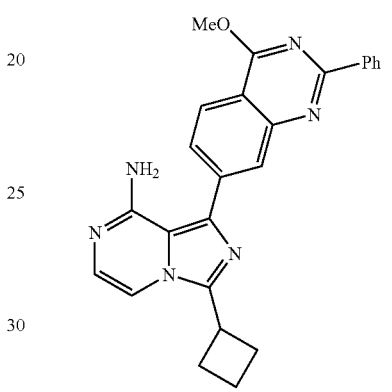
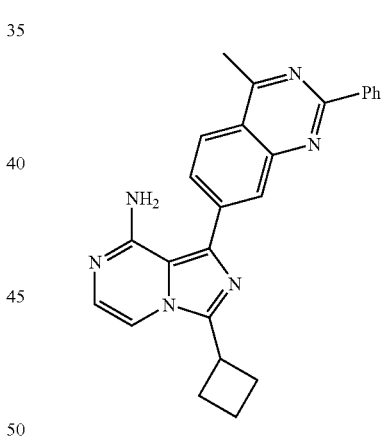
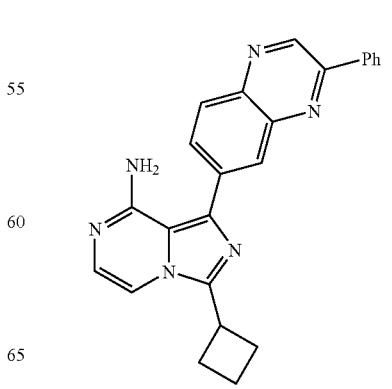

75
-continued
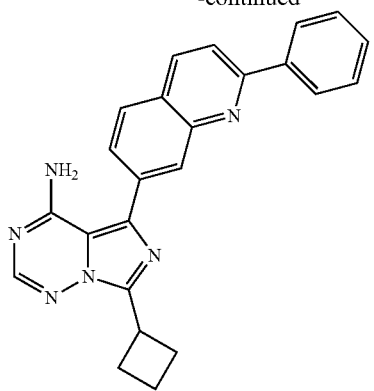
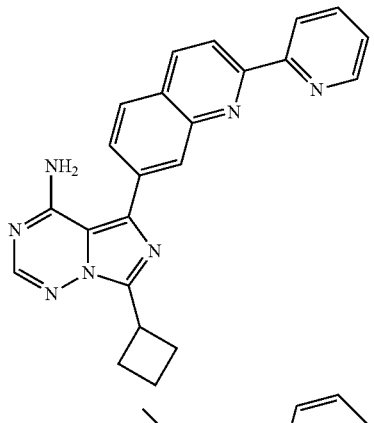
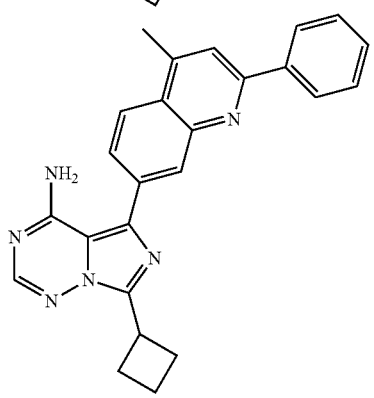
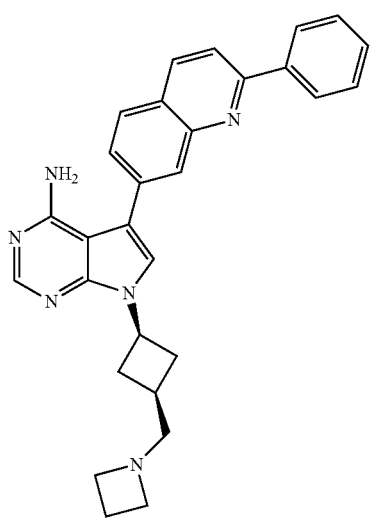
76
-continued
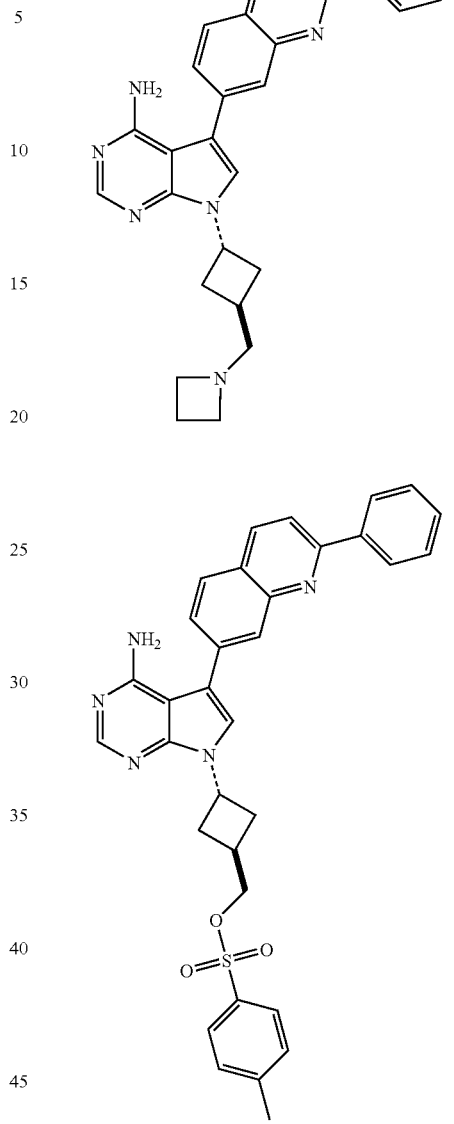
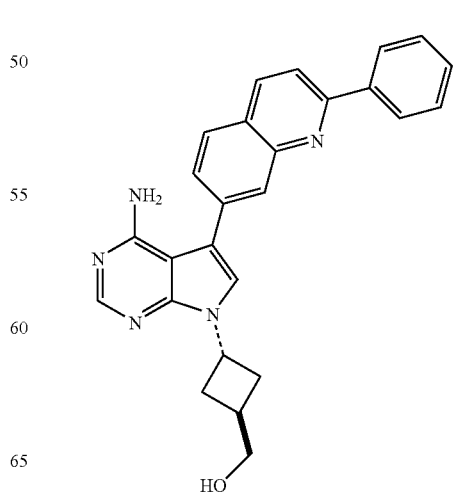

77
-continued
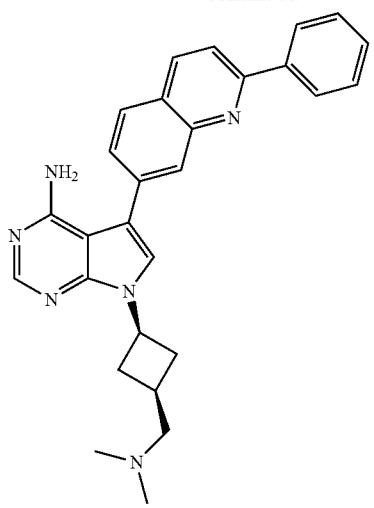
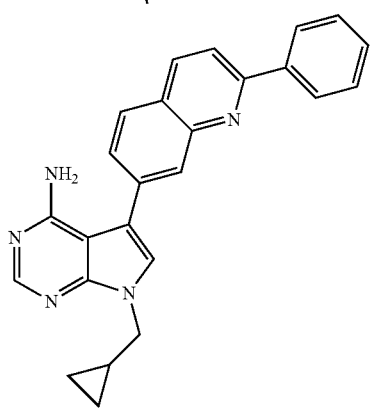
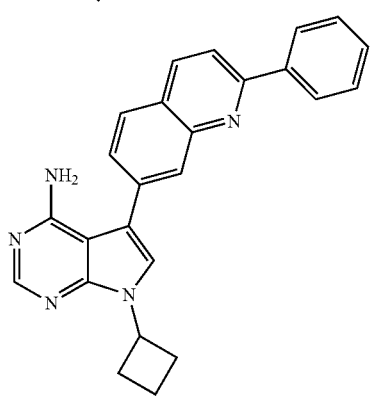
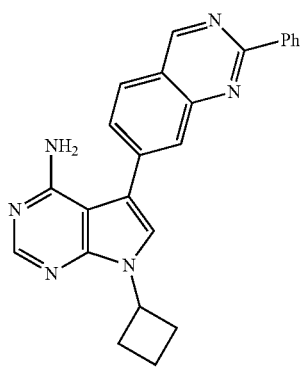
78
-continued
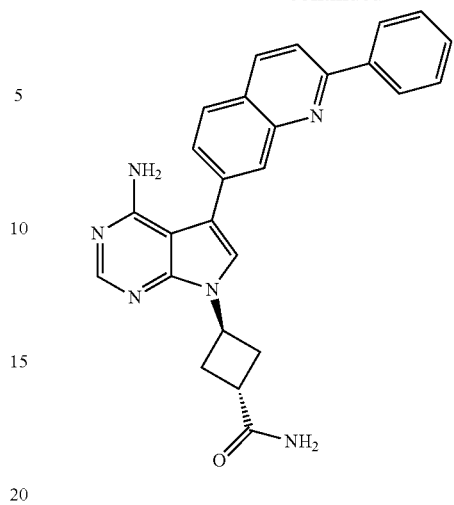
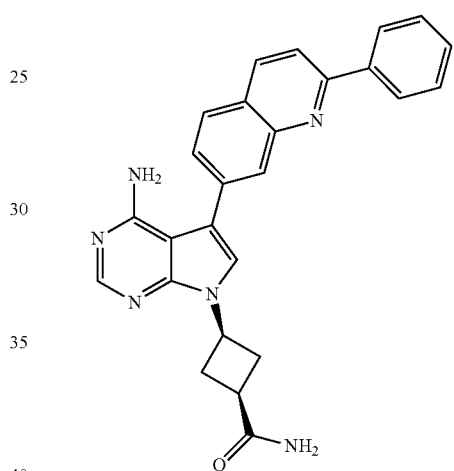
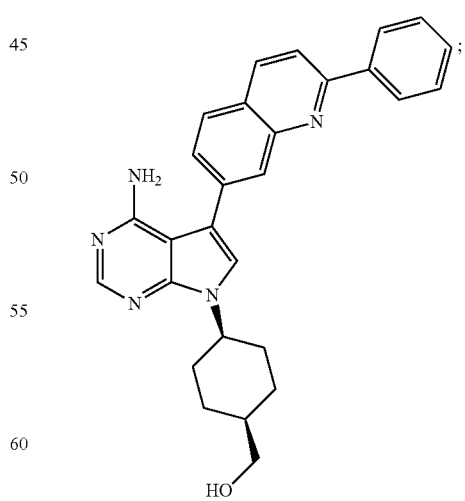
or a pharmaceutically acceptable salt thereof.

The IGF1R inhibitors of the present invention can also include any of,
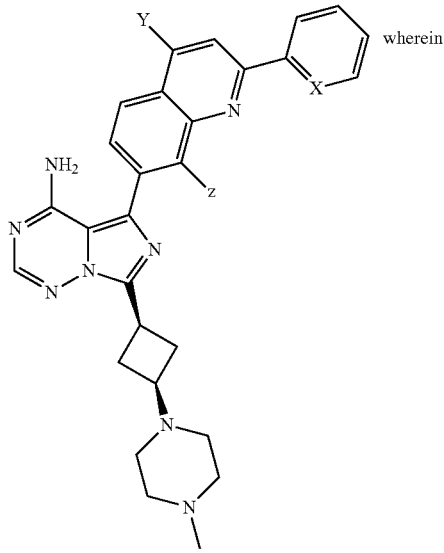
wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
; or wherein
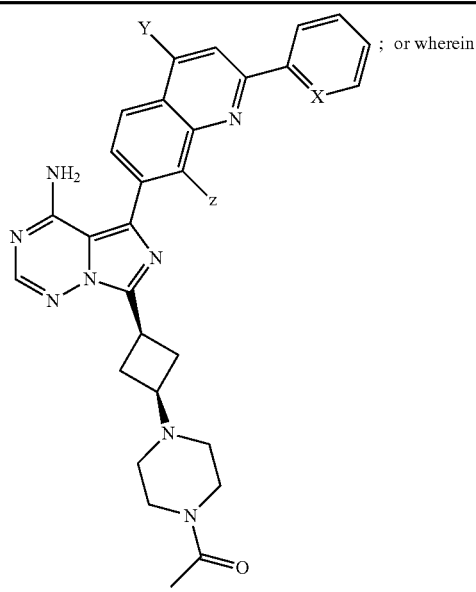
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
; or wherein
[structure continued]
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

81
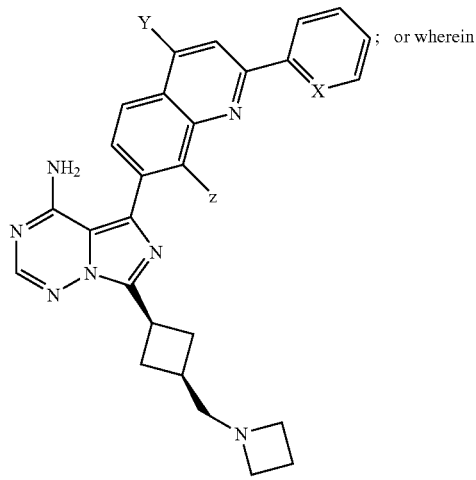
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
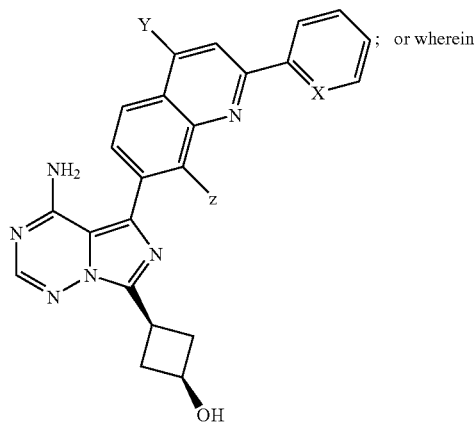
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
82
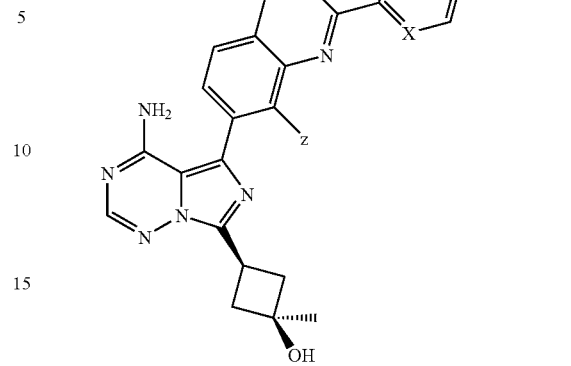
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
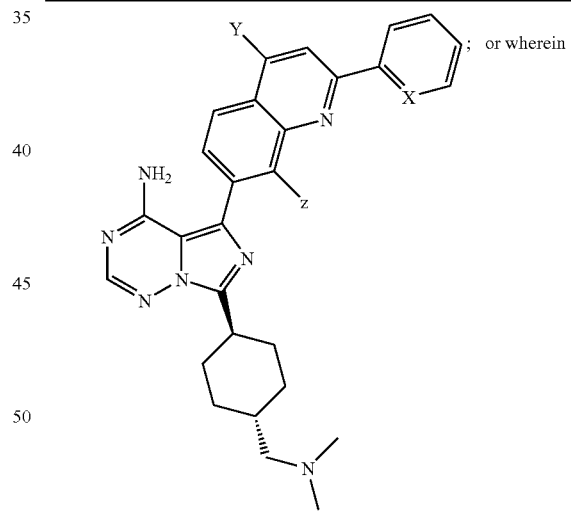
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

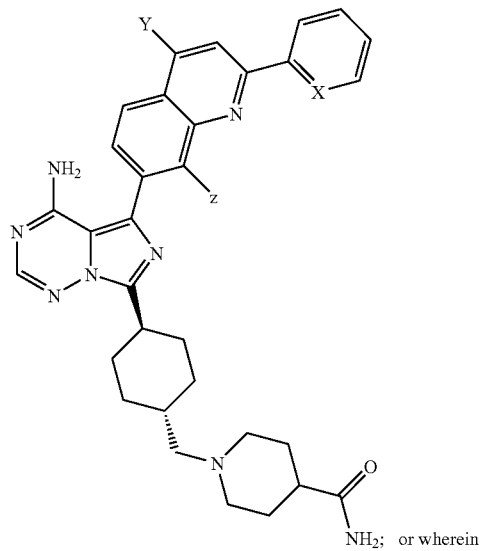
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
; or wherein
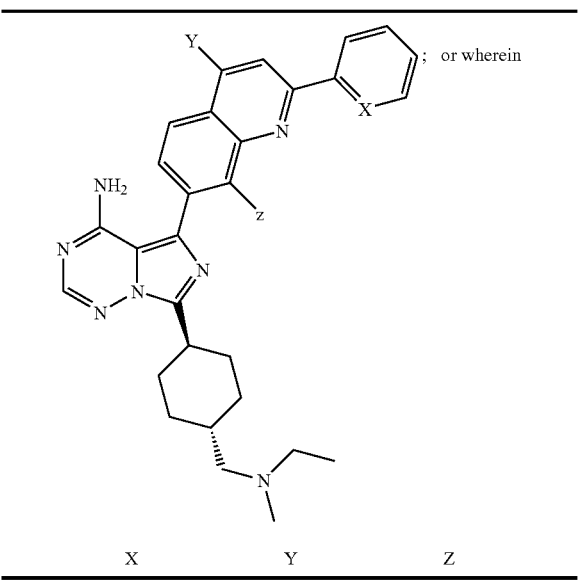
; or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
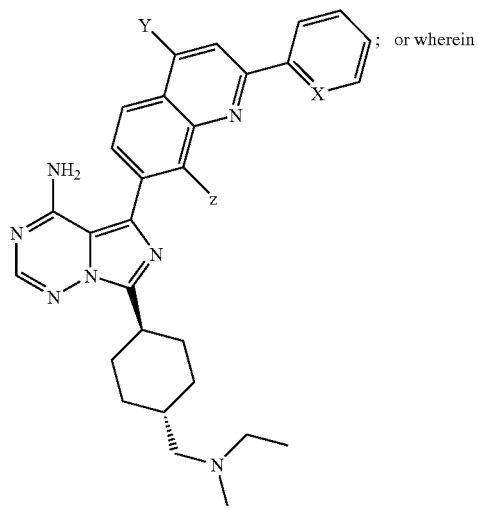
; or wherein
| X | Y | Z |
|---|---|---|
| N | CH₃ | F |
| CF | H | H |
| CF | CH₃ | H |
| CF | H | F |
| CF | CH₃ | F |
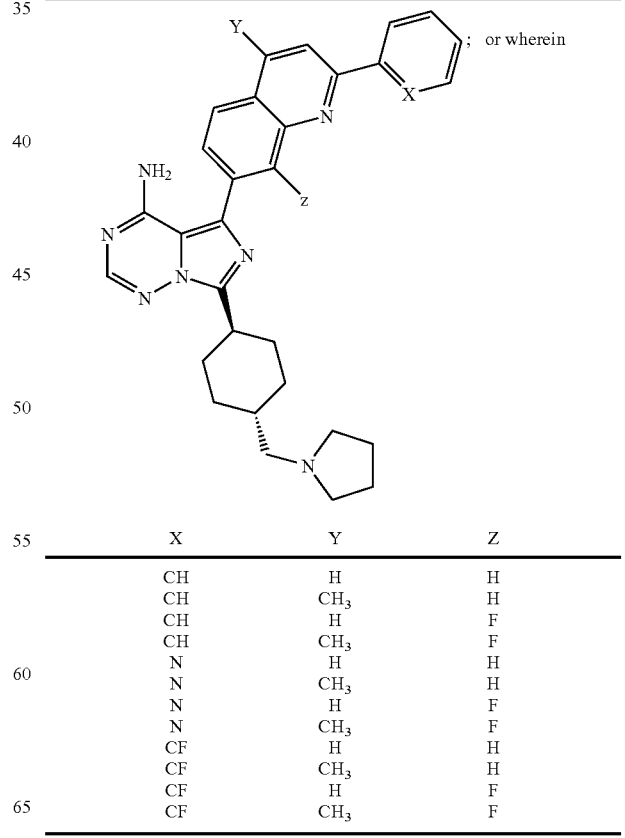
; or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

85
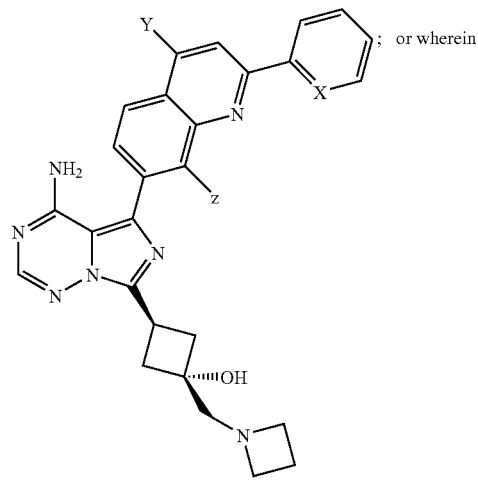
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
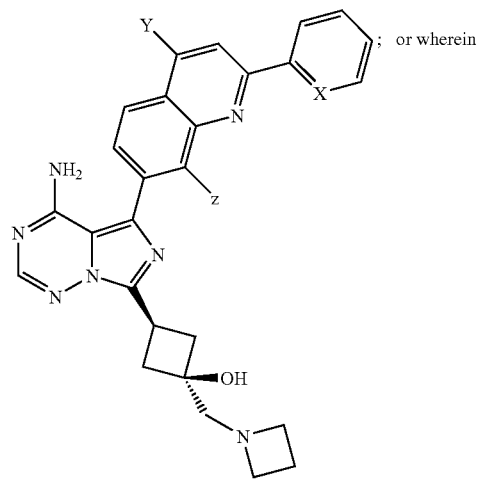
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
86
-continued
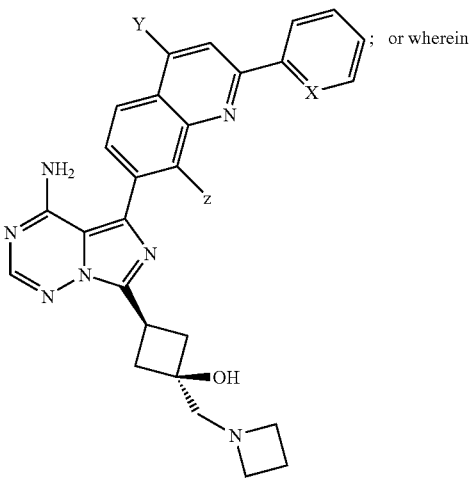
| X | Y | Z |
|---|---|---|
| CF | H | H |
| CF | CH₃ | H |
| CF | H | F |
| CF | CH₃ | F |
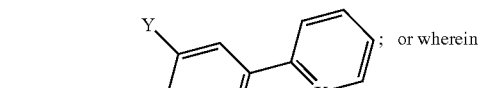
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

87
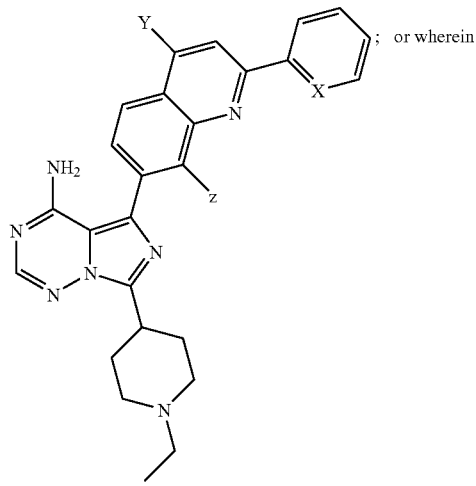
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
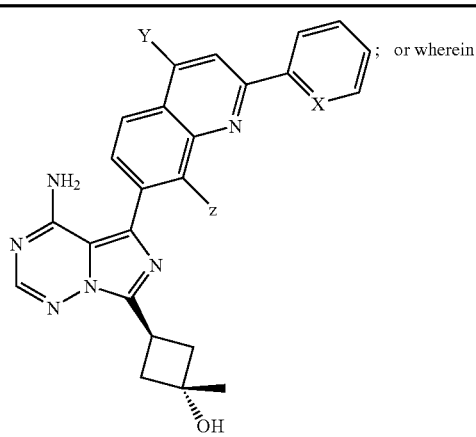
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
88
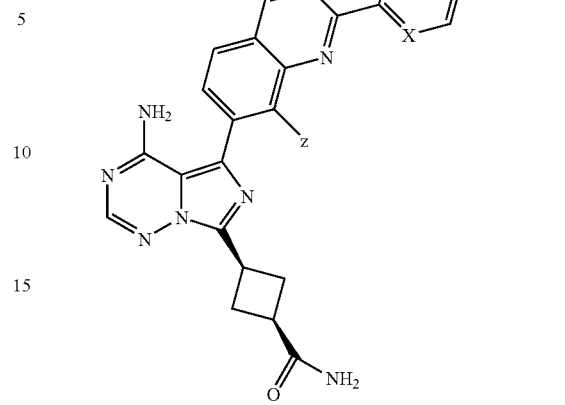
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
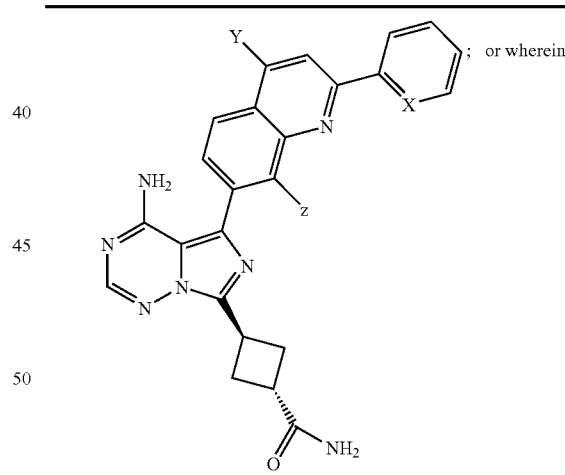
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

89
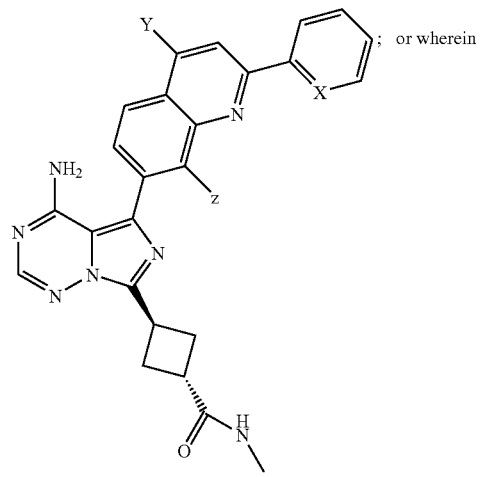
; or wherein
| X | Y | Z |
|---|---|---|
| CH | H | H |
| CH | CH$_3$ | H |
| CH | H | F |
| CH | CH$_3$ | F |
| N | H | H |
| N | CH$_3$ | H |
| N | H | F |
| N | CH$_3$ | F |
| CF | H | H |
| CF | CH$_3$ | H |
| CF | H | F |
| CF | CH$_3$ | F |
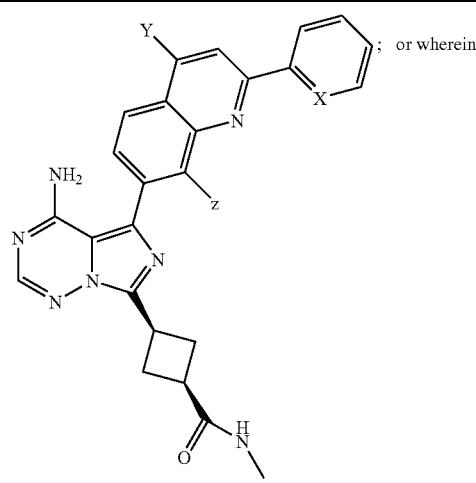
| X | Y | Z |
|---|---|---|
| CH | H | H |
| CH | CH$_3$ | H |
| CH | H | F |
| CH | CH$_3$ | F |
| N | H | H |
| N | CH$_3$ | H |
| N | H | F |
| N | CH$_3$ | F |
| CF | H | H |
90
-continued
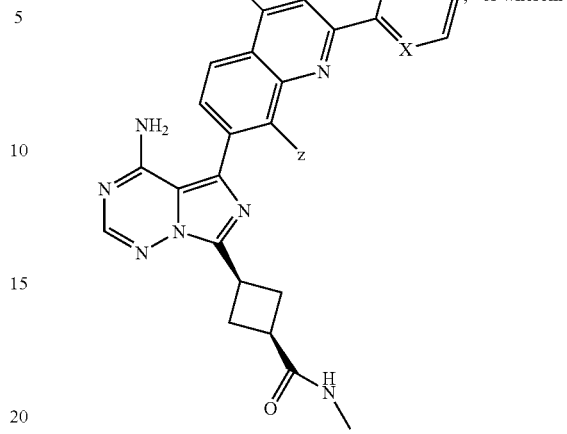
; or wherein
| X | Y | Z |
|---|---|---|
| CF | CH$_3$ | H |
| CF | H | F |
| CF | CH$_3$ | F |
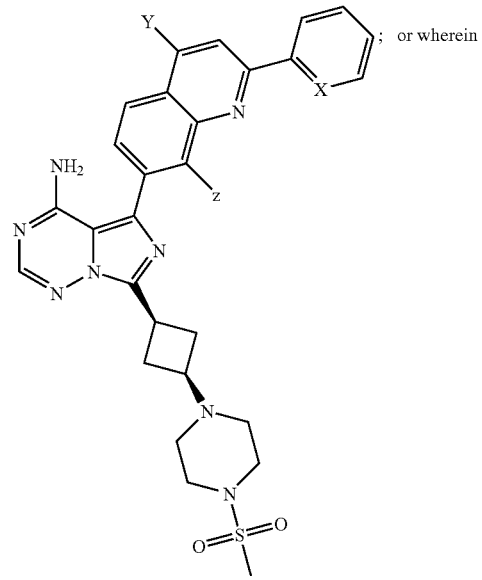
; or wherein
| X | Y | Z |
|---|---|---|
| CH | H | H |
| CH | CH$_3$ | H |
| CH | H | F |
| CH | CH$_3$ | F |
| N | H | H |
| N | CH$_3$ | H |
| N | H | F |
| N | CH$_3$ | F |
| CF | H | H |
| CF | CH$_3$ | H |
| CF | H | F |
| CF | CH$_3$ | F |

| 91 | | |
|---|---|---|
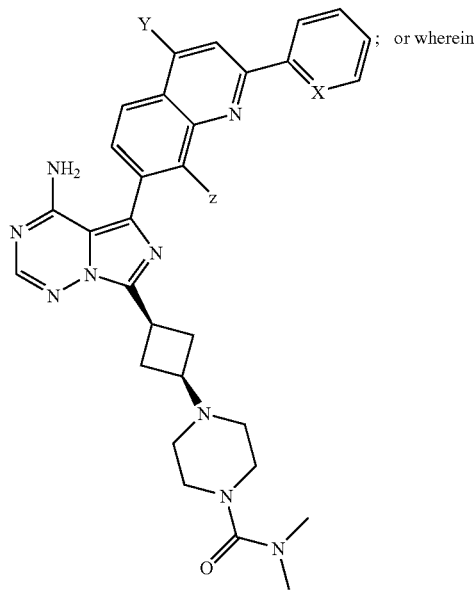
; or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
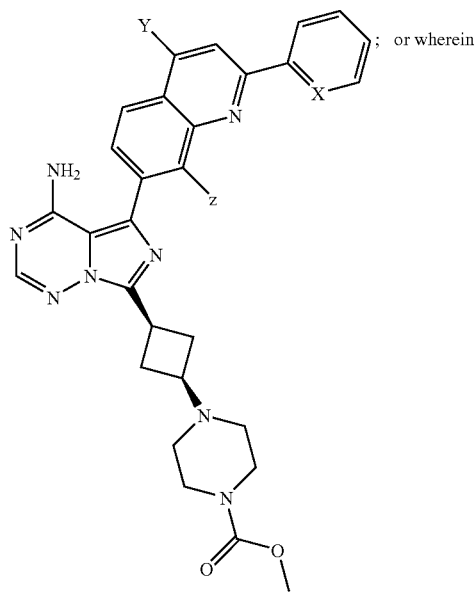
| X | Y | Z |
|---|---|---|
| CH | H | H |
| CH | CH₃ | H |
| CH | H | F |
| 92 -continued | | |
|---|---|---|
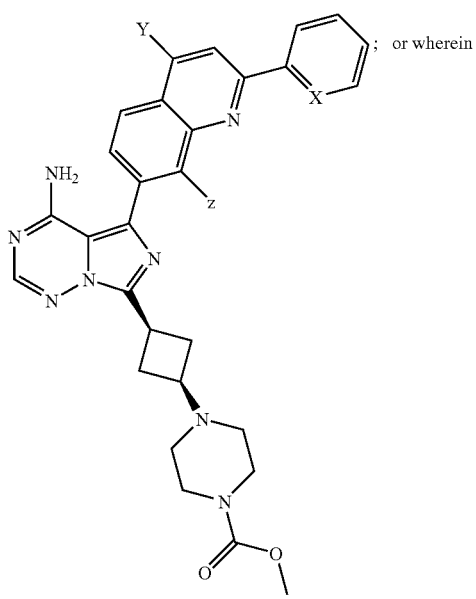
; or wherein
| X | Y | Z |
|---|---|---|
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
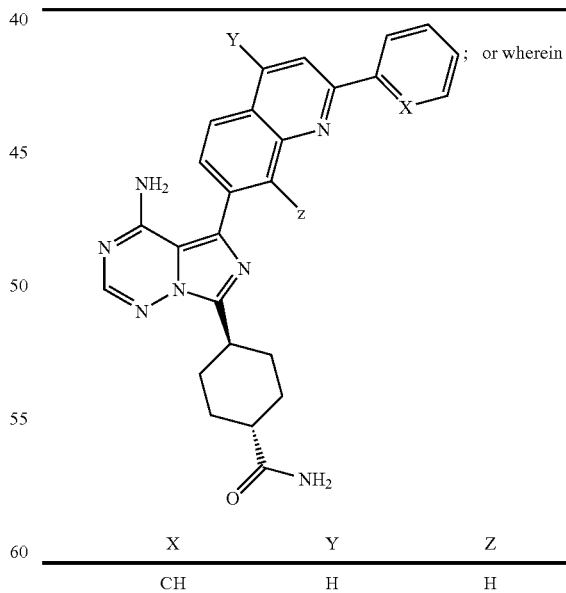
; or wherein
| X | Y | Z |
|---|---|---|
| CH | H | H |
| CH | CH₃ | H |
| CH | H | F |
| CH | CH₃ | F |
| N | H | H |
| N | CH₃ | H |
| N | H | F |

93
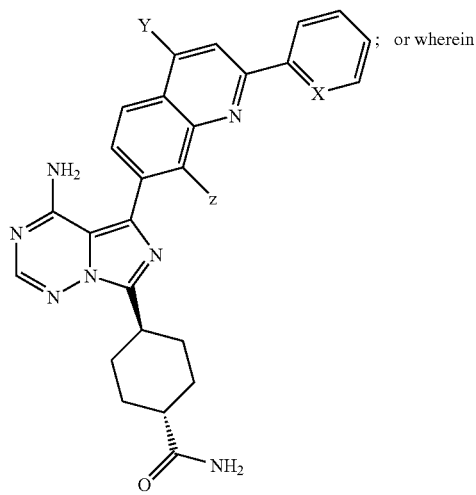
; or wherein
| X | Y | Z |
|---|---|---|
| N | CH₃ | F |
| CF | H | H |
| CF | CH₃ | H |
| CF | H | F |
| CF | CH₃ | F |
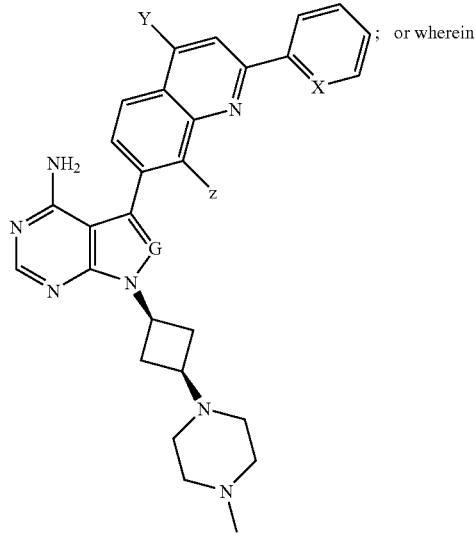
; or wherein
| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
94
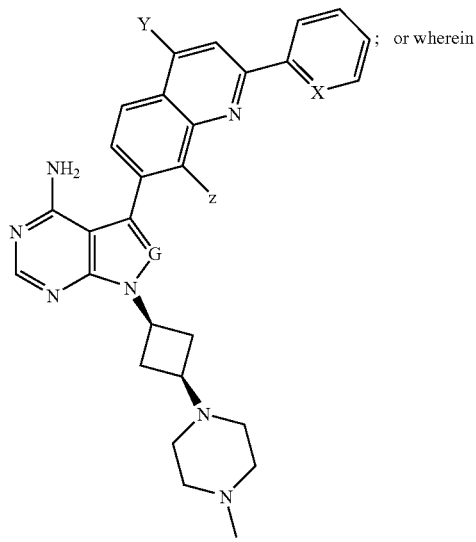
; or wherein
| X | Y | Z | G |
|---|---|---|---|
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |
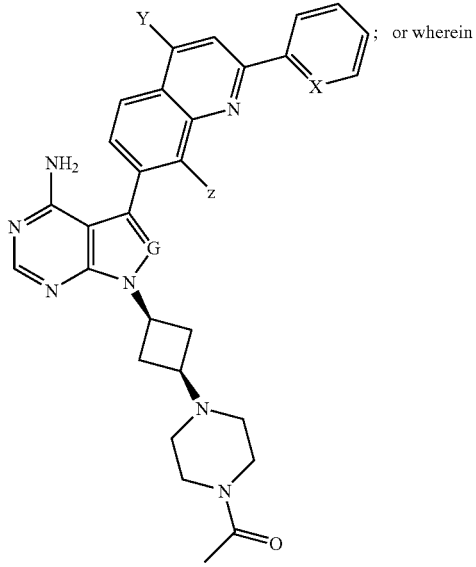
; or wherein
| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |

95
-continued

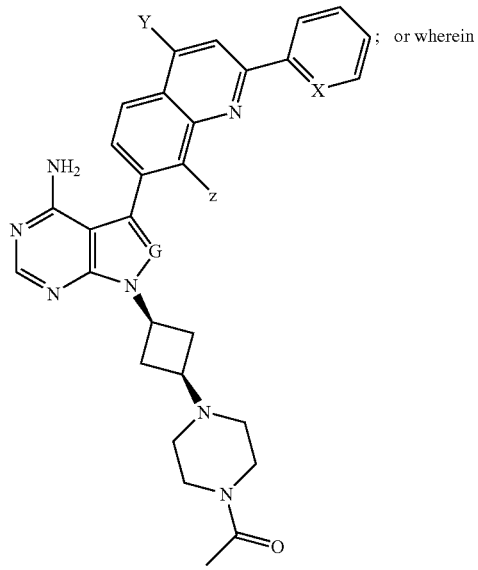
; or wherein

| X | Y | Z | G |
|---|---|---|---|
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

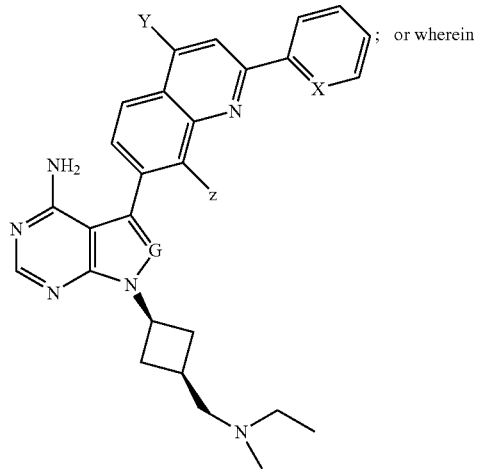

| X | Y | Z | G |
|---|---|---|---|
| CH | H | H | CH |
| CH | CH₃ | H | CH |
| CH | H | F | CH |
| CH | CH₃ | F | CH |

96
-continued

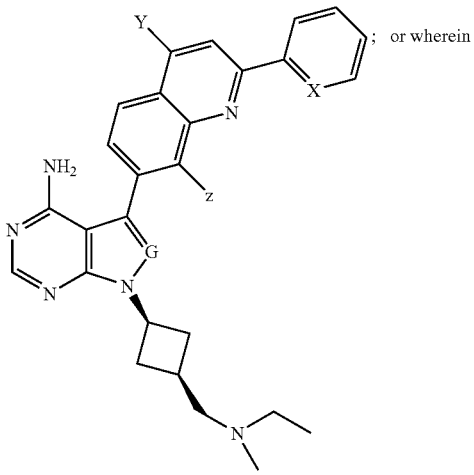
; or wherein

| X | Y | Z | G |
|---|---|---|---|
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

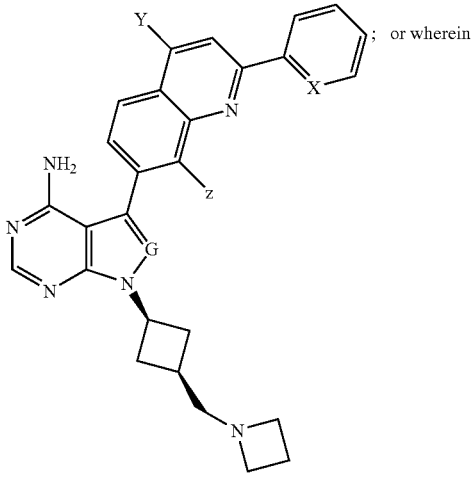
; or wherein

| X | Y | Z | G |
|---|---|---|---|
| CH | H | H | CH |
| CH | CH₃ | H | CH |
| CH | H | F | CH |
| CH | CH₃ | F | CH |

97
-continued

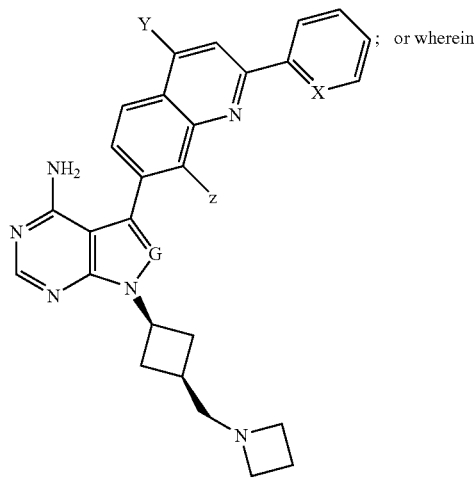
; or wherein

| X | Y | Z | G |
|---|---|---|---|
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

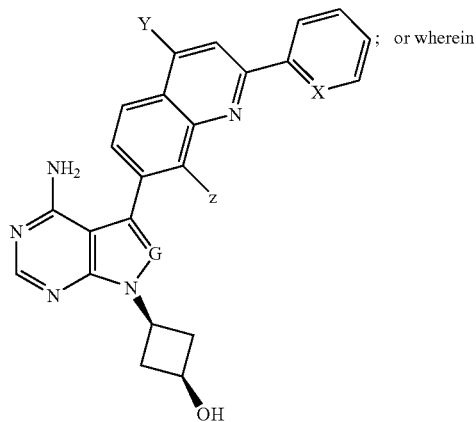
; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |

98
-continued

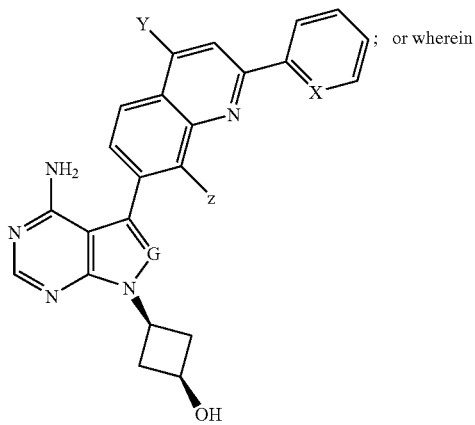
; or wherein

| X | Y | Z | G |
|---|---|---|---|
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

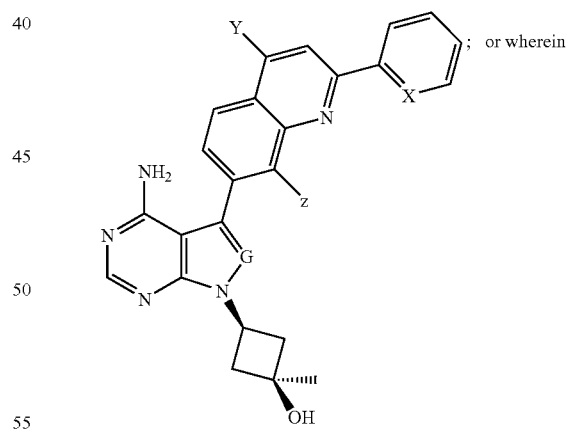
; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |

99

-continued

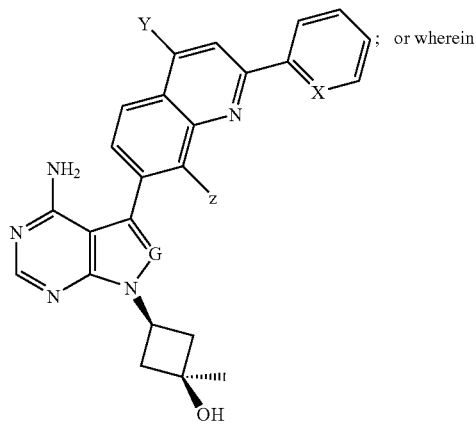
; or wherein

| X | Y | Z | G |
|---|---|---|---|
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

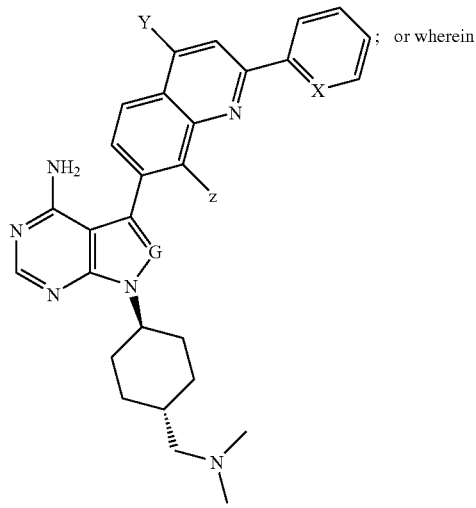
; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |

100

-continued

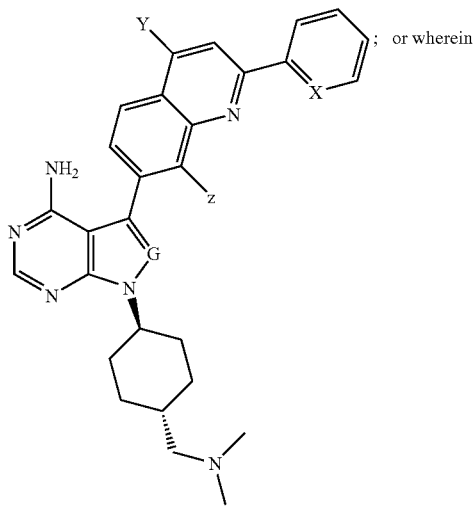
; or wherein

| X | Y | Z | G |
|---|---|---|---|
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

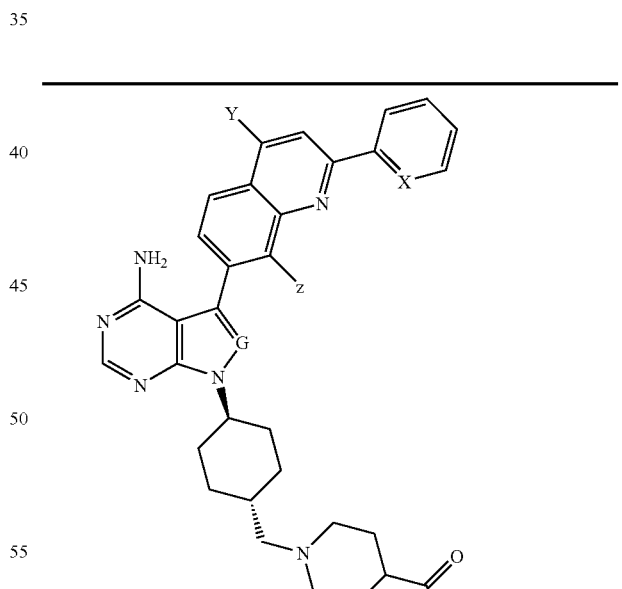
; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |

101
-continued

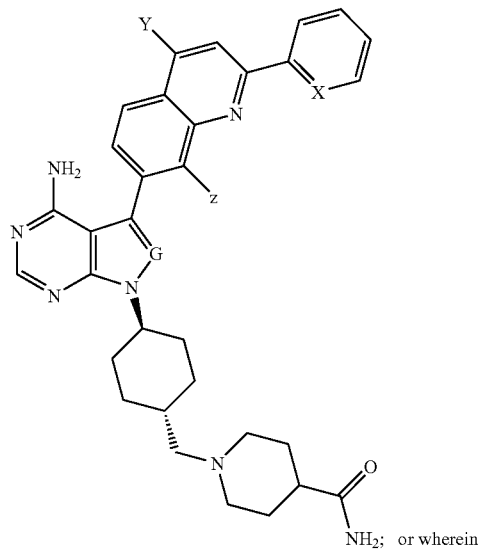

; or wherein

| X | Y | Z | G |
|---|---|---|---|
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

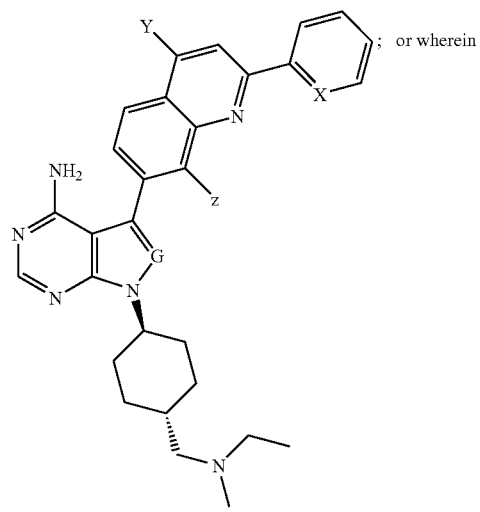

; or wherein

| X | Y | Z | G |
|---|---|---|---|
| CH | H | H | CH |
| CH | CH₃ | H | CH |

102
-continued

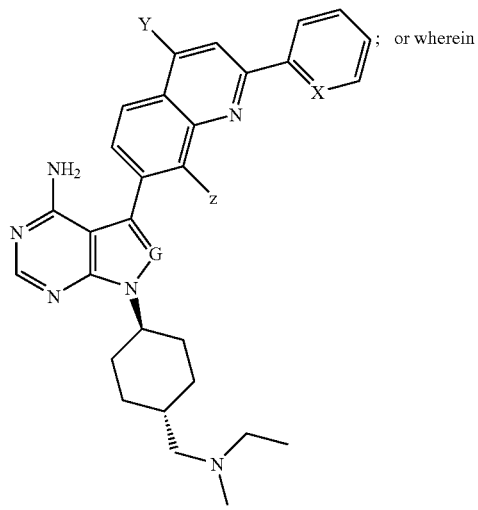

; or wherein

| X | Y | Z | G |
|---|---|---|---|
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

103

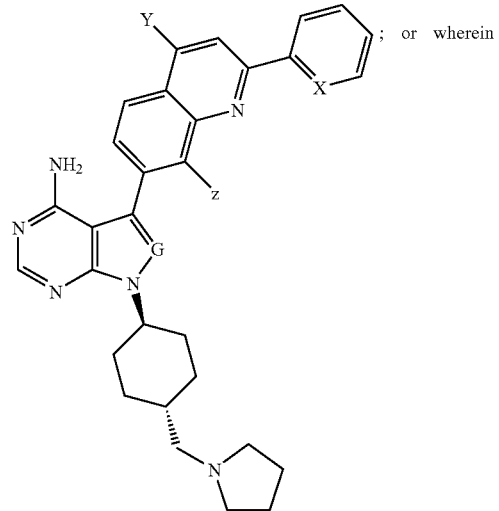

; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

104

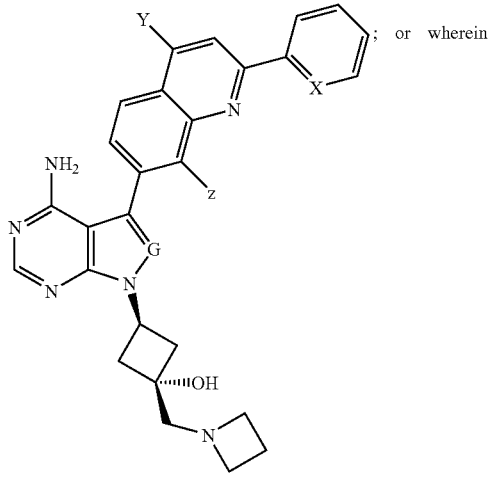

; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

105

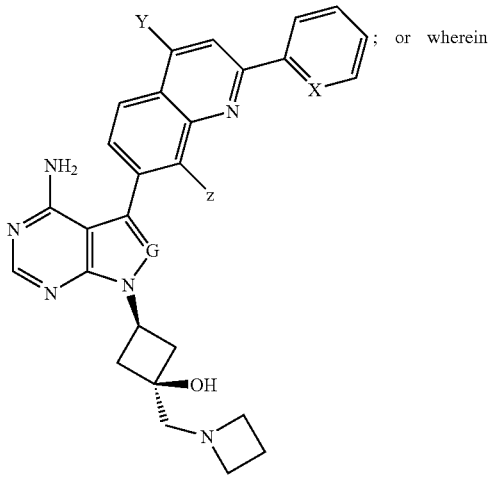

; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

106
-continued

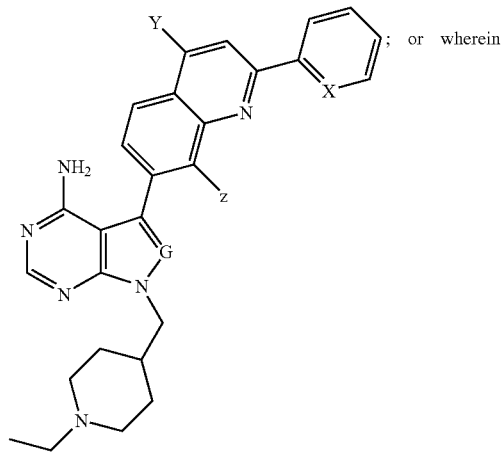

; or wherein

| X | Y | Z | G |
|---|---|---|---|
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

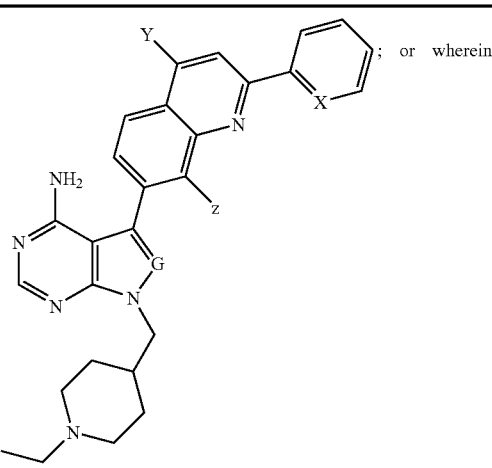

; or wherein

| X | Y | Z | G |
|---|---|---|---|
| CH | H | H | CH |
| CH | CH₃ | H | CH |

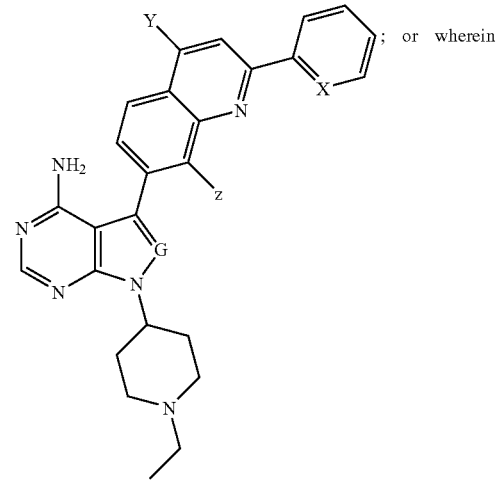

; or wherein

| X | Y | Z | G |
|---|---|---|---|
| CH | H | H | CH |
| CH | CH₃ | H | CH |

107

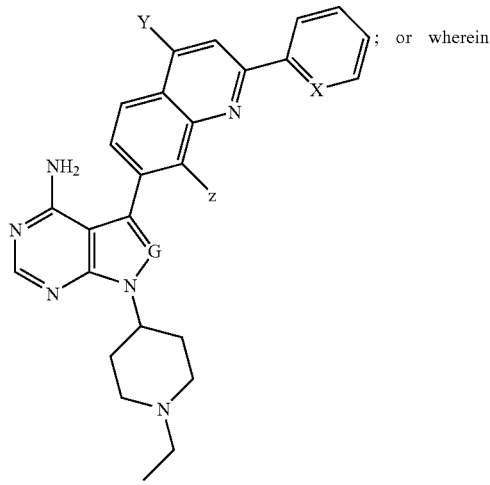

; or wherein

| X | Y | Z | G |
|---|---|---|---|
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

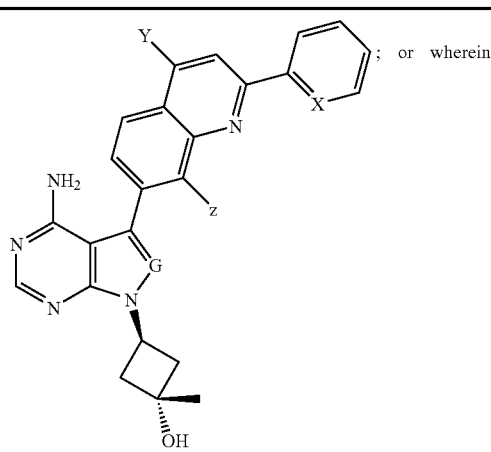

; or wherein

| X | Y | Z | G |
|---|---|---|---|
| CH | H | H | CH |
| CH | CH₃ | H | CH |
| CH | H | F | CH |

108

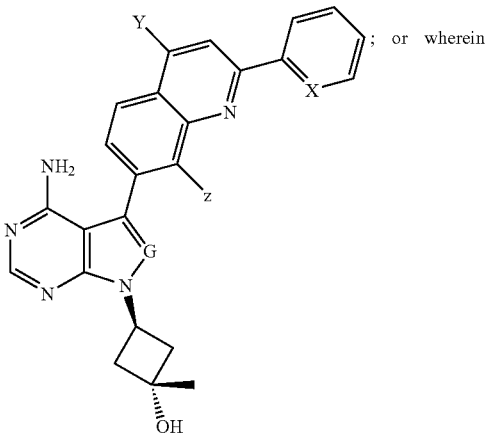

; or wherein

| X | Y | Z | G |
|---|---|---|---|
| CH | CH₃ | F | CH |
| N | H | H | CH |
| N | CH₃ | H | CH |
| N | H | F | CH |
| N | CH₃ | F | CH |
| N | H | H | N |
| N | CH₃ | H | N |
| N | H | F | N |
| N | CH₃ | F | N |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| CF | H | H | N |
| CF | CH₃ | H | N |
| CF | H | F | N |
| CF | CH₃ | F | N |

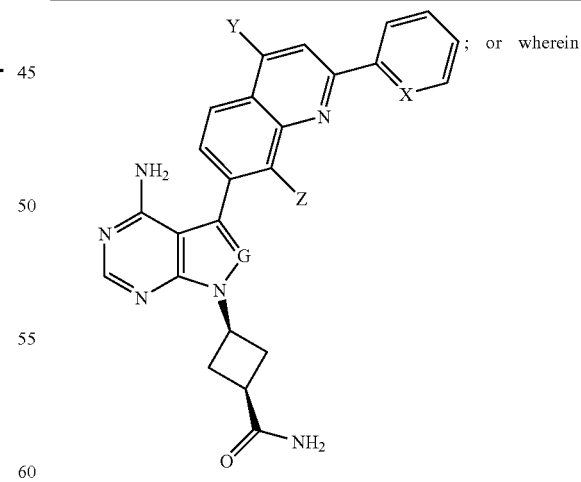

; or wherein

| X | Y | Z | G |
|---|---|---|---|
| CH | H | H | C—CH₃ |
| CH | CH₃ | H | CH |
| CH | H | F | CH |
| CH | CH₃ | F | CH |
| N | H | H | CH |

109
-continued

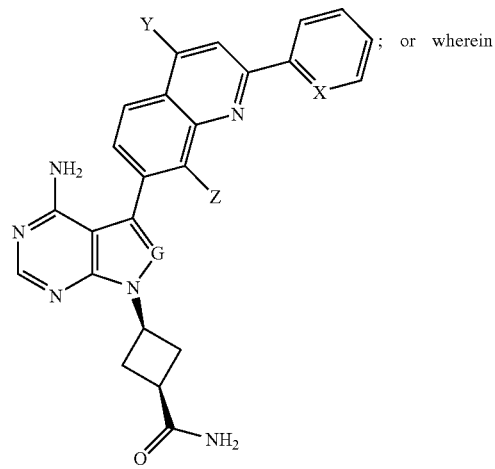
; or wherein

| X | Y | Z | G |
|---|---|---|---|
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

110
-continued

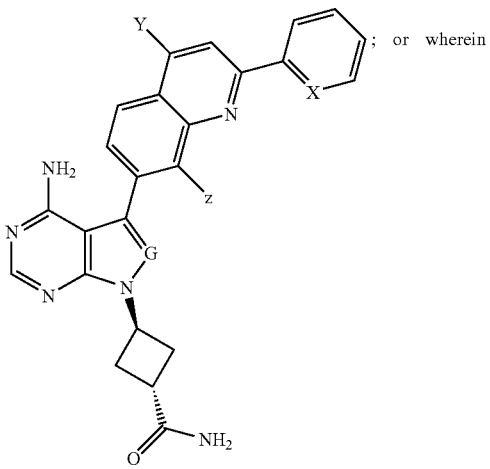
; or wherein

| X | Y | Z | G |
|---|---|---|---|
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | CH |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

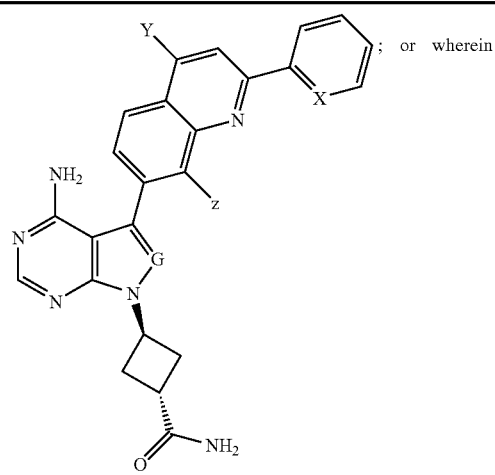
; or wherein

| X | Y | Z | G |
|---|---|---|---|
| CH | H | H | C—CH₃ |
| CH | H | F | CH |
| CH | CH₃ | F | CH |
| N | H | H | CH |
| N | CH₃ | H | CH |
| N | H | F | CH |

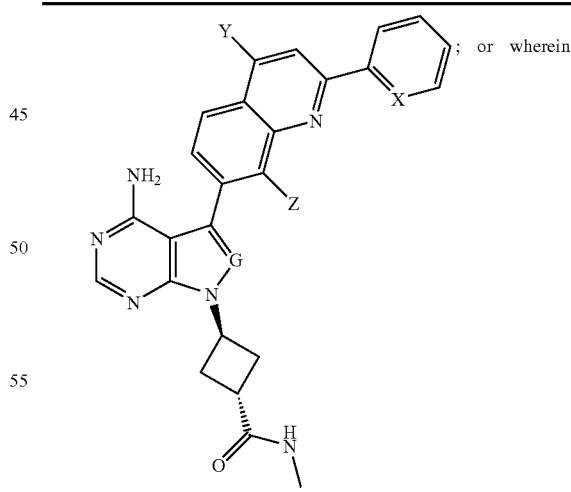
; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |

111
-continued

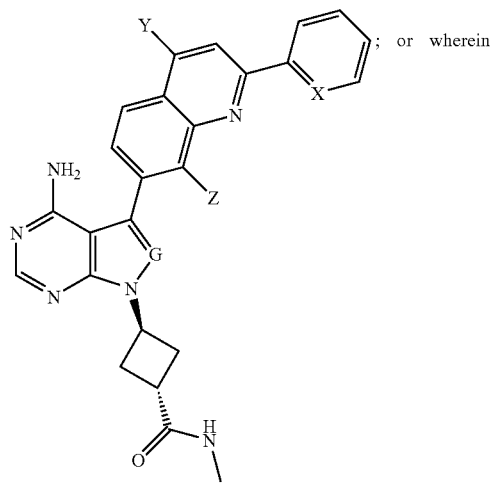

; or wherein

| X | Y | Z | G |
|---|---|---|---|
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

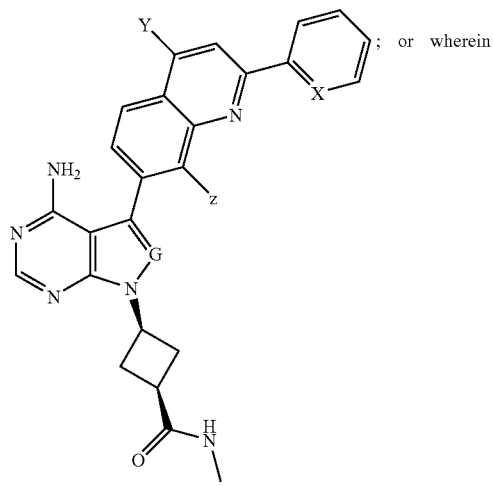

; or wherein

| X | Y | Z | G |
|---|---|---|---|
| CH | H | H | CH |
| CH | CH₃ | H | CH |

112
-continued

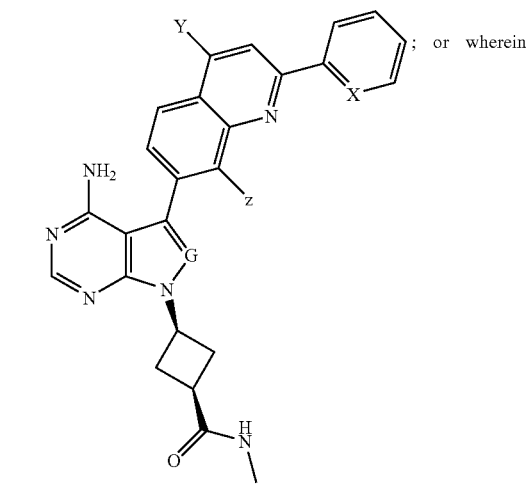

; or wherein

| X | Y | Z | G |
|---|---|---|---|
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

113

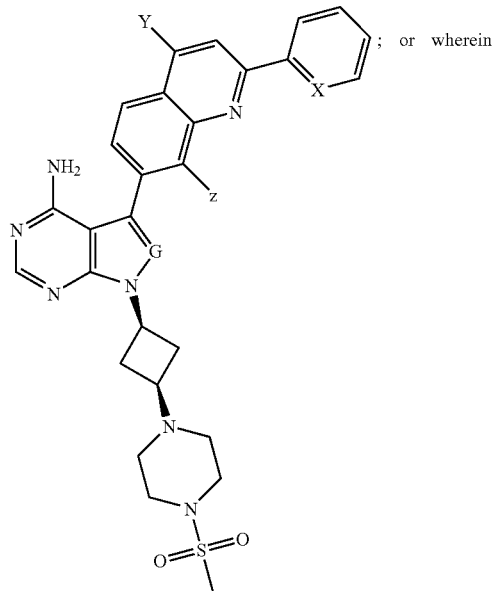

; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

114

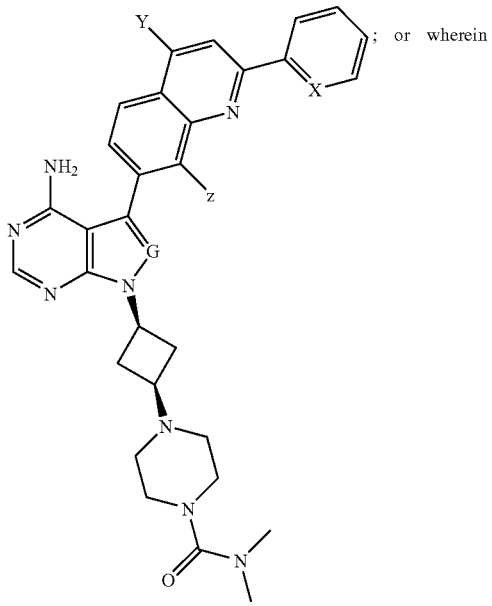

; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

115

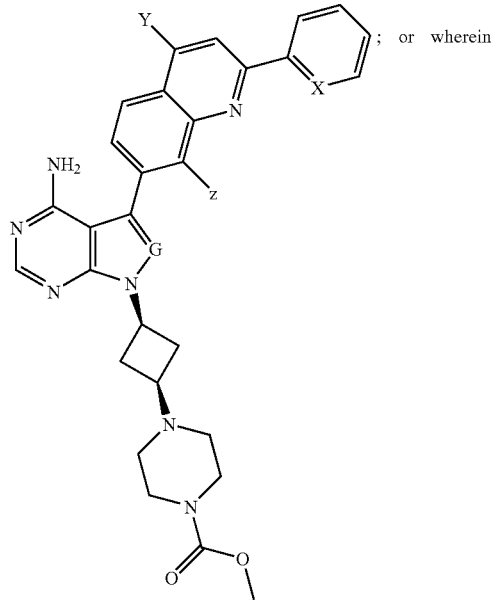

; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

116

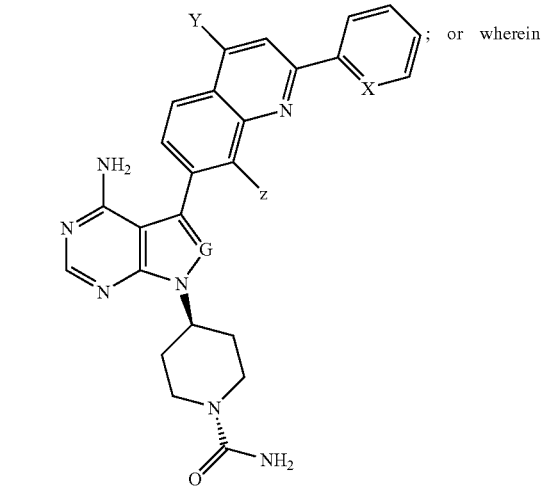

; or wherein

| X | Y | Z | G |
|---|---|---|---|
| CH | H | H | CH |
| CH | CH₃ | H | CH |
| CH | H | F | CH |
| CH | CH₃ | F | CH |
| N | H | H | CH |
| N | CH₃ | H | CH |
| N | H | F | CH |
| N | CH₃ | F | CH |
| CF | H | H | CH |
| CF | CH₃ | H | CH |
| CF | H | F | CH |
| CF | CH₃ | F | CH |
| CH | H | H | N |
| CH | CH₃ | H | N |
| CH | H | F | N |
| CH | CH₃ | F | N |
| N | H | H | N |
| N | CH₃ | H | N |
| N | H | F | N |
| N | CH₃ | F | N |
| CF | H | H | N |
| CF | CH₃ | H | N |
| CF | H | F | N |
| CF | CH₃ | F | N |

117

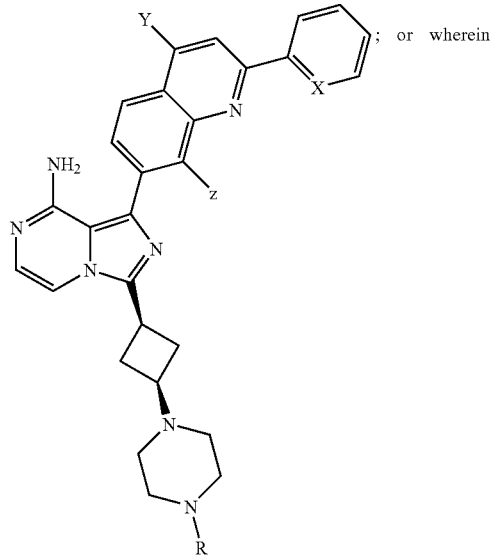

; or wherein

118
-continued

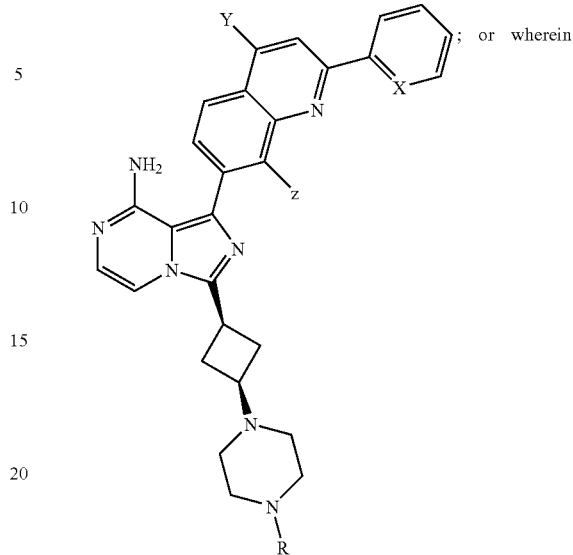

; or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | Ac |
| CH | CH₃ | H | Ac |
| CH | H | F | Ac |
| CH | CH₃ | F | Ac |
| N | H | H | Ac |
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |

| X | Y | Z | R |
|---|---|---|---|
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OCH₃) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NMe₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |

119

-continued

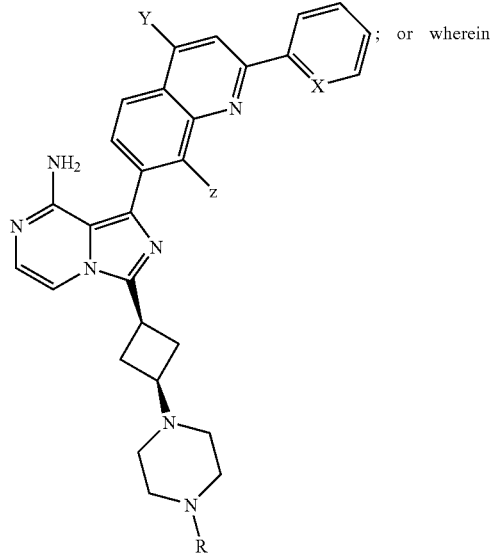

; or wherein

| X | Y | Z | R |
|---|---|---|---|
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | Et |
| CH | CH₃ | H | Et |
| CH | H | F | Et |
| CH | CH₃ | F | Et |
| N | H | H | Et |
| N | CH₃ | H | Et |
| N | H | F | Et |
| N | CH₃ | F | Et |
| CF | H | H | Et |
| CF | CH₃ | H | Et |
| CF | H | F | Et |
| CF | CH₃ | F | Et |

120

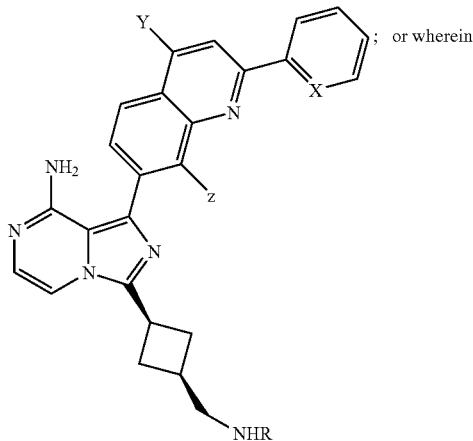

; or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | Ac |
| CH | CH₃ | H | Ac |
| CH | H | F | Ac |
| CH | CH₃ | F | Ac |
| N | H | H | Ac |
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |

121
-continued

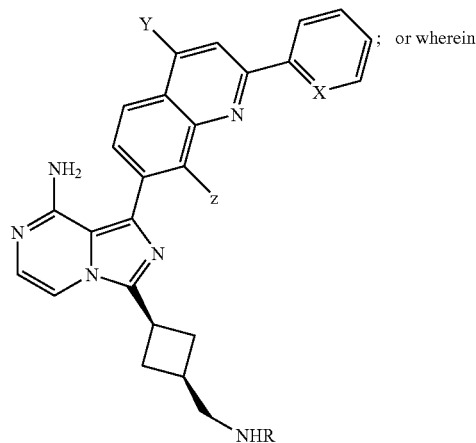
; or wherein

| X | Y | Z | R |
|---|---|---|---|
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OCH₃) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NMe₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |

122
-continued

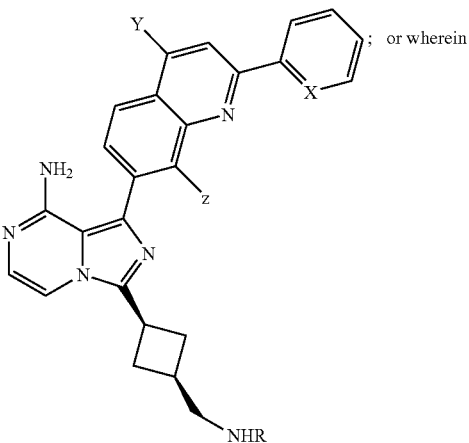
; or wherein

| X | Y | Z | R |
|---|---|---|---|
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | Et |
| CH | CH₃ | H | Et |
| CH | H | F | Et |
| CH | CH₃ | F | Et |
| N | H | H | Et |
| N | CH₃ | H | Et |
| N | H | F | Et |
| N | CH₃ | F | Et |
| CF | H | H | Et |
| CF | CH₃ | H | Et |
| CF | H | F | Et |
| CF | CH₃ | F | Et |

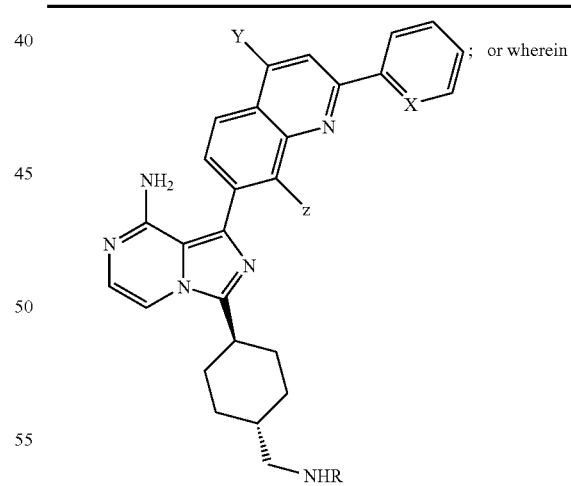
; or wherein

| X | Y | Z | R |
|---|---|---|---|
| CH | CH₃ | F | CH₃ |
| CH | H | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |

123
-continued

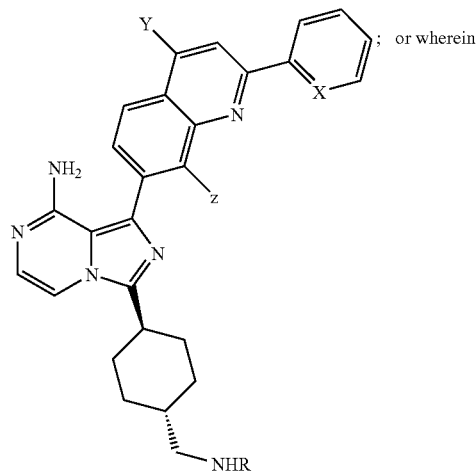

| X | Y | Z | R |
|---|---|---|---|
| CF | CH₃ | F | CH₃ |
| CH | H | H | Ac |
| CH | CH₃ | H | Ac |
| CH | H | F | Ac |
| CH | CH₃ | F | Ac |
| N | H | H | Ac |
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |

124
-continued

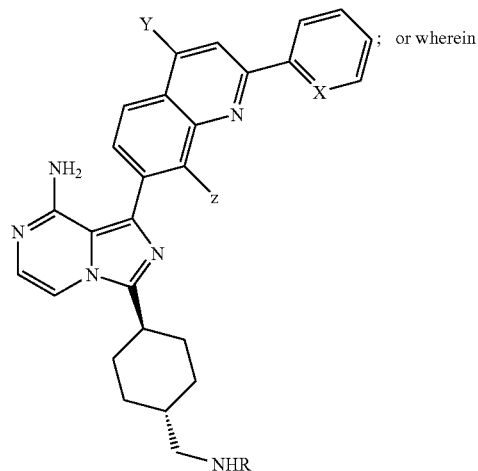

| X | Y | Z | R |
|---|---|---|---|
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OCH₃) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NMe₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | Et |

125
-continued

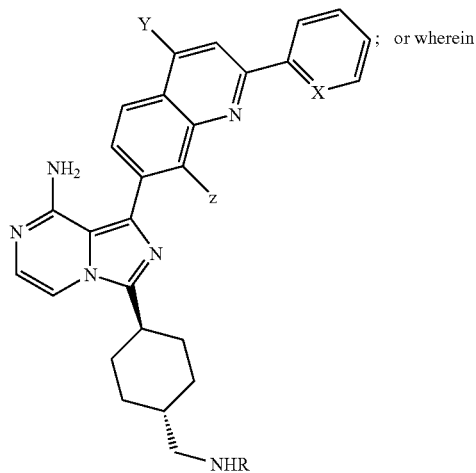

; or wherein

| X | Y | Z | R |
|---|---|---|---|
| CH | CH₃ | H | Et |
| CH | H | F | Et |
| CH | CH₃ | F | Et |
| N | H | H | Et |
| N | CH₃ | H | Et |
| N | H | F | Et |
| N | CH₃ | F | Et |
| CF | H | H | Et |
| CF | CH₃ | H | Et |
| CF | H | F | Et |
| CF | CH₃ | F | Et |

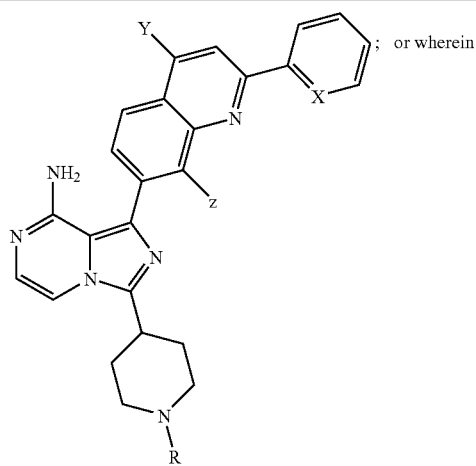

; or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | iPr |
| CH | CH₃ | H | Ac |
| CH | H | F | Ac |
| CH | CH₃ | F | Ac |
| N | H | H | Ac |

126
-continued

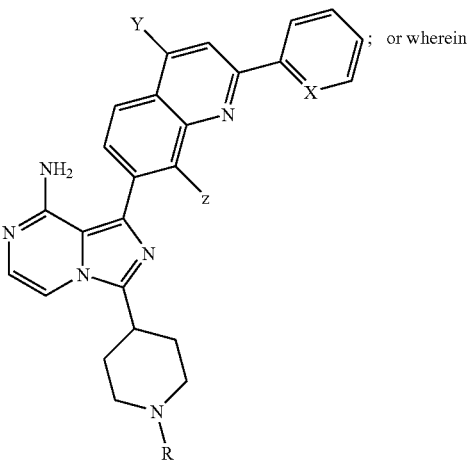

; or wherein

| X | Y | Z | R |
|---|---|---|---|
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |

127
-continued

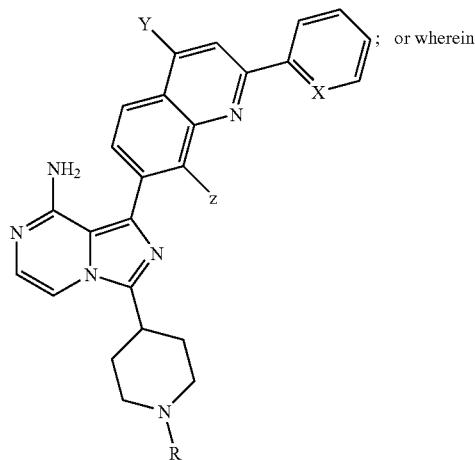
; or wherein

| X | Y | Z | R |
|---|---|---|---|
| CH | H | H | CO(CH₂OCH₃) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NEt₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | Et |
| CH | CH₃ | H | Et |
| CH | H | F | Et |
| CH | CH₃ | F | Et |
| N | H | H | Et |
| N | CH₃ | H | Et |
| N | H | F | Et |

128
-continued

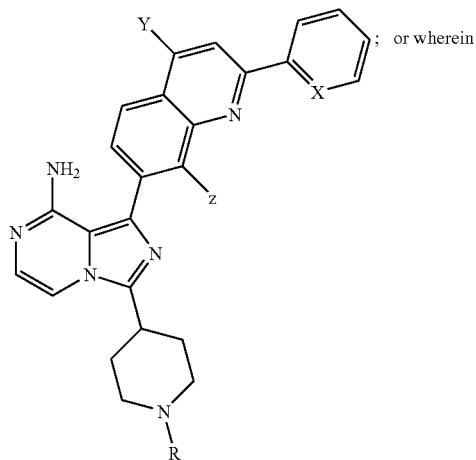
; or wherein

| X | Y | Z | R |
|---|---|---|---|
| N | CH₃ | F | Et |
| CF | H | H | Et |
| CF | CH₃ | H | Et |
| CF | H | F | Et |
| CF | CH₃ | F | Et |

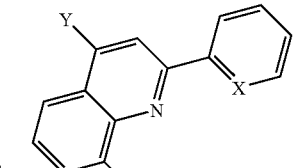
; or wherein

| X | Y | Z | R |
|---|---|---|---|
| CH | CH₃ | F | CH₃ |
| N | H | H | CH₃ |
| N | CH₃ | H | CH₃ |
| N | H | F | CH₃ |
| N | CH₃ | F | CH₃ |
| CF | H | H | CH₃ |
| CF | CH₃ | H | CH₃ |
| CF | H | F | CH₃ |
| CF | CH₃ | F | CH₃ |
| CH | H | H | iPr |
| CH | CH₃ | H | Ac |
| CH | H | F | Ac |
| CH | CH₃ | F | Ac |
| N | H | H | Ac |
| N | CH₃ | H | Ac |
| N | H | F | Ac |
| N | CH₃ | F | Ac |
| CF | H | H | Ac |
| CF | CH₃ | H | Ac |
| CF | H | F | Ac |
| CF | CH₃ | F | Ac |

129
-continued

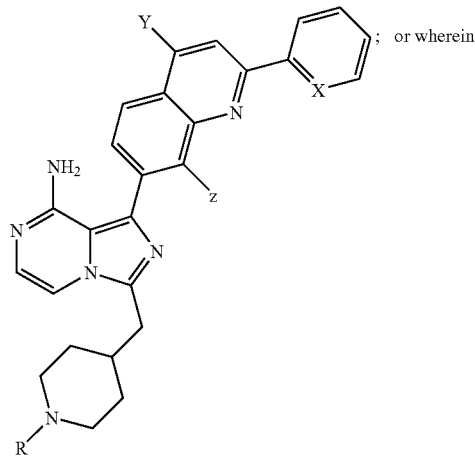

; or wherein

| X | Y | Z | R |
|---|---|---|---|
| CH | H | H | CO(CF₃) |
| CH | CH₃ | H | CO(CF₃) |
| CH | H | F | CO(CF₃) |
| CH | CH₃ | F | CO(CF₃) |
| N | H | H | CO(CF₃) |
| N | CH₃ | H | CO(CF₃) |
| N | H | F | CO(CF₃) |
| N | CH₃ | F | CO(CF₃) |
| CF | H | H | CO(CF₃) |
| CF | CH₃ | H | CO(CF₃) |
| CF | H | F | CO(CF₃) |
| CF | CH₃ | F | CO(CF₃) |
| CH | H | H | CO(CH₂CH₃) |
| CH | CH₃ | H | CO(CH₂CH₃) |
| CH | H | F | CO(CH₂CH₃) |
| CH | CH₃ | F | CO(CH₂CH₃) |
| N | H | H | CO(CH₂CH₃) |
| N | CH₃ | H | CO(CH₂CH₃) |
| N | H | F | CO(CH₂CH₃) |
| N | CH₃ | F | CO(CH₂CH₃) |
| CF | H | H | CO(CH₂CH₃) |
| CF | CH₃ | H | CO(CH₂CH₃) |
| CF | H | F | CO(CH₂CH₃) |
| CF | CH₃ | F | CO(CH₂CH₃) |
| CH | H | H | CO(NMe₂) |
| CH | CH₃ | H | CO(NMe₂) |
| CH | H | F | CO(NMe₂) |
| CH | CH₃ | F | CO(NMe₂) |
| N | H | H | CO(NMe₂) |
| N | CH₃ | H | CO(NMe₂) |
| N | H | F | CO(NMe₂) |
| N | CH₃ | F | CO(NMe₂) |
| CF | H | H | CO(NMe₂) |
| CF | CH₃ | H | CO(NMe₂) |
| CF | H | F | CO(NMe₂) |
| CF | CH₃ | F | CO(NMe₂) |
| CH | H | H | CO(iPr) |
| CH | CH₃ | H | CO(iPr) |
| CH | H | F | CO(iPr) |
| CH | CH₃ | F | CO(iPr) |
| N | H | H | CO(iPr) |
| N | CH₃ | H | CO(iPr) |
| N | H | F | CO(iPr) |
| N | CH₃ | F | CO(iPr) |
| CF | H | H | CO(iPr) |
| CF | CH₃ | H | CO(iPr) |
| CF | H | F | CO(iPr) |
| CF | CH₃ | F | CO(iPr) |
| CH | H | H | CO(CH₂OEt) |
| CH | CH₃ | H | CO(CH₂OCH₃) |
| CH | H | F | CO(CH₂OCH₃) |
| CH | CH₃ | F | CO(CH₂OCH₃) |
| N | H | H | CO(CH₂OCH₃) |
| N | CH₃ | H | CO(CH₂OCH₃) |
| N | H | F | CO(CH₂OCH₃) |

130
-continued

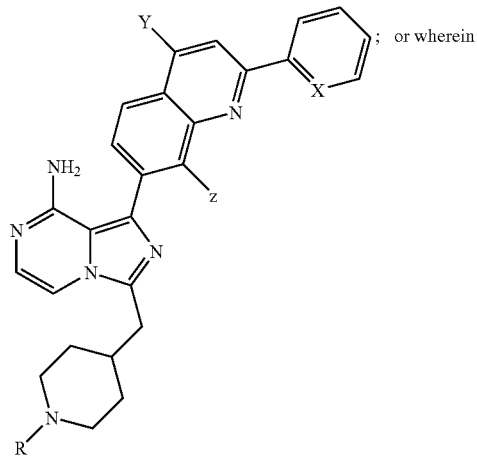

; or wherein

| X | Y | Z | R |
|---|---|---|---|
| N | CH₃ | F | CO(CH₂OCH₃) |
| CF | H | H | CO(CH₂OCH₃) |
| CF | CH₃ | H | CO(CH₂OCH₃) |
| CF | H | F | CO(CH₂OCH₃) |
| CF | CH₃ | F | CO(CH₂OCH₃) |
| CH | H | H | CO(CH₂NEt₂) |
| CH | CH₃ | H | CO(CH₂NMe₂) |
| CH | H | F | CO(CH₂NMe₂) |
| CH | CH₃ | F | CO(CH₂NMe₂) |
| N | H | H | CO(CH₂NMe₂) |
| N | CH₃ | H | CO(CH₂NMe₂) |
| N | H | F | CO(CH₂NMe₂) |
| N | CH₃ | F | CO(CH₂NMe₂) |
| CF | H | H | CO(CH₂NMe₂) |
| CF | CH₃ | H | CO(CH₂NMe₂) |
| CF | H | F | CO(CH₂NMe₂) |
| CF | CH₃ | F | CO(CH₂NMe₂) |
| CH | H | H | CO₂CH₃ |
| CH | CH₃ | H | CO₂CH₃ |
| CH | H | F | CO₂CH₃ |
| CH | CH₃ | F | CO₂CH₃ |
| N | H | H | CO₂CH₃ |
| N | CH₃ | H | CO₂CH₃ |
| N | H | F | CO₂CH₃ |
| N | CH₃ | F | CO₂CH₃ |
| CF | H | H | CO₂CH₃ |
| CF | CH₃ | H | CO₂CH₃ |
| CF | H | F | CO₂CH₃ |
| CF | CH₃ | F | CO₂CH₃ |
| CH | H | H | CO₂CH₂CH₃ |
| CH | CH₃ | H | CO₂CH₂CH₃ |
| CH | H | F | CO₂CH₂CH₃ |
| CH | CH₃ | F | CO₂CH₂CH₃ |
| N | H | H | CO₂CH₂CH₃ |
| N | CH₃ | H | CO₂CH₂CH₃ |
| N | H | F | CO₂CH₂CH₃ |
| N | CH₃ | F | CO₂CH₂CH₃ |
| CF | H | H | CO₂CH₂CH₃ |
| CF | CH₃ | H | CO₂CH₂CH₃ |
| CF | H | F | CO₂CH₂CH₃ |
| CF | CH₃ | F | CO₂CH₂CH₃ |
| CH | H | H | CH₂CH₂OCH₃ |
| CH | CH₃ | H | Et |
| CH | H | F | Et |
| CH | CH₃ | F | Et |
| N | H | H | Et |
| N | CH₃ | H | Et |
| N | H | F | Et |
| N | CH₃ | F | Et |
| CF | H | H | Et |
| CF | CH₃ | H | Et |
| CF | H | F | Et |
| CF | CH₃ | F | Et |

131
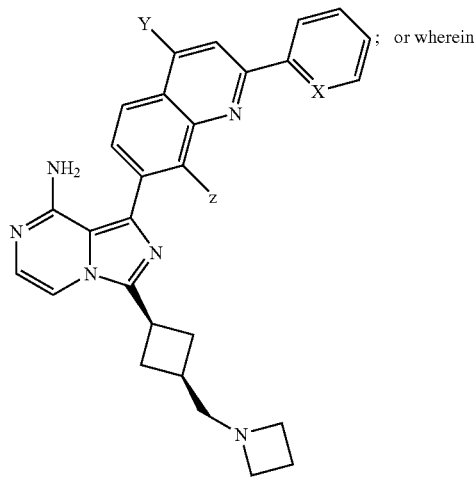
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
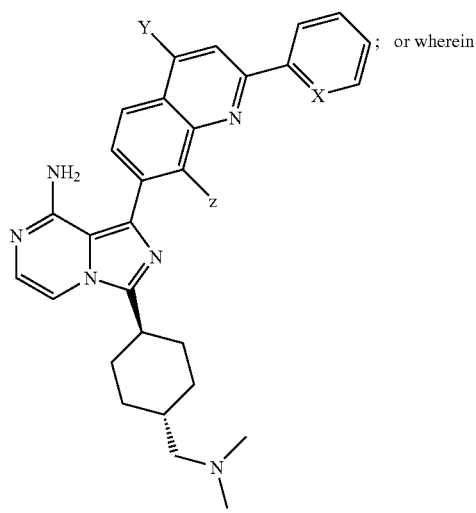
| X | Y | Z |
|---|---|---|
| CH | Et | H |
| CH | H | F |
| CH | CH₃ | F |
| N | H | H |
| N | CH₃ | H |
| N | H | F |
| N | CH₃ | F |
| CF | H | H |
132
-continued
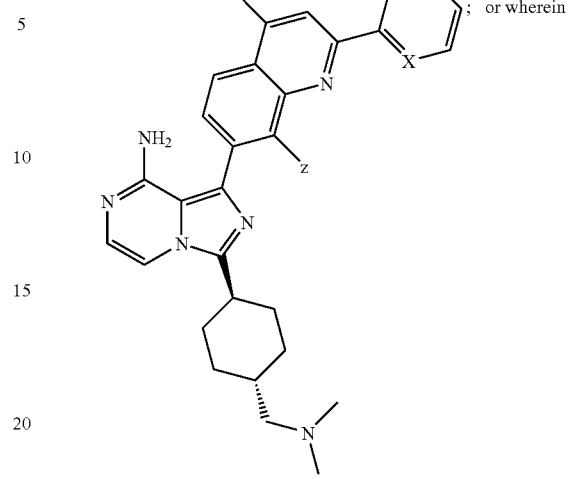
| X | Y | Z |
|---|---|---|
| CF | CH₃ | H |
| CF | H | F |
| CF | CH₃ | F |
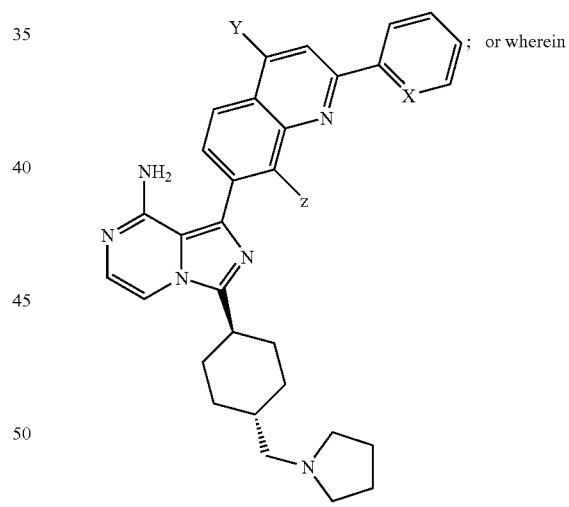
| X | Y | Z |
|---|---|---|
| CH | Et | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

133
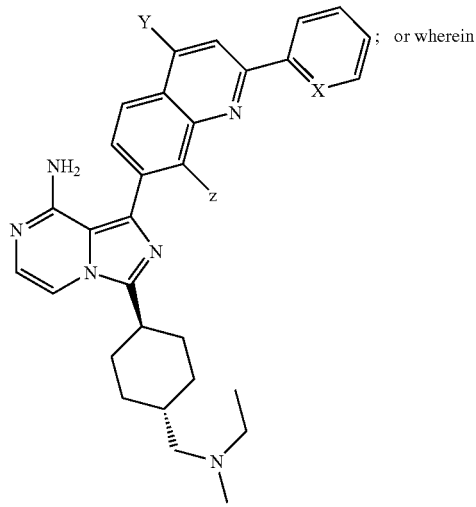
; or wherein
| X | Y | Z |
|---|---|---|
| CH | Et | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
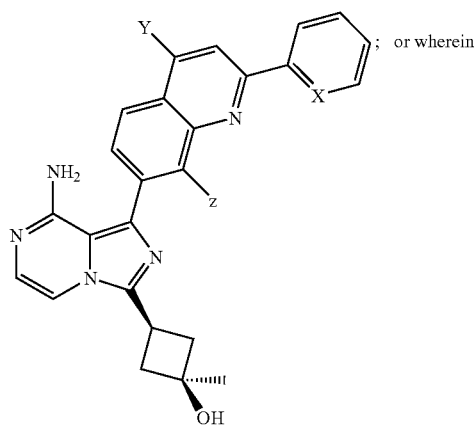
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
134
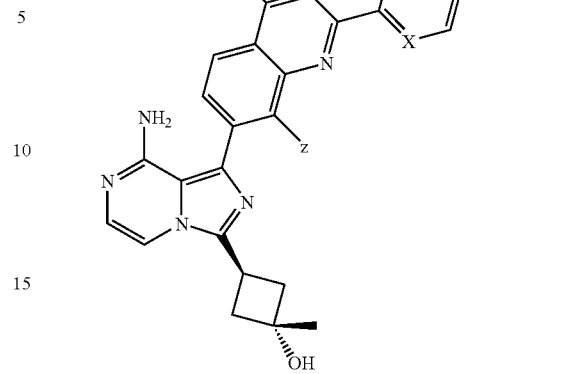
; or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
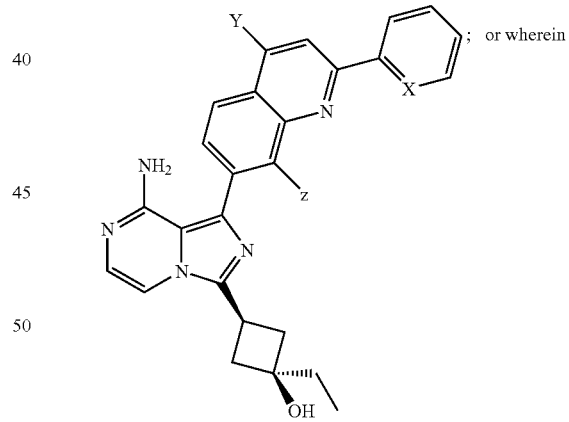
; or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |

135
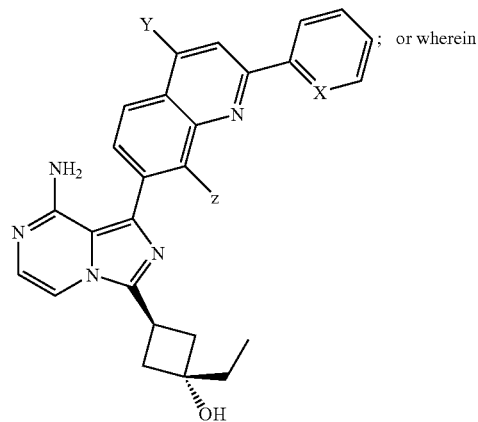
; or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
136
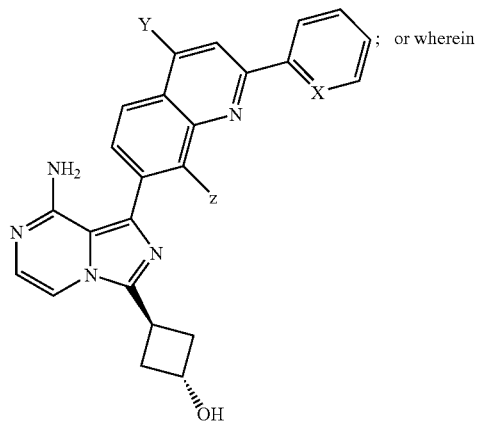
; or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
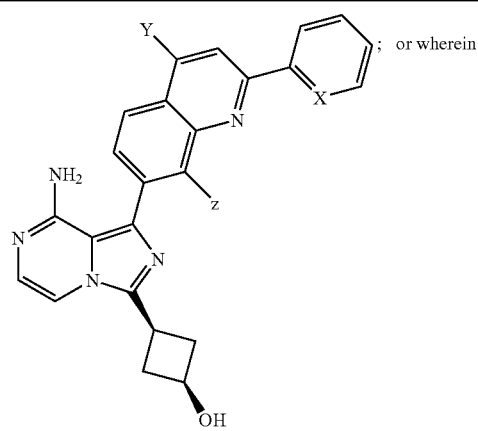
; or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |
| CF | CH₃ | H |
| CF | H | F |
| CF | CH₃ | F |
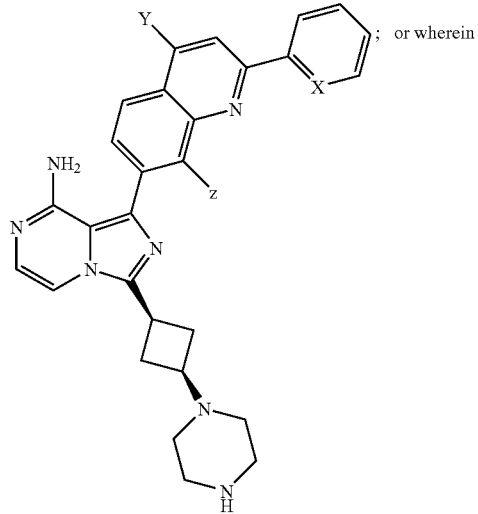
; or wherein
| X | Y | Z |
|---|---|---|
| CH | Et | H |
| CH | CH₃ | H |
| CH | H | F |
| CH | CH₃ | F |
| N | H | H |
| N | CH₃ | H |
| N | H | F |
| N | CH₃ | F |
| CF | H | H |

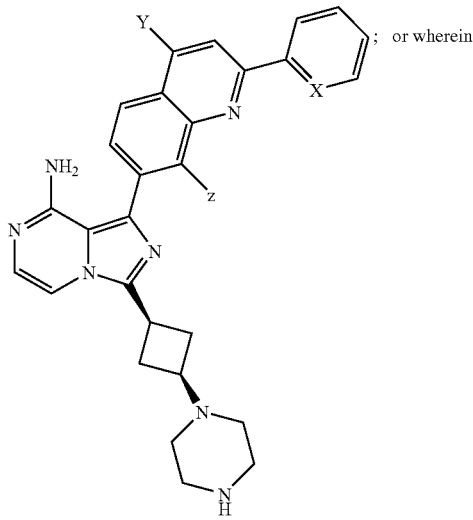

; or wherein

| X | Y | Z |
|---|---|---|
| CF | CH₃ | H |
| CF | H | F |
| CF | CH₃ | F; |

IGF1R inhibitors to be used in accordance with the present invention include those described in US2006/0235031 and include the following inhibitors or pharmaceutically acceptable salts thereof:

3-Cyclobutyl-1-(2-pyridin-2-ylquinolin-7-yl)-imidazo[1,5-a]pyrazin-8-ylamine;
3-Cyclobutyl-1-(2-thiophen-2-ylquinolin-7-yl)-imidazo[1,5-a]pyrazin-8-ylamine;
3-Cyclobutyl-1-(2-phenoxyquinolin-7-yl)-imidazo[1,5-a]pyrazin-8-ylamine;
[7-(8-Amino-3-cyclobutylimidazo[1,5-a]pyrazin-1-yl)-quinolin-2-yl]-phenylamine;
1-(6-Chloro-2-phenylquinolin-7-yl)-3-cyclobutylimidazo[1,5-a]pyrazin-8-ylamine;
1-(6-Chloro-2-pyridin-2-ylquinolin-7-yl)-3-cyclobutylimidazo[1,5-a]pyrazin-8-ylamine;
1-(6-Chloro-2-thiophen-2-ylquinolin-7-yl)-3-cyclobutylimidazo[1,5-a]pyrazin-8-ylamine;
1-(6-Chloro-2-phenoxyquinolin-7-yl)-3-cyclobutylimidazo[1,5-a]pyrazin-8-ylamine;
[7-(8-Amino-3-cyclobutylimidazo[1,5-a]pyrazin-1-yl)-6-chloroquinolin-2-yl]-phenyl-amine;
3-Cyclobutyl-1-(8-fluoro-2-phenylquinolin-7-yl)-imidazo[1,5-a]pyrazin-8-ylamine;
3-Cyclobutyl-1-(8-fluoro-2-pyridin-2-ylquinolin-7-yl)-imidazo[1,5-a]pyrazin-8-ylamine;
3-Cyclobutyl-1-(8-fluoro-2-thiophen-2-ylquinolin-7-yl)-imidazo[1,5-a]pyrazin-8-ylamine;
3-Cyclobutyl-1-(8-fluoro-2-phenoxyquinolin-7-yl)-imidazo[1,5-a]pyrazin-8-ylamine;
[7-(8-Amino-3-cyclobutylimidazo[1,5-a]pyrazin-1-yl)-8-fluoroquinolin-2-yl]-phenyl-amine;
3-Cyclobutyl-1-(4-methyl-2-phenylquinolin-7-yl)-imidazo[1,5-a]pyrazin-8-ylamine;
3-Cyclobutyl-1-(4-methyl-2-pyridin-2-ylquinolin-7-yl)-imidazo[1,5-a]pyrazin-8-ylamine;
3-Cyclobutyl-1-(4-methyl-2-thiophen-2-ylquinolin-7-yl)-imidazo[1,5-a]pyrazin-8-ylamine;
[7-(8-Amino-3-cyclobutylimidazo[1,5-a]pyrazin-1-yl)-4-methylquinolin-2-yl]-phenylamine;
3-Cyclobutyl-1-(4-methyl-2-phenoxyquinolin-7-yl)-imidazo[1,5-a]pyrazin-8-ylamine;
[7-(8-Amino-3-cyclobutylimidazo[1,5-a]pyrazin-1-yl)-2-phenylquinolin-4-yl]-methylamine;
[7-(8-Amino-3-cyclobutylimidazo[1,5-a]pyrazin-1-yl)-2-pyridin-2-ylquinolin-4-yl]-methylamine;
[7-(8-Amino-3-cyclobutylimidazo[1,5-a]pyrazin-1-yl)-2-thiophen-2-ylquinolin-4-yl]-methylamine;
[7-(8-Amino-3-cyclobutylimidazo[1,5-a]pyrazin-1-yl)-2-phenoxyquinolin-4-yl]-methylamine;
7-(8-Amino-3-cyclobutylimidazo[1,5-a]pyrazin-1-yl)-N⁴-methyl-N²-phenylquinoline-2,4-diamine;
3-[8-Amino-1-(2-pyridin-2-ylquinolin-7-yl)-imidazo[1,5-a]pyrazin-3-yl]-cyclobutanol;
3-[8-Amino-1-(2-thiophen-2-ylquinolin-7-yl)-imidazo[1,5-a]pyrazin-3-yl]-cyclobutanol;
3-[8-Amino-1-(2-phenoxyquinolin-7-yl)-imidazo[1,5-a]pyrazin-3-yl]-cyclobutanol;
3-[8-Amino-1-(2-phenylaminoquinolin-7-yl)-imidazo[1,5-a]pyrazin-3-yl]-cyclobutanol;
3-[8-Amino-1-(6-chloro-2-phenylquinolin-7-yl)-imidazo[1,5-a]pyrazin-3-yl]-cyclobutanol;
3-[8-Amino-1-(6-chloro-2-pyridin-2-ylquinolin-7-yl)-imidazo[1,5-a]pyrazin-3-yl]-cyclobutanol;
3-[8-Amino-1-(6-chloro-2-thiophen-2-ylquinolin-7-yl)-imidazo[1,5-a]pyrazin-3-yl]-cyclobutanol;
3-[8-Amino-1-(6-chloro-2-phenylaminoquinolin-7-yl)-imidazo[1,5-a]pyrazin-3-yl]-cyclobutanol;
3-[8-Amino-1-(6-chloro-2-phenoxyquinolin-7-yl)-imidazo[1,5-a]pyrazin-3-yl]-cyclobutanol;
3-[8-Amino-1-(8-fluoro-2-pyridin-2-ylquinolin-7-yl)-imidazo[1,5-a]pyrazin-3-yl]-cyclobutanol;
3-[8-Amino-1-(8-fluoro-2-thiophen-2-ylquinolin-7-yl)-imidazo[1,5-a]pyrazin-3-yl]-cyclobutanol;
3-[8-Amino-1-(8-fluoro-2-phenoxyquinolin-7-yl)-imidazo[1,5-a]pyrazin-3-yl]-cyclobutanol;
3-[8-Amino-1-(8-fluoro-2-phenylaminoquinolin-7-yl)-imidazo[1,5-a]pyrazin-3-yl]-cyclobutanol;
3-[8-Amino-1-(8-fluoro-2-phenylquinolin-7-yl)-imidazo[1,5-a]pyrazin-3-yl]-cyclobutanol;
3-[8-Amino-1-(8-fluoro-4-methyl-2-phenylquinolin-7-yl)-imidazo[1,5-a]pyrazin-3-yl]-cyclobutanol;
3-[8-Amino-1-(8-fluoro-4-methyl-2-thiophen-2-yl-quinolin-7-yl)-imidazo[1,5-a]pyrazin-3-yl]-cyclobutanol;
3-[8-Amino-1-(8-fluoro-4-methyl-2-pyridin-2-ylquinolin-7-yl)-imidazo[1,5-a]pyrazin-3-yl]-cyclobutanol;
3-[8-Amino-1-(8-fluoro-4-methyl-2-phenylaminoquinolin-7-yl)-imidazo[1,5-a]pyrazin-3-yl]-cyclobutanol;
3-[8-Amino-1-(8-fluoro-4-methyl-2-phenoxyquinolin-7-yl)-imidazo[1,5-a]pyrazin-3-yl]-cyclobutanol;
3-(3-Azetidin-1-ylmethylcyclobutyl)-1-(2-pyridin-2-ylquinolin-7-yl)-imidazo[1,5-a]pyrazin-8-ylamine;
3-(3-Azetidin-1-ylmethylcyclobutyl)-1-(2-thiophen-2-ylquinolin-7-yl)-imidazo[1,5-a]pyrazin-8-ylamine;
3-(3-Azetidin-1-ylmethylcyclobutyl)-1-(2-phenoxyquinolin-7-yl)-imidazo[1,5-a]pyrazin-8-ylamine;
{7-[8-Amino-3-(3-azetidin-1-ylmethylcyclobutyl)-imidazo[1,5-a]pyrazin-1-yl]-quinolin-2-yl}-phenylamine;
3-(3-Azetidin-1-ylmethylcyclobutyl)-1-(6-chloro-2-phenylquinolin-7-yl)-imidazo[1,5-a]pyrazin-8-ylamine;
3-(3-Azetidin-1-ylmethylcyclobutyl)-1-(6-chloro-2-pyridin-2-yl-quinolin-7-yl)-imidazo[1,5-a]pyrazin-8-ylamine;
3-(3-Azetidin-1-ylmethylcyclobutyl)-1-(6-chloro-2-thiophen-2-yl-quinolin-7-yl)-imidazo[1,5-a]pyrazin-8-ylamine;

{7-[8-Amino-3-(3-azetidin-1-ylmethylcyclobutyl)-imidazo[1,5-a]pyrazin-1-yl]-6-chloro-quinolin-2-yl}-phenylamine;
3-(3-Azetidin-1-ylmethylcyclobutyl)-1-(6-chloro-2-phenoxyquinolin-7-yl)-imidazo[1,5-a]pyrazin-8-ylamine;
3-(3-Azetidin-1-ylmethylcyclobutyl)-1-(4-methyl-2-phenylquinolin-7-yl)-imidazo[1,5-a]pyrazin-8-ylamine;
3-(3-Azetidin-1-ylmethylcyclobutyl)-1-(4-methyl-2-pyridin-2-ylquinolin-7-yl)-imidazo[1,5-a]pyrazin-8-ylamine;
3-(3-Azetidin-1-ylmethylcyclobutyl)-1-(4-methyl-2-thiophen-2-ylquinolin-7-yl)-imidazo[1,5-a]pyrazin-8-ylamine;
3-(3-Azetidin-1-ylmethylcyclobutyl)-1-(4-methyl-2-phenoxyquinolin-7-yl)-imidazo[1,5-a]pyrazin-8-ylamine;
{7-[8-Amino-3-(3-azetidin-1-ylmethylcyclobutyl)-imidazo[1,5-a]pyrazin-1-yl]-4-methyl-quinolin-2-yl}-phenylamine;
3-(3-Dimethylaminomethylcyclobutyl)-1-(2-phenylquinolin-7-yl)-imidazo[1,5-a]pyrazin-8-ylamine;
3-(3-Dimethylaminomethylcyclobutyl)-1-(2-pyridin-2-ylquinolin-7-yl)-imidazo[1,5-a]pyrazin-8-ylamine;
3-(3-Dimethylaminomethylcyclobutyl)-1-(2-thiophen-2-ylquinolin-7-yl)-imidazo[1,5-a]pyrazin-8-ylamine;
{7-[8-Amino-3-(3-dimethylaminomethylcyclobutyl)-imidazo[1,5-a]pyrazin-1-yl]-quinolin-2-yl}-phenylamine;
3-(3-Dimethylaminomethylcyclobutyl)-1-(2-phenoxyquinolin-7-yl)-imidazo[1,5-a]pyrazin-8-ylamine;
1-(6-Chloro-2-phenylquinolin-7-yl)-3-(3-dimethylaminomethylcyclobutyl)-imidazo[1,5-a]pyrazin-8-ylamine;
1-(6-Chloro-2-pyridin-2-ylquinolin-7-yl)-3-(3-dimethylaminomethylcyclobutyl)-imidazo[1,5-a]pyrazin-8-ylamine;
1-(6-Chloro-2-thiophen-2-ylquinolin-7-yl)-3-(3-dimethylaminomethylcyclobutyl)-imidazo[1,5-a]pyrazin-8-ylamine;
1-(6-Chloro-2-phenoxyquinolin-7-yl)-3-(3-dimethylaminomethylcyclobutyl)-imidazo[1,5-a]pyrazin-8-ylamine;
{7-[8-Amino-3-(3-dimethylaminomethylcyclobutyl)-imidazo[1,5-a]pyrazin-1-yl]-6-chloroquinolin-2-yl}-phenylamine;
3-(3-Dimethylaminomethylcyclobutyl)-1-(4-methyl-2-phenylquinolin-7-yl)-imidazo[1,5-a]pyrazin-8-ylamine;
3-(3-Dimethylaminomethylcyclobutyl)-1-(4-methyl-2-pyridin-2-ylquinolin-7-yl)-imidazo[1,5-a]pyrazin-8-ylamine;
3-(3-Dimethylaminomethylcyclobutyl)-1-(4-methyl-2-thiophen-2-ylquinolin-7-yl)-imidazo[1,5-a]pyrazin-8-ylamine;
{7-[8-Amino-3-(3-dimethylaminomethylcyclobutyl)-imidazo[1,5-a]pyrazin-1-yl]-4-methylquinolin-2-yl}-phenylamine;
3-(3-Dimethylaminomethylcyclobutyl)-1-(4-methyl-2-phenoxyquinolin-7-yl)-imidazo[1,5-a]pyrazin-8-ylamine;
4-[8-Amino-1-(2-pyridin-2-ylquinolin-7-yl)-imidazo[1,5-a]pyrazin-3-yl]-cyclohexanecarboxylic acid amide;
4-[8-Amino-1-(2-thiophen-2-ylquinolin-7-yl)-imidazo[1,5-a]pyrazin-3-yl]-cyclohexanecarboxylic acid amide;
4-[8-Amino-1-(2-phenoxyquinolin-7-yl)-imidazo[1,5-a]pyrazin-3-yl]-cyclohexanecarboxylic acid amide;
4-[8-Amino-1-(2-phenylaminoquinolin-7-yl)-imidazo[1,5-a]pyrazin-3-yl]-cyclohexanecarboxylic acid amide;
4-[8-Amino-1-(6-chloro-2-phenylquinolin-7-yl)-imidazo[1,5-a]pyrazin-3-yl]-cyclohexanecarboxylic acid amide;
4-[8-Amino-1-(6-chloro-2-pyridin-2-ylquinolin-7-yl)-imidazo[1,5-a]pyrazin-3-yl]-cyclohexanecarboxylic acid amide;
4-[8-Amino-1-(6-chloro-2-thiophen-2-ylquinolin-7-yl)-imidazo[1,5-a]pyrazin-3-yl]-cyclohexanecarboxylic acid amide;
4-[8-Amino-1-(6-chloro-2-phenylaminoquinolin-7-yl)-imidazo[1,5-a]pyrazin-3-yl]-cyclohexanecarboxylic acid amide;
4-[8-Amino-1-(6-chloro-2-phenoxyquinolin-7-yl)-imidazo[1,5-a]pyrazin-3-yl]-cyclohexanecarboxylic acid amide;
4-[8-Amino-1-(4-methyl-2-phenylquinolin-7-yl)-imidazo[1,5-a]pyrazin-3-yl]-cyclohexanecarboxylic acid amide;
4-[8-Amino-1-(4-methyl-2-pyridin-2-ylquinolin-7-yl)-imidazo[1,5-a]pyrazin-3-yl]-cyclohexanecarboxylic acid amide;
4-[8-Amino-1-(4-methyl-2-thiophen-2-ylquinolin-7-yl)-imidazo[1,5-a]pyrazin-3-yl]-cyclohexanecarboxylic acid amide;
4-[8-Amino-1-(4-methyl-2-phenoxyquinolin-7-yl)-imidazo[1,5-a]pyrazin-3-yl]-cyclohexanecarboxylic acid amide;
4-[8-Amino-1-(4-methyl-2-phenylaminoquinolin-7-yl)-imidazo[1,5-a]pyrazin-3-yl]-cyclohexanecarboxylic acid amide;
4-[8-Amino-1-(2-pyridin-2-ylquinolin-7-yl)-imidazo[1,5-a]pyrazin-3-yl]-cyclohexanecarboxylic acid methylamide;
4-[8-Amino-1-(2-thiophen-2-ylquinolin-7-yl)-imidazo[1,5-a]pyrazin-3-yl]-cyclohexanecarboxylic acid methylamide;
4-[8-Amino-1-(2-phenylaminoquinolin-7-yl)-imidazo[1,5-a]pyrazin-3-yl]-cyclohexanecarboxylic acid methylamide;
4-[8-Amino-1-(2-phenoxyquinolin-7-yl)-imidazo[1,5-a]pyrazin-3-yl]-cyclohexanecarboxylic acid methylamide;
3-(4-Aminomethylcyclohexyl)-1-(2-pyridin-2-ylquinolin-7-yl)-imidazo[1,5-a]pyrazin-8-ylamine;
3-(4-Aminomethylcyclohexyl)-1-(2-thiophen-2-ylquinolin-7-yl)-imidazo[1,5-a]pyrazin-8-ylamine;
3-(4-Aminomethylcyclohexyl)-1-(2-phenoxyquinolin-7-yl)-imidazo[1,5-a]pyrazin-8-ylamine;
{7-[8-Amino-3-(4-aminomethylcyclohexyl)-imidazo[1,5-a]pyrazin-1-yl]-quinolin-2-yl}-phenylamine;
7-Cyclobutyl-5-(2-phenylquinolin-7-yl)-7H-pyrrolo[2,3-d]pyrimidin-4-ylamine;
7-Cyclobutyl-5-(2-pyridin-2-ylquinolin-7-yl)-7H-pyrrolo[2,3-d]pyrimidin-4-ylamine;
7-Cyclobutyl-5-(2-thiophen-2-ylquinolin-7-yl)-7H-pyrrolo[2,3-d]pyrimidin-4-ylamine;
[7-(4-Amino-7-cyclobutyl-7H-pyrrolo[2,3-d]pyrimidin-5-yl)-quinolin-2-yl]-phenylamine;
7-Cyclobutyl-5-(2-phenoxyquinolin-7-yl)-7H-pyrrolo[2,3-d]pyrimidin-4-ylamine;
5-(6-Chloro-2-phenylquinolin-7-yl)-7-cyclobutyl-7H-pyrrolo[2,3-d]pyrimidin-4-ylamine;
5-(6-Chloro-2-pyridin-2-ylquinolin-7-yl)-7-cyclobutyl-7H-pyrrolo[2,3-d]pyrimidin-4-ylamine;
5-(6-Chloro-2-thiophen-2-ylquinolin-7-yl)-7-cyclobutyl-7H-pyrrolo[2,3-d]pyrimidin-4-ylamine;
5-(6-Chloro-2-phenoxyquinolin-7-yl)-7-cyclobutyl-7H-pyrrolo[2,3-d]pyrimidin-4-ylamine;
[7-(4-Amino-7-cyclobutyl-7H-pyrrolo[2,3-d]pyrimidin-5-yl)-6-chloroquinolin-2-yl]-phenylamine;
3-[4-Amino-5-(2-phenylquinolin-7-yl)-pyrrolo[2,3-d]pyrimidin-7-yl]-cyclobutanol;
3-[4-Amino-5-(2-thiophen-2-ylquinolin-7-yl)-pyrrolo[2,3-d]pyrimidin-7-yl]-cyclobutanol;
3-[4-Amino-5-(2-pyridin-2-ylquinolin-7-yl)-pyrrolo[2,3-d]pyrimidin-7-yl]-cyclobutanol;
3-[4-Amino-5-(2-phenylaminoquinolin-7-yl)-pyrrolo[2,3-d]pyrimidin-7-yl]-cyclobutanol;

3-[4-Amino-5-(2-phenoxyquinolin-7-yl)-pyrrolo[2,3-d]pyrimidin-7-yl]-cyclobutanol;
3-[4-Amino-5-(6-chloro-2-pyridin-2-ylquinolin-7-yl)-pyrrolo[2,3-d]pyrimidin-7-yl]-cyclobutanol;
3-[4-Amino-5-(6-chloro-2-phenylquinolin-7-yl)-pyrrolo[2,3-d]pyrimidin-7-yl]-cyclobutanol;
3-[4-Amino-5-(6-chloro-2-thiophen-2-ylquinolin-7-yl)-pyrrolo[2,3-d]pyrimidin-7-yl]-cyclobutanol;
3-[4-Amino-5-(6-chloro-2-phenoxyquinolin-7-yl)-pyrrolo[2,3-d]pyrimidin-7-yl]-cyclobutanol;
3-[4-Amino-5-(6-chloro-2-phenylaminoquinolin-7-yl)-pyrrolo[2,3-d]pyrimidin-7-yl]-cyclobutanol;
3-[4-Amino-5-(8-fluoro-2-phenylquinolin-7-yl)-pyrrolo[2,3-d]pyrimidin-7-yl]-cyclobutanol;
3-[4-Amino-5-(8-fluoro-2-thiophen-2-ylquinolin-7-yl)-pyrrolo[2,3-d]pyrimidin-7-yl]-cyclobutanol;
3-[4-Amino-5-(8-fluoro-2-pyridin-2-ylquinolin-7-yl)-pyrrolo[2,3-d]pyrimidin-7-yl]-cyclobutanol;
3-[4-Amino-5-(8-fluoro-2-phenylaminoquinolin-7-yl)-pyrrolo[2,3-d]pyrimidin-7-yl]-cyclobutanol;
3-[4-Amino-5-(8-fluoro-2-phenoxyquinolin-7-yl)-pyrrolo[2,3-d]pyrimidin-7-yl]-cyclobutanol;
7-Cyclobutyl-5-(8-fluoro-2-phenylquinolin-7-yl)-7H-pyrrolo[2,3-d]pyrimidin-4-ylamine;
7-Cyclobutyl-5-(8-fluoro-2-pyridin-2-ylquinolin-7-yl)-7H-pyrrolo[2,3-d]pyrimidin-4-ylamine;
7-Cyclobutyl-5-(8-fluoro-2-thiophen-2-yl-quinolin-7-yl)-7H-pyrrolo[2,3-d]pyrimidin-4-ylamine;
7-Cyclobutyl-5-(8-fluoro-2-phenoxyquinolin-7-yl)-7H-pyrrolo[2,3-d]pyrimidin-4-ylamine;
[7-(4-Amino-7-cyclobutyl-7H-pyrrolo[2,3-d]pyrimidin-5-yl)-8-fluoroquinolin-2-yl]-phenylamine;
7-(3-Azetidin-1-ylmethylcyclobutyl)-5-(2-phenylquinolin-7-yl)-7H-pyrrolo[2,3-d]pyrimidin-4-ylamine;
7-(3-Azetidin-1-ylmethylcyclobutyl)-5-(2-pyridin-2-ylquinolin-7-yl)-7H-pyrrolo[2,3-d]pyrimidin-4-ylamine;
7-(3-Azetidin-1-ylmethylcyclobutyl)-5-(2-thiophen-2-ylquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-quinolin-2-yl}-phenylamine;
7-(3-Azetidin-1-ylmethylcyclobutyl)-5-(2-phenoxyquinolin-7-yl)-7H-pyrrolo[2,3-d]pyrimidin-4-ylamine;
7-(3-Azetidin-1-ylmethylcyclobutyl)-5-(6-chloro-2-pyridin-2-ylquinolin-7-yl)-7H-pyrrolo[2,3-d]pyrimidin-4-ylamine;
7-(3-Azetidin-1-ylmethylcyclobutyl)-5-(6-chloro-2-phenylquinolin-7-yl)-7H-pyrrolo[2,3-d]pyrimidin-4-ylamine;
7-(3-Azetidin-1-ylmethylcyclobutyl)-5-(6-chloro-2-thiophen-2-ylquinolin-7-yl)-7H-pyrrolo[2,3-d]pyrimidin-4-ylamine;
7-(3-Azetidin-1-ylmethylcyclobutyl)-5-(6-chloro-2-phenoxyquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-6-chloroquinolin-2-yl}-phenylamine;
7-(3-Azetidin-1-ylmethylcyclobutyl)-5-(8-fluoro-2-phenylquinolin-7-yl)-7H-pyrrolo[2,3-d]pyrimidin-4-ylamine;
7-(3-Azetidin-1-ylmethylcyclobutyl)-5-(8-fluoro-2-pyridin-2-ylquinolin-7-yl)-7H-pyrrolo[2,3-d]pyrimidin-4-ylamine;
7-(3-Azetidin-1-ylmethylcyclobutyl)-5-(8-fluoro-2-thiophen-2-ylquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-8-fluoroquinolin-2-yl}-phenyl-amine;
7-(3-Azetidin-1-ylmethylcyclobutyl)-5-(8-fluoro-2-phenoxyquinolin-7-yl)-7H-pyrrolo[2,3-d]pyrimidin-4-ylamine;
7-(3-Azetidin-1-ylmethylcyclobutyl)-5-(4-methyl-2-pyridin-2-ylquinolin-7-yl)-7H-pyrrolo[2,3-d]pyrimidin-4-ylamine;
7-(3-Azetidin-1-ylmethylcyclobutyl)-5-(4-methyl-2-phenylquinolin-7-yl)-7H-pyrrolo[2,3-d]pyrimidin-4-ylamine;
7-(3-Azetidin-1-ylmethylcyclobutyl)-5-(4-methyl-2-thiophen-2-ylquinolin-7-yl)-7H-pyrrolo[2,3-d]pyrimidin-4-ylamine;
7-(3-Azetidin-1-ylmethylcyclobutyl)-5-(4-methyl-2-phenoxyquinolin-7-yl)-7H-pyrrolo[2,3-d]pyrimidin-4-ylamine;
{7-[4-Amino-7-(3-azetidin-1-ylmethylcyclobutyl)-7H-pyrrolo[2,3-d]pyrimidin-5-yl]-4-methylquinolin-2-yl}-phenylamine;
{7-[4-Amino-7-(3-azetidin-1-ylmethylcyclobutyl)-7H-pyrrolo[2,3-d]pyrimidin-5-yl]-2-phenylquinolin-4-yl}-methylamine;
{7-[4-Amino-7-(3-azetidin-1-ylmethylcyclobutyl)-7H-pyrrolo[2,3-d]pyrimidin-5-yl]-2-pyridin-2-ylquinolin-4-yl}-methylamine;
{7-[4-Amino-7-(3-azetidin-1-ylmethylcyclobutyl)-7H-pyrrolo[2,3-d]pyrimidin-5-yl]-2-thiophen-2-ylquinolin-4-yl}-methylamine;
7-[4-Amino-7-(3-azetidin-1-ylmethylcyclobutyl)-7H-pyrrolo[2,3-d]pyrimidin-5-yl]-$N^4$-methyl-$N^2$-phenylquinoline-2,4-diamine;
{7-[4-Amino-7-(3-azetidin-1-ylmethylcyclobutyl)-7H-pyrrolo[2,3-d]pyrimidin-5-yl]-2-phenoxyquinolin-4-yl}-methylamine;
7-(3-Dimethylaminomethylcyclobutyl)-5-(2-phenylquinolin-7-yl)-7H-pyrrolo[2,3-d]pyrimidin-4-ylamine;
7-(3-Dimethylaminomethylcyclobutyl)-5-(2-pyridin-2-ylquinolin-7-yl)-7H-pyrrolo[2,3-d]pyrimidin-4-ylamine;
7-(3-Dimethylaminomethylcyclobutyl)-5-(2-thiophen-2-ylquinolin-7-yl)-7H-pyrrolo[2,3-d]pyrimidin-4-ylamine;
7-(3-Dimethylaminomethylcyclobutyl)-5-(2-phenoxyquinolin-7-yl)-7H-pyrrolo[2,3-d]pyrimidin-4-ylamine;
{7-[4-Amino-7-(3-dimethylaminomethylcyclobutyl)-7H-pyrrolo[2,3-d]pyrimidin-5-yl]-quinolin-2-yl}-phenylamine;
5-(6-Chloro-2-phenylquinolin-7-yl)-7-(3-dimethylaminomethylcyclobutyl)-7H-pyrrolo[2,3-d]pyrimidin-4-ylamine;
5-(6-Chloro-2-pyridin-2-ylquinolin-7-yl)-7-(3-dimethylaminomethylcyclobutyl)-7H-pyrrolo[2,3-d]pyrimidin-4-ylamine;
5-(6-Chloro-2-thiophen-2-ylquinolin-7-yl)-7-(3-dimethylaminomethylcyclobutyl)-7H-pyrrolo[2,3-d]pyrimidin-4-ylamine;
{7-[4-Amino-7-(3-dimethylaminomethylcyclobutyl)-7H-pyrrolo[2,3-d]pyrimidin-5-yl]-6-chloroquinolin-2-yl}-phenylamine;
5-(6-Chloro-2-phenoxyquinolin-7-yl)-7-(3-dimethylaminomethylcyclobutyl)-7H-pyrrolo[2,3-d]pyrimidin-4-ylamine;
7-(3-Dimethylaminomethylcyclobutyl)-5-(8-fluoro-2-pyridin-2-ylquinolin-7-yl)-7H-pyrrolo[2,3-d]pyrimidin-4-ylamine;
7-(3-Dimethylaminomethylcyclobutyl)-5-(8-fluoro-2-phenylquinolin-7-yl)-7H-pyrrolo[2,3-d]pyrimidin-4-ylamine;

7-(3-Dimethylaminomethylcyclobutyl)-5-(8-fluoro-2-thiophen-2-ylquinolin-7-yl)-7H-pyrrolo[2,3-d]pyrimidin-4-ylamine;

7-(3-Dimethylaminomethylcyclobutyl)-5-(8-fluoro-2-phenoxyquinolin-7-yl)-7H-pyrrolo[2,3-d]pyrimidin-4-ylamine;

7-(3-Dimethylaminomethylcyclobutyl)-5-(4-methyl-2-phenylquinolin-7-yl)-7H-pyrrolo[2,3-d]pyrimidin-4-ylamine;

7-(3-Dimethylaminomethylcyclobutyl)-5-(4-methyl-2-pyridin-2-ylquinolin-7-yl)-7H-pyrrolo[2,3-d]pyrimidin-4-ylamine;

7-(3-Dimethylaminomethylcyclobutyl)-5-(4-methyl-2-thiophen-2-ylquinolin-7-yl)-7H-pyrrolo[2,3-d]pyrimidin-4-ylamine;

7-(3-Dimethylaminomethylcyclobutyl)-5-(4-methyl-2-phenoxyquinolin-7-yl)-7H-pyrrolo[2,3-d]pyrimidin-4-ylamine;

4-[4-Amino-5-(2-phenylquinolin-7-yl)-pyrrolo[2,3-d]pyrimidin-7-yl]-cyclohexanecarboxylic acid amide;

4-[4-Amino-5-(2-pyridin-2-ylquinolin-7-yl)-pyrrolo[2,3-d]pyrimidin-7-yl]-cyclohexanecarboxylic acid amide;

4-[4-Amino-5-(2-thiophen-2-ylquinolin-7-yl)-pyrrolo[2,3-d]pyrimidin-7-yl]-cyclohexanecarboxylic acid amide;

4-[4-Amino-5-(2-phenoxyquinolin-7-yl)-pyrrolo[2,3-d]pyrimidin-7-yl]-cyclohexanecarboxylic acid amide;

4-[4-Amino-5-(2-phenylquinolin-7-yl)-pyrrolo[2,3-d]pyrimidin-7-yl]-cyclohexanecarboxylic acid methylamide;

4-[4-Amino-5-(2-thiophen-2-ylquinolin-7-yl)-pyrrolo[2,3-d]pyrimidin-7-yl]-cyclohexanecarboxylic acid methylamide;

4-[4-Amino-5-(2-phenoxyquinolin-7-yl)-pyrrolo[2,3-d]pyrimidin-7-yl]-cyclohexanecarboxylic acid methylamide;

4-[4-Amino-5-(2-pyridin-2-ylquinolin-7-yl)-pyrrolo[2,3-d]pyrimidin-7-yl]-cyclohexanecarboxylic acid methylamide;

4-[4-Amino-5-(6-chloro-2-pyridin-2-ylquinolin-7-yl)-pyrrolo[2,3-d]pyrimidin-7-yl]-cyclohexanecarboxylic acid methylamide;

4-[4-Amino-5-(6-chloro-2-phenylquinolin-7-yl)-pyrrolo[2,3-d]pyrimidin-7-yl]-cyclohexanecarboxylic acid methylamide;

4-[4-Amino-5-(6-chloro-2-thiophen-2-ylquinolin-7-yl)-pyrrolo[2,3-d]pyrimidin-7-yl]-cyclohexanecarboxylic acid methylamide;

4-[4-Amino-5-(6-chloro-2-phenoxyquinolin-7-yl)-pyrrolo[2,3-d]pyrimidin-7-yl]-cyclohexanecarboxylic acid methylamide;

4-[4-Amino-5-(6-chloro-2-pyridin-2-ylquinolin-7-yl)-pyrrolo[2,3-d]pyrimidin-7-yl]-cyclohexanecarboxylic acid amide;

4-[4-Amino-5-(6-chloro-2-phenylquinolin-7-yl)-pyrrolo[2,3-d]pyrimidin-7-yl]-cyclohexanecarboxylic acid amide;

4-[4-Amino-5-(6-chloro-2-thiophen-2-ylquinolin-7-yl)-pyrrolo[2,3-d]pyrimidin-7-yl]-cyclohexanecarboxylic acid amide;

4-[4-Amino-5-(6-chloro-2-phenoxyquinolin-7-yl)-pyrrolo[2,3-d]pyrimidin-7-yl]-cyclohexanecarboxylic acid amide;

7-(4-Aminomethylcyclohexyl)-5-(2-thiophen-2-ylquinolin-7-yl)-7H-pyrrolo[2,3-d]pyrimidin-4-ylamine;

7-(4-Aminomethylcyclohexyl)-5-(2-phenylquinolin-7-yl)-7H-pyrrolo[2,3-d]pyrimidin-4-ylamine;

7-(4-Aminomethylcyclohexyl)-5-(2-phenoxyquinolin-7-yl)-7H-pyrrolo[2,3-d]pyrimidin-4-ylamine;

7-(4-Aminomethylcyclohexyl)-5-(2-pyridin-2-ylquinolin-7-yl)-7H-pyrrolo[2,3-d]pyrimidin-4-ylamine;

7-(4-Aminomethylcyclohexyl)-5-(6-chloro-2-thiophen-2-ylquinolin-7-yl)-7H-pyrrolo[2,3-d]pyrimidin-4-ylamine;

7-(4-Aminomethylcyclohexyl)-5-(6-chloro-2-pyridin-2-ylquinolin-7-yl)-7H-pyrrolo[2,3-d]pyrimidin-4-ylamine;

7-(4-Aminomethylcyclohexyl)-5-(6-chloro-2-phenoxyquinolin-7-yl)-7H-pyrrolo[2,3-d]pyrimidin-4-ylamine;

7-(4-Aminomethylcyclohexyl)-5-(6-chloro-2-phenylquinolin-7-yl)-7H-pyrrolo[2,3-d]pyrimidin-4-ylamine;

7-(4-Aminomethylcyclohexyl)-5-(4-methyl-2-phenylquinolin-7-yl)-7H-pyrrolo[2,3-d]pyrimidin-4-ylamine;

7-(4-Aminomethylcyclohexyl)-5-(4-methyl-2-thiophen-2-ylquinolin-7-yl)-7H-pyrrolo[2,3-d]pyrimidin-4-ylamine;

7-(4-Aminomethylcyclohexyl)-5-(4-methyl-2-phenoxyquinolin-7-yl)-7H-pyrrolo[2,3-d]pyrimidin-4-ylamine;

7-(4-Aminomethylcyclohexyl)-5-(4-methyl-2-pyridin-2-ylquinolin-7-yl)-7H-pyrrolo[2,3-d]pyrimidin-4-ylamine;

1-(4-Aminomethylcyclohexyl)-3-(2-thiophen-2-ylquinolin-7-yl)-1H-pyrazolo[3,4-d]pyrimidin-4-ylamine;

1-(4-Aminomethylcyclohexyl)-3-(2-pyridin-2-yl-quinolin-7-yl)-1H-pyrazolo[3,4-d]pyrimidin-4-ylamine;

1-(4-Aminomethylcyclohexyl)-3-(2-phenoxyquinolin-7-yl)-1H-pyrazolo[3,4-d]pyrimidin-4-ylamine;

1-(4-Aminomethylcyclohexyl)-3-(2-phenylquinolin-7-yl)-1H-pyrazolo[3,4-d]pyrimidin-4-ylamine;

1-(4-Aminomethylcyclohexyl)-3-(6-chloro-2-phenylquinolin-7-yl)-1H-pyrazolo[3,4-d]pyrimidin-4-ylamine;

1-(4-Aminomethylcyclohexyl)-3-(6-chloro-2-pyridin-2-ylquinolin-7-yl)-1H-pyrazolo[3,4-d]pyrimidin-4-ylamine;

1-(4-Aminomethylcyclohexyl)-3-(6-chloro-2-thiophen-2-ylquinolin-7-yl)-1H-pyrazolo[3,4-d]pyrimidin-4-ylamine;

1-(4-Aminomethylcyclohexyl)-3-(6-chloro-2-phenoxyquinolin-7-yl)-1H-pyrazolo[3,4-d]pyrimidin-4-ylamine;

1-(4-Aminomethylcyclohexyl)-3-(4-methyl-2-thiophen-2-ylquinolin-7-yl)-1H-pyrazolo[3,4-d]pyrimidin-4-ylamine;

1-(4-Aminomethylcyclohexyl)-3-(4-methyl-2-pyridin-2-ylquinolin-7-yl)-1H-pyrazolo[3,4-d]pyrimidin-4-ylamine;

1-(4-Aminomethylcyclohexyl)-3-(4-methyl-2-phenoxyquinolin-7-yl)-1H-pyrazolo[3,4-d]pyrimidin-4-ylamine;

1-(4-Aminomethylcyclohexyl)-3-(4-methyl-2-phenylquinolin-7-yl)-1H-pyrazolo[3,4-d]pyrimidin-4-ylamine;

1-(4-Aminomethylcyclohexyl)-3-(8-fluoro-2-thiophen-2-ylquinolin-7-yl)-1H-pyrazolo[3,4-d]pyrimidin-4-ylamine;

1-(4-Aminomethylcyclohexyl)-3-(8-fluoro-2-phenylquinolin-7-yl)-1H-pyrazoio[3,4-d]pyrimidin-4-ylamine;

1-(4-Aminomethylcyclohexyl)-3-(8-fluoro-2-phenoxyquinolin-7-yl)-1H-pyrazolo[3,4-d]pyrimidin-4-ylamine;

1-(4-Aminomethylcyclohexyl)-3-(8-fluoro-2-pyridin-2-ylquinolin-7-yl)-1H-pyrazolo[3,4-d]pyrimidin-4-ylamine;

4-[4-Amino-3-(2-pyridin-2-ylquinolin-7-yl)-pyrazolo[3,4-d]pyrimidin-1-yl]-cyclohexanecarboxylic acid amide;

4-[4-Amino-3-(2-phenylquinolin-7-yl)-pyrazolo[3,4-d]pyrimidin-1-yl]-cyclohexanecarboxylic acid amide;

4-[4-Amino-3-(2-thiophen-2-ylquinolin-7-yl)-pyrazolo[3,4-d]pyrimidin-1-yl]-cyclohexanecarboxylic acid amide;

4-[4-Amino-3-(2-phenoxyquinolin-7-yl)-pyrazolo[3,4-d]pyrimidin-1-yl]-cyclohexanecarboxylic acid amide;

4-[4-Amino-3-(6-chloro-2-phenylquinolin-7-yl)-pyrazolo[3,4-d]pyrimidin-1-yl]-cyclohexanecarboxylic acid amide;

4-[4-Amino-3-(6-chloro-2-pyridin-2-ylquinolin-7-yl)-pyrazolo[3,4-d]pyrimidin-1-yl]-cyclohexanecarboxylic acid amide;

4-[4-Amino-3-(6-chloro-2-thiophen-2-ylquinolin-7-yl)-pyrazolo[3,4-d]pyrimidin-1-yl]-cyclohexanecarboxylic acid amide;
4-[4-Amino-3-(6-chloro-2-phenoxyquinolin-7-yl)-pyrazolo[3,4-d]pyrimidin-1-yl]-cyclohexanecarboxylic acid amide;
4-[4-Amino-3-(8-fluoro-2-phenylquinolin-7-yl)-pyrazolo[3,4-d]pyrimidin-1-yl]-cyclohexanecarboxylic acid amide;
4-[4-Amino-3-(6-chloro-2-thiophen-2-ylquinolin-7-yl)-pyrazolo[3,4-d]pyrimidin-1-yl]-cyclohexanecarboxylic acid amide;
4-[4-Amino-3-(8-fluoro-2-pyridin-2-ylquinolin-7-yl)-pyrazolo[3,4-d]pyrimidin-1-yl]-cyclohexanecarboxylic acid amide;
4-[4-Amino-3-(8-fluoro-2-phenoxyquinolin-7-yl)-pyrazolo[3,4-d]pyrimidin-1-yl]-cyclohexanecarboxylic acid amide;
4-[4-Amino-3-(4-methyl-2-phenylquinolin-7-yl)-pyrazolo[3,4-d]pyrimidin-1-yl]-cyclohexanecarboxylic acid amide;
4-[4-Amino-3-(4-methyl-2-thiophen-2-ylquinolin-7-yl)-pyrazolo[3,4-d]pyrimidin-1-yl]-cyclohexanecarboxylic acid amide;
4-[4-Amino-3-(4-methyl-2-pyridin-2-ylquinolin-7-yl)-pyrazolo[3,4-d]pyrimidin-1-yl]-cyclohexanecarboxylic acid amide;
4-[4-Amino-3-(4-methyl-2-phenoxyquinolin-7-yl)-pyrazolo[3,4-d]pyrimidin-1-yl]-cyclohexanecarboxylic acid amide;
4-[4-Amino-3-(2-pyridin-2-ylquinolin-7-yl)-pyrazolo[3,4-d]pyrimidin-1-yl]-cyclohexanecarboxylic acid methylamide;
4-[4-Amino-3-(2-phenylquinolin-7-yl)-pyrazolo[3,4-d]pyrimidin-1-yl]-cyclohexanecarboxylic acid methylamide;
4-[4-Amino-3-(2-thiophen-2-ylquinolin-7-yl)-pyrazolo[3,4-d]pyrimidin-1-yl]-cyclohexanecarboxylic acid methylamide;
4-[4-Amino-3-(2-phenoxyquinolin-7-yl)-pyrazolo[3,4-d]pyrimidin-1-yl]-cyclohexanecarboxylic acid methylamide;
4-[4-Amino-3-(6-chloro-2-phenylquinolin-7-yl)-pyrazolo[3,4-d]pyrimidin-1-yl]-cyclohexanecarboxylic acid methylamide;
4-[4-Amino-3-(6-chloro-2-pyridin-2-ylquinolin-7-yl)-pyrazolo[3,4-d]pyrimidin-1-yl]-cyclohexanecarboxylic acid methylamide;
4-[4-Amino-3-(6-chloro-2-thiophen-2-ylquinolin-7-yl)-pyrazolo[3,4-d]pyrimidin-1-yl]-cyclohexanecarboxylic acid methylamide;
4-[4-Amino-3-(6-chloro-2-phenoxyquinolin-7-yl)-pyrazolo[3,4-d]pyrimidin-1-yl]-cyclohexanecarboxylic acid methylamide;
4-[4-Amino-3-(8-fluoro-2-phenylquinolin-7-yl)-pyrazolo[3,4-d]pyrimidin-1-yl]-cyclohexanecarboxylic acid methylamide;
4-[4-Amino-3-(6-chloro-2-thiophen-2-ylquinolin-7-yl)-pyrazolo[3,4-d]pyrimidin-1-yl]-cyclohexanecarboxylic acid methylamide;
4-[4-Amino-3-(8-fluoro-2-pyridin-2-ylquinolin-7-yl)-pyrazolo[3,4-d]pyrimidin-1-yl]-cyclohexanecarboxylic acid methylamide;
4-[4-Amino-3-(8-fluoro-2-phenoxyquinolin-7-yl)-pyrazolo[3,4-d]pyrimidin-1-yl]-cyclohexanecarboxylic acid methylamide;
4-[4-Amino-3-(4-methyl-2-phenylquinolin-7-yl)-pyrazolo[3,4-d]pyrimidin-1-yl]-cyclohexanecarboxylic acid methylamide;
4-[4-Amino-3-(4-methyl-2-thiophen-2-ylquinolin-7-yl)-pyrazolo[3,4-d]pyrimidin-1-yl]-cyclohexanecarboxylic acid methylamide;
4-[4-Amino-3-(4-methyl-2-pyridin-2-ylquinolin-7-yl)-pyrazolo[3,4-d]pyrimidin-1-yl]-cyclohexanecarboxylic acid methylamide;
4-[4-Amino-3-(4-methyl-2-phenoxyquinolin-7-yl)-pyrazolo[3,4-d]pyrimidin-1-yl]-cyclohexanecarboxylic acid methylamide;
1-Cyclobutyl-3-(2-thiophen-2-ylquinolin-7-yl)-1H-pyrazolo[3,4-d]pyrimidin-4-ylamine;
1-Cyclobutyl-3-(2-phenylquinolin-7-yl)-1H-pyrazolo[3,4-d]pyrimidin-4-ylamine;
1-Cyclobutyl-3-(2-phenoxyquinolin-7-yl)-1H-pyrazolo[3,4-d]pyrimidin-4-ylamine;
1-Cyclobutyl-3-(2-pyridin-2-ylquinolin-7-yl)-1H-pyrazolo[3,4-d]pyrimidin-4-ylamine;
3-(6-Chloro-2-phenylquinolin-7-yl)-1-cyclobutyl-1H-pyrazolo[3,4-d]pyrimidin-4-ylamine;
3-(6-Chloro-2-pyridin-2-ylquinolin-7-yl)-1-cyclobutyl-1H-pyrazolo[3,4-d]pyrimidin-4-ylamine;
3-(6-Chloro-2-thiophen-2-ylquinolin-7-yl)-1-cyclobutyl-1H-pyrazolo[3,4-d]pyrimidin-4-ylamine;
3-(6-Chloro-2-phenoxyquinolin-7-yl)-1-cyclobutyl-1H-pyrazolo[3,4-d]pyrimidin-4-ylamine;
1-Cyclobutyl-3-(4-methyl-2-thiophen-2-ylquinolin-7-yl)-1H-pyrazolo[3,4-d]pyrimidin-4-ylamine;
1-Cyclobutyl-3-(4-methyl-2-pyridin-2-ylquinolin-7-yl)-1H-pyrazolo[3,4-d]pyrimidin-4-ylamine;
1-Cyclobutyl-3-(4-methyl-2-phenylquinolin-7-yl)-1H-pyrazolo[3,4-d]pyrimidin-4-ylamine;
1-Cyclobutyl-3-(4-methyl-2-phenoxyquinolin-7-yl)-1H-pyrazolo[3,4-d]pyrimidin-4-ylamine;
3-[4-Amino-3-(2-phenylquinolin-7-yl)-pyrazolo[3,4-d]pyrimidin-1-yl]-cyclobutanol;
3-[4-Amino-3-(2-pyridin-2-ylquinolin-7-yl)-pyrazolo[3,4-d]pyrimidin-1-yl]-cyclobutanol;
3-[4-Amino-3-(2-thiophen-2-ylquinolin-7-yl)-pyrazolo[3,4-d]pyrimidin-1-yl]-cyclobutanol;
3-[4-Amino-3-(2-phenoxyquinolin-7-yl)-pyrazolo[3,4-d]pyrimidin-1-yl]-cyclobutanol;
3-[4-Amino-3-(6-chloro-2-thiophen-2-ylquinolin-7-yl)-pyrazolo[3,4-d]pyrimidin-1-yl]-cyclobutanol;
3-[4-Amino-3-(6-chloro-2-pyridin-2-ylquinolin-7-yl)-pyrazolo[3,4-d]pyrimidin-1-yl]-cyclobutanol;
3-[4-Amino-3-(6-chloro-2-phenylquinolin-7-yl)-pyrazolo[3,4-d]pyrimidin-1-yl]-cyclobutanol;
3-[4-Amino-3-(6-chloro-2-phenoxyquinolin-7-yl)-pyrazolo[3,4-d]pyrimidin-1-yl]-cyclobutanol;
3-[4-Amino-3-(4-methyl-2-phenylquinolin-7-yl)-pyrazolo[3,4-d]pyrimidin-1-yl]-cyclobutanol;
3-[4-Amino-3-(4-methyl-2-pyridin-2-ylquinolin-7-yl)-pyrazolo[3,4-d]pyrimidin-1-yl]-cyclobutanol;
3-[4-Amino-3-(4-methyl-2-thiophen-2-ylquinolin-7-yl)-pyrazolo[3,4-d]pyrimidin-1-yl]-cyclobutanol;
3-[4-Amino-3-(4-methyl-2-phenoxyquinolin-7-yl)-pyrazolo[3,4-d]pyrimidin-1-yl]-cyclobutanol;
1-(3-Azetidin-1-ylmethylcyclobutyl)-3-(2-pyridin-2-ylquinolin-7-yl)-1H-pyrazolo[3,4-d]pyrimidin-4-ylamine;
1-(3-Azetidin-1-ylmethylcyclobutyl)-3-(2-phenylquinolin-7-yl)-1H-pyrazolo[3,4-d]pyrimidin-4-ylamine;
1-(3-Azetidin-1-ylmethylcyclobutyl)-3-(2-thiophen-2-ylquinolin-7-yl)-1H-pyrazolo[3,4-d]pyrimidin-4-ylamine;
1-(3-Azetidin-1-ylmethylcyclobutyl)-3-(2-phenoxyquinolin-7-yl)-1H-pyrazolo[3,4-d]pyrimidin-4-ylamine;

1-(3-Azetidin-1-ylmethylcyclobutyl)-3-(6-chloro-2-thiophen-2-ylquinolin-7-yl)-1H-pyrazolo[3,4-d]pyrimidin-4-ylamine;
1-(3-Azetidin-1-ylmethylcyclobutyl)-3-(6-chloro-2-phenylquinolin-7-yl)-1H-pyrazolo[3,4-d]pyrimidin-4-ylamine;
1-(3-Azetidin-1-ylmethylcyclobutyl)-3-(6-chloro-2-phenoxyquinolin-7-yl)-1H-pyrazolo[3,4-d]pyrimidin-4-ylamine;
1-(3-Azetidin-1-ylmethylcyclobutyl)-3-(6-chloro-2-pyridin-2-ylquinolin-7-yl)-1H-pyrazolo[3,4-d]pyrimidin-4-ylamine;
1-(3-Azetidin-1-ylmethylcyclobutyl)-3-(4-methyl-2-pyridin-2-ylquinolin-7-yl)-1H-pyrazolo[3,4-d]pyrimidin-4-ylamine;
1-(3-Azetidin-1-ylmethylcyclobutyl)-3-(4-methyl-2-phenylquinolin-7-yl)-1H-pyrazolo[3,4-d]pyrimidin-4-ylamine;
1-(3-Azetidin-1-ylmethylcyclobutyl)-3-(4-methyl-2-thiophen-2-ylquinolin-7-yl)-1H-pyrazolo[3,4-d]pyrimidin-4-ylamine;
1-(3-Azetidin-1-ylmethylcyclobutyl)-3-(4-methyl-2-phenoxyquinolin-7-yl)-1H-pyrazolo[3,4-d]pyrimidin-4-ylamine;
1-(3-Dimethylaminomethylcyclobutyl)-3-(2-phenylquinolin-7-yl)-1H-pyrazolo[3,4-d]pyrimidin-4-ylamine;
1-(3-Dimethylaminomethylcyclobutyl)-3-(2-thiophen-2-ylquinolin-7-yl)-1H-pyrazolo[3,4-d]pyrimidin-4-ylamine;
1-(3-Dimethylaminomethylcyclobutyl)-3-(2-pyridin-2-ylquinolin-7-yl)-H-pyrazolo[3,4-d]pyrimidin-4-ylamine;
1-(3-Dimethylaminomethylcyclobutyl)-3-(2-phenoxyquinolin-7-yl)-1H-pyrazolo[3,4-d]pyrimidin-4-ylamine;
3-(6-Chloro-2-phenylquinolin-7-yl)-1-(3-dimethylaminomethylcyclobutyl)-1H-pyrazolo[3,4-d]pyrimidin-4-ylamine;
3-(6-Chloro-2-thiophen-2-ylquinolin-7-yl)-1-(3-dimethylaminomethylcyclobutyl)-1H-pyrazolo[3,4-d]pyrimidin-4-ylamine;
3-(6-Chloro-2-phenoxyquinolin-7-yl)-1-(3-dimethylaminomethylcyclobutyl)-1H-pyrazolo[3,4-d]pyrimidin-4-ylamine;
3-(6-Chloro-2-pyridin-2-ylquinolin-7-yl)-1-(3-dimethylaminomethylcyclobutyl)-1H-pyrazolo[3,4-d]pyrimidin-4-ylamine;
1-(3-Dimethylaminomethylcyclobutyl)-3-(4-methyl-2-pyridin-2-ylquinolin-7-yl)-1H-pyrazolo[3,4-d]pyrimidin-4-ylamine;
1-(3-Dimethylaminomethylcyclobutyl)-3-(4-methyl-2-phenylquinolin-7-yl)-1H-pyrazolo[3,4-d]pyrimidin-4-ylamine;
1-(3-Dimethylaminomethylcyclobutyl)-3-(4-methyl-2-thiophen-2-ylquinolin-7-yl)-1H-pyrazolo[3,4-d]pyrimidin-4-ylamine;
1-(3-Dimethylaminomethylcyclobutyl)-3-(4-methyl-2-phenoxyquinolin-7-yl)-1H-pyrazolo[3,4-d]pyrimidin-4-ylamine;
1-(3-Dimethylaminomethylcyclobutyl)-3-(8-fluoro-2-phenylquinolin-7-yl)-1H-pyrazolo[3,4-d]pyrimidin-4-ylamine;
1-(3-Dimethylaminomethylcyclobutyl)-3-(8-fluoro-2-pyridin-2-ylquinolin-7-yl)-1H-pyrazolo[3,4-d]pyrimidin-4-ylamine;
1-(3-Dimethylaminomethylcyclobutyl)-3-(8-fluoro-2-thiophen-2-ylquinolin-7-yl)-1H-pyrazolo[3,4-d]pyrimidin-4-ylamine;
1-(3-Dimethylaminomethylcyclobutyl)-3-(8-fluoro-2-phenoxyquinolin-7-yl)-1H-pyrazolo[3,4-d]pyrimidin-4-ylamine;
3-Cyclobutyl-1-(3-phenylquinoxalin-6-yl)-imidazo[1,5-a]pyrazin-8-ylamine;
3-[8-Amino-1-(3-phenylquinoxalin-6-yl)-imidazo[1,5-a]pyrazin-3-yl]-cyclobutanol;
3-(3-Azetidin-1-ylmethylcyclobutyl)-1-(3-phenylquinoxalin-6-yl)-imidazo[1,5-a]pyrazin-8-ylamine;
4-[8-Amino-1-(3-phenylquinoxalin-6-yl)-imidazo[1,5-a]pyrazin-3-yl]-cyclohexanecarboxylic acid amide;
4-[8-Amino-1-(3-phenylquinoxalin-6-yl)-imidazo[1,5-a]pyrazin-3-yl]-cyclohexanecarboxylic acid methylamide;
4-[8-Amino-1-(2-phenylquinazolin-7-yl)-imidazo[1,5-a]pyrazin-3-yl]-cyclohexanecarboxylic acid amide;
4-[8-Amino-1-(2-phenylquinazolin-7-yl)-imidazo[1,5-a]pyrazin-3-yl]-cyclohexanecarboxylic acid methylamide;
3-Cyclobutyl-1-(2-phenylquinazolin-7-yl)-imidazo[1,5-a]pyrazin-8-ylamine;
3-[8-Amino-1-(2-phenylquinazolin-7-yl)-imidazo[1,5-a]pyrazin-3-yl]-cyclobutanol;
3-(3-Azetidin-1-ylmethylcyclobutyl)-1-(2-phenylquinazolin-7-yl)-imidazo[1,5-a]pyrazin-8-ylamine;
3-[3-(2-Methoxyethoxy)-cyclobutyl]-1-(2-phenylquinolin-7-yl)-imidazo[1,5-a]pyrazin-8-ylamine;
1-(6-Chloro-2-phenylquinolin-7-yl)-3-[3-(2-methoxyethoxy)-cyclobutyl]-imidazo[1,5-a]pyrazin-8-ylamine;
3-[3-(2-Methoxyethoxy)-cyclobutyl]-1-(4-methyl-2-phenylquinolin-7-yl)-imidazo[1,5-a]pyrazin-8-ylamine;
3-(1-Methyl-1,2,3,6-tetrahydropyridin-4-yl)-1-(2-phenylquinolin-7-yl)-imidazo[1,5-a]pyrazin-8-ylamine;
1-{4-[8-Amino-1-(2-phenylquinolin-7-yl)-imidazo[1,5-a]pyrazin-3-yl]-3,6-dihydro-2H-pyridin-1-yl}-ethanone;
3-Bicyclo[3.1.0]hex-6-yl-1-(2-phenylquinolin-7-yl)-imidazo[1,5-a]pyrazin-8-ylamine;
6-[8-Amino-1-(2-phenylquinolin-7-yl)-imidazo[1,5-a]pyrazin-3-yl]-bicyclo[3.1.0]hexan-3-ol;
7-Cyclobutyl-5-(2-phenylquinolin-7-yl)-imidazo[5,1-f][1,2,4]triazin-4-ylamine;
7-Cyclobutyl-5-(2-thiophen-2-ylquinolin-7-yl)-imidazo[5,1-f][1,2,4]triazin-4-ylamine;
7-Cyclobutyl-5-(2-phenoxyquinolin-7-yl)-imidazo[5,1-f][1,2,4]triazin-4-ylamine;
7-Cyclobutyl-5-(2-pyridin-2-ylquinolin-7-yl)-imidazo[5,1-f][1,2,4]triazin-4-ylamine;
3-[4-Amino-5-(2-phenylquinolin-7-yl)-imidazo[5,1-f][1,2,4]triazin-7-yl]-cyclobutanol;
3-[4-Amino-5-(2-thiophen-2-ylquinolin-7-yl)-imidazo[5,1-f][1,2,4]triazin-7-yl]-cyclobutanol;
3-[4-Amino-5-(2-phenoxyquinolin-7-yl)-imidazo[5,1-f][1,2,4]triazin-7-yl]-cyclobutanol;
3-[4-Amino-5-(2-pyridin-2-ylquinolin-7-yl)-imidazo[5,1-f][1,2,4]triazin-7-yl]-cyclobutanol;
7-(3-Azetidin-1-ylmethylcyclobutyl)-5-(2-phenylquinolin-7-yl)-imidazo[5,1-f][1,2,4]triazin-4-ylamine;
7-(3-Azetidin-1-ylmethylcyclobutyl)-5-(2-thiophen-2-ylquinolin-7-yl)-imidazo[5,1-f][1,2,4]triazin-4-ylamine;
7-(3-Azetidin-1-ylmethylcyclobutyl)-5-(2-phenoxyquinolin-7-yl)-imidazo[5,1-f][1,2,4]triazin-4-ylamine;
7-(3-Azetidin-1-ylmethylcyclobutyl)-5-(2-pyridin-2-ylquinolin-7-yl)-imidazo[5,1-f][1,2,4]triazin-4-ylamine;
7-(3-Dimethylaminomethylcyclobutyl)-5-(2-pyridin-2-ylquinolin-7-yl)-imidazo[5-f][1,2,4]triazin-4-ylamine;
7-(3-Dimethylaminomethylcyclobutyl)-5-(2-thiophen-2-ylquinolin-7-yl)-imidazo[5,1-f][1,2,4]triazin-4-ylamine;
7-(3-Dimethylaminomethylcyclobutyl)-5-(2-phenylquinolin-7-yl)-imidazo[5,1-f][1,2,4]triazin-4-ylamine;

7-(3-Dimethylaminomethylcyclobutyl)-5-(2-phenoxyquinolin-7-yl)-imidazo[5,1-f][1,2,4]triazin-4-ylamine;
4-[4-Amino-5-(2-phenylquinolin-7-yl)-imidazo[5,1-f][1,2,4]triazin-7-yl]-cyclohexanecarboxylic acid amide;
4-[4-Amino-5-(2-thiophen-2-ylquinolin-7-yl)-imidazo[5,1-f][1,2,4]triazin-7-yl]-cyclohexanecarboxylic acid amide;
4-[4-Amino-5-(2-phenoxyquinolin-7-yl)-imidazo[5,1-f][1,2,4]triazin-7-yl]-cyclohexanecarboxylic acid amide;
4-[4-Amino-5-(2-phenylquinolin-7-yl)-imidazo[5,1-f][1,2,4]triazin-7-yl]-cyclohexanecarboxylic acid methylamide;
4-[4-Amino-5-(2-thiophen-2-ylquinolin-7-yl)-imidazo[5,1-f][1,2,4]triazin-7-yl]-cyclohexanecarboxylic acid methylamide;
4-[4-Amino-5-(2-phenoxyquinolin-7-yl)-imidazo[5,1-f][1,2,4]triazin-7-yl]-cyclohexanecarboxylic acid methylamide;
7-(4-Aminomethylcyclohexyl)-5-(2-phenylquinolin-7-yl)-imidazo[5,1-f][1,2,4]triazin-4-ylamine;
7-(4-Aminomethylcyclohexyl)-5-(2-thiophen-2-ylquinolin-7-yl)-imidazo[5,1-f][1,2,4]triazin-4-ylamine;
7-(4-Aminomethylcyclohexyl)-5-(2-phenoxyquinolin-7-yl)-imidazo[5,1-f][1,2,4]triazin-4-ylamine;
7-(4-Aminomethylcyclohexyl)-5-(6-chloro-2-phenylquinolin-7-yl)-imidazo[5,1-f][1,2,4]triazin-4-ylamine;
4-[4-Amino-5-(6-chloro-2-phenylquinolin-7-yl)-imidazo[5,1-f][1,2,4]triazin-7-yl]-cyclohexanecarboxylic acid amide;
4-[4-Amino-5-(6-chloro-2-phenylquinolin-7-yl)-imidazo[5,1-f][1,2,4]triazin-7-yl]-cyclohexanecarboxylic acid methylamide;
5-(6-Chloro-2-phenylquinolin-7-yl)-7-cyclobutylimidazo[5,1-f][1,2,4]triazin-4-ylamine;
3-[4-Amino-5-(6-chloro-2-phenylquinolin-7-yl)-imidazo[5,1-f][1,2,4]triazin-7-yl]-cyclobutanol;
7-(3-Azetidin-1-ylmethylcyclobutyl)-5-(6-chloro-2-phenylquinolin-7-yl)-imidazo[5,1-f][1,2,4]triazin-4-ylamine;
7-(3-Azetidin-1-ylmethylcyclobutyl)-5-(2-phenylquinolin-7-yl)-5H-pyrrolo[3,2-d]pyrimidin-4-ylamine;
3-[4-Amino-5-(2-phenylquinolin-7-yl)-5H-pyrrolo[3,2-d]pyrimidin-7-yl]-cyclobutanol;
7-Cyclobutyl-5-(2-phenylquinolin-7-yl)-5H-pyrrolo[3,2-d]pyrimidin-4-ylamine;
7-Phenyl-5-(2-phenylquinolin-7-yl)-7H-pyrrolo[2,3-d]pyrimidin-4-ylamine;
3-Isopropyl-1-(2-phenylquinolin-7-yl)-imidazo[1,5-a]pyrazin-8-ylamine;
3-tert-Butyl-1-(2-phenylquinolin-7-yl)-imidazo[1,5-a]pyrazin-8-ylamine;
5-[8-Amino-1-(2-phenylquinolin-7-yl)-imidazo[1,5-a]pyrazin-3-yl]-pyrrolidin-3-ol;
3-Cyclobutyl-1-(2-phenylquinolin-7-yl)-2H-imidazo[1,5-a]pyrazin-8-ylamine;
trans-4-[8-Amino-1-(2-phenylquinolin-7-yl)-imidazo[1,5-a]pyrazin-3-yl]-cyclohexanecarboxylic acid amide;
trans-4-[8-Amino-1-(2-phenylquinolin-7-yl)-imidazo[1,5-a]pyrazin-3-yl]-cyclohexanecarboxylic acid methyl ester;
trans-4-[8-Amino-1-(2-phenylquinolin-7-yl)-imidazo[1,5-a]pyrazin-3-yl]-cyclohexanecarboxylic acid;
trans-4-[8-Amino-1-(2-phenylquinolin-7-yl)-imidazo[1,5-a]pyrazin-3-yl]-cyclohexanecarboxylic acid methylamide;
trans-{4-[8-Amino-1(2-phenylquinolin-7-yl)-imidazo[1,5-a]pyrazin-3-yl]-cyclohexyl}-methanol;
trans-2-{4-[8-Amino-1-(2-phenylquinolin-7-yl)-imidazo[1,5-a]pyrazin-3-yl]-cyclohexylmethyl}-isoindole-1,3-dione;
3-(4-Aminomethyl-cyclohexyl)-1-(2-phenyl-quinolin-7-yl)-imidazo[1,5-a]pyrazin-8-ylamine;
trans-3-(4-Aminomethylcyclohexyl)-1-(2-phenylquinolin-7-yl)-imidazo[1,5-a]pyrazin-8-ylamine;
3-(3-Azetidin-1-ylmethyl-cyclobutyl)-1-(2-phenyl-quinolin-7-yl)-imidazo[1,5-a]pyrazin-8-ylamine;
3-(3-Azetidin-1-ylmethylcyclobutyl)-1-(2-phenylquinolin-7-yl)-imidazo[1,5-a]pyrazin-8-ylamine;
cis-3-(3-Azetidin-1-ylmethylcyclobutyl)-1-(2-phenylquinolin-7-yl)-imidazo[1,5-a]pyrazin-8-ylamine;
{3-[8-Amino-1-(2-phenylquinolin-7-yl)-imidazo[1,5-a]pyrazin-3-yl]-cyclobutyl}-methanol;
or a pharmaceutically acceptable salt thereof.

The compounds of Formula I can be prepared according to known methods, such as disclosed in WO2005/097800.

The present invention includes a pharmaceutical composition comprising at least one anti-cancer agent, at least one pharmaceutically acceptable carrier, and at least one IGFR inhibitor represented by Formula I as described herein.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

In practice, the compounds represented by Formula I, or a prodrug, or a metabolite, or a pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous).

The present invention includes a pharmaceutical composition comprising at least one anti-cancer agent such as an IRS1 agent, such as an EGFR inhibitor, optionally at least one pharmaceutically acceptable carrier, and at least one IGFR inhibitor as defined and described above and hereinbelow:

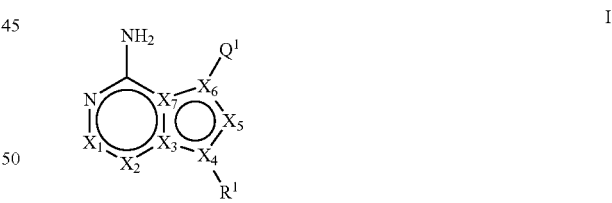

I or a pharmaceutically acceptable salt thereof, wherein:
$X_1$, $X_2$, $X_4$, $X_6$, and $X_7$ are C;
$X_3$ and $X_5$ are N;

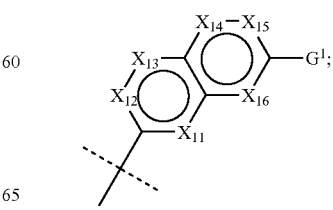

$Q^1$ is $X_{11}$, $X_{12}$, $X_{13}$, $X_{14}$, and $X_{15}$ are C;

$X_{16}$ is N; and $R^1$ is cycloC$_{3-10}$alkyl optionally substituted by one or more independent G$^{11}$ substituents; and the remainder of the substituents are as defined as above.

The present invention includes a pharmaceutical composition comprising an anti-cancer agent, a pharmaceutically acceptable carrier, and an IGFR inhibitor represented by Formula I, wherein the anti-cancer agent is an EGFR kinase inhibitor, MEK inhibitor, VEGFR inhibitor, anti-VEGFR2 antibody, KDR antibody, AKT inhibitors, PDK-1 inhibitors, PI3K inhibitors, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor inhibitor, VEGF-3 receptor antagonist, Raf protein kinase inhibitor, angiogenesis inhibitor, Erb2 inhibitor, mTOR inhibitor, IGF-1R antibody, NFkB inhibitor, proteosome inhibitor, chemotherapy agent, or glucose reduction agent.

The present invention includes a pharmaceutical composition comprising an anti-cancer agent, a pharmaceutically acceptable carrier, and an IGFR inhibitor represented by Formula I, wherein the anti-cancer agent is ARRY-142886, PD-184352, ZD-6474, IMC-1121b, CDP-791, imatinib, sunitinib malate, sorafenib, PTK-787, lapatinib, sirolimus, temsirolimus, everolimus, CP-751871, RAV-12, IMC-A12, 19D12, PS-1145, ororbortezomib.

The present invention includes a pharmaceutical composition comprising an anti-cancer agent, a pharmaceutically acceptable carrier, and an IGFR inhibitor represented by Formula I, wherein the anti-cancer agent is an EGFR kinase inhibitor.

The present invention includes a pharmaceutical composition comprising an anti-cancer agent, a pharmaceutically acceptable carrier, and an IGFR inhibitor represented by Formula I, wherein the anti-cancer agent is an EGFR kinase inhibitor, wherein the EGFR kinase inhibitor is erlotinib, cetuximab, gefitinib, or a salt thereof.

The present invention includes a pharmaceutical composition comprising an anti-cancer agent, a pharmaceutically acceptable carrier, and an IGFR inhibitor represented by Formula I, wherein the anti-cancer agent is an EGFR kinase inhibitor, wherein the EGFR kinase inhibitor is erlotinib or a salt thereof.

The present invention includes a pharmaceutical composition comprising an anti-cancer agent, a pharmaceutically acceptable carrier, and an IGFR inhibitor represented by Formula I

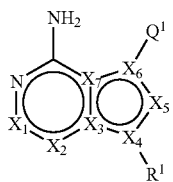

I or a pharmaceutically acceptable salt thereof, wherein:

$X_1$, $X_2$, $X_4$, $X_6$, and $X_7$ are C;

$X_3$ and $X_5$ are N;

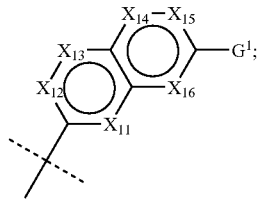

$Q^1$ is $X_{11}$, $X_{12}$, $X_{13}$, $X_{14}$, and $X_{15}$ are C;

$X_{16}$ is N; and $R^1$ is cycloC$_{3-10}$alkyl optionally substituted by one or more independent G$^{11}$ substituents; and the remainder of the substituents are as defined as above; and wherein the EGFR kinase inhibitor is erlotinib or a salt thereof.

The present invention includes a pharmaceutical composition comprising an anti-cancer agent, a pharmaceutically acceptable carrier, and an IGFR inhibitor represented by Formula I, wherein the anti-cancer agent is an EGFR kinase inhibitor, wherein the EGFR kinase inhibitor is erlotinib or a salt thereof, further comprising one or more other anti-cancer agents.

The present invention includes a pharmaceutical composition comprising an anti-cancer agent, a pharmaceutically acceptable carrier, and an IGFR inhibitor represented by Formula I, wherein the anti-cancer agent is an EGFR kinase inhibitor, wherein the EGFR kinase inhibitor is erlotinib or a salt thereof, further comprising one or more other anti-cancer agents, wherein said other anti-cancer agent is an alkylating drug, anti-metabolite, microtubule inhibitor, podophyllotoxin, antibiotic, nitrosourea, hormone therapy, kinase inhibitor, activator of tumor cell apoptosis, antiangiogenic agent, mitotic inhibitor, intercalating antibiotic, growth factor inhibitor, cell cycle inhibitor, an enzyme, a topoisomerase inhibitor, biological response modifier, an anti-hormonal agent, or an anti-androgen.

The present invention includes a pharmaceutical composition comprising an anti-cancer agent, a pharmaceutically acceptable carrier, and an IGFR inhibitor represented by Formula I, wherein the anti-cancer agent is a glucose reduction agent.

The present invention includes a pharmaceutical composition comprising an anti-cancer agent, a pharmaceutically acceptable carrier, and an IGFR inhibitor represented by Formula I, wherein the anti-cancer agent is a glucose reduction agent, wherein the glucose reduction agent is a PPARα agonist, PPARγ agonist, PPAR dual agonist, biguanide, glitazone, or metformin.

The present invention includes a pharmaceutical composition comprising an anti-cancer agent, a pharmaceutically acceptable carrier, and an IGFR inhibitor represented by Formula I, wherein the anti-cancer agent is a glucose reduction agent, wherein the glucose reduction agent is a PPARα agonist, PPARγ agonist, PPAR dual agonist, biguanide, glitazone, or metformin, further comprising one or more other anti-cancer agents.

The present invention includes a pharmaceutical composition comprising an anti-cancer agent, a pharmaceutically acceptable carrier, and an IGFR inhibitor represented by Formula I, wherein the anti-cancer agent is a glucose reduction agent, wherein the glucose reduction agent is a PPARα agonist, PPARγ agonist, PPAR dual agonist, biguanide, glitazone, or metformin, further comprising one or more other anti-cancer agents, wherein said other anti-cancer agent is an alkylating drug, anti-metabolite, microtubule inhibitor, podophyllotoxin, antibiotic, nitrosourea, hormone therapy, kinase inhibitor, activator of tumor cell apoptosis, antiangiogenic agent, mitotic inhibitor, intercalating antibiotic, growth factor inhibitor, cell cycle inhibitor, an enzyme, a topoisomerase inhibitor, biological response modifier, an anti-hormonal agent, or an anti-androgen.

A preferred example of an EGFR kinase inhibitor that can be used in practicing this invention is the compound erlotinib HCl (also known as TARCEVA™).

According to one aspect of the invention, an agent which inhibits serine phosphorylation of IRS1 that can be used in practicing this invention is an EGFR kinase inhibitor.

According to a second aspect of the present invention, an agent which inhibits serine phosphorylation of IRS1 is erlotinib HCl (TARCEVA®, OSI Pharmaceuticals, Inc. Melville, N.Y.).

According to another aspect of the present invention, the agent which inhibits serine phosphorylation of IRS1 that can be used in practicing this invention is a pAkt/MAPK/IRS-1 serine phosphorylation/pS-IRS-1 inhibitor.

According to another aspect of the present invention, the agent which inhibits serine phosphorylation of IRS1 that can be used in practicing this invention is a MEK inhibitor.

According to another aspect of the present invention, the agent which inhibits serine phosphorylation of IRS1 that can be used in practicing this invention is an inhibitor of the MAPK pathway.

According to another aspect of the present invention, the agent which inhibits serine phosphorylation of IRS1 that can be used in practicing this invention is a Raf inhibitor.

According to another aspect of the present invention, the agent which inhibits serine phosphorylation of IRS1 that can be used in practicing this invention is a Ras inhibitor.

According to another aspect of the present invention, the agent which inhibits serine phosphorylation of IRS1 that can be used in practicing this invention is a PKC inhibitor.

The present invention includes a method for treating cancer in a patient, comprising administering to said patient simultaneously or sequentially (i) a therapeutically or sub-therapeutically effective amount of an anti-cancer agent such as an IRS1 agent such as an EGFR inhibitor, or a pharmaceutically salt thereof; and (ii) a therapeutically or sub-therapeutically effective amount an IGFR inhibitor disclosed herein or represented by Formula I in any of its definitions herein.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I

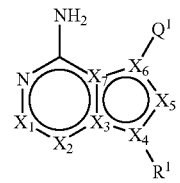

or a pharmaceutically acceptable salt thereof, wherein:
$X_1$, $X_2$, $X_4$, $X_6$, and $X_7$ are C;
$X_3$ and $X_5$ are N;

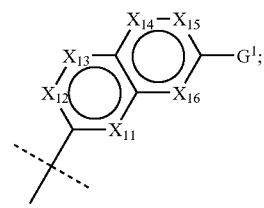

$Q^1$ is
$X_{11}$, $X_{12}$, $X_{13}$, $X_{14}$, and $X_{15}$ are C;
$X_{16}$ is N; and
$R^1$ is cycloC$_{3-10}$alkyl optionally substituted by one or more independent $G^{11}$ substituents, and the remaining substituents are as defined above, and wherein the anticancer agent is erlotinib or a salt thereof.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, Proteosome inhibitor, chemotherapy agent, or glucose reduction agent.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is ARRY-142886, PD-184352, ZD-6474, IMC-1121b, CDP-791, imatinib, sunitinib malate, sorafenib, PTK-787, lapatinib, sirolimus, temsirolimus, everolimus, CP-751871, RAV-12, IMC-A12, 19D12, PS-1145, orbortezomib.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib, cetuximab, gefitinib, or a salt thereof.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor selected from any of those described and defined herein and wherein the anti-cancer agent can be erlotinib or a salt thereof or other anti-cancer agent.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, wherein the cancer is colorectal cancer, non-small cell lung carcinoma, pancreatic cancer, head and neck cancer, breast cancer, or neuroblastoma.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, wherein the cancer is colorectal cancer or non-small cell lung carcinoma.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, and wherein erlotinib and the IGFR inhibitor are co-administered to the patient in the same formulation.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, and wherein erlotinib and the IGFR inhibitor are co-administered to the patient in different formulations.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, and wherein erlotinib and the IGFR inhibitor are co-administered to the patient by the same route.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, and wherein erlotinib and the IGFR inhibitor are co-administered to the patient by different routes.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, and wherein erlotinib is administered to the patient by parenteral or oral administration.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, and wherein the IGFR inhibitor is administered to the patient by parenteral administration.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, additionally comprising one or more other anti-cancer agents.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is an EGFR kinase inhibitor, and wherein the EGFR kinase inhibitor is erlotinib or a salt thereof, and wherein the patient is a human that is being treated for cancer, additionally comprising one or more other anti-cancer agents, wherein the other anti-cancer agents are selected from an alkylating agent, cyclophosphamide, chlorambucil, cisplatin, busulfan, melphalan, carmustine, streptozotocin, triethylenemelamine, mitomycin C, an anti-metabolite, methotrexate, etoposide, 6-mercaptopurine, 6-thioguanine, cytarabine, 5-fluorouracil, raltitrexed, capecitabine, dacarbazine, an antibiotic, actinomycin D, doxorubicin, daunorubicin, bleomycin, mithramycin, an alkaloid, vinblastine, paclitaxel, a glucocorticoid, dexamethasone, a corticosteroid, prednisone, a nucleoside enzyme inhibitors, hydroxyurea, an amino acid depleting enzyme, asparaginase, folinic acid, leucovorin, and a folic acid derivative.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is a MEK inhibitor.

The present invention includes a method for treating cancer in a patient, comprising administering to said patient simultaneously or sequentially (i) a therapeutically or sub-therapeutically effective amount of an anti-cancer agent, or a pharmaceutically salt thereof; and (ii) a therapeutically or sub-therapeutically effective amount an IGFR inhibitor represented by Formula I, wherein the anti-cancer agent is a MEK inhibitor, wherein the MEK inhibitor is ARRY-142886, PD-184352, or PD-98059.

The present invention includes the use of a composition comprising an anti-cancer agent, a pharmaceutically acceptable carrier, and an IGFR inhibitor compound of Formula I for manufacturing a medicament for treating cancer in a mammal.

The present invention includes the use of a composition comprising an anti-cancer agent, a pharmaceutically acceptable carrier, and an IGFR inhibitor compound of Formula I for manufacturing a medicament for treating cancer in a mammal, wherein the cancer is selected from colorectal cancer, non small cell lung cancer, pancreatic cancer, head and neck cancer, breast cancer, or neuroblastoma.

The present invention includes the use of a composition comprising an anti-cancer agent, a pharmaceutically acceptable carrier, and an IGFR inhibitor compound of Formula I, in combination with at least one other anti-cancer agent, for manufacturing a medicament for treating cancer in a mammal.

The present invention includes the use of a composition comprising an anti-cancer agent, a pharmaceutically acceptable carrier, and an IGFR inhibitor compound of Formula I, in combination with at least one other anti-cancer agent, for manufacturing a medicament for treating cancer in a mammal wherein the at least one other anti-cancer agent is selected from an alkylating agent, cyclophosphamide, chlorambucil, cisplatin, busulfan, melphalan, carmustine, streptozotocin, triethylenemelamine, mitomycin C, an anti-metabolite, methotrexate, etoposide, 6-mercaptopurine, 6-thioguanine, cytarabine, 5-fluorouracil, raltitrexed, capecitabine, dacarbazine, an antibiotic, actinomycin D, doxorubicin, daunorubicin, bleomycin, mithramycin, an alkaloid, vinblastine, paclitaxel, a glucocorticoid, dexamethasone, a corticosteroid, prednisone, a nucleoside enzyme inhibitors, hydroxyurea, an amino acid depleting enzyme, asparaginase, folinic acid, leucovorin, and a folic acid derivative.

The present invention includes the use of a composition comprising an anti-cancer agent, a pharmaceutically acceptable carrier, and an IGFR inhibitor compound of Formula I, in combination with at least one other anti-cancer agent, for manufacturing a medicament for treating cancer in a mammal, wherein the cancer is selected from colorectal cancer, non small cell lung cancer, pancreatic cancer, head and neck cancer, breast cancer, or neuroblastoma.

The present invention includes a method for treating cancer in a patient, comprising administering to said patient simultaneously or sequentially (i) a therapeutically effective amount of an agent that inhibits serine phosphorylation of IRS1 such as an EGFR inhibitor, or a pharmaceutically salt thereof; and (ii) a therapeutically effective amount an IGFR inhibitor wherein the IGFR inhibitor is cis-3-[8-Amino-1-(2-phenyl-quinolin-7-yl)-imidazo[1,5-a]pyrazin-3-yl]-1-methyl-cyclobutanol.

The present invention includes a method for treating cancer in a patient, comprising administering to said patient simultaneously or sequentially (i) a therapeutically effective amount of an agent that inhibits serine phosphorylation of IRS1 such as an EGFR inhibitor, or a pharmaceutically salt thereof; and (ii) a therapeutically effective amount an IGFR inhibitor wherein the IGFR inhibitor is wherein the IGFR inhibitor is

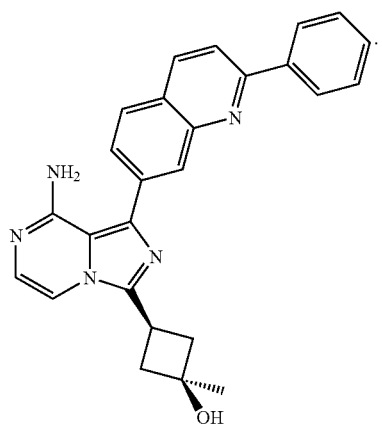 [SMILES: C[C@]1(O)C[C@@H](c2nc(-c3ccc4ccc(-c5ccccc5)nc4c3)c3c(N)nccn32)C1]

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor wherein the agent that inhibits serine phosphorylation of IRS1 is an EGFR kinase inhibitor.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib, cetuximab, gefitinib, panitumumab, or a salt thereof.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR inhibitor wherein the EGFR kinase inhibitor is erlotinib or a salt thereof.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the IGFR inhibitor is cis-3-[8-Amino-1-(2-phenyl-quinolin-7-yl)-imidazo[1,5-a]pyrazin-3-yl]-1-methyl-cyclobutanol and wherein the agent that inhibits serine phosphorylation of IRS1 is erlotinib or a salt thereof.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, wherein the patient is a human that is being treated for cancer, and wherein the cancer is colorectal cancer, non-small cell lung carcinoma, pancreatic cancer, head and neck cancer, breast cancer, or neuroblastoma.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, wherein the patient is a human that is being treated for cancer, and wherein the cancer is colorectal cancer or non-small cell lung carcinoma.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, wherein the patient is a human that is being treated for cancer, and wherein the cancer is colorectal cancer or non-small cell lung carcinoma.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer, and wherein erlotinib and the IGFR inhibitor are co-administered to the patient in the same formulation.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer, and wherein erlotinib and the IGFR inhibitor are co-administered to the patient in different formulations.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer, wherein erlotinib and the IGFR inhibitor are co-administered to the patient by the same route.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer, and wherein erlotinib and the IGFR inhibitor are co-administered to the patient by different routes.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer, and wherein erlotinib is administered to the patient by parenteral or oral administration.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer, and wherein the IGFR inhibitor is administered to the patient by parenteral administration.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 agent is an EGFR kinase inhibitor wherein the EGFR kinase inhibitor is erlotinib or a salt thereof, and wherein the patient is a human that is being treated for cancer, and additionally comprising one or more other anti-cancer agents.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I wherein the agent that inhibits serine phosphorylation of IRS1 is an EGFR kinase inhibitor wherein the EGFR kinase inhibitor is erlotinib or a salt thereof, and wherein the patient is a human that is being treated for cancer, and additionally comprising one or more other anti-cancer agents wherein the other anti-cancer agents are selected from an alkylating agent, cyclophosphamide, chlorambucil, cisplatin, busulfan, melphalan, carmustine, streptozotocin, triethylenemelamine, mitomycin C, an anti-metabolite, methotrexate, etoposide, 6-mercaptopurine, 6-thiocguanine, cytarabine, 5-fluorouracil, raltitrexed, capecitabine, dacarbazine, an antibiotic, actinomycin D, doxorubicin, daunorubicin, bleomycin, mithramycin, an alkaloid, vinblastine, paclitaxel, a glucocorticoid, dexamethasone, a corticosteroid, prednisone, a nucleoside enzyme inhibitors, hydroxyurea, an amino acid depleting enzyme, asparaginase, folinic acid, leucovorin, and a folic acid derivative.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is an inhibitor of the MAPK pathway.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is an inhibitor of the MAPK pathway, wherein the MAPK pathway inhibitor is selected from Ras inhibitors, Raf inhibitors, MEK inhibitors or PKC inhibitors.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is a MEK inhibitor.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is a MEK inhibitor, wherein the MEK inhibitor is ARRY-142886, PD-184352, PD-98059, PD-0325901, XL518, or MEK1.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount of an IGFR inhibitor represented by Formula I, wherein the agent that inhibits serine phosphorylation of IRS1is a Raf protein kinase family inhibitor.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount of an IGFR inhibitor represented by Formula I, wherein the agent that inhibits serine phosphorylation of IRS1 is a Raf protein kinase family inhibitor, wherein the Raf protein kinase family inhibitor is sorafenib.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is a Ras inhibitor.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is a Ras inhibitor is BMS-214662, SCH 66336, R115777, or 6-[(4-chloro-phenyl)-hydroxy-(3-methyl-3H-imidazol-4-yl)-methyl]-4-(3-ethynyl-phenyl)-1-methyl-1H-quinolin-2-one.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is a PKC inhibitor.

The present invention includes a method for treating cancer in a patient, comprising administering to said patient simultaneously or sequentially (i) a therapeutically effective amount of an agent that inhibits serine phosphorylation of IRS1, or a pharmaceutically salt thereof; and (ii) a therapeutically effective amount an IGFR inhibitor represented by Formula I, wherein the agent that inhibits serine phosphorylation of IRS1 is a PKC inhibitor, wherein the PKC inhibitor is byrostatin, staurosporine, a staurosporine analog, UCN-01, CGP41251, or safingol.

The present invention includes a method of preparing a pharmaceutical composition useful for treating tumors or tumor metastases in a patient in any of the methods described herein, comprising combining at least one anti-cancer agent with at least one IGFR inhibitor as described herein.

The present invention includes a method of preparing a pharmaceutical composition useful for treating tumors or tumor metastases in a patient, comprising combining an anti-cancer agent with an IGFR inhibitor of Formula I, wherein the anti-cancer agent is an EGFR kinase inhibitor, MEK inhibitor, VEGFR inhibitor, anti-VEGFR2 antibody, KDR antibody, AKT inhibitor, PDK-1 inhibitor, PI3K inhibitor, c-kit/Kdr tyrosine kinase inhibitor, Bcr-Abl tyrosine kinase inhibitor, VEGFR2 inhibitor, PDGFR-beta inhibitor, KIT inhibitor, Flt3 tyrosine kinase inhibitor, PDGF receptor family inhibitor, Flt3 tyrosine kinase inhibitor, RET tyrosine kinase receptor family inhibitor, VEGF-3 receptor antagonist, Raf protein kinase family inhibitor, angiogenesis inhibitor, Erb2 inhibitor, mTOR inhibitor, IGF-1R antibody, NFkB inhibitor, Proteosome inhibitor, chemotherapy agent, glucose reduction agent, or insulin-sensitizer.

The present invention includes a method of preparing a pharmaceutical composition useful for treating tumors or tumor metastases in a patient, comprising combining an anti-cancer agent with an IGFR inhibitor of Formula I, wherein the anti-cancer agent is ARRY-142886, PD-184352, ZD-6474, IMC-1121b, CDP-791, imatinib, sunitinib malate, sorafenib, PTK-787, lapatinib, sirolimus, temsirolimus, everolimus, CP-751871, RAV-12, IMC-A12, 19D12, PS-1145, or orbortezomib.

The present invention includes a method of preparing a pharmaceutical composition useful for treating tumors or tumor metastases in a patient, comprising combining an anti-cancer agent with an IGFR inhibitor of Formula I, wherein the anti-cancer agent is an EGFR kinase inhibitor.

The present invention includes a method of preparing a pharmaceutical composition useful for treating tumors or tumor metastases in a patient, comprising combining an anti-cancer agent with an IGFR inhibitor of Formula I, wherein the anti-cancer agent is an EGFR kinase inhibitor, wherein the EGFR kinase inhibitor is erlotinib, cetuximab, gefitinib, or a salt thereof.

The present invention includes a method of preparing a pharmaceutical composition useful for treating tumors or tumor metastases in a patient, comprising combining an anti-cancer agent with an IGFR inhibitor of Formula I, wherein the anti-cancer agent is an EGFR kinase inhibitor, wherein the EGFR kinase inhibitor is erlotinib or a salt thereof.

The present invention includes a method of preparing a pharmaceutical composition useful for treating tumors or tumor metastases in a patient, comprising combining an anti-cancer agent with an IGFR inhibitor of Formula I, further comprising combining a pharmaceutically acceptable carrier with the IGFR inhibitor and anti-cancer agent.

The present invention includes anti-cancer agents, for example: EGFR kinase inhibitors; MEK inhibitors, such as ARRY-142886 (also known as AZD6244; Array BioPharma/Astrazeneca), PD-184352 (also known as CI-1040: Pfizer), or PD-98059 (Pfizer); VEGFR/EGFR inhibitors, such as ZD-6474 (ZACTIMA; formerly known as AZD-6474; Astrazeneca); anti-VEGFR2 antibodies or KDR antibodies, such as IMC-1121b (ImClone Systems) or CDP-791 (Celltech/UCB/lmClone Systems); AKT inhibitors; PDK-1 inhibitors (also known as 3'-phosphoinositide-dependent kinase-1 inhibitors); PI3K inhibitors (also known as phosphatidylinositol-3 inhibitors); c-kit/Kdr tyrosine kinase inhibitors; Bcr-Abl tyrosine kinase inhibitors, such as imatinib (also known as STI-571 or GLIVEC or GLEEVEC; Novartis); VEGFR2, PDGFR-beta, KIT and Flt3 tyrosine kinase inhibitors, such as sunitinib malate (also known as SU-11248, SU-11248J, or SUTENT; SUGEN/Pfizer); PDGF, Flt3, Kit, RET, Raf, angiogenesis inhibitors, VEGF-2 or VEGF-3 receptor antagonists, such as sorafenib (also known as NEXAVAR or BAY-43-9006; Bayer/Onyx); EGFR and Erb2 inhibitors, such as Lapatinib (also known as GW-572016, Tykerb, Herceptin; GSK); sirolimus (previously known as rapamycin; Wyeth-Ayerst Pharmaceuticals); mTOR inhibitors, such as temsirolimus (also known as CCI-779; Wyeth Research) or everolimus (also known as RAD-001 or Certican or SDZ-RAD; Novartis); IGF-1R antibodies, such as CP-751871 (Pfizer), RAV-12 (Raven Biotechnologies), IMC-A12 (ImClone Systems), or 19D12 (Schering-Plough); NFkB inhibitors, such as PS-1145 (Millennium Pharmaceuticals); and proteosome inhibitors, such as bortezomib (also known as VELCADE or MLN-341 or LDP-341 or PS-341; Millennium Pharmaceuticals).

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®), oxaliplatin (e.g. ELOXATIN™), busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6 MP), 6-thiocguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and paclitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin, folinic acid, raltitrexed, and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lornustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, cladribine, camptothecin, 10-hydroxy 7-ethyl-camptothecin (SN38), floxuridine, fludarabine, ifosfamide, idarubicin, mesna, interferon alpha, interferon beta, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, or vinorelbine, chlorambucil.

The present invention further provides a method for treating tumors or tumor metastases in a patient, comprising administering to the patient simultaneously or sequentially a therapeutically effective amount of an EGFR kinase inhibitor and an IGF1R protein kinase inhibitor compound of Formula I combination, and in addition, one or more anti-hormonal agents. As used herein, the term "anti-hormonal agent" includes natural or synthetic organic or peptidic compounds that act to regulate or inhibit hormone action on tumors.

Anti-hormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g. ANTIDE®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide (2-methyl-N-[4, 20-nitro-3-(trifluoromethyl)phenylpropanamide), commercially available as EULEXIN® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, of the above additional other cytotoxic, chemotherapeutic or anticancer agents the compounds 5-fluorouracil and raltitrexed are preferred. Conveniently, a combination of 5-fluorouracil with leucovoran or folinic acid can be used with the EGFR kinase inhibitor and an IGF1R protein kinase inhibitor compound of Formula I combination of this invention. Additionally, of the above additional other cytotoxic, chemotherapeutic or anticancer agents the compounds etoposide and cisplatin are also preferred.

The present invention further provides a method for treating tumors or tumor metastases in a patient, comprising administering to the patient simultaneously or sequentially a therapeutically effective amount of an EGFR kinase inhibitor and an IGF1R protein kinase inhibitor compound of Formula I combination, and in addition one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 4,153,0901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271:29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606,046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides a method for treating tumors or tumor metastases in a patient, comprising administering to the patient simultaneously or sequentially a therapeutically effective amount of an EGFR kinase inhibitor and an IGF1R protein kinase inhibitor compound of Formula I combination, and in addition one or more tumor cell pro-apoptotic or apoptosis-stimulating agents.

The present invention further provides a method for treating tumors or tumor metastases in a patient, comprising administering to the patient simultaneously or sequentially a therapeutically effective amount of an EGFR kinase inhibitor and an IGF1R protein kinase inhibitor compound of Formula I combination, and in addition one or more signal transduction inhibitors.

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); ras inhibitors; raf inhibitors; MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

The present invention further thus provides a method for treating tumors or tumor metastases in a patient, comprising administering to the patient simultaneously or sequentially a therapeutically effective amount of an IRS1 agent such as an EGFR kinase inhibitor and an IGF1R protein kinase inhibitor compound of Formula I combination, and in addition an anti-HER2 antibody or an immunotherapeutically active fragment thereof.

The present invention further provides a method for treating tumors or tumor metastases in a patient, comprising administering to the patient simultaneously or sequentially a therapeutically effective amount of an IRS1 agent such as an EGFR kinase inhibitor and an IGF1R protein kinase inhibitor compound of Formula I combination, and in addition one or more additional anti-proliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217.

The present invention further provides a method for treating tumors or tumor metastases in a patient, comprising administering to the patient simultaneously or sequentially a therapeutically effective amount of an IRS1 agent such as an EGFR kinase inhibitor and an IGF1R protein kinase inhibitor compound of Formula I combination, and in addition a COX II (cyclooxygenase II) inhibitor. Examples of useful COX-II inhibitors include alecoxib (e.g. CELEBREX™), valdecoxib, and rofecoxib.

The present invention further provides a method for treating tumors or tumor metastases in a patient, comprising administering to the patient simultaneously or sequentially a therapeutically effective amount of an IRS1 agent such as an EGFR kinase inhibitor and an IGF1R protein kinase inhibitor compound of Formula I combination, and in addition treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides a method for treating tumors or tumor metastases in a patient, comprising administering to the patient simultaneously or sequentially a therapeutically effective amount of an EGFR kinase inhibitor and an IGF1R protein kinase inhibitor compound of Formula I combination, and in addition treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

The present invention further provides a method for reducing the side effects caused by the treatment of tumors or tumor metastases in a patient with an IRS1 agent such as an EGFR kinase inhibitor or an IGF1R protein kinase inhibitor compound of Formula I, comprising administering to the patient simultaneously or sequentially a therapeutically effective amount of an IRS1 agent such as an EGFR kinase inhibitor and irinotecan combination, in amounts that are effective to produce an additive, or a superadditive or synergistic antitumor effect, and that are effective at inhibiting the growth of the tumor.

The present invention further provides a method for the treatment of cancer, comprising administering to a subject in need of such treatment (i) an effective first amount of an EGFR kinase inhibitor, or a pharmaceutically acceptable salt thereof; and (ii) an effective second amount of an IGF1R protein kinase inhibitor compound of Formula I.

The present invention also provides a method for the treatment of cancer, comprising administering to a subject in need of such treatment (i) a sub-therapeutic first amount of the EGFR kinase inhibitor erlotinib, or a pharmaceutically acceptable salt thereof; and (ii) a sub-therapeutic second amount of an IGF1R protein kinase inhibitor compound of Formula I.

Additionally, the present invention provides a pharmaceutical composition comprising an EGFR inhibitor and an IGF1R protein kinase inhibitor compound of Formula I in a pharmaceutically acceptable carrier.

The present invention further provides a method for treating tumors or tumor metastases in a patient, comprising administering to the patient simultaneously or sequentially a therapeutically effective amount of an IRS1 agent such as an EGFR kinase inhibitor and an IGF1R protein kinase inhibitor compound of Formula I combination, and in addition, one or more other cytotoxic, chemotherapeutic or anti-cancer agents, or compounds that enhance the effects of such agents.

In a preferred embodiment, the patient is a human in need of treatment for cancer, or a precancerous condition or lesion. The cancer is preferably any cancer treatable, either partially or completely, by administration of an IRS1 agent such as an EGFR kinase inhibitor. The cancer may be, for example, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, colorectal cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions.

The IRS1 agent will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the IRS1 agent can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of IRS1 agent being used (e.g., small molecule, antibody, RNAi or antisense construct), and the medical judgment of the prescribing physician as based, e.g., on the results of published clinical studies.

The amount of IRS1 agent such as an EGFR kinase inhibitor administered and the timing of IRS1 agent administration will depend on the type (species, gender, age, weight, etc.) and condition of the patient being treated, the severity of the disease or condition being treated, and on the route of administration. For example, a small molecule IRS1 agent can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based IRS1 agents, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The IRS1 agents such as EGFR kinase inhibitors and IGF1R protein kinase inhibitors can be administered either separately or together by the same or different routes, and in a wide variety of different dosage forms. For example, the EGFR kinase inhibitor is preferably administered orally or parenterally, whereas the IGFLR protein kinase inhibitor compound of Formula I is preferably administered parenterally. Where the EGFR kinase inhibitor is erlotinib HCl (TARCEVA™), oral administration is preferable.

The IRS1 agent can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The EGFR kinase inhibitor and IGF1R protein kinase inhibitor compound of Formula I can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous IRS1 agents should be selected so as to avoid denaturation and/or degradation and loss of biological activity of the inhibitor.

Methods of preparing pharmaceutical compositions comprising an EGFR kinase inhibitor are known in the art, and are described, e.g. in International Patent Publication No. WO 01/34574. Methods of preparing pharmaceutical compositions comprising IGF1R protein kinase inhibitor are also known in the art. In view of the teaching of the present invention, methods of preparing pharmaceutical compositions comprising both an EGFR kinase inhibitor and an IGF1R protein kinase inhibitor will be apparent from the above-cited publications and from other known references, such as Remington's Pharmaceutical Sciences, Mack Publishing Company, Easton, Pa., $18^{th}$ edition (1990).

For oral administration of IRS1 agents, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the IRS1 agent may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous IRS1 agents should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising either an IRS1 agent or an IGF1R protein kinase inhibitor compound of Formula I in about 0.1% (w/v) to about 5% (w/v) concentration can be prepared.

For veterinary purposes, the active agents can be administered separately or together to animals using any of the forms and by any of the routes described above. In a preferred embodiment, the IRS1 agent is administered in the form of a capsule, bolus, tablet, liquid drench, by injection or as an implant. As an alternative, the IRS1 agent can be administered with the animal feedstuff, and for this purpose a concentrated feed additive or premix may be prepared for a normal animal feed. The IGF1R protein kinase inhibitor compound of Formula I is preferably administered in the form of liquid drench, by injection or as an implant. Such formulations are prepared in a conventional manner in accordance with standard veterinary practice.

The present invention further provides a kit comprising a single container comprising both an IRS1 agent and an IGF1R protein kinase inhibitor compound of Formula I. The present invention further provides a kit comprising a first container comprising an IRS1 agent and a second container comprising an IGF1R protein kinase inhibitor compound of Formula I. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer.

As used herein, the term "agent which inhibits serine phosphorylation of IRS1" refers to any agent which inhibits serine phosphorylation of IRS1 that is currently known in the art or that will be identified in the future, and includes any chemical entity that, upon administration to a patient, results in inhibition of a biological activity associated with activation of IRS1 in the patient, other than agents that block the mTORC1 signaling pathway. Such IRS1 inhibitors include any agent that can block IRS1 activation or any of the downstream biological effects of IRS1 activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the IRS1 receptor, thereby making the receptor inaccessible to its natural ligand so that its normal biological activity is prevented or reduced. Alternatively, such an inhibitor can act by modulating the dimerization of IRS1 polypeptides, or interaction of IRS1 polypeptide with other proteins, or enhance ubiquitination and endocytotic degradation of IRS1. IRS1 inhibitors include but are not limited to low molecular weight inhibitors, antibodies or antibody fragments, antisense constructs, small inhibitory RNAs (i.e. RNA interference by dsRNA; RNAi), and ribozymes. Agents which inhibit serine phosphorylation of IRS1 include, for example, EGFR kinase inhibitors, MAPK inhibitors, MEK inhibitors, Ras inhibitors, Raf inhibitors, and PKC inhibitors.

The term "MAPK inhibitor" refers to any MAPK inhibitor that is currently known in the art or that will be identified in the future, and includes any chemical entity that, upon administration to a patient, results in inhibition of a biological activity associated with activation of the MAPK receptor in the patient, including any of the downstream biological effects otherwise resulting from the binding to MAPK of its natural ligand. Such MAPK kinase inhibitors include any agent that can block MAPK activation or any of the downstream biological effects of MAPK activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the MAPK receptor, thereby making the receptor inaccessible to its natural ligand so that its normal biological activity is prevented or reduced. Alternatively, such an inhibitor can act by modulating the dimerization of MAPK polypeptides, or interaction of MAPK polypeptide with other proteins, or enhance ubiquitination and endocytotic degradation of MAPK. MAPK kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the MAPK kinase inhibitor is a small organic molecule or an antibody that binds specifically to the human MAPK.

MAPK kinase inhibitors include, for example, Ras inhibitors, Raf inhibitors, MEK inhibitors or PKC inhibitors.

The term "MEK inhibitor" refers to any MEK inhibitor that is currently known in the art or that will be identified in the future, and includes any chemical entity that, upon administration to a patient, results in inhibition of a biological activity associated with activation of the MEK receptor in the patient, including any of the downstream biological effects otherwise resulting from the binding to MEK of its natural ligand. Such MEK kinase inhibitors include any agent that can block MEK activation or any of the downstream biological effects of MEK activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the MEK receptor, thereby making the receptor inaccessible to its natural ligand so that its normal biological activity is prevented or reduced. Alternatively, such an inhibitor can act by modulating the dimerization of MEK polypeptides, or interaction of MEK polypeptide with other proteins, or enhance ubiquitination and endocytotic degradation of MEK. MEK kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the MEK kinase inhibitor is a small organic molecule or an antibody that binds specifically to the human MEK.

A MEK inhibitor is a compound that shows MEK inhibition when tested in the assays titled, "Enzyme Assays" in U.S. Pat. No. 5,525,625, column 6, beginning at line 35. The complete disclosure of U.S. Pat. No. 5,525,625 is hereby incorporated by reference. Specifically, a compound is an MEK inhibitor if a compound shows activity in the assay titled, "Cascade Assay for Inhibitors of the MAP Kinase Pathway," column 6, line 36 to column 7, line 4 of the U.S. Pat. No. 5,525,625 and/or shows activity in the assay titled, "In Vitro MEK Assay" at column 7, lines 4 to 27 of the above-referenced patent. Alternatively, MEK inhibition can be measured in the assay described in WO 02/06213 A1, the complete disclosure of which is hereby incorporated by reference.

MEK kinase inhibitors include, for example, ARRY-142886 (also known as AZD6244; Array BioPharma/Astrazeneca), PD-184352 (also known as CI-1040; Pfizer), XL518 (Exelixis), PD0325901 (Pfizer), PD-98059 (Pfizer), MEK1 (EMD), or 2-(2-amino-3-methoxyphenyl)-4-oxo-4H-[1]benzopyran and 2-(2-chloro-4-iodo-phenylamino)-N-cyclopropylmethoxy-3,4-difluoro-benzamide.

Specific preferred examples of MEK inhibitors that can be used according to the present invention include ARRY-142886, PD-184352, PD-98059, PD-0325901, XL518, or MEK1.

The term "Ras inhibitor" refers to any Ras inhibitor that is currently known in the art or that will be identified in the future, and includes any chemical entity that, upon administration to a patient, results in inhibition of a biological activity associated with activation of the Ras receptor in the patient, including any of the downstream biological effects otherwise resulting from the binding to Ras of its natural ligand. Such Ras kinase inhibitors include any agent that can block Ras activation or any of the downstream biological effects of Ras activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the Ras receptor, thereby making the receptor inaccessible to its natural ligand so that its normal biological activity is prevented or reduced. Alternatively, such an inhibitor can act by modulating the dimerization of Ras polypeptides, or interaction of Ras polypeptide with other proteins, or enhance ubiquitination and endocytotic degradation of Ras. Ras kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the Ras kinase inhibitor is a small organic molecule or an antibody that binds specifically to the human Ras.

Ras kinase inhibitors include, for example, BMS-214662 (Bristol-Myers Squibb), SCH 66336 (also known as Ionafarnib; Schering-Plough), L-778,123 (Merck), R115777 (also known as Zarnestra or Tipifarnib; Johnson and Johnson), and 6-[(4-chloro-phenyl)-hydroxy-(3-methyl-3H-imidazol-4-yl)-methyl]-4-(3-ethynyl-phenyl)-1-methyl-1H-quinolin-2-one (OSI Pharmaceuticals, Inc.). Ras inhibitors disclosed in U.S. Pat. Nos. 6,150,377 and 6,645,982 are included. The complete disclosures of U.S. Pat. Nos. 6,150,377 and 6,645,982 are incorporated by reference.

A specific preferred example of a Ras inhibitors that can be used according to the present invention includes 6-[(4-chloro-phenyl)-hydroxy-(3-methyl-3H-imidazol-4-yl)-methyl]-4-(3-ethynyl-phenyl)-1-methyl-1H-quinolin-2-one.

The term "Raf inhibitor" refers to any Raf inhibitor that is currently known in the art or that will be identified in the future, and includes any chemical entity that, upon administration to a patient, results in inhibition of a biological activity associated with activation of the Raf receptor in the patient, including any of the downstream biological effects otherwise resulting from the binding to Raf of its natural ligand. Such Raf kinase inhibitors include any agent that can block Raf activation or any of the downstream biological effects of Raf activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the Raf receptor, thereby making the receptor inaccessible to its natural ligand so that its normal biological activity is prevented or reduced. Alternatively, such an inhibitor can act by modulating the dimerization of Raf polypeptides, or interaction of Raf polypeptide with other proteins, or enhance ubiquitination and endocytotic degradation of Raf. Raf kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the Raf kinase inhibitor is a small organic molecule or an antibody that binds specifically to the human Raf.

Raf kinase inhibitors include, for example, sorafenib (also known as BAY 43-9006; Bayer).

The term "PKC inhibitor" refers to any PKC inhibitor that is currently known in the art or that will be identified in the future, and includes any chemical entity that, upon administration to a patient, results in inhibition of a biological activity associated with activation of the PKC receptor in the patient, including any of the downstream biological effects otherwise resulting from the binding to PKC of its natural ligand. Such PKC kinase inhibitors include any agent that can block PKC activation or any of the downstream biological effects of Raf activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the PKC receptor, thereby making the receptor inaccessible to its natural ligand so that its normal biological activity is prevented or reduced. Alternatively, such an inhibitor can act by modulating the dimerization of PKC polypeptides, or interaction of PKC polypeptide with other proteins, or enhance ubiquitination and endocytotic degradation of PKC. PKC kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the PKC kinase inhibitor is a small organic molecule or an antibody that binds specifically to the human PKC.

PKC kinase inhibitors include, for example, Byrostatin, staurosporine, staurosporine analogs including UCN-01 or CGP41251, or safingol.

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase inhibitors that include, for example quinazoline EGFR kinase inhibitors, pyrido-pyrimidine EGFR kinase inhibitors, pyrimido-pyrimidine EGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Opin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl) amine (also known as OSI-774, erlotinib, or TARCEVA™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or IRESSA™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl) amine (i.e. erlotinib), its hydrochloride salt (i.e. erlotinib HCl, TARCEVA™), or other salt forms (e.g. erlotinib mesylate).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

Additional antibody-based EGFR kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against EGFR can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Natl. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-EGFR single chain antibodies. Antibody-based EGFR kinase inhibitors useful in practicing the present invention also include anti-EGFR antibody fragments including but not limited to $F(ab')_2$ fragments, which can be generated by pepsin digestion of an intact antibody molecule, and Fab fragments, which can be generated by reducing the disulfide bridges of the $F(ab')_2$ fragments. Alternatively, Fab and/or scFv expression libraries can be constructed (see, e.g., Huse et al., 1989, Science 246: 1275-1281) to allow rapid identification of fragments having the desired specificity to EGFR.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-EGFR antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24): 3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

The invention also encompasses a pharmaceutical composition that is comprised of an EGFR kinase inhibitor and an IGF1R protein kinase inhibitor compound of Formula I combination with a pharmaceutically acceptable carrier.

Preferably the composition is comprised of a pharmaceutically acceptable carrier and a non-toxic therapeutically effective amount of an IRS1 agent such as an EGFR kinase inhibitor compound and an IGF1R protein kinase inhibitor compound of Formula I combination (including pharmaceutically acceptable salts of each component thereof).

Moreover, within this preferred embodiment, the invention encompasses a pharmaceutical composition for the treatment of disease, the use of which results in the inhibition of growth of neoplastic cells, benign or malignant tumors, or metastases, comprising a pharmaceutically acceptable carrier and a non-toxic therapeutically effective amount of an IRS1 agent such as an EGFR kinase inhibitor compound and an IGF1R protein kinase inhibitor compound of Formula I combination (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise an IRS1 agent such as an EGFR kinase inhibitor compound and an IGF1R protein kinase inhibitor of Formula I combination (including pharmaceutically acceptable salts of each component thereof) as active ingredient, a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by an IRS1 agent such as an EGFR kinase inhibitor compound and an IGF1R protein kinase inhibitor compound of Formula I combination (including pharmaceutically acceptable salts of each component thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an IRS1 agent such as an EGFR kinase inhibitor compound and an IGF1R protein kinase inhibitor compound of Formula I combination (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and an IRS1 agent such as an EGFR kinase inhibitor compound and an IGF1R protein kinase inhibitor compound of Formula I combination (including pharmaceutically acceptable salts of each component thereof). An IRS1 agent such as an EGFR kinase inhibitor compound and an IGF1R protein kinase inhibitor compound of Formula I combination (including pharmaceutically acceptable salts of each component thereof, can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, a pharmaceutical composition can comprise an IRS1 agent such as an EGFR kinase inhibitor compound and an IGF1R protein kinase inhibitor compound of Formula I in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing an IRS1 agent such as an EGFR kinase inhibitor compound and an IGF1R protein kinase inhibitor compound of Formula I combination (including pharmaceutically acceptable salts of each component thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an IRS1 agent such as an EGFR kinase inhibitor compound and an IGF1R protein kinase inhibitor compound of Formula I combination (including pharmaceutically acceptable salts of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

The data presented below demonstrate that co-administration of an IGF1R protein kinase inhibitor compound of Formula I with an EGFR kinase inhibitor is effective for treatment of cancers, such as colorectal and non small cell lung (NSCL) cancer. Accordingly, the present invention provides a method for treating tumors or tumor metastases in a patient, comprising administering to the patient simultaneously or sequentially a therapeutically effective amount of an EGFR kinase inhibitor and an IGF1R protein kinase inhibitor combination. In one embodiment the tumors or tumor metastases to be treated are colorectal tumors or tumor metastases. In another embodiment the tumors or tumor metastases to be treated are non small cell lung (NSCL) tumors or tumor metastases.

Experiment Details: Effect of Pharmacological Combination of TARCEVA™, an EGF-1R inhibitor, and IGF-1R inhibitors (imidazopyrazines), Compound-A, Compound-B, and Compound-C, on cell survival and viability of cancer cells in vitro and tumor growth in vivo.

Compound A: 3-(4-Aminomethyl-cyclohexyl)-1-(2-phenyl-quinolin-7-yl)-imidazo[1,5-a]pyrazin-8-ylamine represented by the following structure

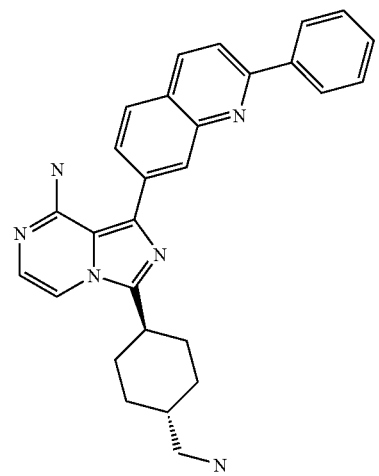 [SMILES: NC[C@H]1CC[C@H](c2nc(-c3ccc4ccc(-c5ccccc5)nc4c3)c3c(N)nccn32)CC1]

Compound B: 3-(3-Azetidin-1-ylmethyl-cyclobutyl)-1-(2-phenyl-quinolin-7-yl)-imidazo[1,5-a]pyrazin-8-ylamine) represented by the following structure:

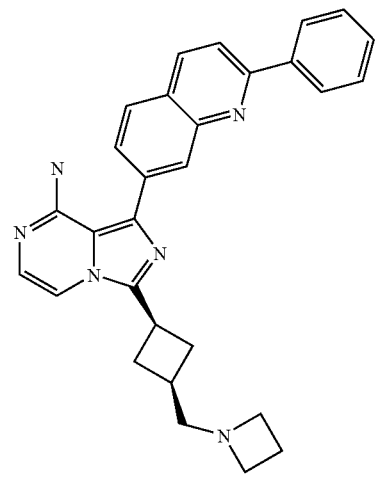 [SMILES: Nc1nccn2c1c(-c1ccc3ccc(-c4ccccc4)nc3c1)nc2[C@H]1C[C@@H](CN2CCC2)C1]

Compound C: cis-3-[3-(4-Methyl-piperazin-1-yl)-cyclobutyl]1-(2-phenyl-quinolin-7-yl)-imidazo[1,5-a]pyrazin-8-ylamine represented by the following structure:

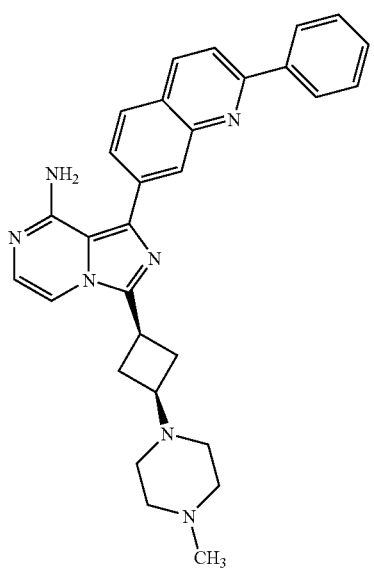 [SMILES: CN1CCN([C@H]2C[C@@H](c3nc(-c4ccc5ccc(-c6ccccc6)nc5c4)c4c(N)nccn43)C2)CC1]

Recently, the EGFR has emerged as a key target for anti-cancer therapeutics. Erlotnib (TARCEVA™, OSI-774) is a potent, orally active and bioavailable, selective small molecule inhibitor of epidermal growth factor receptor (HER1, erbB1) tyrosine kinase (TK), which blocks signal transaction pathways implicated in proliferation and survival of cancer cells, and is in phase III clinical trial. Erlotinib inhibits phosphorylation of the EGFR tyrosine kinase domain, thereby blocking key signal transduction molecules downstream from the receptor. Erlotinib is being tested in Phase III clinical trials in NSCLC, and is also being tested in other types of solid tumors.

Human colorectal cancer represents one of the most prevalent human carcinomas. Surgical resection is the only curative treatment. Since the majority of patients present in an advanced stage of disease with metastatic spread, surgery alone is not a good enough clinical approach. Newer treatments are being sought to better manage this disease. Ideally these would come in the form of new single agent entities. The trend for novel agents, however, is to pursue targets inherent only to the cancer cells. With this precise targeting comes the assumption of a better toxicity profile compared to traditional cytotoxic agents.

Many traditional cytotoxics have single-agent activity in cancer. Since only modest objective responses were seen with monotherapy regimens, a combination approach is considered a better approach. The ideal regimen would be two agents with different mechanisms which could therefore potentially achieve synergic or additive efficacy with toxicity reduced or similar to monotherapy treatment. Epidermal growth factor receptor-inhibitor seems to have the promising perspective for achieving this goal when combined with traditional chemotherapeutics.

Several EGFR inhibitors are in the later stages of clinical development. Two antibodies against EGFR have been developed. Cetuximab (C225, ERBITUX™), a chimeric antibody which competitively inhibits the activation of EGFR, and ABX-EGF, a fully humanized antibody to EGFR that is postulated to escape degradation post-internalization and therefore gets recycled. Impressive clinical results have been seen with Cetuximab, and Phase II results from ABX-EGF are pending. Several small molecules are also in development. Of particular interest are IRESSA™ (ZD1839), CI-1033 and TARCEVA™ (OSI-774). CI-1033, being earliest in development, is a nonspecific irreversible inhibitor of all EGFR family members. Data from later stage trials with this compound are pending. IRESSA™ received FDA approval as third line treatment for NSCLC in May 2003.

The goal of this study is to assess the ability of IGF-1R inhibitors to potentiate TARCEVA™ (erlotinib) effects on cell survival in the presence of IGF-1, and the ability of IGF-1R inhibitors in combination with TARCEVA™ to reduce cell viability and modulate downstream signaling pathways, namely Ras-MAPK and PI3K-AKT, and to promote apoptosis in human non small cell lung carcinoma (NSCLC) cells, colorectal cancer (CRC), breast, and pancreatic cancer cells in vitro, as well as to inhibit the tumor growth in mouse xenograft models.

The in vitro and in vivo efficacy of both IGF-1R inhibitors and an EGFR inhibitor, TARCEVA™ is significantly enhanced when used in combination, which was demonstrated and resulted in methods for the treatment of various cancers by using combinations of an EGFR inhibitor, TARCEVA™, and IGF-1R inhibitors. In addition, the modulation of downstream Ras-MAPK and PI3K-AKT pathways can be used for cancer patient selection for such treatment.

Cell lines from NSCLC, colorectal, breast, and pancreatic were maintained under standard cell culture conditions described by ATCC unless otherwise noted.

Drug stock concentration was 10 mM in 100% DMSO (dimethyl sulfoxide). Serial dilutions (1:3 or 1:4) were used to establish the 50% inhibitory dose of TARCEVA™ and IGF-1R inhibitors. Before dosing, drugs were diluted in 100% DMSO, and then added to the cells at desired final concentrations in duplicates. The final DMSO concentration was between 0.3-0.5%.

For measuring cell viability, Cell-Titer Glo assay was used, which is available as a kit from Promega. The basis of the assay is a luminescent quantitation of ATP present in a cell culture plate well. In essence, the greater the number of viable cells in the well, the greater the level of ATP present. The assay utilizes a substrate that binds ATP to produce a luminescent signal which can be read on a luminometer. Unless otherwise noted, the manufacturers instructions were followed exactly. Briefly, on Day 1, cells were plated in 120 ul of 10% serum-containing growth media at a density of 4000 cells/well in a white polystyrene 96 well assay plate. On day 2, cells were treated with 15 ul of 10× concentrations of drugs or DMSO alone for a final well volume of 150 ul. After 72 h incubation with the drugs, the cells were assayed. Results were calculated as a fraction of the DMSO controlled cells.

To monitor cell apoptosis, DNA fragmentation was measured by using a commercially available kit from Roche. Cells were plated in 90 ul of 10% serum-containing growth media at a density of 5000 cells/well in a 96-well culture plate. On day 2, cells were treated with 10 ul of 10× concentrations of drugs or DMSO alone for a final well volume of 100 ul. After 48 h treatment with the drugs, the cells were assayed for DNA fragmentation according to the manufacture instructions. Results were calculated as fold of induction of DNA fragmentation of the DMSO controlled cells. In addition, apoptosis markers, cleaved PARP and cleaved caspase-3, in the tumor cell lines treated with IGF-IR inhibitor alone, erlotinib alone or the two drug together were also measured by a immunoblotting.

Modulations of IGF-1R activity and downstream pathways were measured by phosphorylation states of IGF-1R (Tyr), AKT (Ser 473) and MAPK using immunoprecipitation/Western blotting. In brief, cells were plated in regular media containing 10% FCS overnight. On Day 2, cells were treated with IGF-1R inhibitor alone, TARCEVA™ alone or the two drugs together in the presence or absence of IGF-1 for 2 h. Following rinsing with cold PBS (phosphate-buffered saline) the cells were lysed with cold TGH buffer supplemented with fresh protease and phosphatase inhibitors. Approximately 300 µg of the total lysate were incubated with 2 µg of a specific anti-IGF-IR pre-coupled to Protein G sepharose overnight at 4° C. with rotating. The Protein G captured antibody-protein complexes were washed three times with cold TGH buffer. The samples were boiled, and the immunoprecipitates were separated on a 4-12% gradient Tris-Glycine gel. Following transfer to nitrocellulose membranes, phospho-IGF-1R was probed with anti-phosphotyrosine antibody (pY-20 HRP) for 2 h at RT. The bound antibody was detected by enhanced chemiluminescence (ECL). The total IGF-1R levels were determined with a specific antibody by direct Western blotting. To monitor influence of the drugs on downstream pathways emanated from IGF-1R and EGFR, antibodies specific for phospho-PKB (Ser473), or phospho-p44/42 MAPK (Thr202/Tyr204) was used in direct Western blotting. Approximately 20 µg of total cell lysates was resolved on 4-12% gradient Tris-Glycine gel. Detection was performed using ECL.

Anti-tumor efficacy of IGF-IR inhibitor plus erlotinib was evaluated using mouse xenograft tumor models derived from H292, H441, H460, GEO and HT29 cells. A fixed once daily dose of 100 mg/kg of erlotinib was chosen, and was co-administered orally with or without compound-C at three different doses (25, 50 and 75 mg/kg). Female CD-1 and athymic nude nu/nu CD-1 mice (6-8 wks, 22-29 g) were obtained from Charles River Laboratories (Wilmington, Mass.). Animals were allowed to acclimate for a minimum of one week prior to initiation of a study. Throughout the studies, animals were allowed sterile rodent chow and water ad libitum, and immunocompromised animals were maintained under specific pathogen free conditions. All animal studies were conducted at OSI facilities with the approval of the Institutional Animal Care and Use Committee in an American Association for Accreditation of Laboratory Animal Care (AAALAC)-accredited vivarium and in accordance with the Institute of Laboratory Animal Research (Guide for the Care and Use of Laboratory Animals, NIH, Bethesda, Md.). Tumor cells were harvested from cell culture flasks during exponential cell growth, washed twice with sterile PBS, counted and resuspended in PBS to a suitable concentration before s.c. implantation on the right flank of female nu/nu CD-1 mice. Tumors were established to 200+/−50 mm$^3$ in size before randomization into treatment groups of 8 mice each. Compound-C or vehicle (25 mM tartaric acid) was administered orally as indicated. Body weights were determined twice weekly along with tumor volume {V=[length×(width)2]/2} measurements using Vernier calipers during the study. Tumor growth inhibition (% TGI) was determined by the following formula: % TGI={1−[($T_t/T_0$)/($C_t/C_0$)]/1−[$C_0/C_t$]}×100. $T_t$ is tumor volume of treated at time t; $T_0$ is tumor volume of treated at time 0; $C_t$ is tumor volume of control at time t; and $C_0$ is tumor volume of control at time 0. Antitumor activity was defined as a minimum tumor growth inhibition of 50% at the end of treatment. Furthermore, we evaluated the effect of drug treatment on tumor growth delay (GD or T−C value), defined as the difference in time (days) required for the treated tumors (T) to reach 400% of the initial tumor volume compared with those of the control group (C). Cures were excluded from this particular calculation.

Results

Activation of IGF-IR Pathways Protects Cells from Growth Inhibition and Apoptosis by TARCEVA™ in H292 Cells As shown in FIGS. 1A and 1B, TARCEVA™, an EGFR inhibitor, inhibited cell proliferation and induced apoptosis in a significant fraction of H292 human non-small cell lung carcinoma cell line in culture conditions. This effect could be prevented by concomitant exposure to IGF-1, by providing alternative survival signal pathways (FIG. 1C). When they were combined together, IGF-1R inhibitor potentiated TARCEVA™ effects, and further enhanced activity of inhibition of cell proliferation and induction of cell apoptosis as well as effectively blocking both cell proliferation and cell survival pathways.

Drug Combination of TARCEVA™ and IGF-1R Inhibitors Achieves Synergistic Effects on Inhibition of Cell Viability in Human Non-Small Cell Lung Carcinoma, Colorectal, Breast, and Pancreatic Cancer Cell Lines Effects on cell viability by either TARCEVA™ or IGF-1R inhibitor alone or combination of the two drugs were assayed. The data were expressed in three ways:

1. Isobogram of either drug alone or combination of the two drugs. To assess synergistic effects, concentration of each drug alone or combination of the two drugs that blocked growth by 50% (IC50) were calculated. See, Berenbaum M C. *Critreial for analyzing interactions between biologically active agents. Cancer Res.* (1981) 35: 269-335. Assuming zero interaction between the two drugs, these points on the axes can be joined by a straight line (isobole) that indicates combinations of TARCEVA™ and IGF-1R inhibitors that are isoeffective with either drug alone. The isoeffect is the IC50. When drug combination fall alone this straight line they are assumed to be additive. When the drug combinations are more effective than expected, lower concentrations are required to produce the isoeffects (IC50) and are considered synergistic. These points will fall below the zero interaction isobole. When drug combinations require higher concentrations than expected to produce the isoeffect, they are considered antagonistic and the points will fall above the zero interaction isobole. All of the combination tested all at or below the zero interaction isobole as depicted in FIGS. 2 and 6.

2. Bar charts illustrating effect of single concentration of TARCEVA™ or IGF-1R inhibitor alone or combination of the two drugs. No inhibition of cell viability as indicated by the DMSO control is expressed as value of one. 100% inhibition of cell viability will be zero. All of the single drug or the combinations fall below the value of one as depicted by FIGS. 3, 7, and 8.

3. Heat maps demonstrating a percentage difference of the combination of drugs over Bliss equation calculated pure additivity based on the effects of drugs as single drugs. Bliss transformation of data was calculated as described in Borisy et al., *Systematic discovery of multicomponent therapeutics. Proc Natl Acad Sci USA.* (2003) 100: 7977-82. *The Bliss equation compares the effects of individual drugs alone with the effect of the combination.* Positive values represent a percentage effect greater than that of additivity alone, and negative numbers represent an effect less than that predicted from the single drug activities. Almost all of the combinations tested have positive numbers as shown in FIG. 4. Alternatively, Bliss additivity curves were also generated to illustrate effect of the drug combination. For dose response curves, the bliss additivity value was calculated for varying doses of compound-C when combined with a constant dose of erlotinib. The dashed line is the BLISS additivity curve and represents the theoretical expectation if the combined effects of erlotinib with PQIP were exactly additive All plots were generated using Prism Graphpad software (FIGS. 10 and 11).

IGF-1R Inhibitor Enhances Anti-Tumor Activity of TARCEVA™ in NSCLC and Colorectal Cancer Xenograft Tumor Models As shown in FIG. 13 and FIG. 13A, IGF-1R inhibitor enhanced anti-tumor efficacy of TARCEVA™ in both NSCLC and colorectal cancer xenograft models when orally co-administering compound-C and erlotinib. Tumor growth of H292 exhibited a durable cure in 3/8 mice when erlotinib was co-administrated with this IGF-IR inhibitor orally once daily. Significant tumor regression was also observed in H441 and GEO tumors in response to the combination treatment (FIG. 13 and FIG. 13A).

The combination of TARCEVA™, an EGFR inhibitor, and IGF1R inhibitors demonstrates synergistic effects on inhibition of cell viability (FIGS. 2, 3, 4, 6, 7, 8, 10 and 11) and promotion of apoptosis (FIGS. 1A, 12A and 12B) in a number of human NSCLC, colorectal, breast and pancreatic cancer cell lines in culture. This synergy is apparent irrespective of the sensitivities of the cell lines to either drug alone, which corresponding to the modulations of downstream pathways, namely Ras-MAPK and PI3K-PKB pathways (FIGS. 5, 9 and 12). Furthermore, the downstream modulations of pAkt and pErk observed in these cells correlated with induction of cell apoptosis and with their responsiveness to erlotinib and IGF-IR inhibitor treatment when grown as xenografts in vivo. The combination treatment resulted better anti-tumor activity than either single agent alone.

The data presented below demonstrate that co-administration of an IGF1R protein kinase inhibitor compound of Formula I with an agent that inhibits serine phosphorylation of IRS1 is effective for treatment of cancers, such as colorectal cancer, non-small cell lung (NSCL) cancer, pancreatic cancer, head and neck cancer, breast cancer, neuroblastoma, or ovarian cancer. Accordingly, the present invention provides a method for treating tumors or tumor metastases in a patient, comprising administering to the patient simultaneously or sequentially a therapeutically effective amount of an agent that inhibits serine phosphorylation of IRS1 and an IGF1R protein kinase inhibitor combination. In one embodiment the tumors or tumor metastases to be treated is non small cell lung (NSCL) cancer.

In addition to the above EGFR inhibitors, specific agent that inhibits serine phosphorylation of IRS1 include MEK inhibitors. Examples of MEK inhibitors that can be used according to the present invention include ARRY-142886 (also known as AZD6244; Array BioPharma/Astrazeneca), PD-184352 (also known as CI-1040; Pfizer), XL518 (Exelixis), PD0325901 (Pfizer), PD-98059 (Pfizer), and Meki (EMD). Particularly preferred MEK inhibitors that can be used according to the present invention are MEK1 or PD-98059.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

Experiment Details: Effect of Pharmacological Combination of Tarceva, an EGF-1R Inhibitor, and IGF-1R Inhibitor, Compound-D, on Cell Survival and Viability of Cancer Cells In Vitro and Tumor Growth In Vivo Compound D: cis-3-[8-Amino-1-(2-phenyl-quinolin-7-yl)-imidazo[1,5-a]pyrazin-3-yl]-1-methyl-cyclobutanol is represented by the following structure

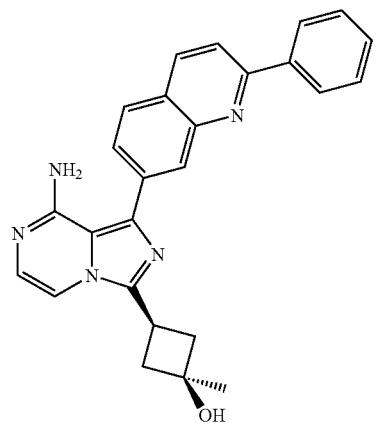 [SMILES: C[C@]1(O)C[C@@H](c2nc(-c3ccc4ccc(-c5ccccc5)nc4c3)c3c(N)nccn32)C1]

The ability of IGF-1R inhibitors to potentiate TARCEVA (erlotinib) effects on cell survival in the presence of IGF-1, and the ability of IGF-1R inhibitors in combination with TARCEVA to reduce cell viability and modulate downstream signaling pathways, namely Ras-MAPK and PI3K-AKT, and to promote apoptosis in colorectal cancer (CRC), breast, and pancreatic cancer cells in vitro, as well as to inhibit the tumor growth in mouse xenograft models was assessed.

Measurement of Cell Proliferation and Apoptosis:

The models identified in experiments are for all the cell lines. Cell proliferation was determined using the Cell Titer Glo assay (Promega), and apoptosis was determined using the Caspase Glo assay (Promega). Cell lines were seeded at a density of 3000 cells per well in a 96-well plate. 24 hours after plating cells were dosed with varying concentrations of drug, either as a single agent or in combination. The signal for Cell Titer Glo was determined 72 hours after dosing, and fold induction for apoptosis was measured 48 hours after dosing Analysis of Additivity and Synergy The Bliss additivism model was used to classify the effect of combining Compound D and erlotinib as additive, synergistic, or antagonistic. A theoretical curve was calculated for combined inhibition using the equation: Ebliss=EA+EB−EA*EB, where EA and EB are the fractional inhibitions obtained by drug A alone and drug B alone at specific concentrations. Here, Ebliss is the fractional inhibition that would be expected if the combination of the two drugs was exactly additive. If the experimentally measured fractional inhibition is less than Ebliss the combination was said to be synergistic. If the experimentally measured fractional inhibition is greater than Ebliss the combination was said to be antagonistic. For dose response curves, the bliss additivity value was calculated for varying doses of drug A when combined with a constant dose of drug B. This allowed an assessment as to whether drug B affected the potency of drug A or shifted its intrinsic activity. All plots were generated using Prism Graphpad software.

Xenograft Studies in Nude Mice:

Female CD-1 nu/nu mice (Charles River Laboratories) were implanted with harvested BxPC3 (pancreatic) or GEO (colorectal) tumor cells in a single subcutaneous site on the flank of the mice in the axillary region. Tumors were allowed to grow to 200±50 mm3, at which time the animals were sorted into treatment groups of 8 animals per group based on weight (+/−1 g body weight) and tattooed on the tail for permanent identification. Tumor volumes and body weights were determined twice weekly. The tumor volume was determined by measuring in two directions with vernier calipers and calculated using the formula: Tumor volume=(length× width2)/2. The data were plotted as the % change in mean values of tumor volume and body weight for each group. The tumor growth inhibition (% TGI) was determined as % TGI= $(1-\{Tt/T0/Ct/C0\}/1-\{C0/Ct\})\times 100$ where Tt=median tumor volume of treated at time t, T0=median tumor volume of treated at time 0, Ct=median tumor volume of control at time t and C0=median tumor volume of control at time 0. Mean % TGI was determined for the dosing period of each study. Erlotinib was dosed in a 6% Captisol (CyDex, Inc) in WFI (Water for Injection) solution, Compound D was dosed in 25 mM Tartaric acid solution, combination treated mice were dosed with 2× concentrated erlotinib in 6% captisol and 2× concentrated Compound D in 25 mM Tartaric Acid mixed 50:50 just prior to dosing and control animals were dosed with a 50:50 mix of both vehicles. All mice were dosed by oral gavage once a day for 14 days, unless otherwise noted.

% tumor growth inhibition (TGI) as calculated by the following formula:

$$(1-\{Tt/T0/Ct/C0\}/1-\{C0/Ct\})\times 100$$

$T_t$=median tumor volume of treated at time t
$T_0$=median tumor volume of treated at time 0
$C_t$=median tumor volume of control at time t
$C_0$=median tumor volume of control at time 0
Mean % TGI determined for the dosing period of each study.

As seen in FIGS. 14-18, the combination of Compound D with erlotinib is more efficacious than either drug alone in both in vitro and in vivo.

In FIG. 14, the combination of Compound D and Erlotinib produces synergist effect on inhibiting cell proliferation and promoting apoptosis in the epithelial pancreatic cancer cell line BxPC3.

As seen in FIGS. 15A and 15B, the combination of Compound D and Erlotinib by co-administration leads to much greater anti-tumor effect than either drug alone in vivo, and only the combination achieves early growth regression of the tumor during the treatment period. Approximately 26% of tumor regression is achieved on day 4 of dosing (maximum regression). The average tumor regression for the treatment period is approximately 13.2%.

Figure 16B:
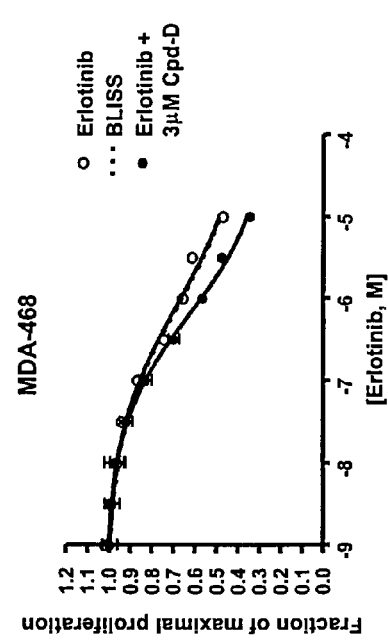

In FIG. 16, the combination of Compound D and Erlotinib has synergist effect on inhibiting cell proliferation in the epithelial breast tumor cell line MDA-MB-468. The additive effect of the combination treatment on growth inhibition is observed in the breast tumor cell line BT20.

Figure 17A:
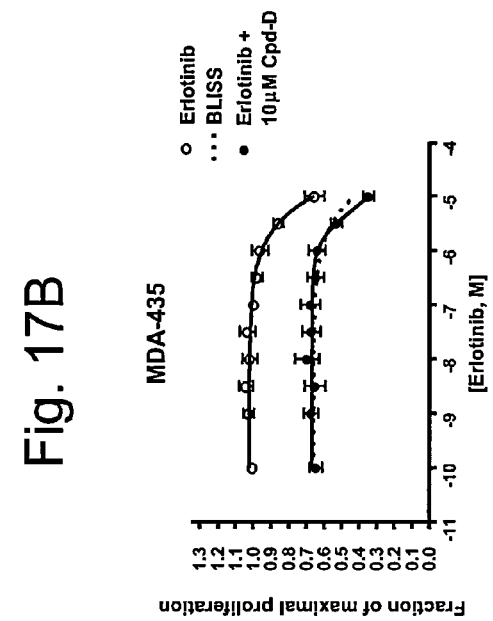
FIGS. 17A and 17B: Plots depicting effect of IGF-1R inhibitor Compound D (cis-3-[8-Amino-1-(2-phenyl-quinolin-7-yl)-imidazo[1,5-a]pyrazin-3-yl]-1-methyl-cyclobutanol) in combination with Erlotinib (TARCEVA) on inhibiting cell proliferation in two mesenchymal breast tumor cell lines DU4475 and MDA-MB-435. Synergistic effect achieved in DU4475 cell line (A), and additive effect is observed in MDA-MB-435 cell line (B).
Figure 17B:
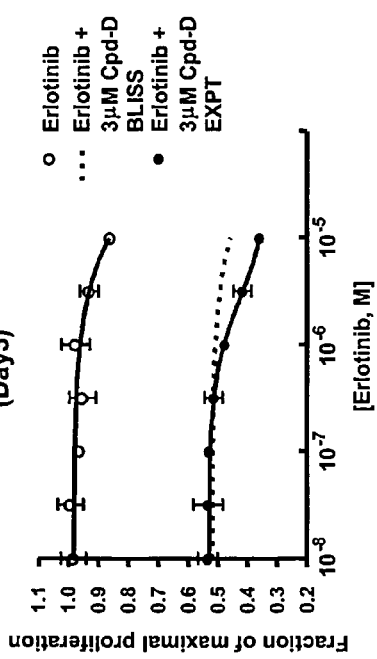

In FIG. 17, the combination of Compound D and Erlotinib produces synergistic effect on inhibiting cell proliferation in mesenchymal breast tumor cell lines DU4475. The combination treatment has additive effect on cell growth inhibition of mesenchymal breast cancer cell line MDA-MB-435.

In FIG. 18, the combination of Compound D and Erlotinib by co-administration achieves much greater anti-tumor effect than either drug alone in GEO human colorectal cancer xenograft model, and only the combination leads growth regression of the tumor during the treatment period. Approximately 18%, 5% and 20% of maximum tumor regression are seen with Erlotinib at 100 mg/kg in combination with doses of Compound D at 7.5 mg/kg, 15 mg/kg and 30 mg/kg, respectively. The average tumor regression is approximately 10%, 4% and 13% at the three doses of Compound D in combination with Erlotinib, respectively.

Experimental Procedures: Effect of Pharmacological Combination of a MEK Inhibitor, and IGF-1R Inhibitor, Compound-D, on Cell Survival and Viability of Cancer Cells In Vitro and Tumor Growth In Vivo Cell lines: The cell lines NCI-H292, GEO, BxPC3, MDA-MB-435, DU4475, and MDA-MB-468, and BT-20 were routinely cultured in media as prescribed by the ATCC containing 10% FCS. With the exception of GEO tumor cells (obtained from RPCI, Roswell Park Cancer Institute), all tumor cells were obtained from the ATCC.

Measurement of Cell Proliferation:

Cell proliferation was determined using the Cell Titer Glo assay (Promega), and apoptosis was determined by measuring caspase 3/7 activity with Caspase Glo (Promega). Cell lines were seeded at a density of 3000 cells per well in a 96-well plate. 24 hours after plating cells were dosed with varying concentrations of drug, either as a single agent or in combination. The signal for Cell Titer Glo was determined 72 hours after dosing, and the signal for Caspase Glo was determined 48 hours after dosing.

Analysis of Additivity and Synergy:

The Bliss additivism model was used to classify the effect of combining Compd D or PD98059 or MEK1 and erlotinib as additive, synergistic, or antagonistic. A theoretical curve was calculated for combined inhibition using the equation: $E_{bliss}=E_A+E_B-E_A*E_B$, where $E_A$ and $E_B$ are the fractional inhibitions obtained by drug A alone and drug B alone at specific concentrations, wherein drug A is Compd D and drug B is a MEK inhibitor PD98059 or MEK1. Here, $E_{bliss}$ is the fractional inhibition that would be expected if the combination of the two drugs was exactly additive. If the experimentally measured fractional inhibition is less than $E_{bliss}$ the combination was said to be synergistic. If the experimentally measured fractional inhibition is greater than $E_{bliss}$ the combination was said to be antagonistic. For dose response curves, the bliss additivity value was calculated for varying doses of drug A when combined with a constant dose of drug B. This allowed an assessment as to whether drug B affected the potency of drug A or shifted its intrinsic activity. All plots were generated using Prism Graphpad software.

Animals: Female athymic nude nu/nu CD-1 mice (6-8 wks, 22-29 g) were obtained from Charles River Laboratories (Wilmington, Mass.). Animals were allowed to acclimate for a minimum of one week prior to initiation of a study. Throughout the studies, animals were allowed sterile rodent chow and water ad libitum, and animals were maintained under specific pathogen free conditions. All animal studies were conducted at OSI facilities with the approval of the Institutional Animal Care and Use Committee in an American Association for Accreditation of Laboratory Animal Care (AAALAC)-accredited vivarium and in accordance with the Institute of Laboratory Animal Research (Guide for the Care and Use of Laboratory Animals, NIH, Bethesda, Md.).

In Vivo Anti-Tumor Efficacy Study:

Cells were harvested from cell culture flasks during exponential cell growth, washed twice with sterile PBS, counted and resuspended in PBS to a suitable concentration before s.c. implantation on the right flank of female nu/nu CD-1 mice. Tumors were established to 200+/−50 mm³ in size before randomization into treatment groups of 8 mice each. Compound D or vehicle was administered orally as indicated. Body weights were determined twice weekly along with tumor volume {V=[length×(width)2]/2} measurements using Vernier calipers during the study. Tumor growth inhibition (% TGI) was determined twice weekly during the dosing period by the following formula: % TGI=$(1-\{T_t/T_0/C_t/C_0\}/1-\{C_0/C_t\})\times 100$ where $T_t$=median tumor volume of treated at time t, $T_0$=median tumor volume of treated at time 0, $C_t$=median tumor volume of control at time t and $C_0$=median tumor volume of control at time 0. Tumor growth inhibition of >50% is considered meaningful. Growth delay is calculated as T–C where T and C are the times in days for mean tumor size in the treated (T) and control (C) groups to reach 400% of the initial tumor volume. Cures are excluded from this calculation. Percent regression is measured by the following formula: $100 \times (T_0-T_t)/T_0$, where $T_0$ is the median tumor volume of a treatment group on day 0, and $T_t$ is the median tumor volume of the same group on day t. Durable cures were determined by the absence of palpable tumor 60 days post final dose of drug. Tarceva was dosed in a 6% Captisol (CyDex, Inc) in WFI (Water for Injection) solution and all control animals were dosed with an equal volume of the vehicle. Compd D was dosed in 25 mM tartaric acid at the appropriate concentration in 20 ml/kg dose volume. All mice were dosed daily by oral gavage for the indicated time periods.

Figure 19A:
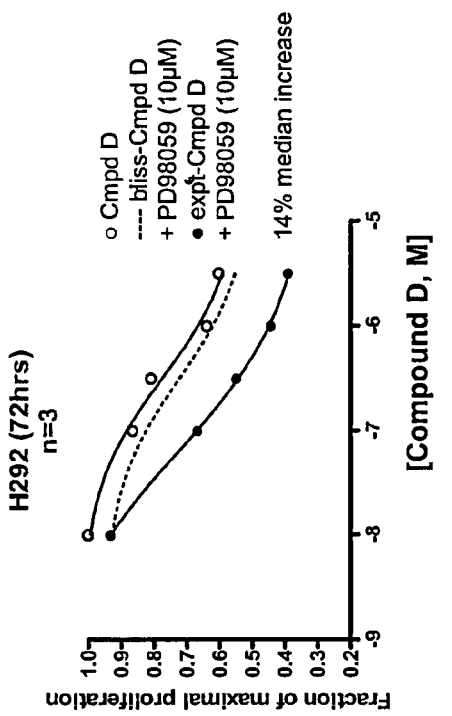
FIGS. 19A and 19B: Plots depicting synergistic effect of IGF-1R inhibitor Compound D (cis-3-[8-Amino-1-(2-phenyl-quinolin-7-yl)-imidazo[1,5-a]pyrazin-3-yl]-1-methyl-cyclobutanol) in combination with MEK1 (6A) and with PD-98059 (6B) on inhibiting cell proliferation in the non-small cell lung carcinoma cell line H292.
Figure 19B:
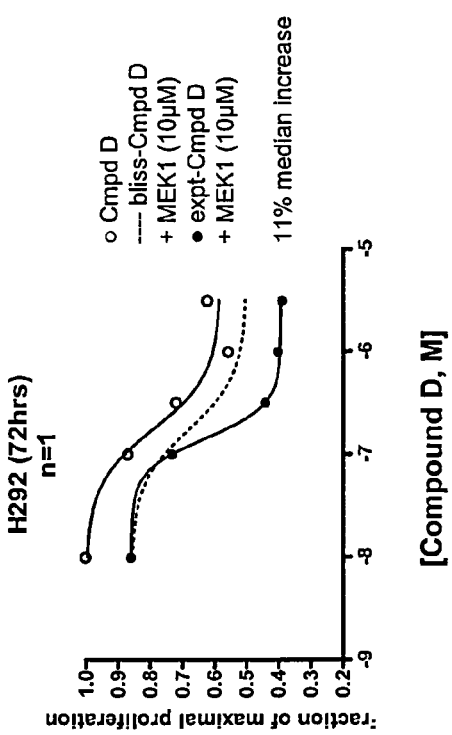

As seen in FIGS. 19A and 19B, the combination of Compound D with MEK1 and PD-98059 is more efficacious than either drug alone in both in vitro and in vivo.

In FIG. 19A, the combination of Compound D and MEK1 produces synergist effect on inhibiting cell proliferation and promoting apoptosis in the non-small cell lung carcinoma cell line H292.

In FIG. 19B, the combination of Compound D and PD-98059 produces synergist effect on inhibiting cell proliferation and promoting apoptosis in the non-small cell lung carcinoma cell line H292.

Unless otherwise stated, the connections of compound name moieties are at the rightmost recited moiety. That is, the substituent name starts with a terminal moiety, continues with any bridging moieties, and ends with the connecting moiety. For example, heteroarylthio$C_{1-4}$alkyl has a heteroaryl group connected through a thio sulfur to a $C_{1-4}$ alkyl that connects to the chemical species bearing the substituent.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group. Further, C0alkyl includes being a substituted bond—that is, for example, —X—Y—Z is —C(O)—$C_{2-4}$alkyl when X is $C_0$alkyl, Y is $C_0$alkyl, and Z is —C(O)—$C_{2-4}$alkyl.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like.

The term "halo" refers to fluoro, chloro, bromo, or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl, and the like.

The term "acyl" refers to the structure —C(=O)—R, in which R is a general substituent variable such as, for example $R^1$ described above. Examples include, but are not limited to, (bi)(cyclo)alkylketo, (cyclo)alkenylketo, alkynylketo, arylketo, hetarylketo, heterocyclylketo, heterobicycloalkylketo, spiroalkylketo.

Unless otherwise specified, the term "cycloalkyl" refers to a 3-8 carbon cyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "bicycloalkyl" refers to a structure consisting of two cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" refers to a structure consisting of two cycloalkyl moieties that have exactly one atom in common. Examples include, but are not limited to, spiro[4.5]decyl, spiro[2.3]hexyl, and the like.

The term "heterobicycloalkyl" refers to a bicycloalkyl structure in which at least one carbon atom is replaced with a heteroatom independently selected from oxygen, nitrogen, and sulfur.

The term "heterospiroalkyl" refers to a spiroalkyl structure in which at least one carbon atom is replaced with a heteroatom independently selected from oxygen, nitrogen, and sulfur.

The term "alkylcarbonyloxyalkyl" refers to an ester moiety, for example acetoxymethyl, n-butyryloxyethyl, and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl, and the like.

The term "alkylsulfonylalkyl" refers to an alkyl group substituted with an alkylsulfonyl moiety, for example mesylmethyl, isopropylsulfonylethyl, and the like.

The term "alkylsulfonyl" refers to a sulfonyl moiety substituted with an alkyl group, for example mesyl, n-propylsulfonyl, and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl, and the like.

The term "haloalkenyl" refers to an alkenyl group substituted with one or more halo groups.

Unless otherwise specified, the term "cycloalkenyl" refers to a cyclic aliphatic 3 to 8 ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

The term "alkynyl" refers to an unsaturated hydrocarbon group, straight or branched, having at least one acetylenic bond, for example ethynyl, propargyl, and the like.

The term, "haloalkynyl" refers to an alkynyl group substituted with one or more independent halo groups.

The term "alkylcarbonyl" refers to an alkylketo functionality, for example acetyl, n-butyryl, and the like.

The term "alkenylcarbonyl" refers to an alkenylketo functionality, for example, propenoyl and the like.

The term "aryl" refers to phenyl or naphthyl which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The terms "heteroaryl" or "hetaryl" or "heteroar-" or "hetar-" refer to a substituted or unsubstituted 5- or 6-membered unsaturated ring containing one, two, three, or four independently selected heteroatoms, preferably one or two heteroatoms independently selected from oxygen, nitrogen, and sulfur or to a bicyclic unsaturated ring system containing up to 10 atoms including at least one heteroatom selected from oxygen, nitrogen, and sulfur. Examples of hetaryls include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. The heterocyclic ring may be optionally substituted with one or more substituents.

The terms "aryl-alkyl" or "arylalkyl" or "aralkyl" are used to describe a group wherein the alkyl chain can be branched or straight chain forming a bridging portion with the terminal aryl, as defined above, of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl) propyl, 3-(2-methylphenyl)propyl, 3-(4-methoxyphenyl) propyl, 3-(4-(trifluoromethyl)phenyl)propyl, 3-(2,4-dichlorophenyl)propyl, 4-phenylbutyl, 4-(4-chlorophenyl) butyl, 4-(2-methylphenyl)butyl, 4-(2,4-dichlorophenyl) butyl, 4-(2-methoxphenyl)butyl, and 10-phenyldecyl.

The terms "aryl-cycloalkyl" or "arylcycloalkyl" are used to describe a group wherein the terminal aryl group is attached to a cycloalkyl group, for example phenylcyclopentyl and the like.

The terms "aryl-alkenyl" or "arylalkenyl" or "aralkenyl" are used to describe a group wherein the alkenyl chain can be branched or straight chain forming a bridging portion of the aralkenyl moiety with the terminal aryl portion, as defined above, for example styryl (2-phenylvinyl), phenpropenyl, and the like.

The terms "aryl-alkynyl" or "arylalkynyl" or "aralkynyl" are used to describe a group wherein the alkynyl chain can be branched or straight chain forming a bridging portion of the aryl-alkynyl moiety with the terminal aryl portion, as defined above, for example 3-phenyl-1-propynyl, and the like.

The terms "aryl-oxy" or "aryloxy" or "aroxy" are used to describe a terminal aryl group attached to a bridging oxygen atom. Typical aryl-oxy groups include phenoxy, 3,4-dichlorophenoxy, and the like.

The terms "aryl-oxyalkyl" or "aryloxyalkyl" or "aroxyalkyl" are used to describe a group wherein an alkyl group is substituted with a terminal aryl-oxy group, for example pentafluorophenoxymethyl and the like.

The term "heterocycloalkenyl" refers to a cycloalkenyl structure in which at least one carbon atom is replaced with a heteroatom selected from oxygen, nitrogen, and sulfur.

The terms "hetaryl-oxy" or "heteroaryl-oxy" or "hetaryloxy" or "heteroaryloxy" or "hetaroxy" or "heteroaroxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "hetaryl-alkyl" or "heteroaryl-alkyl" or "hetaralkyl" or "heteroaralkyl" are used to describe a group wherein the alkyl chain can be branched or straight chain forming a bridging portion of the heteroaralkyl moiety with the terminal heteroaryl portion, as defined above, for example 3-furylmethyl, thenyl, furfuryl, and the like.

The terms "hetarylalkenyl" or "heteroarylalkenyl" or "hetaryl-alkenyl" or "heteroaryl-alkenyl" or "hetaralkenyl" or heteroaralkenyl" are used to describe a group wherein the alkenyl chain can be branched or straight chain forming a bridging portion of the heteroaralkenyl moiety with the terminal heteroaryl portion, as defined above, for example 3-(4-pyridyl)-1-propenyl.

The terms "hetarylalkynyl" or "heteroarylalkynyl" or "hetaryl-alkynyl" or "heteroaryl-alkynyl" or "hetaralkynyl" or "heteroaralkynyl" are used to describe a group wherein the alkynyl chain can be branched or straight chain forming a bridging portion of the heteroaralkynyl moiety with the heteroaryl portion, as defined above, for example 4-(2-thienyl)-1-butynyl.

The term "heterocyclyl" or "hetcyclyl" refers to a substituted or unsubstituted 4-, 5-, or 6-membered saturated or partially unsaturated ring containing one, two, or three heteroatoms, preferably one or two heteroatoms independently selected from oxygen, nitrogen and sulfur; or to a bicyclic ring system containing up to 10 atoms including at least one heteroatom independently selected from oxygen, nitrogen, and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl, and 5-methyl-6-chromanyl.

The terms "heterocyclylalkyl" or "heterocyclyl-alkyl" or "hetcyclylalkyl" or "hetcyclyl-alkyl" are used to describe a group wherein the alkyl chain can be branched or straight chain forming a bridging portion of the heterocyclylalkyl moiety with the terminal heterocyclyl portion, as defined above, for example 3-piperidinylmethyl and the like.

The terms "heterocyclylalkenyl" or "heterocyclyl-alkenyl" or "hetcyclylalkenyl" or "hetcyclyl-alkenyl" are used to describe a group wherein the alkenyl chain can be branched or straight chain forming a bridging portion of the heterocyclylalkenyl moiety with the terminal heterocyclyl portion, as defined above, for example 2-morpholinyl-1-propenyl and the like.

The terms "heterocyclylalkynyl" or "heterocyclyl-alkynyl" or "hetcyclylalkynyl" or "hetcyclyl-alkynyl" are used to describe a group wherein the alkynyl chain can be branched or straight chain forming a bridging portion of the heterocyclylalkynyl moiety with the terminal heterocyclyl portion, as defined above, for example 2-pyrrolidinyl-1-butynyl and the like.

The term "carboxylalkyl" refers to a terminal carboxyl (—COOH) group attached to branched or straight chain alkyl groups as defined above.

The term "carboxylalkenyl" refers to a terminal carboxyl (—COOH) group attached to branched or straight chain alkenyl groups as defined above.

The term "carboxylalkynyl" refers to a terminal carboxyl (—COOH) group attached to branched or straight chain alkynyl groups as defined above.

The term "carboxylcycloalkyl" refers to a terminal carboxyl (—COOH) group attached to a cyclic aliphatic ring structure as defined above.

The term "carboxylcycloalkenyl" refers to a terminal carboxyl (—COOH) group attached to a cyclic aliphatic ring structure having ethylenic bonds as defined above.

The terms "cycloalkylalkyl" or "cycloalkyl-alkyl" refer to a terminal cycloalkyl group as defined above attached to an alkyl group, for example cyclopropylmethyl, cyclohexylethyl, and the like.

The terms "cycloalkylalkenyl" or "cycloalkyl-alkenyl" refer to a terminal cycloalkyl group as defined above attached to an alkenyl group, for example cyclohexylvinyl, cycloheptylallyl, and the like.

The terms "cycloalkylalkynyl" or "cycloalkyl-alkynyl" refer to a terminal cycloalkyl group as defined above attached to an alkynyl group, for example cyclopropylpropargyl, 4-cyclopentyl-2-butynyl, and the like.

The terms "cycloalkenylalkyl" or "cycloalkenyl-alkyl" refer to a terminal cycloalkenyl group as defined above attached to an alkyl group, for example 2-(cyclopenten-1-yl) ethyl and the like.

The terms "cycloalkenylalkenyl" or "cycloalkenyl-alkenyl" refer to terminal a cycloalkenyl group as defined above attached to an alkenyl group, for example 1-(cyclohexen-3-yl)allyl and the like.

The terms "cycloalkenylalkynyl" or "cycloalkenyl-alkynyl" refer to terminal a cycloalkenyl group as defined above attached to an alkynyl group, for example 1-(cyclohexen-3-yl)propargyl and the like.

The term "carboxylcycloalkylalkyl" refers to a terminal carboxyl (—COOH) group attached to the cycloalkyl ring portion of a cycloalkylalkyl group as defined above.

The term "carboxylcycloalkylalkenyl" refers to a terminal carboxyl (—COOH) group attached to the cycloalkyl ring portion of a cycloalkylalkenyl group as defined above.

The term "carboxylcycloalkylalkynyl" refers to a terminal carboxyl (—COOH) group attached to the cycloalkyl ring portion of a cycloalkylalkynyl group as defined above.

The term "carboxylcycloalkenylalkyl" refers to a terminal carboxyl (—COOH) group attached to the cycloalkenyl ring portion of a cycloalkenylalkyl group as defined above.

The term "carboxylcycloalkenylalkenyl" refers to a terminal carboxyl (—COOH) group attached to the cycloalkenyl ring portion of a cycloalkenylalkenyl group as defined above.

The term "carboxylcycloalkenylalkynyl" refers to a terminal carboxyl (—COOH) group attached to the cycloalkenyl ring portion of a cycloalkenylalkynyl group as defined above.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy, and the like.

The term "alkoxyalkoxyalkyl" refers to an alkyl group substituted with an alkoxy moiety which is in turn is substituted with a second alkoxy moiety, for example methoxymethoxymethyl, isopropoxymethoxyethyl, and the like.

The term "alkylthio" includes both branched and straight chain alkyl groups attached to a bridging sulfur atom, for example methylthio and the like.

The term "haloalkylthio" refers to an alkylthio group substituted with one or more halo groups, for example trifluoromethylthio and the like.

The term "alkoxyalkyl" refers to an alkyl group substituted with an alkoxy group, for example isopropoxymethyl and the like.

The term "alkoxyalkenyl" refers to an alkenyl group substituted with an alkoxy group, for example 3-methoxyallyl and the like.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined above substituted with an alkoxycarbonyl, for example 4-(ethoxycarbonyl)-2-butenyl and the like.

The term "alkoxycarbonylalkynyl" refers to a straight chain or branched alkynyl as defined above substituted with an alkoxycarbonyl, for example 4-(ethoxycarbonyl)-2-butynyl and the like.

The term "haloalkoxyalkyl" refers to a straight chain or branched alkyl as defined above substituted with a haloalkoxy, for example 2-chloroethoxymethyl, trifluoromethoxymethyl and the like.

The term "haloalkoxyalkenyl" refers to a straight chain or branched alkenyl as defined above substituted with a haloalkoxy, for example 4-(chloromethoxy)-2-butenyl and the like.

The term "haloalkoxyalkynyl" refers to a straight chain or branched alkynyl as defined above substituted with a haloalkoxy, for example 4-(2-fluoroethoxy)-2-butynyl and the like.

The term "alkylthioalkyl" refers to a straight chain or branched alkyl as defined above substituted with an alkylthio group, for example methylthiomethyl, 3-(isobutylthio)heptyl, and the like.

The term "alkylthioalkenyl" refers to a straight chain or branched alkenyl as defined above substituted with an alkylthio group, for example 4-(methylthio)-2-butenyl and the like.

The term "alkylthioalkynyl" refers to a straight chain or branched alkynyl as defined above substituted with an alkylthio group, for example 4-(ethylthio)-2-butynyl and the like.

The term "haloalkylthioalkyl" refers to a straight chain or branched alkyl as defined above substituted with an haloalkylthio group, for example 2-chloroethylthiomethyl, trifluoromethylthiomethyl and the like.

The term "haloalkylthioalkenyl" refers to a straight chain or branched alkenyl as defined above substituted with an haloalkylthio group, for example 4-(chloromethylthio)-2-butenyl and the like.

The term "haloalkylthioalkynyl" refers to a straight chain or branched alkynyl as defined above substituted with a haloalkylthio group, for example 4-(2-fluoroethylthio)-2-butynyl and the like.

The term "dialkoxyphosphorylalkyl" refers to two straight chain or branched alkoxy groups as defined above attached to a pentavalent phosphorous atom, containing an oxo substituent, which is in turn attached to an alkyl, for example diethoxyphosphorylmethyl and the like.

One in the art understands that an "oxo" requires a second bond from the atom to which the oxo is attached. Accordingly, it is understood that oxo cannot be substituted onto an aryl or heteroaryl ring.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

As used herein, the term "patient" preferably refers to a human in need of treatment with an IRS1 agent such as an EGFR kinase inhibitor for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an IRS1 agent.

In the context of this invention, an "effective amount" of an agent or therapy is as defined above. A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

For purposes of the present invention, "co-administration of" and "co-administering" of an IGF1R protein kinase inhibitor compound of Formula I with an IRS1 agent such as an EGFR kinase inhibitor (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. An IGF1R protein kinase inhibitor compound of Formula I can be administered prior to, at the same time as, or subsequent to administration of the IRS1 agent, or in some combination thereof. Where the IRS1 agent is administered to the patient at repeated intervals, e.g., during a standard course of treatment, an IGF1R protein kinase inhibitor compound of Formula I can be administered prior to, at the same time as, or subsequent to, each administration of the IRS1 agent, or some combination thereof, or at different intervals in relation to the IRS1 agent treatment, or in a single dose prior to, at any time during, or subsequent to the course of treatment with the IRS1 agent.

All patents, published patent applications and other references disclosed herein are hereby expressly incorporated herein by reference.

The invention claimed is:

1. A method for treating cancer, wherein the cancer is non-small cell lung cancer, colorectal cancer, pancreatic cancer or breast cancer, comprising administering to a patient simultaneously or sequentially:

(i) a therapeutically or sub-therapeutically effective amount of an anti-cancer agent that inhibits serine phosphorylation of IRS1, or a pharmaceutically salt thereof; and (ii) a therapeutically or sub-therapeutically effective amount an IGF-1R inhibitor represented by the formula:

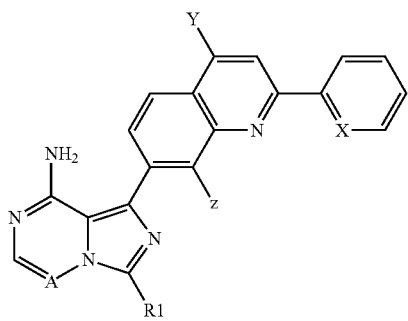

wherein:
A is CH or N;
X is CH or N;
Y and Z are independently H, methyl, ethyl, or halogen; and
$R^1$ is cycloC$_{3-10}$alkyl substituted by one or more independent $G^{11}$ substituents;

$G^{11}$ is halo, oxo, —CF$_3$, —OCF$_3$, OR$^{21}$, —NR$^{21}$R$^{31}$ (R$^{2a1}$)$_{j4}$, —C(O)R$^{21}$, —CO$_2$R$^{21}$, —C(=O)NR$^{21}$R$^{31}$, —NO$_2$, —CN, —S(O)$_{j4}$R$^{21}$, —SO$_2$NR$^{21}$R$^{31}$, NR$^{21}$(C=O)R$^{31}$, NR$^{21}$C(=O)OR$^{31}$, NR$^{21}$C(=O)NR$^{31}$R$^{2a1}$, NR$^{21}$S(O)$_{j4}$R$^{31}$, —C(=S)OR$^{21}$, —C(=O)SR$^{21}$, —NR$^{21}$C(=NR$^{31}$)NR$^{2a1}$R$^{3a1}$, —NR$^{21}$C(=NR$^{31}$)OR$^{2a1}$, —NR$^{21}$C(=NR$^{31}$)SR$^{2a1}$, —OC(=O)OR$^{21}$, —OC(=O)NR$^{21}$R$^{31}$, —OC(=O)SR$^{21}$, —SC(=O)OR$^{21}$, —SC(=O)NR$^{21}$R$^{31}$, —P(O)OR$^{21}$OR$^{31}$, C$_{1-10}$alkylidene, C$_{0-10}$alkylidene, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkyl C$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(=O)NR$^{2221}$R$^{3331}$, —NO$_2$, —CN, —S(O)$_{j4a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j4a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —C(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

or $G^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{222a1}$, R$^{2221a1}$)$_{j5a}$, —C(O)R$^{2221}$, —CO$_2$R$^{2221}$, —C(=O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(=O)R$^{3331}$, —NR$^{2221}$C(=O)OR$^{3331}$, —NR$^{2221}$C(=O)NR$^{3331}$R$^{222a1}$, —NR$^{2221}$S(O)$_{j5a}$R$^{3331}$, —C(=S)OR$^{2221}$, —C(=O)SR$^{2221}$, —NR$^{2221}$C(=NR$^{3331}$)NR$^{222a1}$R$^{333a1}$, —NR$^{2221}$C(=NR$^{3331}$)OR$^{222a1}$, —NR$^{2221}$C(=NR$^{3331}$)SR$^{222a1}$, —C(=O)OR$^{2221}$, —OC(=O)NR$^{2221}$R$^{3331}$, —OC(=O)SR$^{2221}$, —SC(=O)OR$^{2221}$, —P(O)OR$^{2221}$OR$^{3331}$, or —SC(=O)NR$^{2221}$R$^{3331}$ substituents;

$R^{21}$, $R^{2a1}$, $R^{31}$, $R^{3a1}$, $R^{2221}$, $R^{222a1}$, $R^{3331}$, and $R^{333a1}$ are each independently C$_{0-10}$alkyl, C$_{2-10}$alkenyl, C$_{2-10}$alkynyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkyl C$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted by one or more independent $G^{111}$ substituents;

or in the case of —NR$^{21}$R$^{31}$(R$^{2a1}$)$_{j4}$ or —NR$^{2221}$R$^{3331}$(R$^{222a1}$)$_{j4a}$ or —NR$^{2221}$R$^{3331}$(R$^{222a1}$)$_{j5a}$, then R$^{2221}$ and R$^{3331}$ are optionally taken together with the nitrogen atom to which they are attached to form a 3-10 membered saturated or unsaturated ring, wherein said ring is optionally substituted by one or more independent $G^{1111}$ substituents and wherein said ring optionally includes one or more heteroatoms other than the nitrogen to which R$^{2221}$ and R$^{3331}$ are attached;

each $G^{111}$ is independently C$_{0-10}$alkyl, C$_{2-10}$alkenyl, C$_{2-10}$alkynyl, C$_{1-10}$alkoxyC$_{1-10}$alkyl, C$_{1-10}$alkoxy C$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenyl C$_{2-10}$alkynyl, heterocyclyl-C$_{0-10}$alkyl, heterocyclyl-C$_{2-10}$alkenyl, heterocyclyl-C$_{2-10}$alkynyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, —NR$^{77}$C(=O)R$^{87}$, —NR$^{77}$C(=O)OR$^{87}$, —NR$^{77}$C(=O)NR$^{78}$R$^{87}$, —NR$^{77}$S(O)$_{j5a}$R$^{87}$, —C(=S)OR$^{77}$, —C(=O)SR$^{77}$, —NR$^{77}$C(=NR$^{87}$)NR$^{78}$R$^{88}$, —NR$^{77}$C(=NR$^{87}$)OR$^{78}$, —NR$^{77}$C(=NR$^{87}$)SR$^{78}$, —OC(=O)OR$^{77}$, —OC(=O)NR$^{77}$R$^{87}$, —OC(=O)SR$^{77}$, —SC(=O)OR$^{77}$, —P(O)OR$^{77}$OR$^{87}$, or —SC(=O)NR$^{77}$R$^{87}$ substituents;

or in the case of —NR$^{78}$R$^{88}$, R$^{78}$ and R$^{88}$ are optionally taken together with the nitrogen atom to which they are attached to form a 3-10 membered saturated or unsaturated ring, wherein said ring is optionally substituted with one or more independent halo, cyano, hydroxy, nitro, C$_{1-10}$alkoxy, —SO$_2$NR$^{778}$R$^{888}$, or —NR$^{778}$R$^{888}$ substituents, and wherein said ring optionally includes one or more heteroatoms other than the nitrogen to which R$^{78}$ and R$^{88}$ are attached;

R$^{77}$, R$^{78}$, R$^{87}$, R", R$^{778}$, and R$^{888}$ are each independently C$_{0-10}$alkyl, C$_{2-10}$alkenyl, C$_{2-10}$alkynyl, C$_{1-10}$alkoxy C$_{1-10}$alkyl, C$_{1-10}$alkoxyC$_{2-10}$alkenyl, C$_{1-10}$alkoxy C$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkyl C$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenyl C$_{2-10}$alkynyl, heterocyclyl-C$_{0-10}$alkyl, heterocyclyl-C$_{2-10}$alkenyl, heterocyclyl-C$_{2-10}$alkynyl, C$_{1-10}$alkylcarbonyl, C$_{2-10}$alkenylcarbonyl, C$_{2-10}$alkynylcarbonyl, C$_{1-10}$alkoxycarbonyl, C$_{1-10}$alkoxycarbonylC$_{1-10}$alkyl, monoC$_{1-6}$alkylaminocarbonyl, diC$_{1-6}$alkylaminocarbonyl, mono(aryl)aminocarbonyl, di(aryl)aminocarbonyl, or C$_{1-10}$alkyl(aryl)aminocarbonyl, any of which is optionally substituted with one or more independent halo, cyano, hydroxy, nitro, C$_{1-10}$alkoxy, —SO$_2$N(C$_{0-4}$alkyl)(C$_{0-4}$alkyl), or —N(C$_{0-4}$alkyl)(C$_{0-4}$alkyl) substituents;

or R$^{77}$, R$^{78}$, R$^{87}$, R$^{88}$, R$^{778}$, and R$^{888}$ are each independently aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, hetaryl-C$_{2-10}$alkynyl, mono(C$_{1-6}$alkyl)aminoC$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, or —N(C$_{1-6}$alkyl)-C$_{1-6}$alkykaryl, any of which is optionally substituted with one or more independent halo, cyano, nitro, —O(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CON(C$_{0-4}$alkyl)(C$_{0-10}$alkyl), —SO$_2$N(C$_{0-4}$alkyl)(C$_{0-4}$alkyl), or —N(C$_{0-4}$alkyl)(C$_{0-4}$alkyl) substituents;

j4, j4a, and j5a are each independently 0, 1, or 2.

2. The method of claim 1, wherein the cancer comprises non-small cell lung cancer.

3. The method of claim 1, wherein the IGFR inhibitor comprises cis-3-[8-amino-1-(2-phenyl-quinolin-7-yl)-imidazo[1,5-a]pyrazin-3-yl]-1-methyl-cyclobutanol, or a pharmaceutically acceptable salt thereof.

4. The method of claim 1, wherein the IGFR inhibitor comprises cis-3-[4-Amino-5-(8-fluoro-2-phenyl-quinolin-7-yl)-imidazo[5,1f][1,2,4]triazin-7-yl]-1-methyl-cyclobutanol, or a pharmaceutically acceptable salt thereof.

5. The method of claim 3, wherein the anti-cancer agent comprises erlotinib, cetuximab, gefitinib, or a pharmaceutically acceptable salt thereof.

6. The method of claim 3, wherein the anti-cancer agent comprises erlotinib or a pharmaceutically acceptable salt thereof.

7. The method of claim 6, wherein the cancer comprises non-small cell lung cancer.

8. The method of claim 1, wherein the anticancer agent is selected from Ras inhibitors, Raf inhibitors, MEK inhibitors, or PKC inhibitors.

9. The method of claim 1, wherein the anti-cancer agent is a MEK inhibitor.

10. The method of claim 1, wherein the anti-cancer agent is an MEK inhibitor, or a pharmaceutically acceptable salt thereof, and the IGFR inhibitor is cis-3-[8-amino-1-(2-phenyl-quinolin-7-yl)-imidazo[1,5-a]pyrazin-3-yl]-1-methyl-cyclobutanol, or a pharmaceutically acceptable salt thereof.

11. The method of claim 1, wherein the anti-cancer agent is a Raf protein kinase family inhibitor.

12. The method of claim 1, wherein the anti-cancer agent is sorafenib.

13. The method of claim 1, wherein the anti-cancer agent is a Raf protein kinase family inhibitor, or a pharmaceutically acceptable salt thereof, and the IGFR inhibitor is cis-3-[8-Amino-1-(2-phenyl-quinolin-7-yl)-imidazo[1,5-a]pyrazin-3-yl]-1-methyl-cyclobutanol, or a pharmaceutically acceptable salt thereof.

14. The method of claim 1, wherein the anti-cancer agent is ZD-6474, IMC-1121b, CDP-791, imatinib, sunitinib malate, PTK-787, lapatinib, sirolimus, temsirolimus, everolimus, CP-751871, RAV-12, IMC-A12, 19D12, PS-1145, or orbortezomib.

* * * * *